US011008395B2

(12) United States Patent
Yamniuk et al.

(10) Patent No.: US 11,008,395 B2
(45) Date of Patent: May 18, 2021

(54) ANTIBODIES AGAINST IL-7R ALPHA SUBUNIT AND USES THEREOF

(71) Applicant: Bristol Myers-Squibb Company, Princeton, NJ (US)

(72) Inventors: Aaron Paul Yamniuk, Lawrenceville, NJ (US); Scott Ronald Brodeur, New Hope, PA (US); Ekaterina Deyanova, Lawrenceville, NJ (US); Richard Yu-Cheng Huang, Bridgewater, NJ (US); Yun Wang, Plainsboro, NJ (US); Alfred Robert Langish, Feasterville, PA (US); Guodong Chen, East Brunswick, NJ (US); Stephen Michael Carl, Howell, NJ (US); Hong Shen, Belle Mead, NJ (US); Achal Mukundrao Pashine, Mahwah, NJ (US); Lin Hui Su, Somerville, MA (US)

(73) Assignee: Bristol Myers-Squibb Company, Princeton, NJ (US)

( * ) Notice: Subject to any disclaimer, the term of this patent is extended or adjusted under 35 U.S.C. 154(b) by 0 days.

(21) Appl. No.: 16/748,518

(22) Filed: Jan. 21, 2020

(65) Prior Publication Data
US 2020/0231687 A1 Jul. 23, 2020

Related U.S. Application Data

(60) Provisional application No. 62/795,378, filed on Jan. 22, 2019, provisional application No. 62/868,791, filed on Jun. 28, 2019.

(51) Int. Cl.
| | | |
|---|---|---|
| *C07K 16/28* | (2006.01) | |
| *A61P 29/00* | (2006.01) | |
| *C12N 15/63* | (2006.01) | |
| *A61K 39/00* | (2006.01) | |

(52) U.S. Cl.
CPC .......... *C07K 16/2866* (2013.01); *A61P 29/00* (2018.01); *C12N 15/63* (2013.01); *A61K 2039/505* (2013.01); *C07K 2317/565* (2013.01)

(58) Field of Classification Search
CPC ................................................ C07K 16/2866
See application file for complete search history.

(56) References Cited

U.S. PATENT DOCUMENTS

| | | | |
|---|---|---|---|
| 4,399,216 A | 8/1983 | Axel et al. | |
| 4,439,196 A | 3/1984 | Higuchi | |
| 4,447,224 A | 5/1984 | Decant, Jr. et al. | |
| 4,447,233 A | 5/1984 | Mayfield | |
| 4,475,196 A | 10/1984 | La Zor | |
| 4,486,194 A | 12/1984 | Ferrara | |
| 4,487,603 A | 12/1984 | Harris | |
| 4,596,556 A | 6/1986 | Morrow et al. | |
| 4,634,665 A | 1/1987 | Axel et al. | |
| 4,790,824 A | 12/1988 | Morrow et al. | |
| 4,816,567 A | 3/1989 | Cabilly et al. | |
| 4,881,175 A | 11/1989 | Ladner | |
| 4,941,880 A | 7/1990 | Burns | |
| 4,946,778 A | 8/1990 | Ladner et al. | |
| 5,013,653 A | 5/1991 | Huston et al. | |
| 5,064,413 A | 11/1991 | McKinnon et al. | |
| 5,091,513 A | 2/1992 | Huston et al. | |
| 5,132,405 A | 7/1992 | Huston et al. | |
| 5,179,017 A | 1/1993 | Axel et al. | |
| 5,223,409 A | 6/1993 | Ladner et al. | |
| 5,225,539 A | 7/1993 | Winter | |
| 5,258,498 A | 11/1993 | Huston et al. | |
| 5,260,203 A | 11/1993 | Ladner et al. | |
| 5,312,335 A | 5/1994 | McKinnon et al. | |
| 5,383,851 A | 1/1995 | McKinnon, Jr. et al. | |
| 5,399,163 A | 3/1995 | Peterson et al. | |
| 5,403,484 A | 4/1995 | Ladner et al. | |
| 5,427,908 A | 6/1995 | Dower et al. | |
| 5,455,030 A | 10/1995 | Ladner et al. | |
| 5,476,786 A | 12/1995 | Huston | |
| 5,476,996 A | 12/1995 | Wilson et al. | |
| 5,482,858 A | 1/1996 | Huston et al. | |
| 5,530,101 A | 6/1996 | Queen et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,571,698 A | 11/1996 | Ladner et al. | |
| 5,580,717 A | 12/1996 | Dower et al. | |
| 5,585,089 A | 12/1996 | Queen et al. | |
| 5,624,821 A | 4/1997 | Winter et al. | |
| 5,625,126 A | 4/1997 | Lonberg et al. | |
| 5,633,425 A | 5/1997 | Lonberg et al. | |
| 5,648,260 A | 7/1997 | Winter et al. | |
| 5,661,016 A | 8/1997 | Lonberg et al. | |
| 5,677,425 A | 10/1997 | Bodmer et al. | |
| 5,693,762 A | 12/1997 | Queen et al. | |
| 5,698,767 A | 12/1997 | Wilson et al. | |

(Continued)

FOREIGN PATENT DOCUMENTS

| | | |
|---|---|---|
| EP | 0338841 B1 | 3/1995 |
| WO | WO-8704462 A1 | 7/1987 |

(Continued)

OTHER PUBLICATIONS

Acosta-Rodriguez, E.V.A., et al., "Surface phenotype and antigenic specificity of human interleukin 17-producing T helper memory cells," Nature Immunology 8(6):639-646, Nature Publishing Group, United States (Jun. 2007).

(Continued)

*Primary Examiner* — Prema M Mertz
(74) *Attorney, Agent, or Firm* — McCarter & English, LLP

(57) ABSTRACT

Provided herein are antibodies that bind to the alpha subunit of an IL-7 receptor (IL-7Rα). Also provided are uses of these antibodies in therapeutic applications, such as treatment of inflammatory diseases. Further provided are cells that produce the antibodies, polynucleotides encoding the heavy and/or light chain regions of the antibodies, and vectors comprising the polynucleotides.

25 Claims, 39 Drawing Sheets

Figure 1:
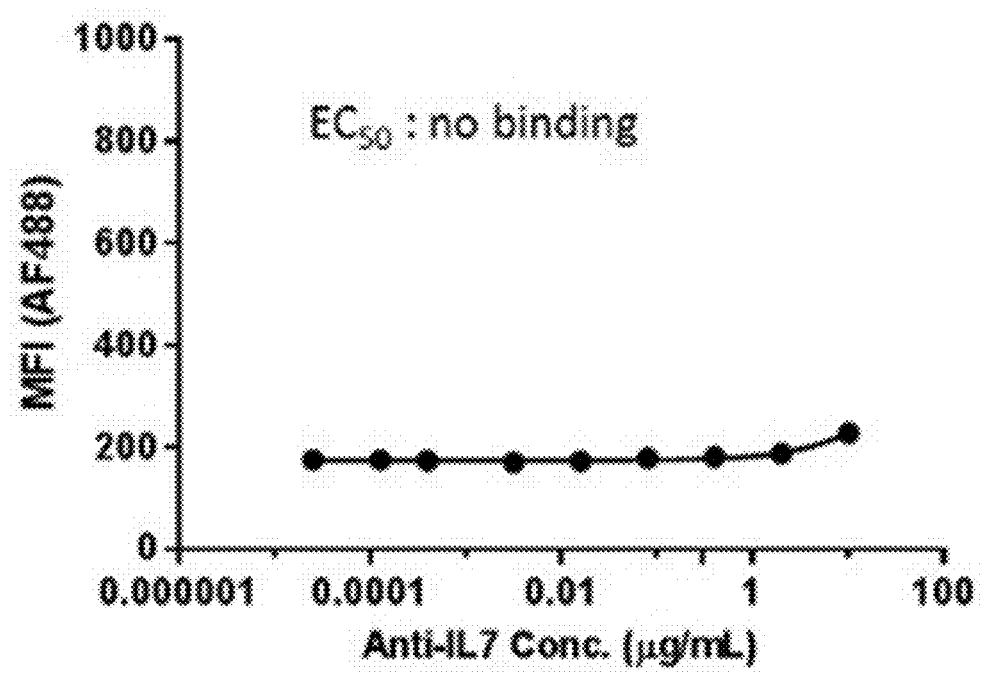

Specification includes a Sequence Listing.

(56) References Cited

U.S. PATENT DOCUMENTS

| | | |
|---|---|---|
| 5,714,350 A | 2/1998 | Co et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,869,046 A | 2/1999 | Presta et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,939,598 A | 8/1999 | Kucherlapati et al. |
| 5,969,108 A | 10/1999 | McCafferty et al. |
| 6,075,181 A | 6/2000 | Kucherlapati et al. |
| 6,114,598 A | 9/2000 | Kucherlapati et al. |
| 6,121,022 A | 9/2000 | Presta et al. |
| 6,150,584 A | 11/2000 | Kucherlapati et al. |
| 6,162,963 A | 12/2000 | Kucherlapati et al. |
| 6,165,745 A | 12/2000 | Ward et al. |
| 6,172,197 B1 | 1/2001 | McCafferty et al. |
| 6,180,370 B1 | 1/2001 | Queen et al. |
| 6,194,551 B1 | 2/2001 | Idusogie et al. |
| 6,277,375 B1 | 8/2001 | Ward |
| 6,350,861 B1 | 2/2002 | Co et al. |
| 6,437,095 B1 | 8/2002 | Lilie et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,737,056 B1 | 5/2004 | Presta |
| 6,989,452 B2 | 1/2006 | Ng et al. |
| 7,087,600 B2 | 8/2006 | Ng et al. |
| 7,129,261 B2 | 10/2006 | Ng et al. |
| 7,317,091 B2 | 1/2008 | Lazar et al. |
| 8,101,720 B2 | 1/2012 | Lazar et al. |
| 9,150,653 B2 | 10/2015 | Kirby et al. |
| 2003/0153043 A1 | 8/2003 | Carr et al. |
| 2006/0004081 A1 | 1/2006 | Chen et al. |
| 2006/0024317 A1 | 2/2006 | Boyd et al. |
| 2006/0247295 A1 | 11/2006 | Gangwar et al. |
| 2010/0069614 A1 | 3/2010 | Houtzager et al. |
| 2013/0295111 A1 | 11/2013 | Gonzalez-Quintial et al. |
| 2018/0251561 A1 | 9/2018 | Durum et al. |

FOREIGN PATENT DOCUMENTS

| | | |
|---|---|---|
| WO | WO-8901036 A1 | 2/1989 |
| WO | WO-1990015870 A1 | 12/1990 |
| WO | WO-9203918 A1 | 3/1992 |
| WO | WO-9312227 A1 | 6/1993 |
| WO | WO-9425585 A1 | 11/1994 |
| WO | WO-9429351 A2 | 12/1994 |
| WO | WO-1994028160 A1 | 12/1994 |
| WO | WO-9517886 A1 | 7/1995 |
| WO | WO-9632478 A1 | 10/1996 |
| WO | WO-9713852 A1 | 4/1997 |
| WO | WO-9734631 A1 | 9/1997 |
| WO | WO-9824884 A1 | 6/1998 |
| WO | WO-9945962 A1 | 9/1999 |
| WO | WO-9954342 A1 | 10/1999 |
| WO | WO-0042072 A2 | 7/2000 |
| WO | WO-0114424 A2 | 3/2001 |
| WO | WO-0158957 A2 | 8/2001 |
| WO | WO-0206919 A2 | 1/2002 |
| WO | WO-0243478 A2 | 6/2002 |
| WO | WO-2002068646 A1 | 9/2002 |
| WO | WO-02092780 A2 | 11/2002 |
| WO | WO-02096910 A1 | 12/2002 |
| WO | WO-03035835 A2 | 5/2003 |
| WO | WO-03074679 A2 | 9/2003 |
| WO | WO-2004016750 A2 | 2/2004 |
| WO | WO-2004029207 A2 | 4/2004 |
| WO | WO-2004035752 A2 | 4/2004 |
| WO | WO-2004063351 A2 | 7/2004 |
| WO | WO-2004074455 A2 | 9/2004 |
| WO | WO-2004099249 A2 | 11/2004 |
| WO | WO2005040217 A2 | 5/2005 |
| WO | WO-2005070963 A1 | 8/2005 |
| WO | WO-2005092925 A2 | 10/2005 |
| WO | WO-2006020114 A2 | 2/2006 |
| WO | WO-2006052660 A2 | 5/2006 |
| WO | WO-2007038658 A2 | 4/2007 |
| WO | WO2007051081 A1 | 5/2007 |
| WO | WO-2007059404 A2 | 5/2007 |
| WO | WO-2008083312 A2 | 7/2008 |
| WO | WO-2008103693 A2 | 8/2008 |
| WO | WO-2009157771 A1 | 2/2009 |
| WO | WO-2009059278 A1 | 5/2009 |
| WO | WO-2010017468 A1 | 2/2010 |
| WO | WO-2010085643 A1 | 7/2010 |
| WO | WO-2011072204 A1 | 6/2011 |
| WO | WO-2011097603 A1 | 8/2011 |
| WO | WO-2011104687 A1 | 9/2011 |
| WO | WO-2011163311 A1 | 12/2011 |
| WO | WO-2011163314 A1 | 12/2011 |
| WO | WO-2012148873 A2 | 11/2012 |
| WO | WO-2013056984 A1 | 4/2013 |
| WO | WO-2015189302 A1 | 12/2015 |
| WO | WO-2016059512 A1 | 4/2016 |
| WO | WO-2017062035 A1 | 4/2017 |
| WO | WO-2018013818 A2 | 1/2018 |
| WO | WO-2018104483 A1 | 6/2018 |

OTHER PUBLICATIONS

Annunziato F, et al., "Phenotypic and functional features of human Th17 cells," J Exp Med. 204(8):1849-61, University Press, United States (Aug. 2007).

Boettler, T., et al., "IL-7 receptor alpha blockade, an off-switch for autoreactive T cells," Proc Natl Acad Sci. 109(31):12270-1, National Academy of the Sciences, United States (Jul. 2012).

Boyman, O., et al., "IL-7/anti-IL-7 mAb complexes restore T cell development and induce homeostatic T Cell expansion without lymphopenia." J Immunol 180(11):7265-75, American Association of Immunologists, United States (Jun. 2008).

Bradley,L., et al., "IL-7: maintaining T-cell memory and achieving homeostasis," Trends Immunol. 26(3):172-6, Cell Pres, United States (Mar. 2005).

Carette, F., et al., "IL-7 signaling and CD127 receptor regulation in the control of T cell homeostasis," Semin Immunol. 24(3):209-17, Elsevier, Netherlands (Jun. 2012).

Chakrabarti, S., et al., "T-cell depletion with Campath-1H 'in the bag' for matched related allogeneic peripheral blood stem cell transplantation is associated with reduced graft-versus-host disease, rapid immune constitution and improved survival," Br J Haematol. 21(1):109-18, Wiley-Blackwell, Britain (Apr. 2003).

Chazen, G.D., et al., "Interleukin 7 is a T-cell growth factor," Proc Natl Acad Sci 86(15):5923-7, National Academy of Sciences, United States (Aug. 1989).

Clarke, D., et al., "Interaction of interleukin 7 (IL-7) with glycosaminoglycans and its biological relevance," Cytokine 7(4):325-30, Elsevier, Netherlands (May 1995).

Fry, T.J., et al., "The many faces of IL-7: from lymphopoiesis to peripheral T cell maintenance," J Immunol 174(11):6571-6, American Association of Immunologist, United States (Jun. 2005).

Gasper, D.J., "CD4 T-cell memory generation and maintenance." Crit Rev Immunol.;34(2):121-46, Begel House, United States (Dec. 2014).

Hakim, F.T., et al., "Age-dependent incidence, time course, and consequences of thymic renewal in adults," J Clin Invest. 115(4):930-9, American Society for Clinical Investigation, United States (Apr. 2005).

Hara, T, et al., "Identification of IL-7-producing cells in primary and secondary lymphoid organs using IL-7-GFP knock-in mice," J Immunol. 189(4):1577-84, American Association of Immunologists, United States (Aug. 2012).

Jacobs, SR, et al., "IL-7 is essential for homeostatic control of T cell metabolism in vivo," J Immunol. 184(7):3461-9, American Association of Immunologists, United Sates (Apr. 2010).

(56) References Cited

OTHER PUBLICATIONS

Kern, B., et al., "Receptor occupancy and blocking of STAT5 signaling by an anti-IL-7 receptor alpha antibody in cynomolgus monkeys," Cytometry B Clin Cytom. 90(2):191-8, Wiley, United States (Mar. 2016).

Lee, L.F., et al., "Anti-IL-7 receptor-alpha reverses established type 1 diabetes in nonobese diabetic mice by modulating effector T-cell function," Proc Natl Acad Sci :109(31):12674-9, National Academy of the Science, United States (Jul. 2012).

Mackall, L., et al., "Age, thymopoiesis, and CD4+ T-lymphocyte regeneration after intensive chemotherapy," N Engl J Med. 332(3):143-9, Massachusetts Medical Society, United States (Jan. 1995).

Maggi, L., et al., "CD161 is a marker of all human IL-17-producing T-cell subsets and is induced by RORC," Eur J Immunol.40(8):2174-81, Wiley-VCH, Germany (Aug. 2010).

Mazzucchelli, RI., et al, "Visualization and identification of IL-7 producing cells in reporter mice," PLoS One 4(11):e7637, Public Library of Science, United States (Nov. 2009).

Menard, L., et al., "Signaling lymphocytic activation molecule (SLAM)/SLAM-associated protein pathway regulates human B-cell tolerance," J Allergy Clin Immunol.133(4):1149-61, Nature Publishing Group, Britain (Apr. 2014).

Mertsching, E,et al., "IL-7 transgenic mice: analysis of the role of IL-7 in the differentiation of thymocytes in vivo and in vitro," Int Immunol.7(3):401-14, Oxford University Press, England (Mar. 1995).

Miyaura, C., et al., "Increased B-lymphopoiesis by interleukin 7 induces bone loss in mice with intact ovarian function: similarity to estrogen deficiency," Proc Natl Acad Sci U S A94(17):9360-5, National Academy of the Sciences, United States (Aug. 1997).

Murray, R., et al., "IL-7 is a growth and maintenance factor for mature and immature thymocyte subsets," Int Immunol.1(5):526-3, Oxford University Press, England (Nov. 1989).

Okoye, AA., et al., "Effect of IL-7 Therapy on Naive and Memory T Cell Homeostasis in Aged Rhesus Macaques," J Immunol. 195(9):4292-305, American Association of Immunologist, United States (Nov. 2015).

Penaranda, C., et al., "IL-7 receptor blockade reverses autoimmune diabetes by promoting inhibition of effector/memory T cells," Proc Natl Acad Sci U S A. 109(31):12668-73 (Jul. 2012).

Peschon, JJ, et al., "Early lymphocyte expansion is severely impaired in interleukin 7 receptor-deficient mice," J Exp Med.180(5):1955-60, Rockefeller, United States (Nov. 1994).

Puel, A. et al., "Mutations in the gene for the IL-7 receptor result in T(−)B(+)NK(+) severe combined immunodeficiency disease," Curr Opin Immunol 12(4):468-73, Elsevier, Netherlands (Aug. 2000).

Qi, Q., et al., "Mechanisms shaping the naive T cell repertoire in the elderly—thymic involution or peripheral homeostatic proliferation?," Exp Gerontol.54:71-4, Elsevier, Netherlands (Jun. 2014).

Roifman, CM, et al., "A partial deficiency of interleukin-7R alpha is sufficient to abrogate T-cell development and cause severe combined immunodeficiency," Blood. 96(8):2803-7, American Association of Hematology, United States (Oct. 2000).

Sportes, C., et al., "Administration of rhIL-7 in humans increases in vivo TCR repertoire diversity by preferential expansion of naive T cell subsets," J Exp Med. 205(7):1701-14, Rockefeller, United States (Jul. 2008).

Surh, C.D., et al., "Homeostasis of naive and memory T cells," Immunity. 29(6):848-62, Cell Press, England (Dec. 2008).

Totsuka, T, et al., "IL-7 Is essential for the development and the persistence of chronic colitis," J Immunol. 178(8):4737-48, American Association of Immunologists, United States (Apr. 2007).

Vignali, D., et al., "IL-7 Mediated Homeostatic Expansion of Human CD4+CD25+FOXP3+ Regulatory T Cells After Depletion With Anti-CD25 Monoclonal Antibody," Transplantation 100(9):1853-61, Wolters Kluwer, Netherlands (Sep. 2016).

Von Freeden-Jeffry, U., et al., "Lymphopenia in interleukin (IL)-7 gene-deleted mice identifies IL-7 as a nonredundant cytokine," J Exp Med. 181(4):1519-26, Rockefeller Press, United States (Apr. 1995).

Wang, X.S., et al., "Perspectives of the relationship between IL-7 and autoimmune diseases," Clin Rheumatol. 32(12):1703-9, Springer, United States (Dec. 2013).

Watanabe, B., et al., "Mucosal IL-7-mediated immune responses in chronic colitis-IL-7 transgenic mouse model," Immunol Res. 20(3):251-9, Hindawi, India (Nov. 1999).

Watanabe, M, et al., "Interleukin 7 transgenic mice develop chronic colitis with decreased interleukin 7 protein accumulation in the colonic mucosa." J Exp Med. 187(3):389-402, Rockefeller, United States (Feb. 1998).

Watanabe, M., et al., "Interleukin 7 is produced by human intestinal epithelial cells and regulates the proliferation of intestinal mucosal lymphocytes," J Clin Invest. 95(6):2945-53, American Society for Clinical Investigation, United States (Jun. 1995).

Welch, P.A., et al., "Human IL-7: a novel T cell growth factor," J Immunol. 143(11):3562-7, American Association of Immunologist, United States (Dec. 1989).

Willis, C.R., et al., "Interleukin-7 receptor blockade suppresses adaptive and innate inflammatory responses in experimental colitis," J Inflamm (Lond) 9(1):39, BMC, England (Oct. 2012).

Yamaji, O, et al., "The development of colitogenic CD4(+) T cells is regulated by IL-7 in collaboration with NK cell function in a murine model of colitis," J Immunol. 188(6):2524-36, American Association of Immunologist, United States (Mar. 2012).

Yamazaki, M., et al., "Mucosal T cells expressing high levels of IL-7 receptor are potential targets for treatment of chronic colitis," J Immunol. 171(3):1556-63, American Association of Immunologist, United States (Aug. 2003).

Yang, H., et al., "Specific overexpression of IL-7 in the intestinal mucosa: the role in intestinal intraepithelial lymphocyte development," Am J Physiol Gastrointest Liver Physiol 294(6):G1421-30, American Physiological Society, United States (Jun. 2008).

Younas, M., et al., "IL-7 modulates in vitro and in vivo human memory T regulatory cell functions through the CD39/ATP axis," J Immunol. 191(6):3161-8, American Association of Immunologist, United States (Sep. 2013).

International Search Report and Written Opinion in PCT/US2020/014413, European Patent Office, Netherlands, dated Jun. 23, 2020, 19 pages.

Alexander, A.J. and Hughes, D.E., "Monitoring of IgG Antibody Thermal Stability by Micellar Electrokinetic Capillary Chromatography and Matrix-assisted Laser Desorption/ionization Mass Spectrometry," Analytical Chemistry 67(20):3626-3632, American Chemical Society, United States (Oct. 1995).

Berge, S.M., et al., "Pharmaceutical Salts," Journal of Pharmaceutical Sciences 66(1):1-19, Wiley, United States (Jan. 1977).

Bird, R.E., et al., "Single-chain Antigen-binding Proteins," Science 242(4877):423-426, Association for the Advancement of Science, United States (Oct. 1988).

Bordusa, F., "F C-N Protease Catalyzed Bond Formation Using," Highlights in Bioorganic Chemistry 389-403, (Jan. 2004).

Boss, M.A. and Wood, C.R., "Genetically Engineered Antibodies," Immunology today 6(1):12-13, Elsevier Science Publishers, England (1985).

Brennan, M., et al., "Preparation of Bispecific Antibodies by Chemical Recombination of Monoclonal Immunoglobulin G1 Fragments," Science 229(4708):81-83, American Association for the Advancement of Science, United States (Jul. 1985).

Brummell, D.A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (Feb. 1993).

Burks, E.A., et al., "In vitro Scanning Saturation Mutagenesis of an Antibody Binding Pocket," Proceedings of the National Academy of Sciences USA 94(2):412-417, Plenum Publishing Corporation , United States (Jan. 1997).

Chen, B., et al., "Influence of Histidine on the Stability and Physical Properties of a Fully Human Antibody in Aqueous and Solid Forms," Pharmaceutical Research 20(12):1952-1960, Kluwer Academic, United States (Dec. 2003).

Chen, J., et al., "B Cell Development in Mice That Lack One or Both Immunoglobulin Kappa Light Chain Genes," The EMBO Journal 12(3):821-830, Wiley Blackwell, England (Mar. 1993).

(56) References Cited

OTHER PUBLICATIONS

Chen, J., et al., "Immunoglobulin Gene Rearrangement in B Cell Deficient Mice Generated by Targeted Deletion of the JH Locus," International Immunology 5(6):647-656, Oxford University Press, England (Jun. 1993).

Cheung, R.C., et al., "Epitope-specific Antibody Response to the Surface Antigen of Duck Hepatitis B Virus in Infected Ducks," Virology 176(2):546-552, Academic Press, United States (Jun. 1990).

Choi, T.K., et al., "Transgenic Mice Containing a Human Heavy Chain Immunoglobulin Gene Fragment Cloned in a Yeast Artificial Chromosome," Nature Genetics 4(2):117-123, Nature Pub. Co., United States (Jun. 1993).

Cox, J.P., et al., "A Directory of Human Germ-line V kappa Segments Reveals a Strong Bias in their Usage," European Journal of Immunology 24(4):827-836, Verlag Chemie GmbH, Germany (Apr. 1994).

Dall'Acqua, W.F., et al., "Increasing the Affinity of a Human IgG1 for the Neonatal Fc Receptor: Biological Consequences," The Journal of Immunology 169(9):5171-5180, American Association of Immunologists, United States (Nov. 2002).

Dall'Acqua, W.F., et al., "Properties of Human IgG1s Engineered for Enhanced Binding to the Neonatal Fc Receptor (FcRn)," The Journal of Biological Chemistry 281(33):23514-23524, American Society for Biochemistry and Molecular Biology, United States (Aug. 2006).

De Graaf, A.J., et al., "Nonnatural Amino Acids for Site-specific Protein Conjugation," Bioconjugate Chemistry 20(7):1281-1295, American Chemical Society, United States (Feb. 2009).

Durum, S.K., "IL-7 and TSLp Receptors: Twisted Sisters," Blood 124(1):4-5, American Society of Hematology, United States (Jul. 2014).

Fishwild, D.M., et al., "High-Avidity Human IgG Kappa Monoclonal Antibodies from a Novel Strain of Minilocus Transgenic Mice," Nature Biotechnology 14(7):845-851, Nature America Publishing, United States (Jul. 1996).

Frese, M.A. and Dierks, T., "Formylglycine Aldehyde Tag-protein Engineering Through a Novel Post-translational Modification," Chembiochem 10(3):425-427, Wiley-VCH Verlag, Germany (Jan. 2009).

Gala, F.A. and Morrison, S.L., "V Region Carbohydrate and Antibody Expression," The Journal of Immunology 172(9):5489-5494, Williams & Wilkins, United States (May 2004).

Gautier, A., et al., "An Engineered Protein Tag for Multiprotein Labeling in Living Cells," Chemistry & Biology 15(2):128-136, Elsevier, United States (Feb. 2008).

Ghirlando, R., et al., "Glycosylation of Human IgG-Fc: Influences on Structure Revealed by Differential Scanning Micro-Calorimetry," Immunology Letters 68(1):47-52, Elsevier/North-Holland Biomedical Press, Netherlands (May 1999).

Glennie, M.J., et al., "Preparation and Performance of Bispecific F(Ab' Gamma)2 Antibody Containing Thioether-linked Fab' Gamma Fragments," Journal of Immunology 139(7):2367-2375, American Association of Immunologists, United States (Oct. 1987).

Gu, J., et al., "Human Cd39hi Regulatory T Cells Present Stronger Stability and Function Under Inflammatory Conditions," Cellular & Molecular Immunology 14(6):521-528, Chinese Society of Immunology, China (Jun. 2017).

Hackenberger, C.P. and Schwarzer, D., "Chemoselective Ligation and Modification Strategies for Peptides and Proteins," Angewandte Chemie 47(52):10030-10074, Wiley-VCH, Germany (Dec. 2008).

Harding, F.A. and Lonberg, N., "Class Switching in Human Immunoglobulin Transgenic Mice," Annals of the New York Academy of Sciences 764:536-546, The Academy, United States (Sep. 1995).

Heninger, A.K., et al., "Il-7 Abrogates Suppressive Activity of Human Cd4+cd25+foxp3+Regulatory T Cells and Allows Expansion of Alloreactive and Autoreactive T Cells," Journal of Immunology, 189(12):5649-5658, American Association of Immunologists, United States (Dec. 2012).

Hinton, P.R., et al., "An Engineered Human IgG1 Antibody with Longer Serum Half-Life," Journal of Immunology 176(1):346-356, American Association of Immunologists, United States (Jan. 2006).

Hinton, P.R., et al., "Engineered Human IgG Antibodies With Longer Serum Half-lives in Primates," The Journal of Biological Chemistry 279(8):6213-6216, American Society for Biochemistry and Molecular Biology, United States (Feb. 2004).

Hoeppli, R.E., et al., "The Environment of Regulatory T Cell Biology: Cytokines, Metabolites, and the Microbiome," Frontiers in Immunology 6:61, Frontiers Research Foundation, Switzerland (Feb. 2015).

Huston, J.S., et al., "Protein Engineering of Antibody Binding Sites: Recovery of Specific Activity in an Anti-digoxin Single-chain Fv Analogue Produced in *Escherichia coli*," Proceedings of the National Academy of Sciences USA 85(16):5879-5883, National Academy of Sciences, United States (Aug. 1988).

Igawa, T., et al., "Antibody Recycling by Engineered Ph-dependent Antigen Binding Improves the Duration of Antigen Neutralization," Nature Biotechnology 28(11):1203-1207, Nature America Publishing, United States (Oct. 2010).

Jefferis, R., et al., "Human Immunoglobulin Allotypes: Possible Implications for Immunogenicity," Mabs 1(4):332-338, Taylor & Francis, United States (Jul.-Aug. 2009).

Jones, P.T., et al., "Replacing the Complementarity-determining Regions in a Human Antibody with those from a Mouse," Nature 321(6069):522-525, Nature Publishing Group, England (May 1986).

Kabat, E.A., et al., "Sequences of Proteins of Immunological Interest," 5th Edition, U.S. Department of Public Health and Human Services, Public Health Service, NIH publication No. 91-3242, National Institutes of Health, Bethesda (1991).

Karpovsky, B., et al., "Production of Target-specific Effector Cells Using Hetero-cross-linked Aggregates Containing Anti-target Cell and Anti-fc Gamma Receptor Antibodies," The Journal of Experimental Medicine 160(6):1686-1701, Rockefeller University Press, United States (Dec. 1984).

Kaufman, R.J. and Sharp, P.A., "Amplification and Expression of Sequences Cotransfected with a Modular Dihydrofolate Reductase Complementary DNA Gene," Journal of Molecular Biology 159(4):601-621, Academic Press, Inc. Ltd., England (Aug. 1982).

Kirkland, T.N., et al., "Analysis of the Fine Specificity and Cross-reactivity of Monoclonal Anti-lipid A Antibodies," Journal of Microbiology 137(11):3614-3619, Microbiological Society of Korea, Korea (Dec. 1986).

Kobayashi, H., et al., "Tryptophan H33 Plays an Important Role in Pyrimidine (6-4) Pyrimidone Photoproduct Binding by a High-Affinity Antibody," Protein Engineering Design and Selection 12(10):879-884, Oxford University Press, United States (Oct. 1999).

Kohler, G. and Milstein, C., "Continuous Cultures of Fused Cells Secreting Antibody of Predefined Specificity," Nature 256(5517):495-497, Macmillan Journals Ltd., England (Aug. 1975).

Kostelny, S.A., et al., "Formation of a Bispecific Antibody by the Use of Leucine Zippers," The Journal of Immunology 148(5):1547-1553, American Association of Immunologists, United States (Mar. 1992).

Krishnamurthy, R. and Manning, M.C., "The Stability Factor: Importance in Formulation Development," Current Pharmaceutical Biotechnology 3(4):361-371, Bentham Science Publishers, Netherlands (Dec. 2002).

Kuroiwa, Y., et al., "Cloned Transchromosomic Calves Producing Human Immunoglobulin," Nature Biotechnology 20(9):889-894, Nature America Publishing, United States (Sep. 2002).

Kurz M., et al., "Psoralen Photo-crosslinked Mrna-puromycin Conjugates: a Novel Template for the Rapid and Facile Preparation of Mrna-protein Fusions, " Nucleic Acids Research 28(18):E83 Oxford University Press, England (Sep. 2000).

Lazar, G.A., et al., "Engineered Antibody Fc Variants with Enhanced Effector Function," Proceedings of the National Academy of Sciences USA 103(11):4005-4010, National Academy of Sciences, United States (Mar. 2006).

Liu, M.A., et al., "Heteroantibody Duplexes Target Cells for Lysis by Cytotoxic T Lymphocytes," Proceedings of the National Academy of Sciences of the United States of America 82(24):8648-8652, National Academy of Sciences, United States (Dec. 1985).

(56) References Cited

OTHER PUBLICATIONS

Lonberg, N. and Huszar, D., "Human Antibodies from Transgenic Mice," International Reviews of Immunology 13(1):65-93, Informa Healthcare, England (1995).
Lonberg, N., et al., "Antigen-specific Human Antibodies from Mice Comprising Four Distinct Genetic Modifications," Nature 368(6474):856-859, Nature Publishing Group, United States (Apr. 1994).
Lonberg, N., "Handbook of Experimental Pharmacology," The Pharmacology of Monoclonal Antibodies 113:49-101 (1994).
Marshall, R.D., "Glycoproteins," Annual Review of Biochemistry 41:673-702, Annual Reviews, United States (Jul. 1972).
Mimura, Y., et al., "The Influence of Glycosylation on the Thermal Stability and Effector Function Expression of Human IgG1-Fc: Properties of a Series of Truncated Glycoforms," Molecular Immunology 37(12-13):697-706, Pergamon Press, England (Aug.-Sep. 2000).
Moldenhauer, G., et al., "Identity of HML-1 Antigen on Intestinal Intraepithelial T Cells and of B-Iy7 Antigen on Hairy Cell Leukaemia," Scandinavian Journal of Immunology 32(2):77-82, Blackwell Scientific Publications, England (Aug. 1990).
Morel, G.A., et al., "Monoclonal Antibodies to Bovine Serum Albumin: Affinity and Specificity Determinations," Molecular Immunology 25(1):7-15, Pergamon Press, England (Jan. 1988).
Morrison, S.L., "Transfectomas Provide Novel Chimeric Antibodies," Science 229(4719):1202-1207, Association for the Advancement of Science, United States (Sep. 1985).
Murray, A., et al., "Epitope Affinity Chromatography and Biophysical Studies of Monoclonal Antibodies and Recombinant Antibody Fragments," Journal of Chromatographic Science 40(6):343-349, Oxford University Press, United States (Jul. 2002).
Myers, E.W and Miller, W., "Optical Alignments in linear space," Computer Applications in the Biosciences 4(1):11-17, Oxford University Press, England (1988).
Carrette, F and Surh, C.D., "Il-7 Signaling and Cd127 Receptor Regulation in the Control of T Cell Homeostasis," Seminars in Immunology 24(3):209-217, Academic Press, England (Jun. 2012).
Lonberg, N., "Human Antibodies From Transgenic Animals," Nature Biotechnology, 23(9):1117-1125, Nature America Publishing, United States (Sep. 2005).
Maraskovsky, E., et al., "Impaired Survival and Proliferation in Il-7 Receptor-deficient Peripheral T Cells," Journal of Immunology 157(12):5315-5323, American Association of Immunologists, United States (Dec. 1996).
Needleman, S.B. and Wunsch, C.D., "A General Method Applicable to the Search for Similarities in the Amino Acid Sequence of Two Proteins," Journal of Molecular Biology 48(3):443-453, Academic Press, England (Mar. 1970).
Nguyen, V., et al., "Interleukin-7 and Immunosenescence," Journal of Immunology Research 2017:4807853, Hindawi Publishing Corporation, Egypt (Apr. 2017).
Nordstrom, J. L., et al., "Anti-Tumor Activity and Toxicokinetics Analysis of MGAH22, an Anti-HER2 Monoclonal Antibody with Enhanced Fcγ Receptor Binding Properties," Breast Cancer Research 13(6):R123, BioMed Central Ltd, England (Nov. 2011).
Parekh, R.B., et al., "Association of Rheumatoid Arthritis and Primary Osteoarthritis with Changes in the Glycosylation Pattern of Total Serum IgG," Nature 316(6027):452-457, Nature Publishing Group, England (Aug. 1985).
Paulus, H., et al., "Preparation and Biomedical Applications of Bispecific Antibodies," Behring Institute Mitteilungen 78:118-132, Behringwerke Ag, Germany (Dec. 1985).
Queen, C., et al., "A Humanized Antibody that Binds to the Interleukin 2 Receptor," Proceedings of the National Academy of Sciences USA 86(24):10029-10033, National Academy of Sciences, United States (Dec. 1989).
Ren, H., et al., "A Biocompatible Condensation Reaction for the Labeling of Terminal Cysteine Residues on Proteins," Angewandte Chemie 48(51):9658-9662, Wiley-VCH, Germany (Dec. 2009).

Riechmann, L., et al., "Reshaping Human Antibodies for Therapy," Nature 332(6162):323-327, Nature Publishing Group, United States (Mar. 1988).
Roberts, R.W. and Szostak, J.W., "RNA-Peptide Fusions for the in Vitro Selection of Peptides and Proteins," Proceedings of the National Academy of Sciences of the USA 94(23):12297-12302, National Academy of Sciences, United States (Nov. 1997).
Sanchez-Munoz, F., et al., "Role of Cytokines in Inflammatory Bowel Disease," World Journal of Gastroenterology 14(27):4280-4288, Baishideng Publishing Group, United States (Jul. 2008).
Sarmay, G., et al., "Mapping and Comparison of the Interaction Sites on the Fc Region of IgG Responsible for Triggering Antibody Dependent Cellular Cytotoxicity (ADCC) Through Different Types of Human Fc Gamma Receptor," Molecular Immunology 29(5):633-639, Pergamon Press, England (May 1992).
Senter, P.D., "Potent Antibody Drug Conjugates for Cancer Therapy," Current Opinion in Chemical Biology 13(3):235-244, Elsevier, England (Jun. 2009).
Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (Mar. 2001).
Shields, R.L., et al., "Lack of Fucose on Human IgG1 N-linked Oligosaccharide Improves Binding to Human Fcgamma RIII and Antibody-Dependent Cellular Toxicity," The Journal of Biological Chemistry 277(30):26733-26740, American Society for Biochemistry and Molecular Biology, United States (Jul. 2002).
Songsivilai, S. and Lachmann, P.J., "Bispecific Antibody: A Tool for Diagnosis and Treatment of Disease," Clinical and Experimental Immunology 79(3):315-321, Blackwell Scientific Publications, England (Mar. 1990).
Spiro, R.G., "Protein Glycosylation: Nature, Distribution, Enzymatic Formation, and Disease Implications of Glycopeptide Bonds," Glycobiology 12(4):43R-56R, IRL Press at Oxford University Press, England (Apr. 2002).
Stahli, C., et al., "Distinction of Epitopes by Monoclonal Antibodies.," Methods in Enzymology 92:242-253, Academic Press, United States (1983).
Stavenhagen, J.B., et al., "Fc Optimization of Therapeutic Antibodies Enhances Their Ability to Kill Tumor Cells in Vitro and Controls Tumor Expansion in Vivo via Low-affinity Activating Fcgamma Receptors," Cancer Research 67(18):8882-8890, American Association for Cancer Research, United States (Sep. 2007).
Strohl, W.R., "Optimization of Fc-mediated Effector Functions of Monoclonal Antibodies," Current Opinion in Biotechnology 20(6):685-691, Elsevier, England (Dec. 2009).
Sunbul, M. and Yin, J., "Site Specific Protein Labeling by Enzymatic Posttranslational Modification," Organic & Biomolecular Chemistry 7(17):3361-3371, Royal Society of Chemistry, England (Sep. 2009).
Takebe, T., et al., "SR Alpha Promoter: An Efficient and Versatile Mammalian Cdna Expression System Composed of the Simian Virus 40 Early Promoter and the R-U5 Segment of Human T-Cell Leukemia Virus Type 1 Long Terminal Repeat," Molecular and Cell Biology 8(1):466-472, American Society for Microbiology, United States (Jan. 1988).
Taki, M., et al., "Transglutaminase-mediated N- and C-terminal Fluorescein Labeling of a Protein Can Support the Native Activity of the Modified Protein," Protein Engineering, Design & Selection 17(2):119-126, Oxford University Press, England (Jan. 2004).
Taylor, E.V., et al., "Native Chemical Ligation: SemiSynthesis of Post-translationally Modified Proteins and Biological Probes," Protein Engineering, 22:65-96, (2009).
Taylor, L.D., et al., "A Transgenic Mouse That Expresses a Diversity of Human Sequence Heavy and Light Chain Immunoglobulins," Nucleic Acids Research 20(23):6287-6295, Oxford University Press, England (Dec. 1992).
Taylor, L.D., et al., "Human Immunoglobulin Transgenes Undergo Rearrangement, Somatic Mutation and Class Switching in Mice That Lack Endogenous IgM," International Immunology 6(4):579-591, University Press, England (Apr. 1994).

(56) References Cited

OTHER PUBLICATIONS

Tomita, T., et al., "Systemic, but Not Intestinal, Il-7 is Essential for the Persistence of Chronic Colitis," Journal of Immunology 180(1):383-390, American Association of Immunologists, United States (Jan. 2008).

Tomizuka, K., et al., "Double Trans-chromosomic Mice: Maintenance of Two Individual Human Chromosome Fragments Containing Ig Heavy and kappa loci and Expression of Fully Human Antibodies," Proceedings of the National Academy of Sciences USA 97(2):722-727, National Academy of Sciences, United States (Jan. 2000).

Tomlinson, I.M., et al., "The Repertoire of Human Germline VH Sequences Reveals about Fifty Groups of VH Segments with Different Hypervariable Loops," Journal of Molecular Biology 227(3):776-798, Elsevier, Netherlands (Oct. 1992).

Tuaillon, N., et al., "Biased Utilization of DHQ52 and JH4 Gene Segments in a Human Ig Transgenic Minilocus Is Independent of Antigenic Selection," The Journal of Immunology 152(6):2912-2920, Williams & Wilkins, United States (Mar. 1994).

Tuaillon, N., et al., "Human Immunoglobulin Heavy-chain Minilocus Recombination in Transgenic Mice: Gene-segment Use in Mu and Gamma Transcripts," Proceedings of the National Academy of Sciences of the United States of America 90(8):3720-3724, National Academy of Sciences, United States (Apr. 1993).

Umana, P., et al., "Engineered Glycoforms of an Antineuroblastoma IgG1 with Optimized Antibody-Dependent Cellular Cytotoxic Activity," Nature Biotechnology 17(2):176-180, Nature America Publishing, United States (Feb. 1999).

Urlaub, G. and Chasin, L.A., "Isolation of Chinese Hamster Cell Mutants Deficient in Dihydrofolate Reductase Activity," Proceedings of the National Academy of Sciences USA 77(7):4216-4220, National Academy of Sciences, United States (Jul. 1980).

Wallick, S.C., et al., "Glycosylation of a Vh Residue of a Monoclonal Antibody Against Alpha (1—6) Dextran Increases Its Affinity for Antigen," The Journal of Experimental Medicine 168(3):1099-1109, Rockefeller University Press, United States (Sep. 1988).

Ward, E.S., et al., "Binding Activities of a Repertoire of Single Immunoglobulin Variable Domains Secreted from *Escherichia coli*," Nature 341(6242):544-546, Nature Publishing Group, England (Oct. 1989).

Xu, L., et al., "Directed Evolution of High-affinity Antibody Mimics Using mRNA Display," Chemistry & Biology 9: 933-942, Elsevier Science Ltd., The Netherlands (Aug. 2002).

Yeung, Y.A., et al., "Engineering Human IgG1 Affinity to Human Neonatal Fc Receptor: Impact of Affinity Improvement on Pharmacokinetics in Primates," Journal of Immunology 182(12):7663-7671, American Association of Immunologists, United States (Jun. 2009).

SPR data at 37C:

|  | ka (1/Ms) | kd (1/s) | KD (nM) |
|---|---|---|---|
| 18B1 | 3.11e5 | 4.03e-04 | 1.3 |

| Light Chain | | | | | | | | | | | | | | | |
|---|---|---|---|---|---|---|---|---|---|---|---|---|---|---|---|
| LCDR1 | 24 | 25 | 26 | 27 | 28 | 29 | 30 | 31 | 32 | 33 | 34 | | | | |
| | R | A | S | Q | G | I | S | S | A | L | A | | | | |
| LCDR2 | 50 | 51 | 52 | 53 | 54 | 55 | 56 | | | | | | | | |
| | D | A | S | S | L | E | S | | | | | | | | |
| LCDR3 | 89 | 90 | 91 | 92 | 93 | 94 | 95 | 95A | 95B | 96 | 97 | | | | |
| | Q | Q | F | N | S | Y | P | L | W | I | T | | | | |
| Heavy Chain | | | | | | | | | | | | | | | |
| HCDR1 | 26 | 27 | 28 | 29 | 30 | 31 | 32 | 33 | 34 | 35 | | | | | |
| | G | F | T | F | D | D | H | A | M | H | | | | | |
| HCDR2 | 50 | 51 | 52 | 52a | 53 | 54 | 55 | 56 | 57 | 58 | 59 | 60 | 61 | 62 | 63 | 64 | 65 |
| | G | I | S | W | N | S | R | G | I | G | Y | A | D | S | V | K | G |
| HCDR3 | 95 | 96 | 97 | 98 | 99 | 100 | a | b | c | d | 101 | 102 | | | |
| | D | E | Y | S | R | G | Y | Y | V | L | D | V | | | |
| Framework | F89L | | | | | | | | | | | | | | |

| Antibody Variant | KD Relative to 18B1 | 0.2 nM NGS |
|---|---|---|
| 18B1_LC_R24A | 1.15 | 0.91 |
| 18B1_LC_S26A | 1.28 | 1.32 |
| 18B1_LC_Q27A | 1.06 | 1.27 |
| 18B1_LC_G28A | 0.85 | 1.05 |
| 18B1_LC_I29A | 1.46 | 1.44 |
| 18B1_LC_S30A | 0.88 | 0.70 |
| 18B1_LC_S31A | 0.74 | 0.60 |
| 18B1_LC_L33A | 1.08 | 1.05 |
| 18B1_LC_Q89A | 0.23 | 0.07 |
| 18B1_LC_Q90A | 1.46 | 1.63 |
| 18B1_LC_F91A | 0.19 | 0.05 |
| 18B1_LC_N92A | 0.63 | 0.34 |
| 18B1_LC_S93A | 1.86 | 1.84 |
| 18B1_LC_Y94A | 0.01 | 0.01 |
| 18B1_LC_P95A | 0.08 | 0.03 |
| 18B1_LC_L95aA | 0.01 | 0.01 |
| 18B1_LC_I96A | 0.16 | 0.02 |
| 18B1_LC_T97A | 1.16 | 0.92 |
| 18B1_HC F89LG26A | 0.71 | 0.47 |
| 18B1_HC F89LF27A | 0.18 | 0.05 |
| 18B1_HC F89LT28A | 0.98 | 1.25 |
| 18B1_HC F89LF29A | 0.05 | 0.01 |
| 18B1_HC F89LD30A | 0.46 | 0.30 |
| 18B1_HC F89LD31A | 0.03 | 0.02 |
| 18B1_HC F89LH32A | 0.01 | 0.01 |
| 18B1_HC F89LM34A | 0.25 | 0.08 |
| 18B1_HC F89LH35A | 0.02 | 0.01 |
| 18B1_HC F89LG50A | 1.02 | 0.87 |
| 18B1_HC F89LI51A | 0.28 | 0.20 |
| 18B1_HC F89LS52A | 0.22 | 0.07 |
| 18B1_HC F89LW52aA | 1.28 | 0.00 |
| 18B1_HC F89LN53A | 0.02 | 0.00 |
| 18B1_HC F89LS54A | 0.57 | 0.61 |
| 18B1_HC F89LR55A | 0.42 | 0.07 |
| 18B1_HC F89LG56A | 0.08 | 0.01 |
| 18B1_HC F89LI57A | 0.54 | 0.36 |
| 18B1_HC F89LG58A | 0.16 | 0.04 |
| 18B1_HC F89LY59A | 0.78 | 0.42 |
| 18B1_HC F89LD61A | 0.78 | 0.85 |
| 18B1_HC F89LS62A | 0.93 | 1.24 |
| 18B1_HC F89LV63A | 0.88 | 0.89 |
| 18B1_HC F89LK64A | 1.23 | 1.22 |
| 18B1_HC F89LG65A | 1.03 | 0.87 |
| 18B1_HC F89LE96A | 0.04 | 0.01 |
| 18B1_HC F89LY97A | 0.07 | 0.02 |
| 18B1_HC F89LS98A | 0.55 | 0.59 |

FIG. 19 (cont'd)

| | | |
|---|---|---|
| 18B1_HC F89LR99A | 0.63 | 0.53 |
| 18B1_HC F89LG100A | 0.01 | 0.01 |
| 18B1_HC F89LY100aA | 0.31 | 0.34 |
| 18B1_HC F89LV100cA | 1.17 | 1.46 |
| 18B1_HC F89LL100dA | 0.27 | 0.01 |
| 18B1_HC F89LD101A | 0.14 | 0.02 |
| 18B1_HC F89LV102A | 1.14 | 0.90 |
| 18B1 parent | 1.00 | 1.00 |
| 18B1_LC_D50A | 0.77 | 0.30 |
| 18B1_LC_S52A | 0.93 | 1.09 |
| 18B1_LC_S53A | 0.79 | 1.07 |
| 18B1_LC_L54A | 0.93 | 0.99 |
| 18B1_LC_E55A | 0.57 | 0.23 |
| 18B1_LC_S56A | 0.98 | 0.96 |
| 18B1_LC_R24A | 1.15 | 0.91 |

- hu IL-7R (30nM, 10nM, 3.3nM)
- Running buffer: HBS-P+ pH 7.4
- Temperature: 37°C
- Capture: HMEP_0216-01 mAbs
  - 12.5nM, 20sec at 10μL/min
- Regeneration: 2X 30sec with $MgCl_2$ CM5 chip:
Chip #4573

ANTIBODIES AGAINST IL-7R ALPHA SUBUNIT AND USES THEREOF

CROSS-REFERENCE TO RELATED APPLICATIONS

This application claims priority benefit of U.S. Provisional Application No. 62/795,378, filed Jan. 22, 2019; and 62/868,791, filed Jun. 28, 2019, each of which is incorporated herein by reference in its entirety.

REFERENCE TO SEQUENCE LISTING SUBMITTED ELECTRONICALLY VIA EFS-WEB

The content of the electronically submitted sequence listing in ASCII text file (Name: 4521.0010003_Seqlisting_ST25.txt; Size: 100,565 bytes; and Date of Creation: Jan. 21, 2020) filed with the application is herein incorporated by reference in its entirety.

BACKGROUND OF THE DISCLOSURE

Interleukin-7 (IL-7) is a member of the common γ chain (γc) family of cytokines that also include IL-2, IL-4, IL-9, IL-15, and IL-21. Nguyen V., et al., *J Immunol Res* 2017: 4807853 (2017). Like other members, IL-7 signals via a ternary complex formed with its unique α-receptor, IL-7Rα (CD127), and the common γ receptor. Carrette, F., et al., *Semin Immunol* 24(3): 209-17 (2012). This interaction stimulates the Janus kinase (JAK) and signal transducer and activator of transcription (STAT) proteins with subsequent activation of the phosphoinositol 3-kinase (PI3K)/Akt, or Src pathways to facilitate target gene transcription. IL-7 Rα is also used by thymic stromal-derived lymphopoietin (TSLP) as part of a complex that contains a second receptor chain, TSLPR. Durum, S. K., *Blood* 124(1):4-5 (2014).

IL-7 plays a critical role in the development of a normal immune system, as it is essential for the thymic development, peripheral maintenance, and survival of lymphocytes. Maraskovsky, E., et al., *J Immunol* 157(12): 5315-5323 (1996). Thymic T cell precursors require IL-7 for proliferation, differentiation, and survival. In the periphery, IL-7 regulates T cell hemostasis by enhancing the survival and proliferation of naïve and memory T cells.

IL-7 is a tissue-derived cytokine, and is primarily produced from stromal and epithelial cells in various tissues. For instance, in the small and large intestines, IL-7 is produced by the intestinal goblet epithelial cells and has been described as being essential for the persistence of chronic colitis in animal models. Tomita, T., et al., *J Immunol* 180(1): 383-390 (2008). IL-7 has also been shown to interfere with the immunosuppressive capabilities of regulatory T cells (Tregs). Heninger, A. K., et al., *J Immunol* 189(12): 5649-5658 (2012). Thus, agents that can modulate the activity of IL-7 in vivo and thereby decrease the survival/function of pathogenic T cells and/or increase the induction of regulatory T cells are highly desirable for the treatment of inflammatory diseases, such as inflammatory bowel disease.

SUMMARY OF THE DISCLOSURE

Provided herein is an isolated antibody or antigen binding portion thereof, which specifically binds to an alpha-chain of a human IL-7 receptor ("anti-IL-7R antibody"), comprising a heavy chain CDR1, CDR2, and CDR3 and a light chain CDR1, CDR2, and CDR3, wherein the antibody (a) is capable of binding to T cells (CD4$^+$CD45RA$^+$, CD4$^+$CD45RA$^-$, CD8$^+$CD45RA$^+$, and/or CD8$^+$CD45RA$^-$) in whole blood with an EC$_{50}$ of about 5 nM or less (e.g., less than about 3 nM);
(b) is not capable of binding to non-T cells in whole blood;
(c) is not capable of effectively blocking thymic stromal lymphopoietin (TSLP)-mediated activation of monocytes;
(d) does not agonize IL-7 receptor signaling upon binding to the IL-7 receptor, e.g., minimal pSTAT5 activation; or
(e) any combination thereof.

In some embodiments, a heavy chain CDR3 of an anti-IL-7R antibody (e.g., disclosed herein) comprises the amino acid sequence set forth in SEQ ID NO: 15 (DEYSRGYYVLDV).

In some embodiments, an anti-IL-7R antibody of the present disclosure has one or more properties selected from the group consisting of:
(a) is capable of selectively binding to an alpha-chain of a human and cynomolgus IL-7 receptor (IL-7R);
(b) is capable of binding to an alpha-chain of soluble and membrane bound IL-7R;
(c) is capable of blocking an expansion and/or survival of pathogenic T cells when administered to a subject in need thereof;
(d) is capable of restoring a T regulatory cell (Treg) function and/or promoting a Treg survival when administered to a subject in need thereof;
(e) is capable of maintaining a drug free remission longer than that by CTLA4-Ig (ORENCIA®);
(f) is capable of blocking inflammation and mucosal damage, e.g., induced by pathogenic T cells, within an intestinal tissue of a subject in need thereof;
(g) is capable of decreasing a frequency of T effector cells in the mesenteric lymph nodes (MLN) and/or lamina propria (LP) in a subject in need thereof;
(h) is capable of reducing or inhibiting IL-7 mediated pSTAT activation in T cells (e.g., CD4$^+$CD45RA$^-$);
(i) is capable of blocking expansion of IL-17 and/or IFN-gamma producing cells;
(j) is capable of treating a subject with an inflammatory disease (e.g., inflammatory bowel disease); and
(k) any combination thereof.

In some embodiments, an anti-IL-7R antibody comprises a heavy chain CDR1, wherein the heavy chain CDR1 comprises the amino acid sequence set forth in SEQ ID NO: 13 (DHAMH). In some embodiments, an anti-IL-7R antibody comprises a heavy chain CDR2, wherein the heavy chain CDR2 comprises the amino acid sequence set forth in SEQ ID NO: 14 (GISWNSRGIGYADSVKG). In some embodiments, an anti-IL-7R antibody comprises a light chain CDR1, wherein the light chain CDR1 comprises the amino acid sequence set forth in SEQ ID NO: 16 (RASQGISSALA). In some embodiments, an anti-IL-7R antibody comprises a light chain CDR2, wherein the light chain CDR2 comprises the amino acid sequence set forth in SEQ ID NO: 17 (DASSLES). In some embodiments, an anti-IL-7R antibody comprises a light chain CDR3, wherein the light chain CDR3 comprises the amino acid sequence set forth in SEQ ID NO: 18 (QQFNSYPLWIT).

In some embodiments, an anti-IL-7R antibody comprises a heavy chain variable region (VH) and a light chain variable region (VL), wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 19. In certain embodiments, the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 20.

In some embodiments, an anti-IL-7R antibody disclosed herein specifically binds to the alpha-chain of the human IL-7 receptor at an epitope selected from the group consisting of: $^{24}$SQLEVNGSQHSLTCAF$^{39}$ (SEQ ID NO: 8); $^{73}$FIETKKFLLIGKSNIC$^{88}$ (SEQ ID NO: 9); $^{89}$VKVGEKSLTCKKIDLTT$^{105}$ (SEQ ID NO: 10); $^{136}$QKKYVKVLMHDVAY$^{149}$ (SEQ ID NO: 11); $^{181}$YEIKVRSIPDHYFKGF$^{196}$ (SEQ ID NO: 12); and combinations thereof. In certain embodiments, an anti-IL-7R antibody specifically binds to the alpha-chain of the human IL-7 receptor at an epitope comprising one or more amino acid residues selected from the group consisting of H33, E75, F79, I82, K84, M144, R186, H191, Y192, and combinations thereof.

In some embodiments, an anti-IL-7R antibody of the present disclosure is selected from the group consisting of an IgG1, IgG2, IgG3, IgG4, and a variant thereof. In certain embodiments, an IL-7R antibody is an IgG1 antibody. In some embodiments, an anti-IL-7R antibody comprises an effectorless IgG1 Fc.

Also disclosed herein is an isolated antibody or antigen binding portion thereof, which specifically binds to an alpha-chain of a human IL-7 receptor ("anti-IL-7R antibody"), comprising a heavy chain and a light chain, wherein the heavy chain comprises the amino acid sequence set forth in SEQ ID NO: 21 and wherein the light chain comprises the amino acid sequence set forth in SEQ ID NO: 22.

In some embodiments, an anti-IL-7R antibody binds to the alpha-chain of the human IL-7 receptor with a $K_D$ of less than 10 nM, 9 nM, 8 nM, 7 nM, 6 nM, 5 nM, 4 nM, 3 nM, 2 nM, or 1 nM (e.g., 1.3 nM), as measured by surface plasmon resonance. In certain embodiments, an anti-IL-7R antibody binds to the alpha-chain of the cynomolgus IL-7 receptor with a $K_D$ of less than 10 nM, 9 nM, 8 nM, 7 nM, 6 nM, 5 nM, 4 nM, 3 nM, 2 nM, or 1 nM (e.g., 1.7 nM), as measured by surface plasmon resonance. In some embodiments, the binding to the alpha-chain of the human IL-7 receptor or the alpha-chain of the cynomolgus IL-7 receptor is pH-dependent. In certain embodiments, an anti-IL-7R antibody binds to the alpha-chain of the human IL-7 receptor with a $K_D$ of about 1.3 nM at pH 7.4 and with a $K_D$ of about 5.3 nM at pH 6. In some embodiments, an anti-IL-7R antibody binds to the alpha-chain of the cynomolgus IL-7 receptor with a $K_D$ of about 1.7 nM at pH 7.4 and with a $K_D$ of about 7.0 nM at pH 6.

Provided herein is an isolated antibody or antigen binding portion thereof, which specifically binds to an alpha-chain of a human IL-7 receptor ("anti-IL-7R antibody") comprising a heavy chain (HC) CDR1, CDR2, and CDR3, and a light chain (LC) CDR1, CDR2, and CDR3, wherein the HC CDR1 comprises the amino acid sequence $GX_1X_2FDDHAX_3H$ (SEQ ID NO: 260), wherein $X_1$ is F or Y; $X_2$ is T, P, A, S, V, L, I, M, H, F, Y, N, D, E, or Q; and $X_3$ is L or M. In certain aspects, $X_2$ is D or E.

In some aspects, the HC CDR2 comprises the amino acid sequence $GIX_1WX_2SRGX_3GYX_4X_5X_6X_7X_8X_9$ (SEQ ID NO: 261), wherein X1 is S or T; X2 is H or N; X3 is I or V; X4 is G, A, S, T, V, L, I, R, H, or N; X5 is P, T, N, D, E, Q, S, H, or Y; X6 is P, G, A, S, T, V, R, H, F, Y, N, D, or E; X7 is V or I; X8 is A, S, T, V, L, I, M, K, R, H, F, Y, N, D, E, or Q; and X9 is G, H, D, or Q. In certain aspects, $X_1$ is T.

In some aspects, the HC CDR3 comprises the amino acid sequence $DEYX_1X_2GYYX_3LDX_4$ (SEQ ID NO: 262), wherein X1 is S, T, N, D, or E; $X_2$ is L, M, R, or S; $X_3$ is G, A, S, T, V, M, N, E, or Q; and $X_4$ is A, S, T, V, R, H, Y, W, N, E, Q, or M. In certain aspects, $X_3$ is A, S, or T. In some aspects, $X_4$ is E.

In some aspects, the LC CDR1 comprises the amino acid sequence $X_1X_2X_3X_4X_5X_6X_7SX_8X_9A$ (SEQ ID NO: 263), wherein $X_1$ is S, T, V, K, R, H, Y, or I; $X_2$ is A, S, T, or V; $X_3$ is P, G, A, S, T, V, L, I, M, K, R, H, N, E, or Q; $X_4$ is P, G, A, S, T, V, L, I, M, H, F, Y, N, D, E, or Q; $X_5$ is P, G, A, S, T, H, E, Q, M, N, or D; $X_6$ is P, G, A, S, T, V, L, I, or N; $X_7$ is S, T, V, L, I, M, H, F, Y, N, D, E, or Q; $X_8$ is P or A; and $X_9$ is A, L, or V. In certain aspects, $X_6$ is P. In further aspects, $X_8$ is P. In some aspects, $X_7$ is D or E.

In some aspects, the LC CDR2 comprises the amino acid sequence $DX_1X_2X_3X_4X_5X_6$ (SEQ ID NO: 264), wherein $X_1$ is G, A, S, M, H, N, D, E, or Q; $X_2$ is G, A, S, T, V, M, H, F, Y, N, D, E, or Q; $X_3$ is A, S, F, Y, W, N, D, E, or L; $X_4$ is P, S, T, L, K, H, or N; $X_5$ is D, E, or Q; and $X_6$ is G, S, T, N, D, Q, P, or E.

In some aspects, the LC CDR3 comprises the amino acid sequence $X_1X_2FX_3X_4YPLX_5X_6X_7$ (SEQ ID NO: 265), wherein $X_1$ is M or Q; $X_2$ is G, A, D, E, or Q; $X_3$ is N or E; $X_4$ is P, A, or S; $X_5$ is T, I, M, K, W, N, E, or Q; $X_6$ is L or I; and $X_7$ is T, M, K, H, Y, E, or Q. In certain aspects, $X_2$ is A. In further aspects, $X_4$ is P or A.

In some aspects, the heavy chain CDR1 comprises an amino acid sequence set forth in SEQ ID NOs: 31 to 46. In certain aspects, the heavy chain CDR1 comprises an amino acid sequence set forth in SEQ ID NO: 43 or SEQ ID NO: 44. In some aspects, the heavy chain CDR2 comprises an amino acid sequence set forth in SEQ ID NOs: 47 to 96. In certain aspects, the heavy chain CDR2 comprises an amino acid sequence set forth in SEQ ID NO: 47. In further aspects, the heavy chain CDR3 comprises an amino acid sequence set forth in SEQ ID NOs: 97 to 122. In certain aspects, the heavy chain CDR3 comprises an amino acid sequence set forth in SEQ ID NO: 105, SEQ ID NO: 106, SEQ ID NO: 107, or SEQ ID NO: 120. In some aspects, the light chain CDR1 comprises an amino acid sequence set forth in SEQ ID NOs: 123 to 194. In certain aspects, the light chain CDR1 comprises an amino acid sequence set forth in SEQ ID NO: 172, SEQ ID NO: 189, SEQ ID NO: 190, or SEQ ID NO: 192. In some aspects, the light chain CDR2 comprises an amino acid sequence set forth in SEQ ID NOs: 195 to 237. In some aspects, the light chain CDR3 comprises an amino acid sequence set forth in SEQ ID NOs: 238 to 259. In certain aspects, the light chain CDR3 comprises an amino acid sequence set forth in SEQ ID NO: 240, SEQ ID NO: 244, or SEQ ID NO: 245.

Provided herein is an isolated antibody or antigen binding portion thereof, which specifically binds to an alpha-chain of a human IL-7 receptor ("anti-IL-7R antibody") comprising a heavy chain (HC) CDR1, CDR2, and CDR3, and a light chain (LC) CDR1, CDR2, and CDR3, wherein: (i) the heavy chain CDR1 comprises an amino acid sequence set forth in SEQ ID NOs: 31 to 46; (ii) the heavy chain CDR2 comprises an amino acid sequence set forth in SEQ ID NO: 14; (iii) the heavy chain CDR3 comprises an amino acid sequence set forth in SEQ ID NO: 15; (iv) the light chain CDR1 comprises an amino acid sequence set forth in SEQ ID NO: 16; (v) the light chain CDR2 comprises an amino acid sequence set forth in SEQ ID NO: 17; and (vi) the light chain CDR3 comprises an amino acid sequence set forth in SEQ ID NO:

18. In certain aspects, the heavy chain CDR1 comprises an amino acid sequence set forth in SEQ ID NO: 43 or SEQ ID NO: 44.

Also provided herein is an isolated antibody or antigen binding portion thereof, which specifically binds to an alpha-chain of a human IL-7 receptor ("anti-IL-7R antibody") comprising a heavy chain (HC) CDR1, CDR2, and CDR3, and a light chain (LC) CDR1, CDR2, and CDR3, wherein: (i) the heavy chain CDR1 comprises an amino acid sequence set forth in SEQ ID NO: 13; (ii) the heavy chain CDR2 comprises an amino acid sequence set forth in SEQ ID NOs: 47 to 96; (iii) the heavy chain CDR3 comprises an amino acid sequence set forth in SEQ ID NO: 15; (iv) the light chain CDR1 comprises an amino acid sequence set forth in SEQ ID NO: 16; (v) the light chain CDR2 comprises an amino acid sequence set forth in SEQ ID NO: 17; and (vi) the light chain CDR3 comprises an amino acid sequence set forth in SEQ ID NO: 18. In certain aspects, the heavy chain CDR2 comprises an amino acid sequence set forth in SEQ ID NO: 47.

Present disclosure provides an isolated antibody or antigen binding portion thereof, which specifically binds to an alpha-chain of a human IL-7 receptor ("anti-IL-7R antibody") comprising a heavy chain (HC) CDR1, CDR2, and CDR3, and a light chain (LC) CDR1, CDR2, and CDR3, wherein: (i) the heavy chain CDR1 comprises an amino acid sequence set forth in SEQ ID NO: 13; (ii) the heavy chain CDR2 comprises an amino acid sequence set forth in SEQ ID NO: 14; (iii) the heavy chain CDR3 comprises an amino acid sequence set forth in SEQ ID NOs: 97 to 122; (iv) the light chain CDR1 comprises an amino acid sequence set forth in SEQ ID NO: 16; (v) the light chain CDR2 comprises an amino acid sequence set forth in SEQ ID NO: 17; and (vi) the light chain CDR3 comprises an amino acid sequence set forth in SEQ ID NO: 18. In some aspects, the heavy chain CDR3 comprises an amino acid sequence set forth in SEQ ID NO: 105, SEQ ID NO: 106, SEQ ID NO: 107, or SEQ ID NO: 120.

Provided herein is an isolated antibody or antigen binding portion thereof, which specifically binds to an alpha-chain of a human IL-7 receptor ("anti-IL-7R antibody") comprising a heavy chain (HC) CDR1, CDR2, and CDR3, and a light chain (LC) CDR1, CDR2, and CDR3, wherein: (i) the heavy chain CDR1 comprises an amino acid sequence set forth in SEQ ID NO: 13; (ii) the heavy chain CDR2 comprises an amino acid sequence set forth in SEQ ID NO: 14; (iii) the heavy chain CDR3 comprises an amino acid sequence set forth in SEQ ID NO: 15; (iv) the light chain CDR1 comprises an amino acid sequence set forth in SEQ ID NOs: 123 to 194; (v) the light chain CDR2 comprises an amino acid sequence set forth in SEQ ID NO: 17; and (vi) the light chain CDR3 comprises an amino acid sequence set forth in SEQ ID NO: 18. In certain aspects, the light chain CDR1 comprises an amino acid sequence set forth in SEQ ID NO: 172, SEQ ID NO: 189, SEQ ID NO: 190, or SEQ ID NO: 192.

Also provided herein is an isolated antibody or antigen binding portion thereof, which specifically binds to an alpha-chain of a human IL-7 receptor ("anti-IL-7R antibody") comprising a heavy chain (HC) CDR1, CDR2, and CDR3, and a light chain (LC) CDR1, CDR2, and CDR3, wherein: (i) the heavy chain CDR1 comprises an amino acid sequence set forth in SEQ ID NO: 13; (ii) the heavy chain CDR2 comprises an amino acid sequence set forth in SEQ ID NO: 14; (iii) the heavy chain CDR3 comprises an amino acid sequence set forth in SEQ ID NO: 15; (iv) the light chain CDR1 comprises an amino acid sequence set forth in SEQ ID NO: 16; (v) the light chain CDR2 comprises an amino acid sequence set forth in SEQ ID NOs: 195 to 237; and (vi) the light chain CDR3 comprises an amino acid sequence set forth in SEQ ID NO: 18.

Provided herein is an isolated antibody or antigen binding portion thereof, which specifically binds to an alpha-chain of a human IL-7 receptor ("anti-IL-7R antibody") comprising a heavy chain (HC) CDR1, CDR2, and CDR3, and a light chain (LC) CDR1, CDR2, and CDR3, wherein: (i) the heavy chain CDR1 comprises an amino acid sequence set forth in SEQ ID NO: 13; (ii) the heavy chain CDR2 comprises an amino acid sequence set forth in SEQ ID NO: 14; (iii) the heavy chain CDR3 comprises an amino acid sequence set forth in SEQ ID NO: 15; (iv) the light chain CDR1 comprises an amino acid sequence set forth in SEQ ID NO: 16; (v) the light chain CDR2 comprises an amino acid sequence set forth in SEQ ID NO: 17; and (vi) the light chain CDR3 comprises an amino acid sequence set forth in SEQ ID NOs: 238 to 259. In certain aspects, the light chain CDR3 comprises an amino acid sequence set forth in SEQ ID NO: 240, SEQ ID NO: 244, or SEQ ID NO: 245.

Present disclosure also provides nucleic acids encoding an anti-IL-7R antibody of the present disclosure, vectors comprising the nucleic acids, and cells comprising the vectors. In some embodiments, the cell is CHO cells, HEK293 cells, HBK cells, COS cells, NSO cells, or HT1080 cells.

Provided herein are also immunoconjugates comprising an anti-IL-7R antibody, as disclosed herein, linked to an agent.

Present disclosure further provides compositions comprising an anti-IL-7R antibody, nucleic acid, vector, cell, or immunoconjugate, as disclosed herein, and a carrier.

Also provided in the present disclosure are kits comprising an anti-IL-7R antibody, nucleic acid, vector, cell, or immunoconjugate, as disclosed herein, and an instruction for use.

Provided herein is a method of inhibiting IL-7 activity in a subject in need thereof, comprising administering an anti-IL-7R antibody, nucleic acid, vector, cell, or immunoconjugate, as disclosed herein, to the subject.

Provided herein is a method of inhibiting proliferation of effector T cells and/or inducing generation and/or survival of regulatory T cells in a subject in need thereof, comprising administering an anti-IL-7R antibody, nucleic acid, vector, cell, or immunoconjugate, as disclosed herein, to the subject.

Also provided herein is a method of treating an inflammatory disease or an autoimmune disease in a subject in need thereof, comprising administering an anti-IL-7R antibody, nucleic acid, vector, cell, or immunoconjugate, as disclosed herein, to the subject. In certain embodiments, the inflammatory disease or the autoimmune disease is selected from the group consisting of an inflammatory bowel disease (IBD), irritable bowel syndrome, rheumatoid arthritis (RA), psoriasis, psoriatic arthritis, systemic lupus erythematosus (SLE), lupus nephritis, vasculitis, sepsis, systemic inflammatory response syndrome (SIRS), type I diabetes, Grave's disease, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogren's syndrome, autoimmune nephritis, Goodpasture syndrome, chronic inflammatory demyelinating polyneuropathy, allergy, asthma, other autoimmune diseases that are a result of either acute or chronic inflammation, and any combinations thereof. In some embodiments, the inflammatory disease or the autoimmune disease is inflammatory bowel disease. In further embodiments, the inflammatory bowel disease is ulcerative colitis or Crohn's disease.

In some embodiments, a subject (e.g., described herein) did not adequately respond to previous TNF-α inhibitor therapy (anti-TNF-α inadequate responder).

In some embodiments, a method disclosed herein can further comprise administering one or more additional therapeutics. In certain embodiments, the additional therapeutics comprise an anti-TNF-α antibody.

In some embodiments, an anti-IL-7R antibody disclosed herein is administered to the subject at a flat dose or a body weight based dose. In some embodiments, an anti-IL-7R antibody is administered intravenously, subcutaneously, intramuscularly, intradermally, or intraperitoneally. In certain embodiments, an anti-IL-7R antibody is administered intravenously or subcutaneously.

Also provided herein is a method of producing an antibody which specifically binds to an alpha-chain of a human IL-7 receptor ("anti-IL-7R antibody), comprising culturing a cell described herein under suitable conditions and isolating the antibody.

BRIEF DESCRIPTION OF THE DRAWINGS/FIGURES

FIG. 1 shows the binding curve of the anti-IL-7R antibody to CD3⁻ cells (i.e., non-Tcells) as measured by flow cytometry. The x-axis shows the concentration (μg/mL) of the anti-IL-7R antibody and the y-axis shows the mean fluorescence intensity (MFI) of the binding.

Figure 2A:
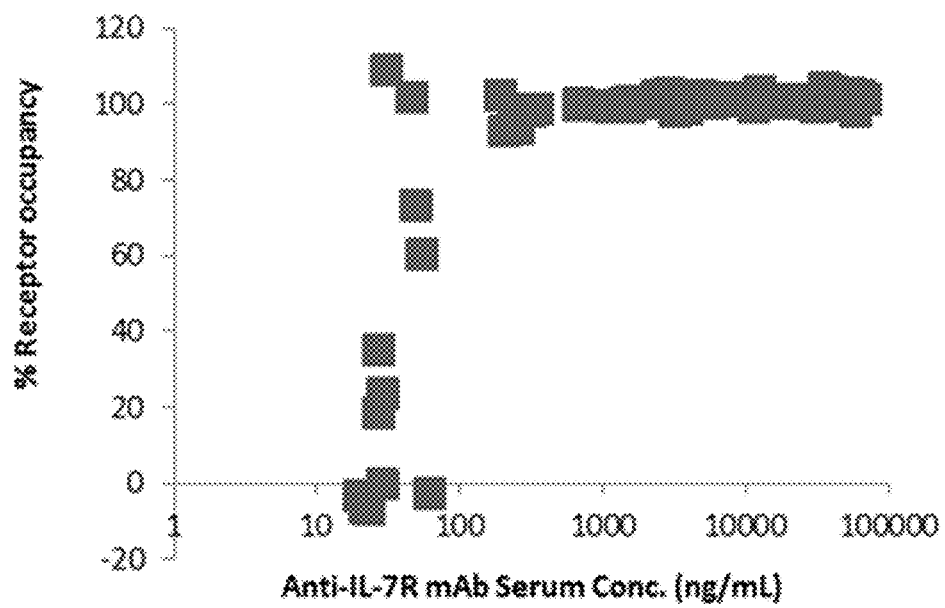
Figure 2B:
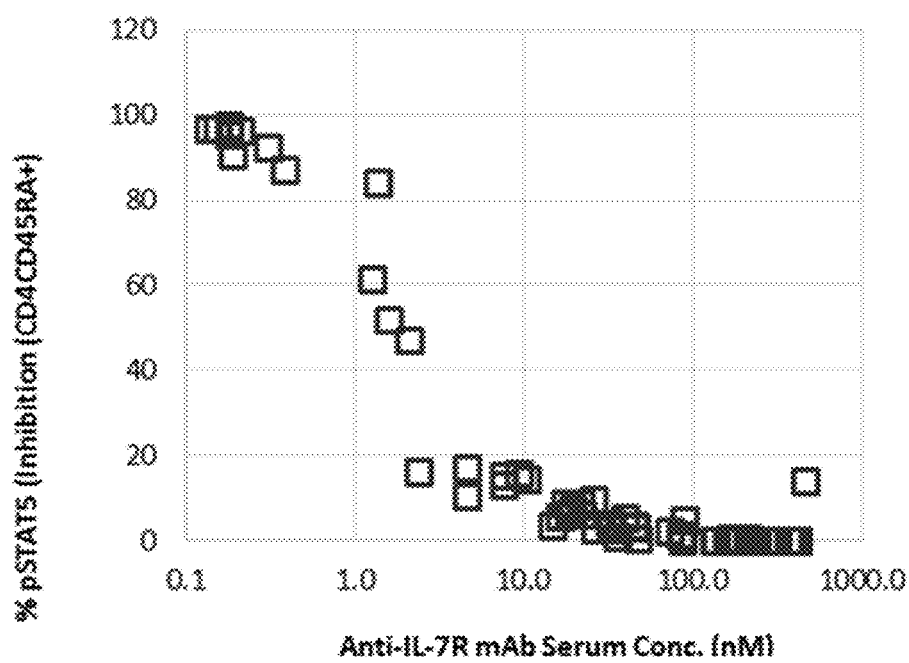

FIGS. 2A and 2B show the cross-reactivity of the anti-IL-7R antibody to cynomolgus IL-7Rα following a single intravenous administration of the antibody in cynomolgus monkeys. FIG. 2A shows the percentage of the total IL-7Rα expressed on $CD4^+CD45RA^+$ T cell that are occupied as a function of anti-IL-7R antibody serum concentration (ng/mL). FIG. 2B shows pSTAT5 activation in $CD4^+CD45RA^+$ T cells as a function of anti-IL-7R antibody concentration (nM) in the serum. pSTAT5 activation is shown as a percentage of total STAT5 that is phorphorylated. In both FIGS. 2A and 2B, the antibody concentration in the serum is intended to represent the measured exposure of the $CD4^+CD45RA^+$ T cells to the anti-IL-7R antibody.

Figure 3:
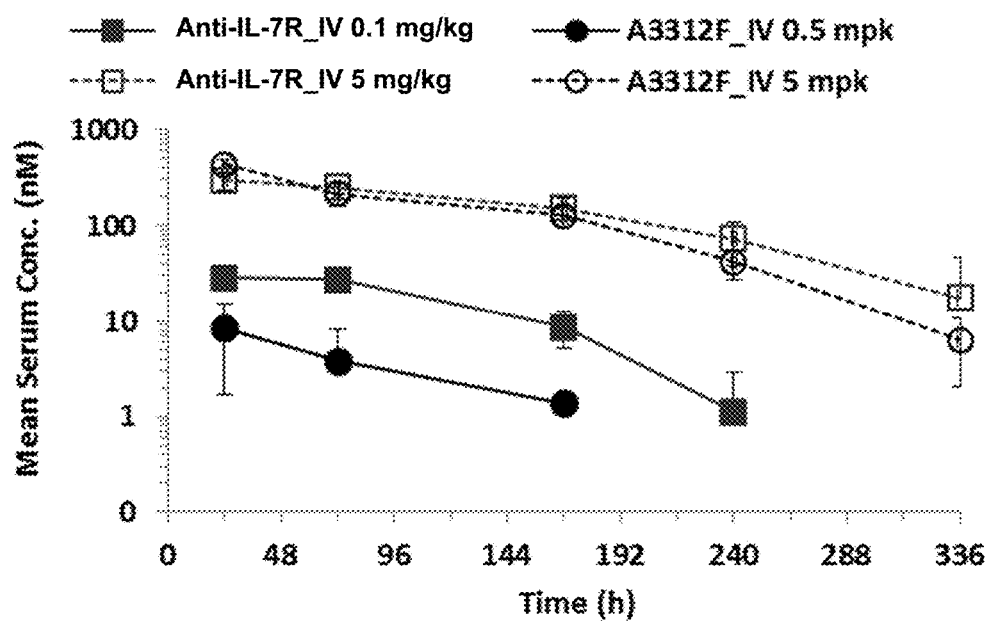

FIG. 3 shows the pharmacokinetics (serum concentration) of the anti-IL-7R antibody following a single intravenous administration in NOD SCID gamma (NSG)-human PBMC transfer mice. The mice received one of two doses of the anti-IL-7R antibody: 0.5 mg/kg (closed square with solid line) or 5 mg/kg (open square with dashed line). Control mice received the A3312F antibody: 0.5 mg/kg (closed circle with solid line) or 5 mg/kg (open circle with dashed line). Data are shown as mean±standard deviation.

Figure 4:
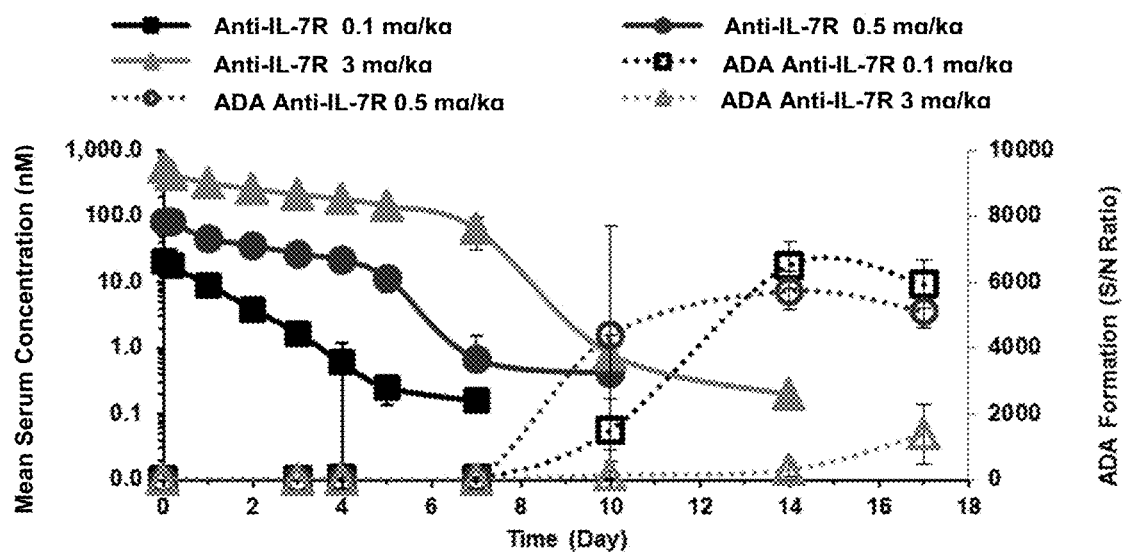

FIG. 4 shows both the pharmacokinetics (serum concentration) and anti-drug antibody (ADA) formation following a single intravenous administration of the anti-IL-7R antibody in cynomolgus monkeys. The animals received one of three doses of the antibody: 0.1 mg/kg (square), 0.5 mg/kg (circle), or 3 mg/kg (triangle). The serum concentrations (left y-axis) of the antibody at the different doses are shown as solid lines. The anti-drug antibody (i.e., against the administered anti-IL-7R antibody) formation (right y-axis) is shown as dashed lines. Data are shown as mean±standard deviation.

Figure 5:
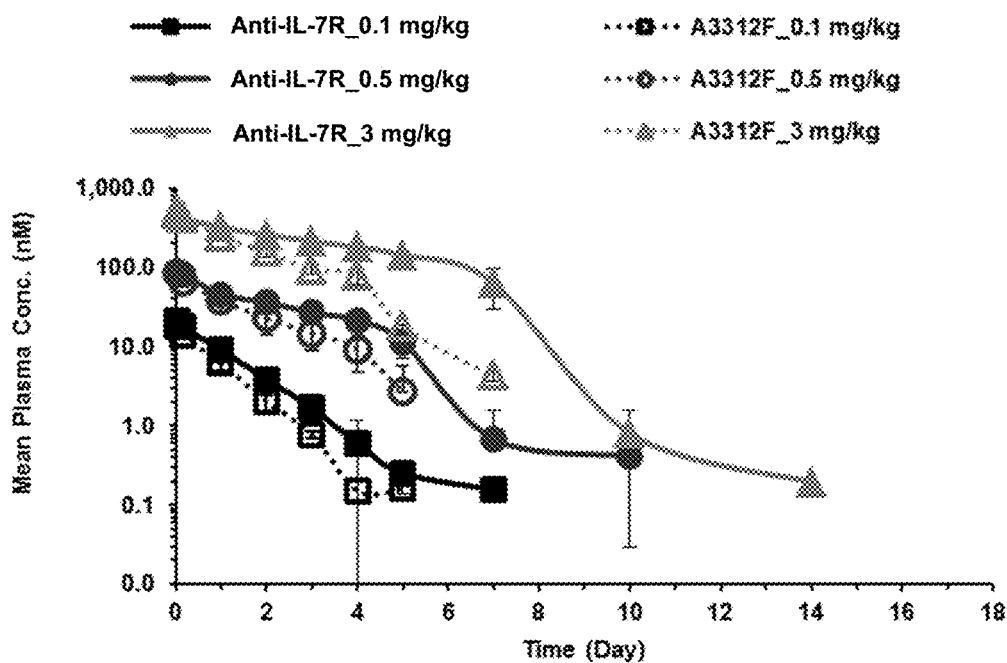

FIG. 5 shows a comparison of the pharmacokinetics (serum concentration) of the anti-IL-7R antibody and A3312F antibody following a single intravenous administration in cynomolgus monkeys. The animals received one of three doses of the anti-IL-7R antibody: 0.1 mg/kg (closed square with solid line), 0.5 mg/kg (closed circle with solid line), or 3 mg/kg (closed triangle with solid line). Control animals received the A3312F antibody at one of the following doses: 0.1 mg/kg (open square with dashed line), 0.5 mg/kg (open circle with dashed line), or 3 mg/kg (open triangle with dashed line). Data are shown as mean±standard deviation.

Figure 6:
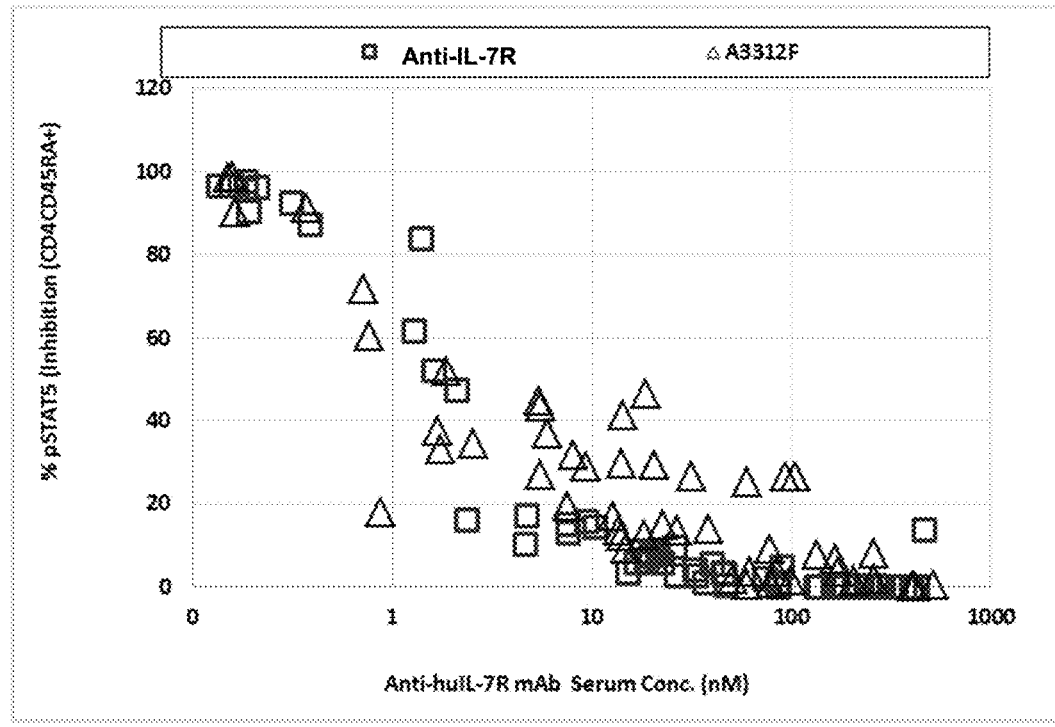

FIG. 6 shows the pSTAT5 activation in $CD4^+CD45RA^+$ T cells following a single intravenous administration of the anti-IL-7R antibody (square) or the A3312F antibody (triangle) in cynomolgus monkeys. pSTAT5 activation is shown as a percentage of total STAT5 that is phorphorylated. The antibody concentration in the serum is intended to represent the measured exposure of the $CD4^+CD45RA^+$ T cells to the antibody.

Figure 7A:
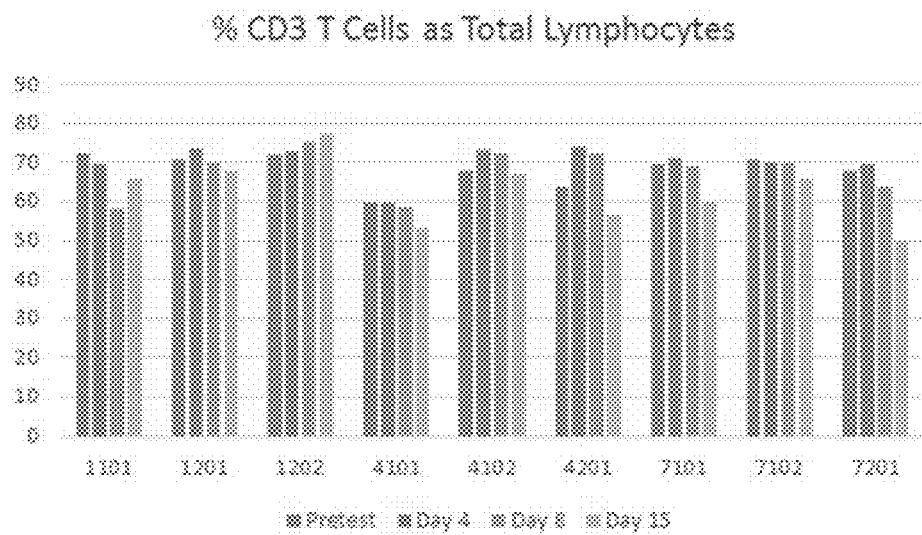
Figure 7B:
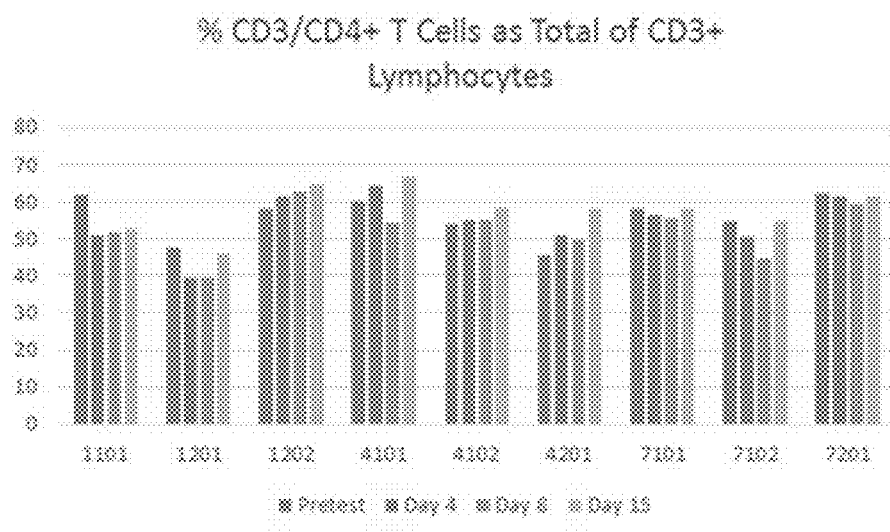
Figure 7C:
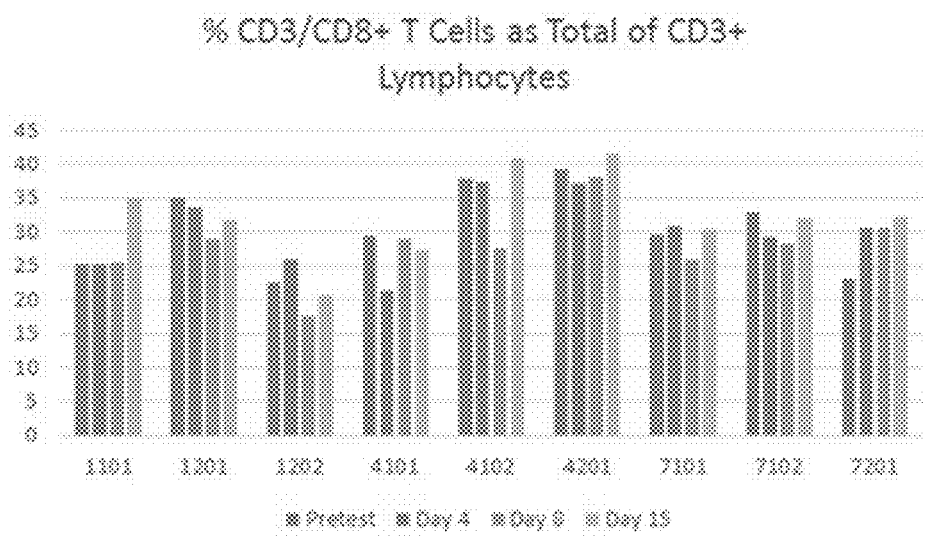

FIGS. 7A, 7B, and 7C show the frequency of different T cell populations observed in peripheral blood following single intravenous administration of the anti-IL-7R antibody (3 mg/kg) in different cynomolgus monkeys. FIG. 7A shows the frequency of $CD3^+$ T cells as a percentage of the total lymphocytes. FIG. 7B and FIG. 7C show the frequency of $CD4^+$ T cells and $CD8^+$ T cells, respectively, as a percentage of the total $CD3^+$ T cell population. In FIGS. 7A, 7B, and 7C, the frequency of the different T cell populations was observed at pre-administration (the first bar from the left in each set of bars for an individual monkey) and at days 4 (the second bar from the left in each set of bars for an individual monkey), 8 (the third bar from the left in each set of bars for an individual monkey), and 15 (the fourth bar from the left in each set of bars for an individual monkey) post antibody administration. The x-axis provides the identification number for each of the monkeys.

Figure 8:
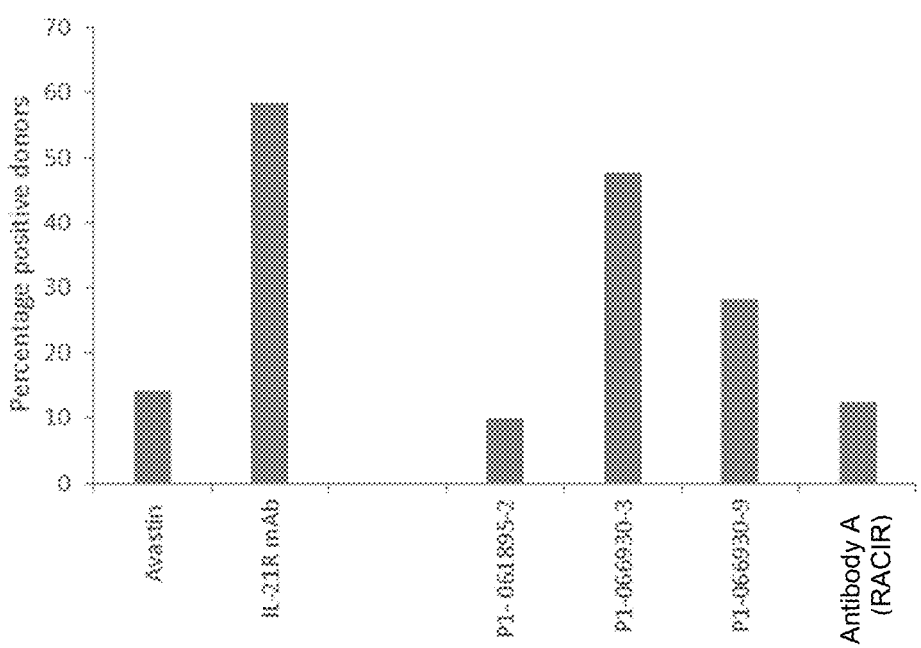

FIG. 8 shows the potential risk of immunogenicity of different production lots of the anti-IL-7R antibody as measured in vitro using a dendritic cell:T cell proliferation assay. The different anti-IL-7R antibodies tested include: (i) P1-061895-2, (ii) P1-066930-3, (iii) P1-066930-9, and (iv) Antibody A RACIR. Avastin and anti-IL-21R antibody (IL-21R mAb) are shown as negative and positive controls, respectively.

Figure 9:
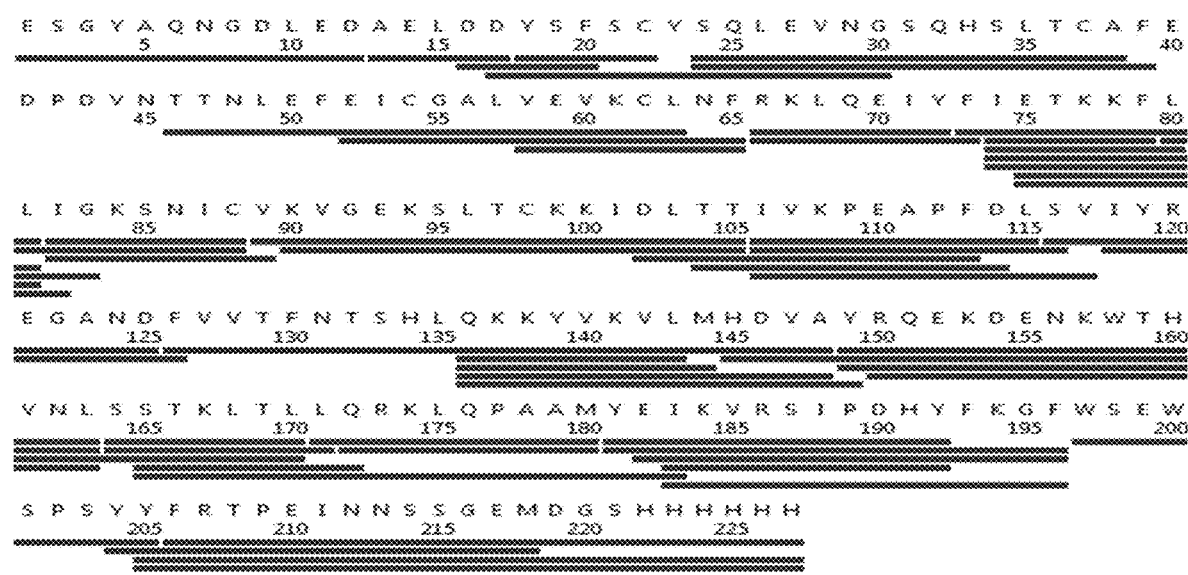

FIG. 9 shows the sequence coverage of the human IL-7Rα using HDX-MS epitope mapping analysis. Each bar indicates a peptic peptide.

Figure 10:
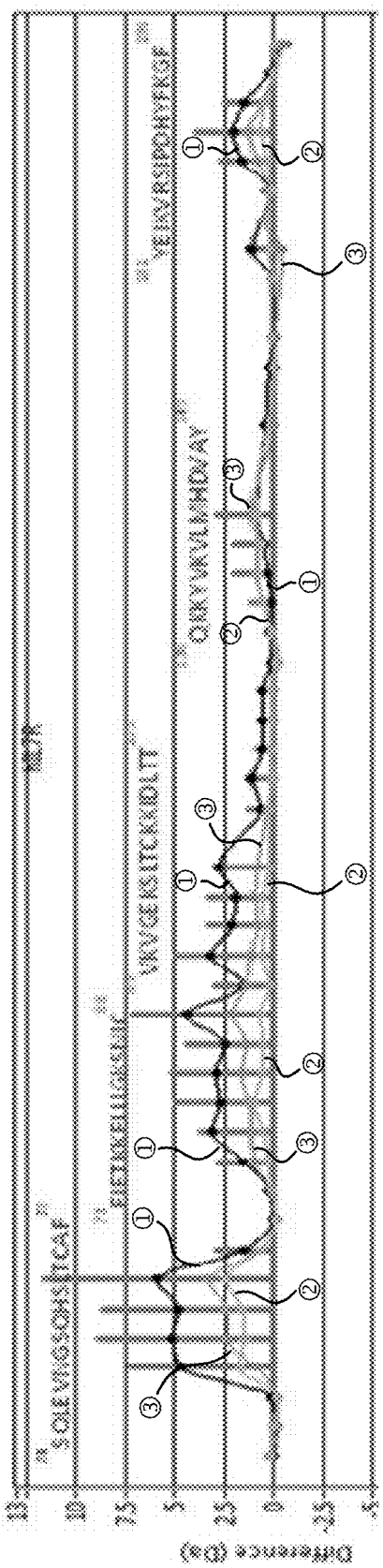

FIG. 10 shows the deuterium uptake differences for the five epitopes of the anti-IL-7R antibody identified using the HDX-MS epitope mapping analysis. The five epitopes shown include: (i) $^{24}$SQLEVNGSQHSLTCAF$^{39}$; (ii) $^{73}$FIETKKFLLIGKSNIC$^{88}$; (iii) $^{89}$VKVGEKSLTCK-KIDLTT$^{105}$; (iv) $^{136}$QKKYVKVLMHDVAY$^{149}$; and (v) $^{181}$YEIKVRSIPDHYFKGF$^{196}$. The black vertical bars indicate the summed differences in deuteration for each peptide. The lines represent differences in deuteration for each peptide at different time points, i.e., 1 minute ("(2)"), 10 minutes ("(3)"), and 240 minutes ("(1)").

Figure 11A:
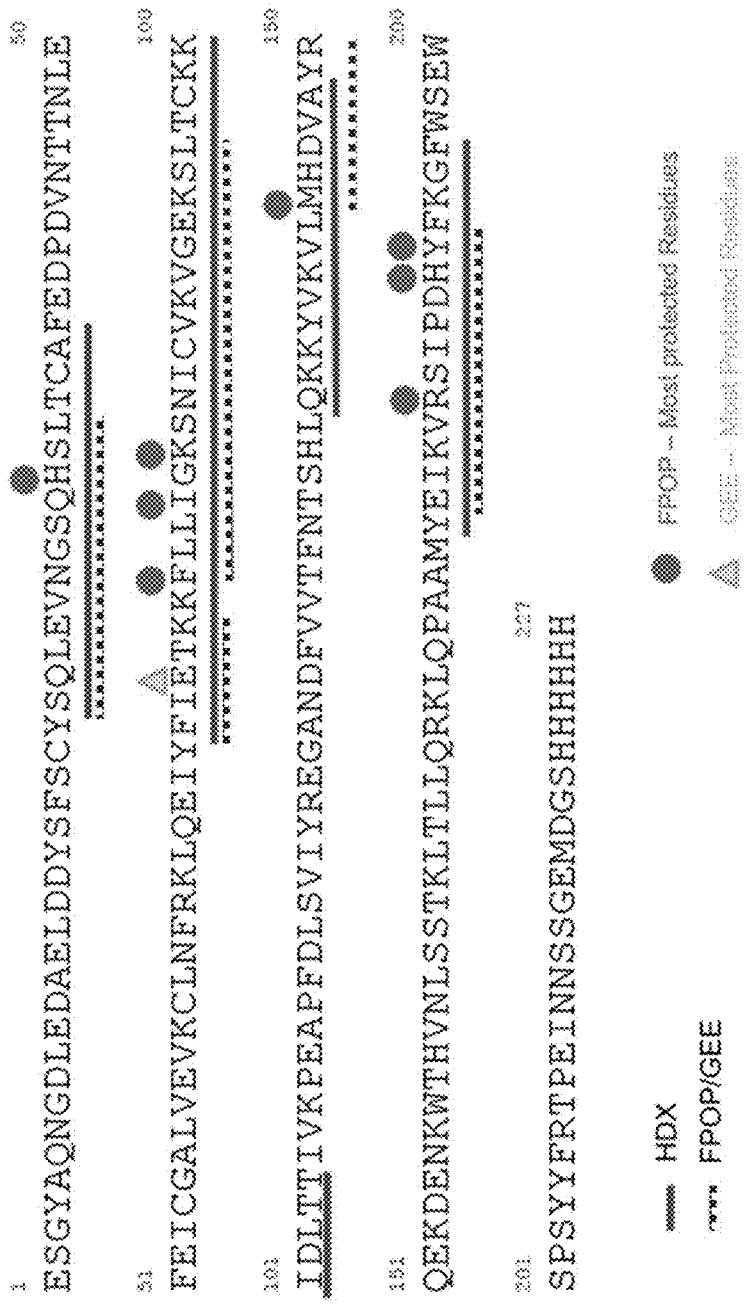
Figure 11B:
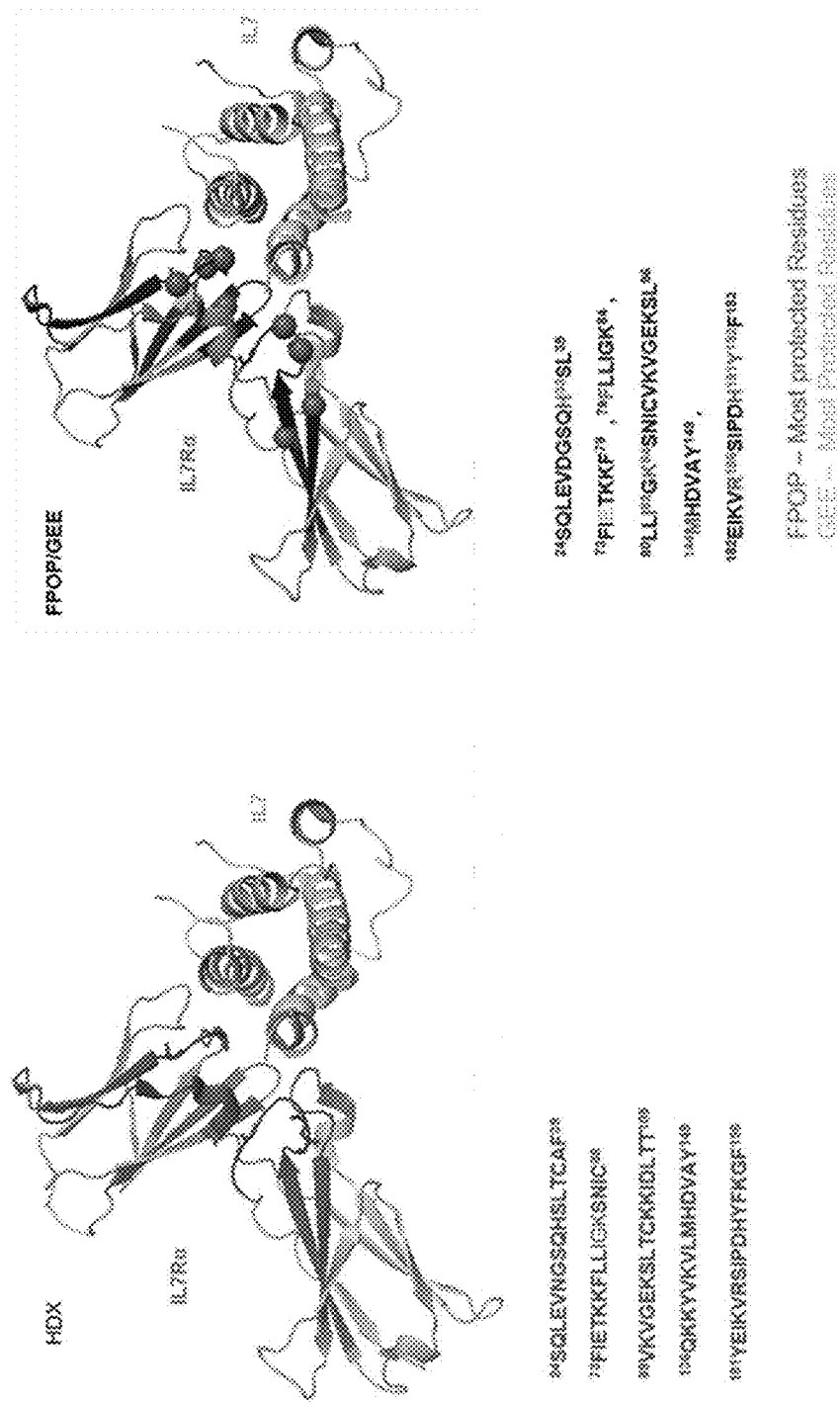

FIGS. 11A and 11B shows a summary of the epitope mapping analysis for the anti-IL-7R antibody. In FIG. 11A, the epitopes were mapped to a linear sequence of human IL-7Rα. The epitopes identified using the HDX-MS analysis are indicated by the solid line. The epitopes identified using the FPOP/GEE analysis are indicated by the dotted line. The most protected residues of the epitopes identified using FPOP analysis are indicated by circles. The most protected residues of the epitopes identified using GEE analysis are indicated by triangles. The numbering shown correspond to the mature sequence of human IL-7Rα. In FIG. 11B, the epitopes are mapped to the crystal structure of human IL-7Rα. The crystal structure on the left shows the epitopes identified using the HDX-MS analysis. The crystal structure on the right shows the epitopes identified using FPOP/GEE analysis. The sequences of the epitopes are provided below the crystal structures.

Figure 12A:
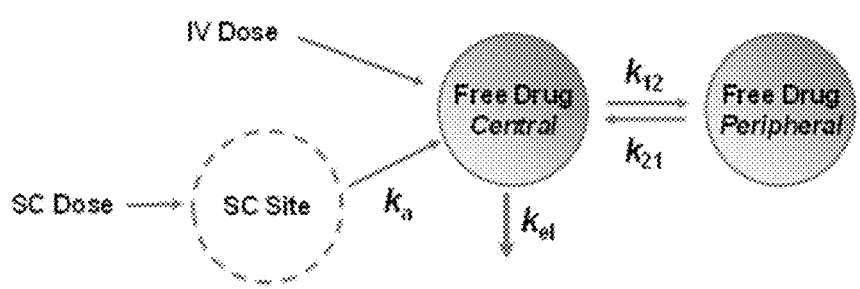
Figure 12B:
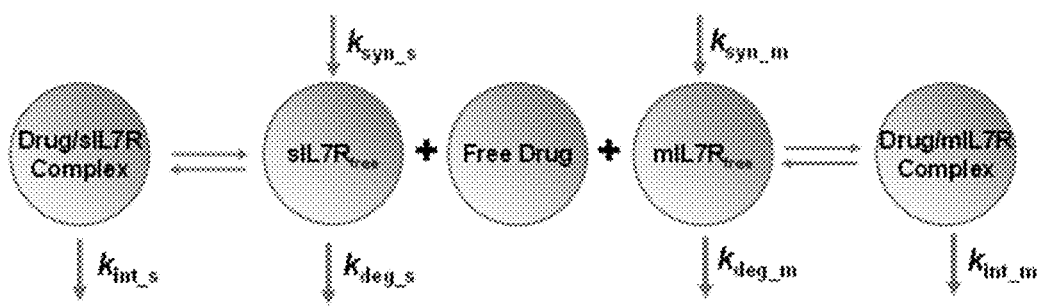

FIGS. 12A and 12B show the schematic diagram of the PK model of anti-IL-7R antibody (FIG. 12A) and the mechanistic PK/OD model (FIG. 12B) used to characterize the PK and PD data in monkeys and humans.

Figure 13:
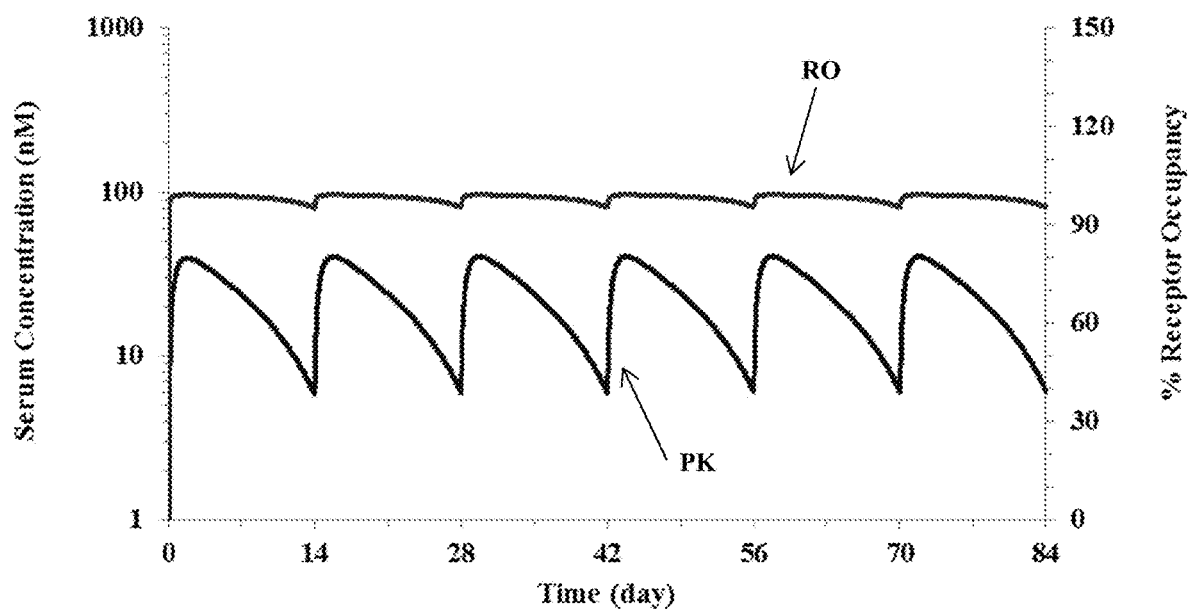

FIG. 13 shows the predicted human pharmacokinetics (based on serum concentration of the anti-IL-7R antibody) (left y-axis) and receptor occupancy (right y-axis) curve at the projected human dose (110 mg every other week subcutaneously for a 70-kg adult) of the anti-IL-7R antibody. The top line ("RO") shows the receptor occupancy data. The bottom line ("PK") shows the pharmacokinetics data.

Figures 14A, 14B:
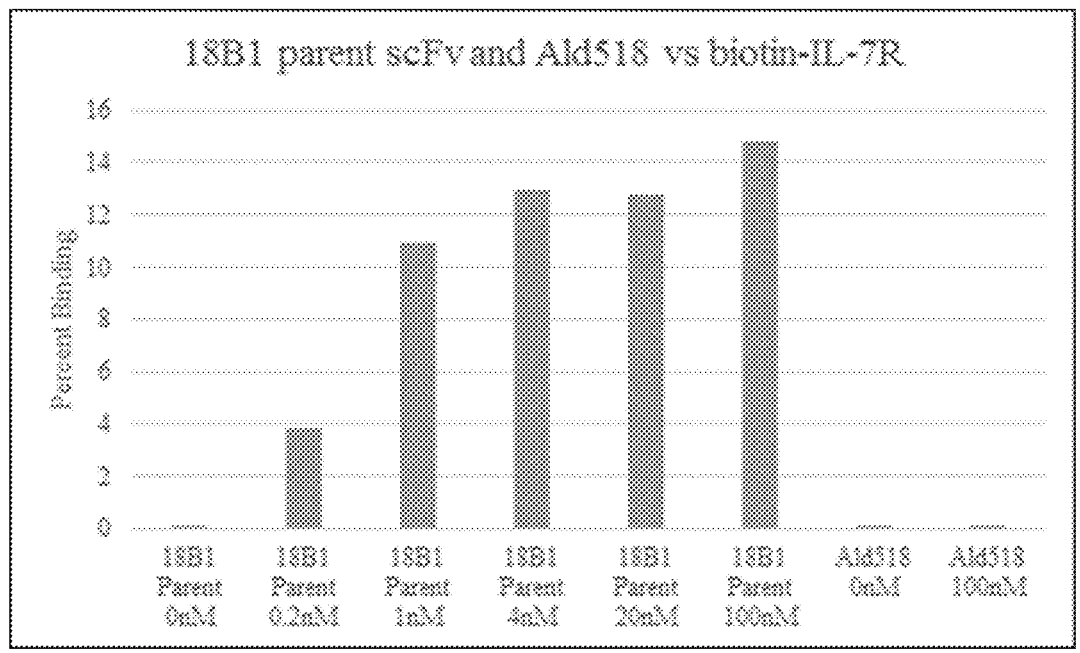

FIGS. 14A and 14B show the binding of the 18B1 (Antibody A) antibody to human IL-7R after being reformatted as scFv. FIG. 14A provides a comparison of binding of the 18B1 scFv at different concentrations. FIG. 14B provides the ka, kd, and KD values.

FIG. 15 shows the specific amino acid residues within the heavy and light chain CDRs, which were individually mutated for the mutational scan analysis described in Example 11.

Figure 16:
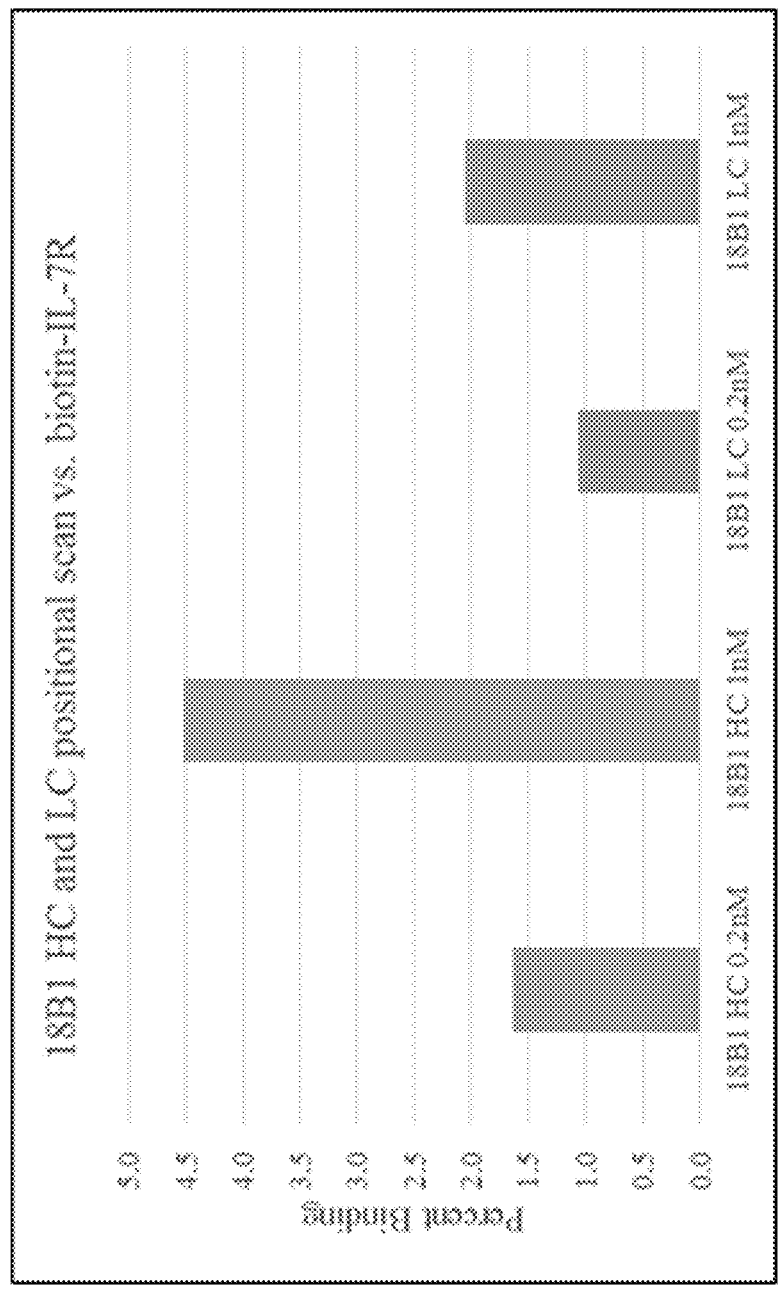

FIG. 16 shows the results from a single round of selection for the 18B1 scFv. Percent binding of the 18B1 heavy chain and light chain to human IL-7R is shown as compared to biotin-IL-7R. The 18B1 heavy chain and light chain were tested at two different concentrations (0.2 nM and 1 nM).

Figure 17A:
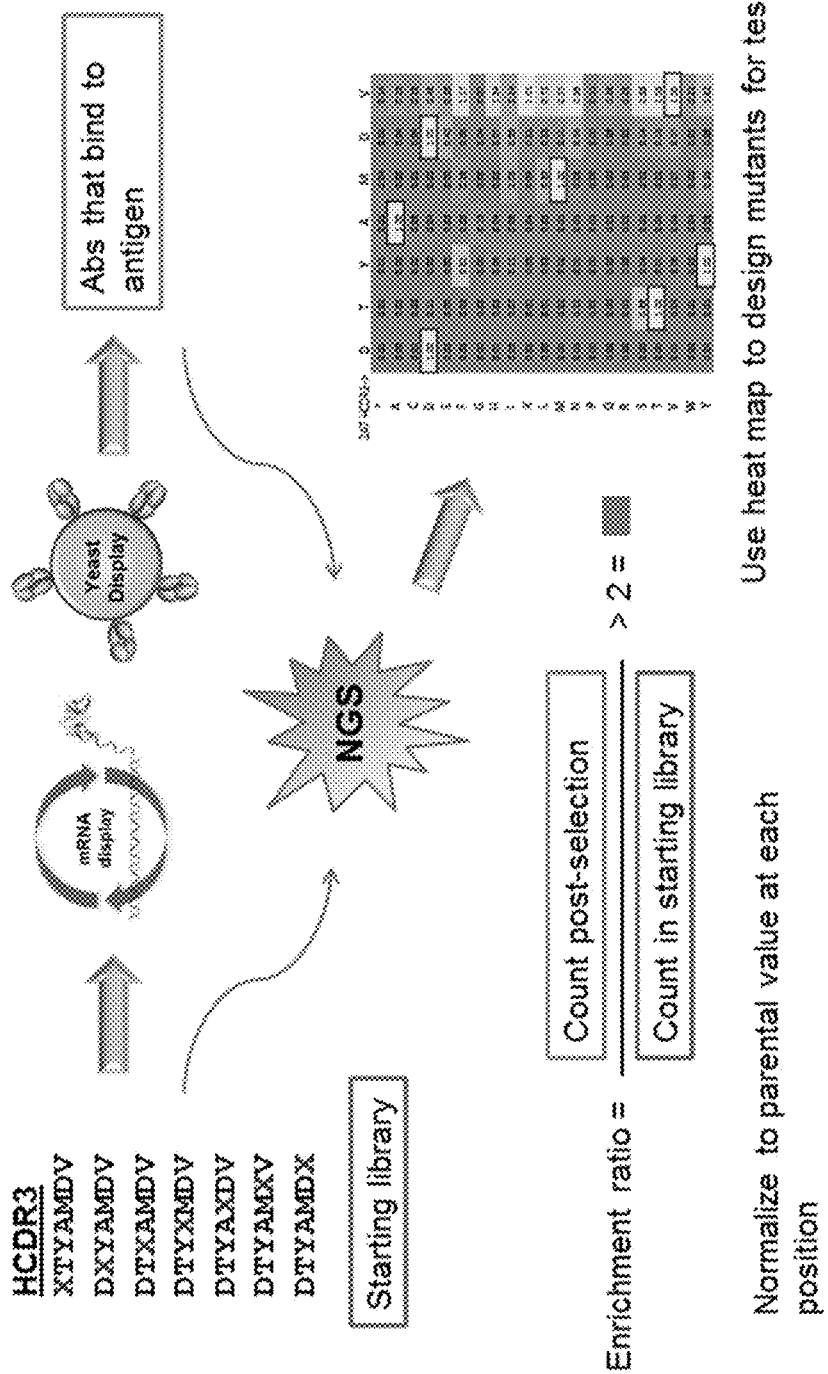
Figure 17B:
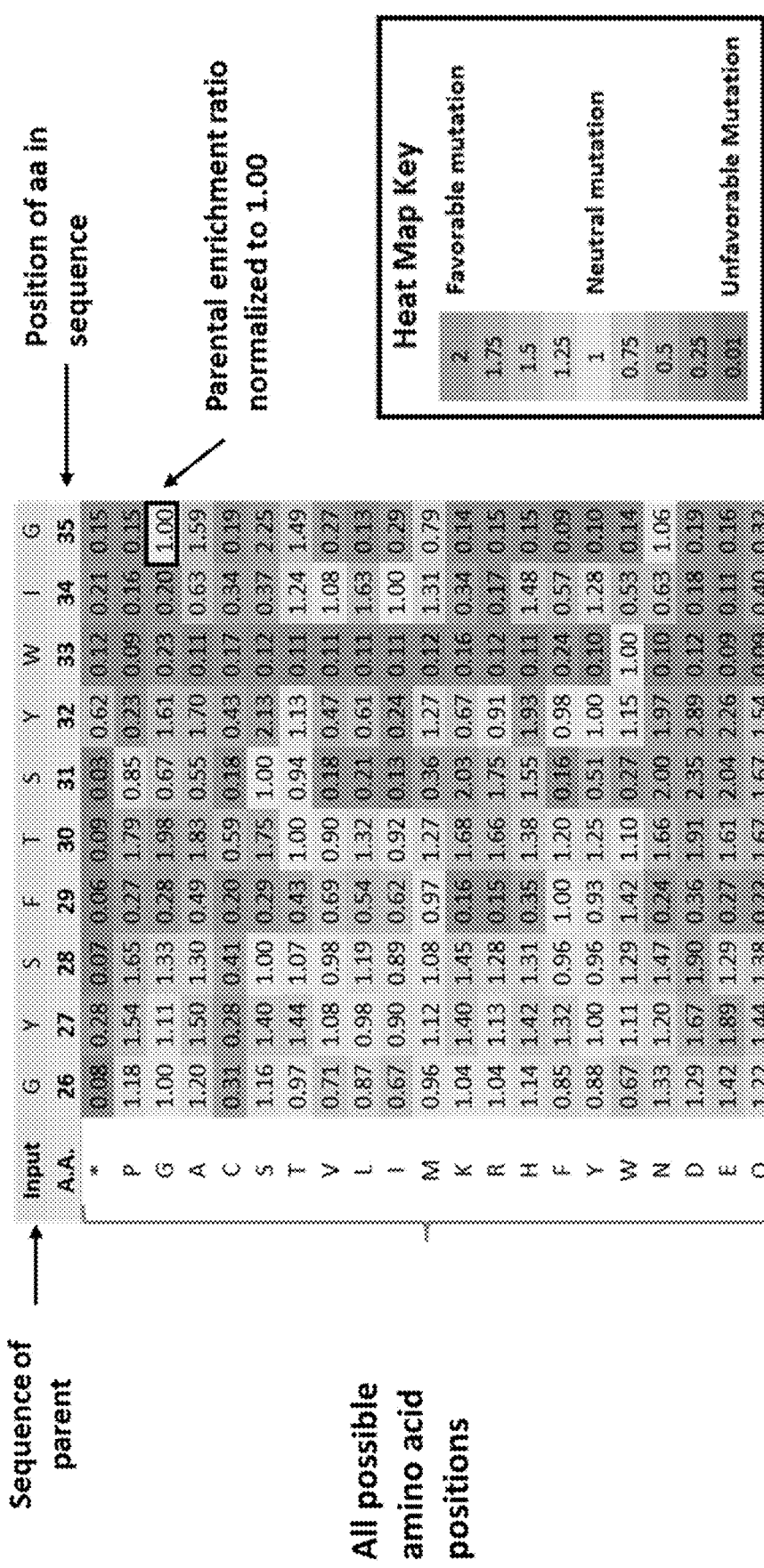

FIGS. 17A and 17B provide a schematic of the overall process involved in constructing the mutational scan library described in Example 11 and using next generation sequencing (NGS) to identify 1) CDR positions critical for binding, 2) CDR positions where mutations are tolerated, and 3) mutations that can improve binding of the antibody to hIL-7R. FIG. 17A illustrates the different aspects of the process itself. FIG. 17B provides a brief description of interpreting the results from the heat maps.

FIGS. 18A, 18B, 18C, 18D, 18E, and 18F provide the heat map results for 18B1 antibody variants with a mutation in LC CDR3, HC CDR3, LC CDR1, LC CDR2, HC CDR1, and HC CDR2, respectively. For each of the figures, the antibody variants were tested at two different concentrations (0.2 nM and 1 nM). In each of the figures, the left most column provides the specific mutation made at a particular amino acid residue. The enrichment score for the different mutations are provided in the relevant boxes. As explained in FIG. 17B, an enrichment score of >1 suggests a favorable mutation (i.e., improves binding), with a higher enrichment score suggesting a more favorable mutation. An enrichment score of 1 suggests a neutral mutation (i.e., does not significantly affect binding). An enrichment score of <1 suggests an unfavorable mutation (i.e., impairs binding).

FIG. 19 provides (i) the KD value (shown as a ratio of the parent 18B1 antibody to the variant antibody), and (ii) the enrichment ratio obtained through NGS heat map analysis for different 18B1 antibody variants.

Figure 20A:
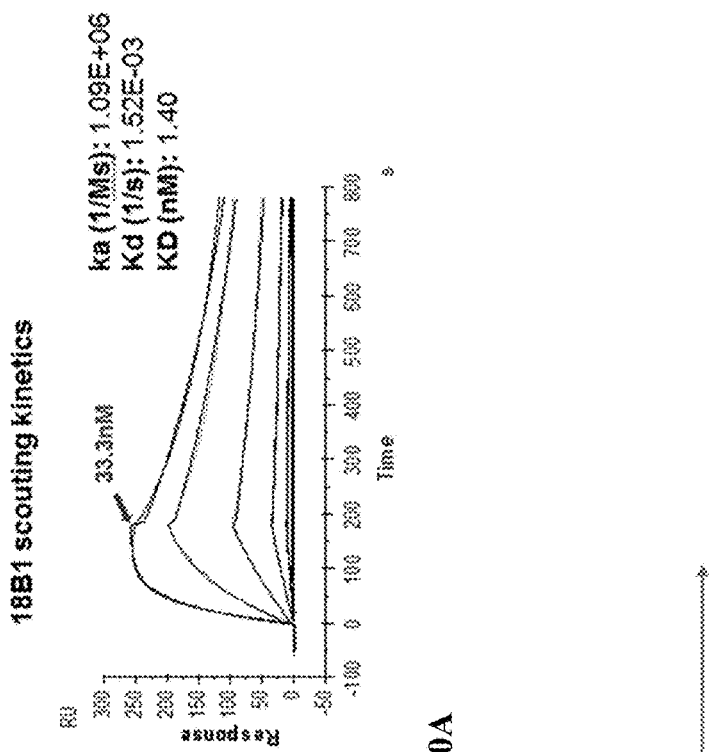
Figure 20B:
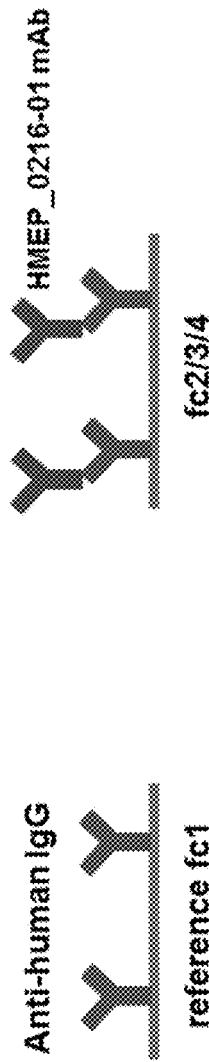

FIGS. 20A and 20B provide an overview of the Biacore kinetics format used to assess the binding of 18B1 (Antibody A) and 18B1 alanine variants described in Example 11. The specific conditions used are provided in the left portion of FIG. 20A. Biacore sensorgram for the 18B1 antibody is provided in the right portion of FIG. 20A. FIG. 20B shows a schematic of the Biacore assay used.

Figure 21:
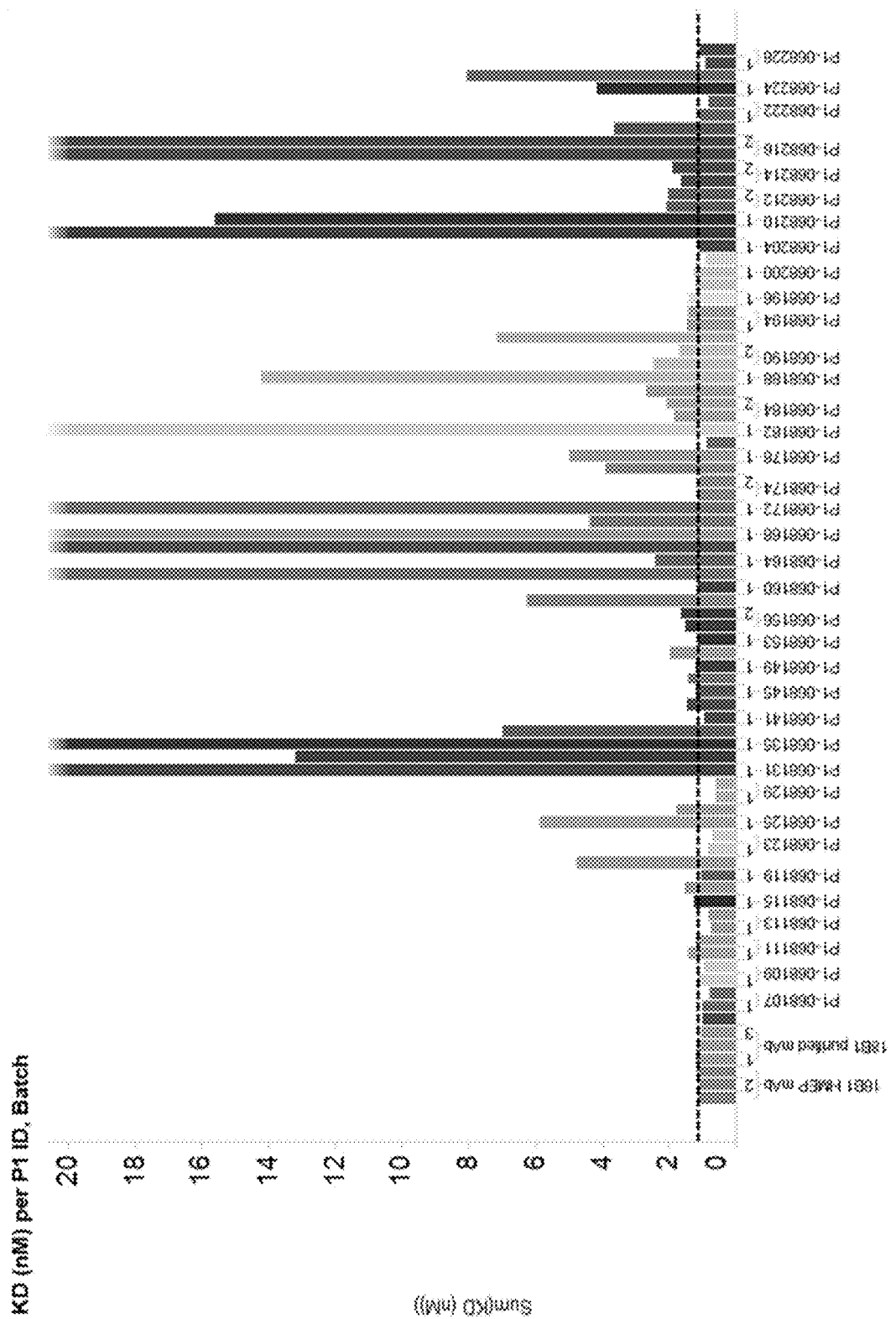

FIG. 21 provides the binding data for the different 18B1 antibody variants to human IL-7R, as measured by Biacore analysis.

Figure 22:
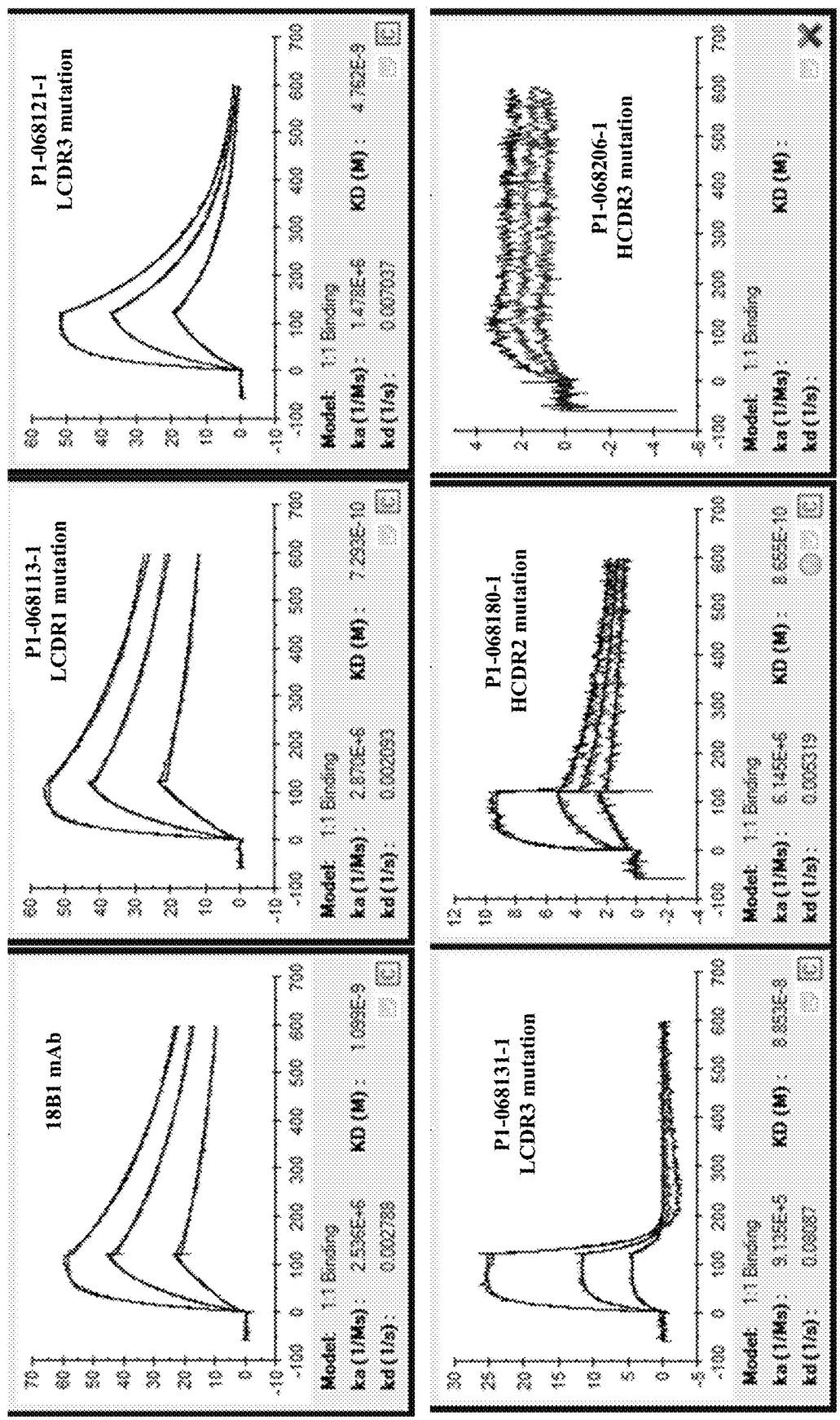

FIG. 22 provides surface plasmon resonance (SPR) profile of exemplary 18B1 antibody variants. For each of the antibody variants, the ka, kd, and KD values are provided below the SPR profile.

Figure 23:
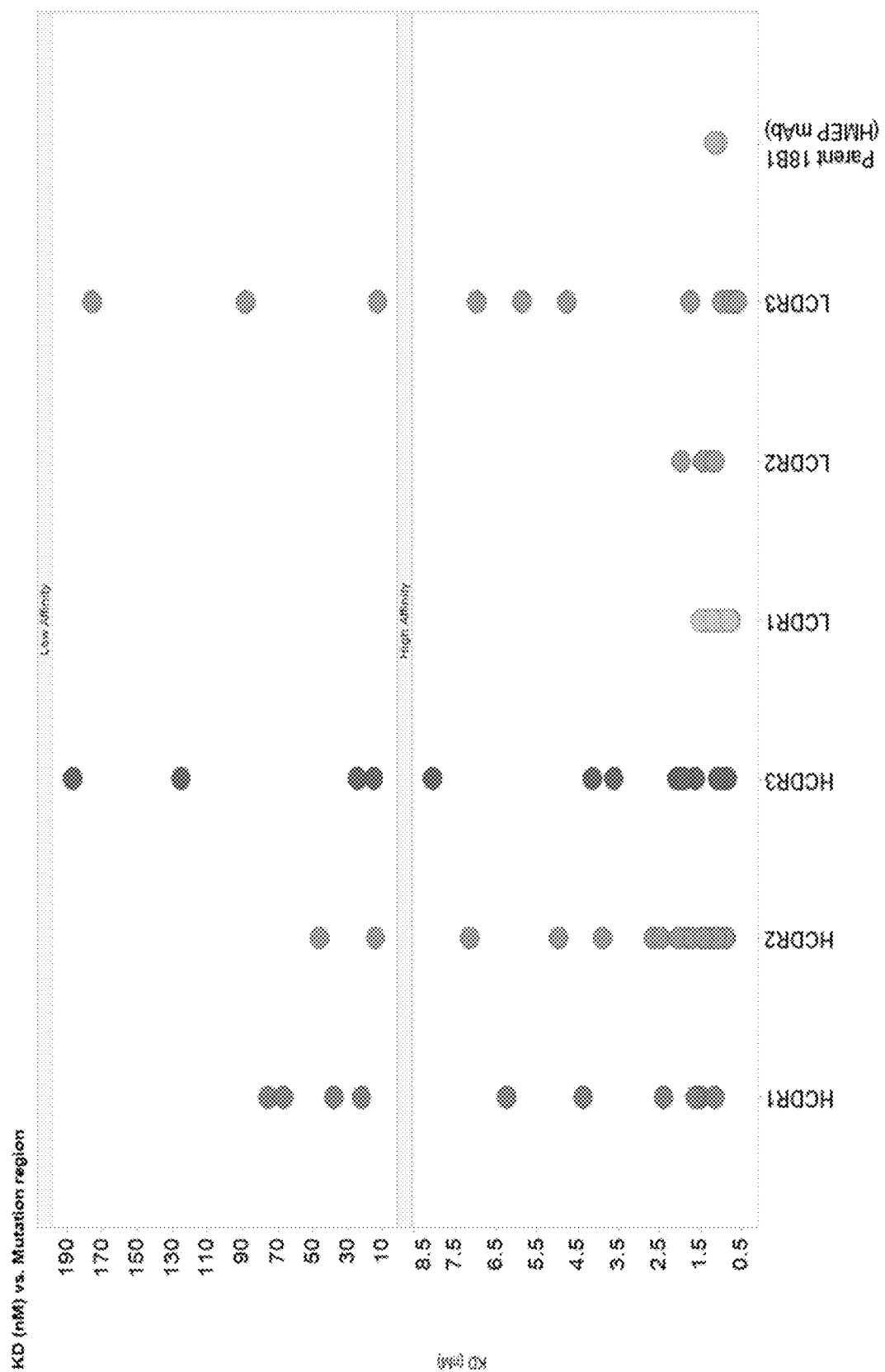

FIG. 23 provides a graphical summary of the distribution of KD values for different 18B1 antibody variants. Each of the antibody variants are divided based on which of the CDRs were mutated. Each circle represents an individual antibody.

Figure 24:
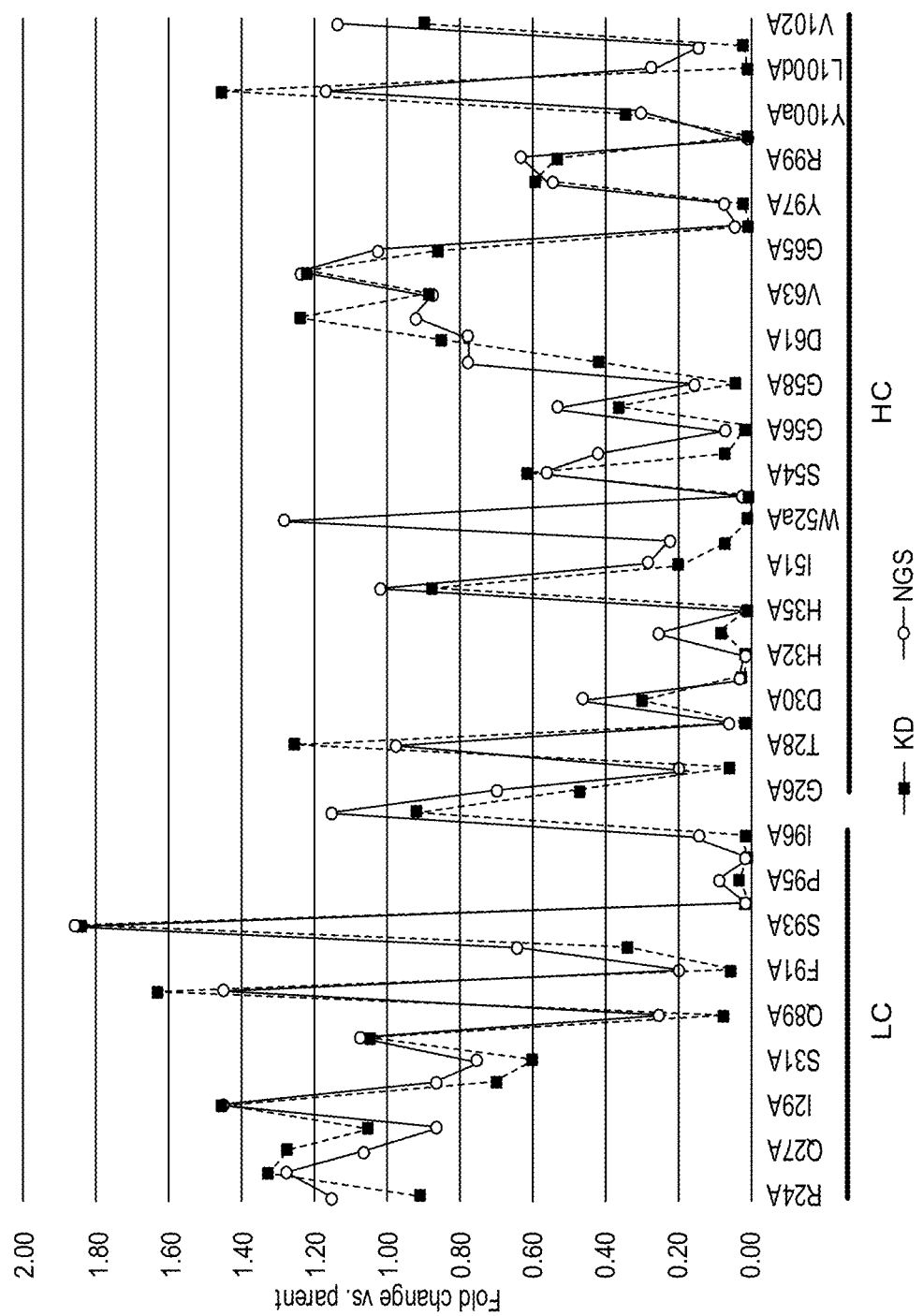

FIG. 24 shows the correlation between KD values (square) and the heat map results generated using NGS (open circle) for different alanine variants. The specific mutations (either in the light chain CDRs or the HC CDRs) are provided along the X-axis.

Figure 25B:
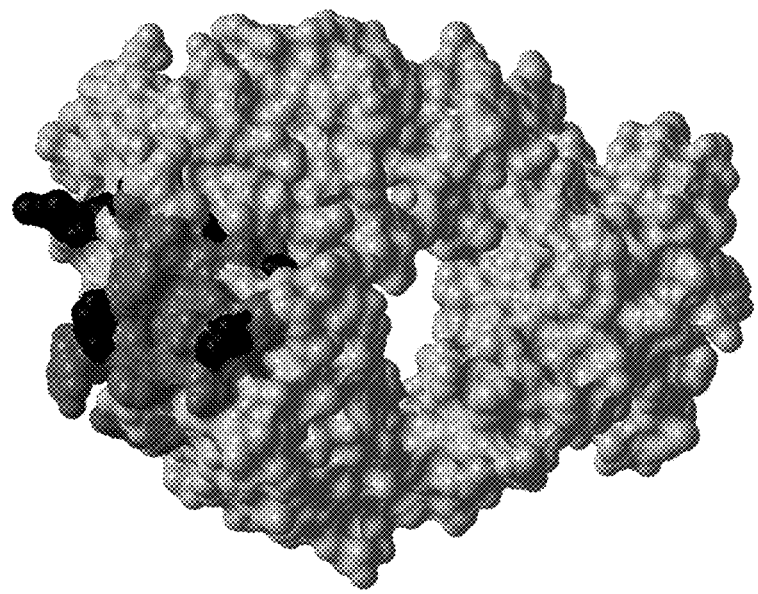
Figure 25A:
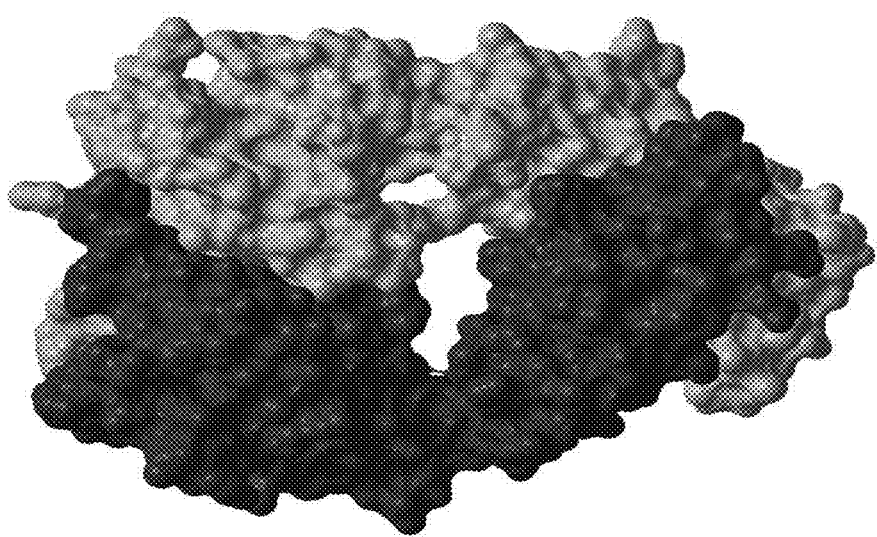

FIGS. 25A and 25B provide a crystal structure of the Fab fragment of the 18B1 antibody. In FIG. 25A, the heavy (dark gray) and light chains (light gray) of the 18B1 antibody are denoted. In FIG. 25B, residues that are important for binding to IL-7Rα are shown in dark gray. Residues that could be modified to improve binding are shown in black.

Figure 26:
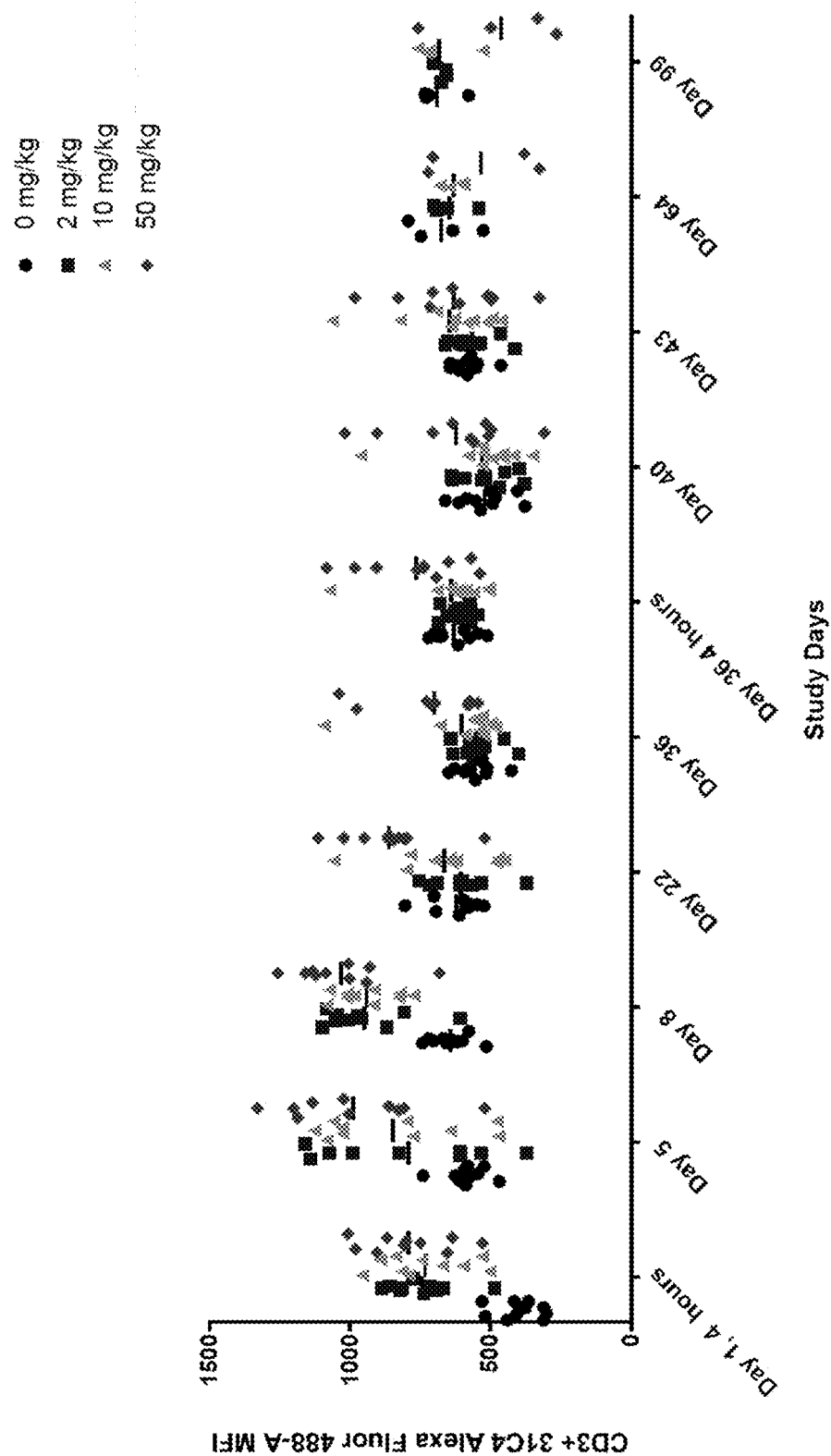

FIG. 26 provides a comparison of IL-7Rα expression on CD3$^+$ leukocytes isolated from monkeys that received a subcutaneous administration of the 18B1 antibody at one of the following doses: (i) 2 mg/kg ("square"), (ii) 10 mg/kg ("triangle"), and (iii) 50 mg/kg ("diamond"). Animals that did not receive the 18B1 antibody were used as controls ("circle"). IL-7Rα expression is shown as mean fluorescence intensity (MFI) as measured using flow cytometry. IL-7Rα expression was measured on the following days post antibody administration: day 1, 4 hours; day 5; day 8; day 22; day 36; day 36, 4 hours; day 40; day 43; day 64; and day 99.

Figure 27A:
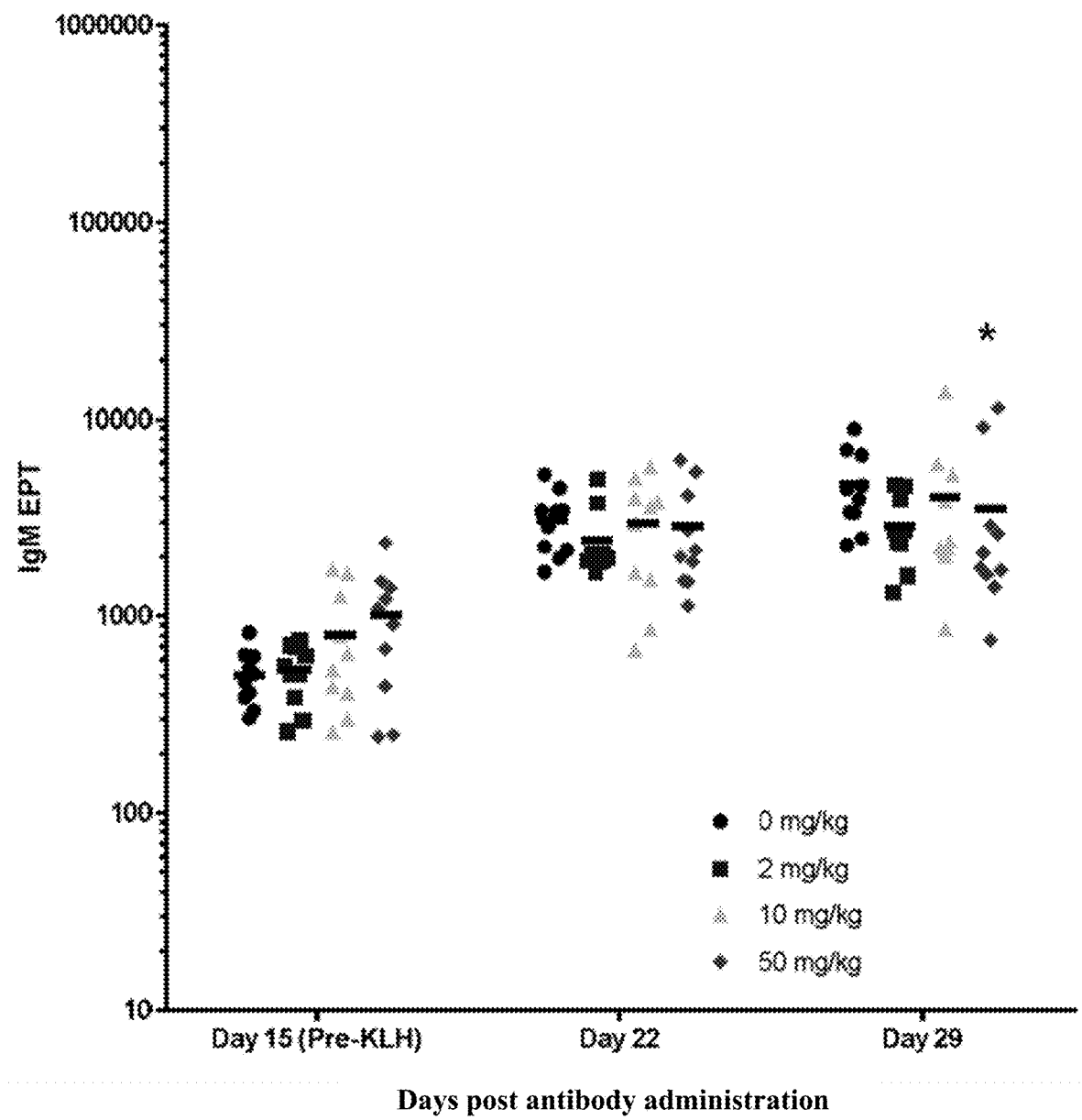
Figure 27B:
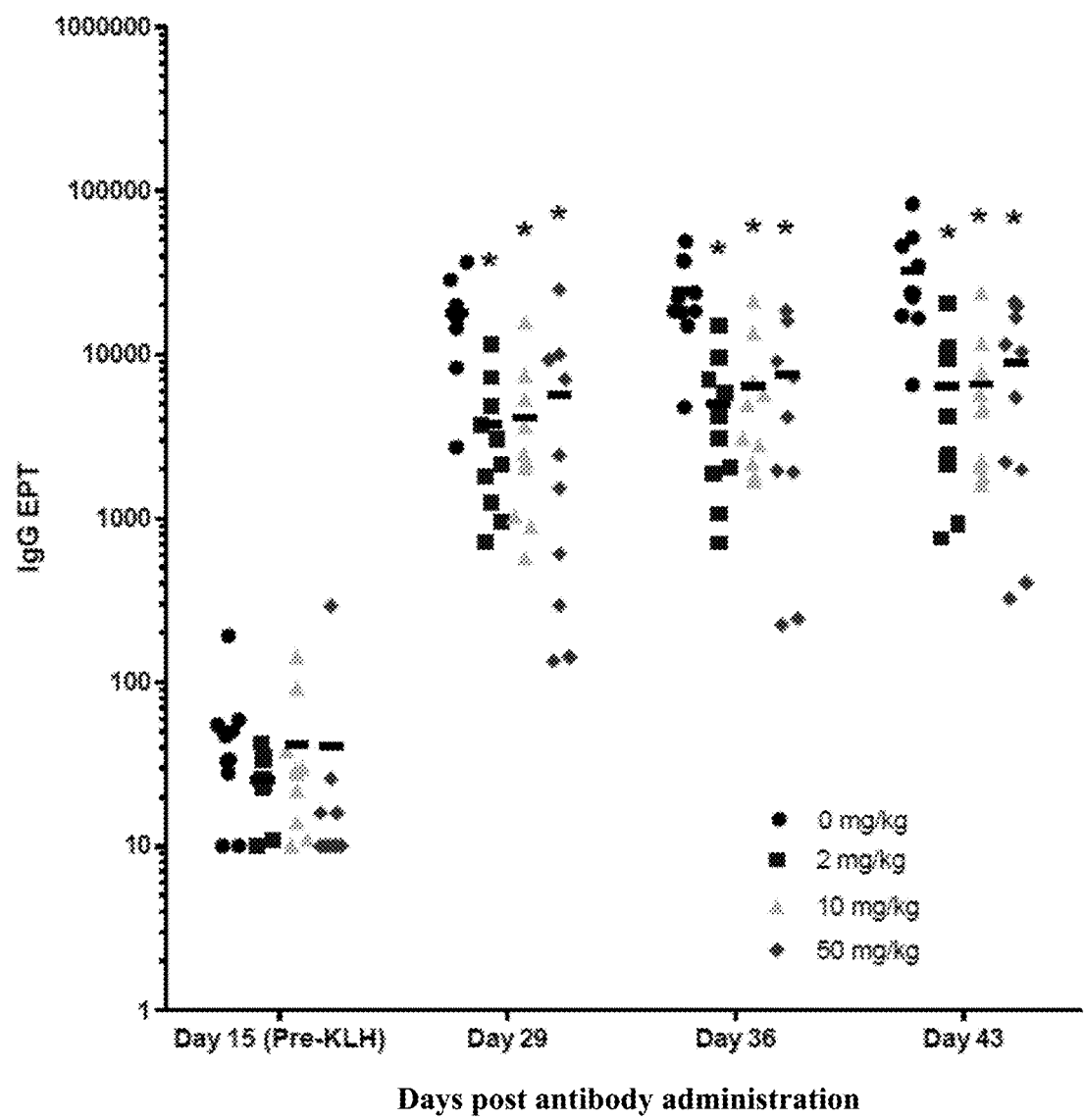

FIGS. 27A and 27B provide a comparison of the keyhole limpet hemocyanin (KLH)-induced IgM (FIG. 27A) and IgG (FIG. 27B) antibody responses in monkeys that received a subcutaneous administration of the 18B1 antibody at one of the following doses: (i) 2 mg/kg ("square"), (ii) 10 mg/kg ("triangle"), and (iii) 50 mg/kg ("diamond"). Animals that did not receive the 18B1 antibody were used as controls ("circle"). The KLH-induced IgM and IgG responses are shown by providing the endpoint titers KLH-specific IgM and IgG antibody measured in the sera of the animals using ELISA. As shown in FIG. 27A, KLH-specific IgM was measured on days 15, 22, and 29 post 18B1 antibody administration (i.e., days 0, 7, and 14 post-KLH immunization, respectively). As shown in FIG. 27B, KLH-specific IgG was measured on days 15, 29, 36, and 43 post 18B1 antibody administration (i.e., days 0, 14, 21, and 28 post-KLH immunization, respectively).

Figure 28A:
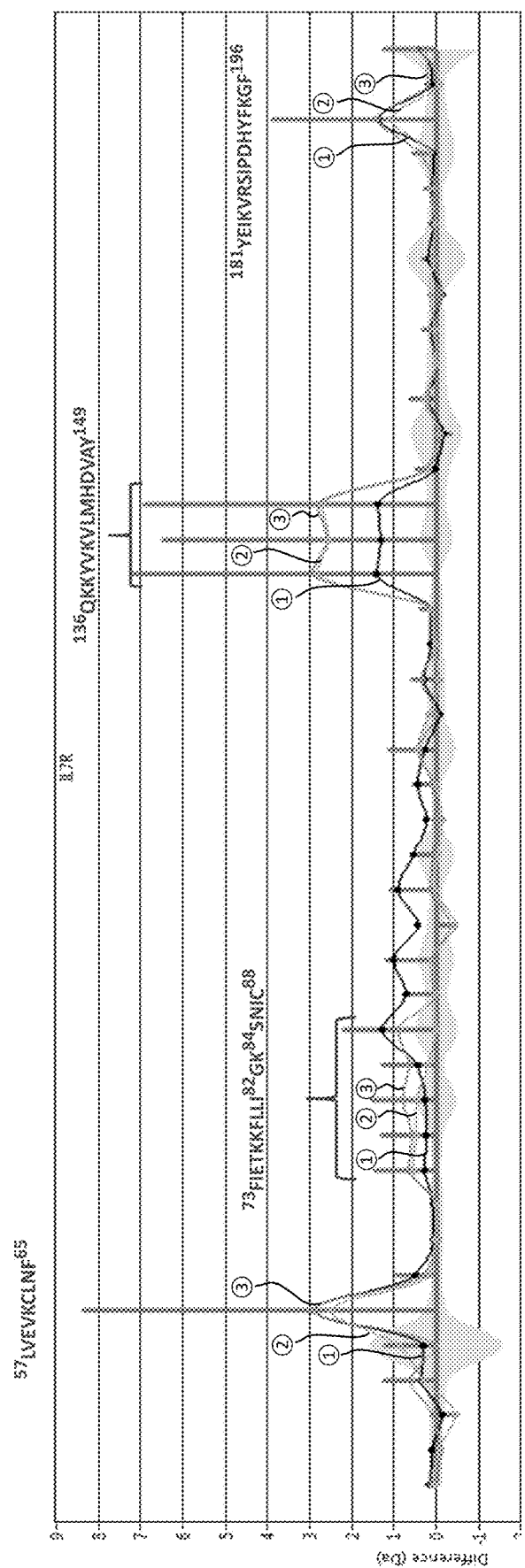
Figure 28B:
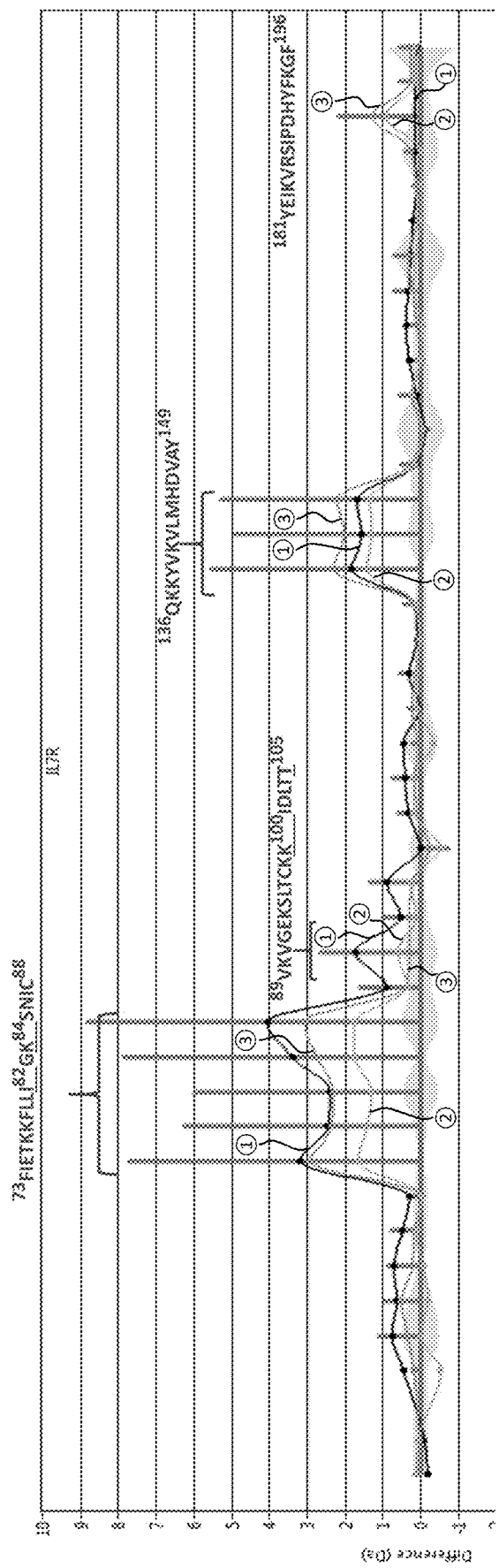
Figure 28C:
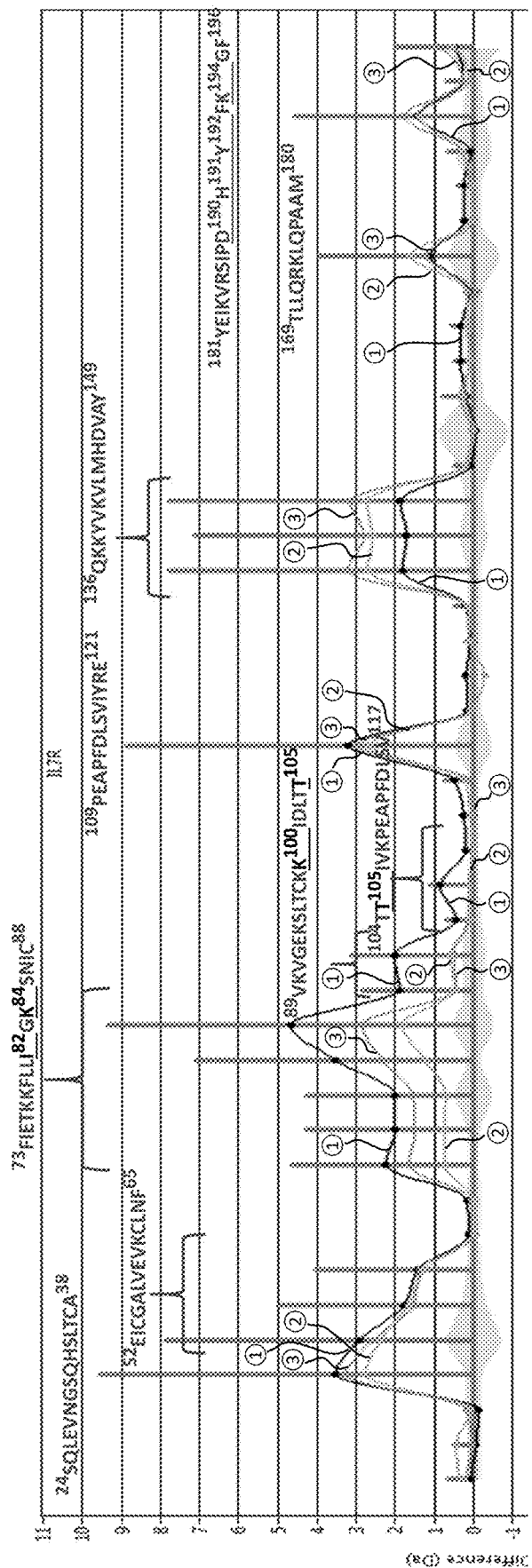

FIGS. 28A, 28B, and 28C show the deuterium uptake differences for the different epitopes of three reference anti-IL-7R antibodies (4A8, 13A10, and PFE A3312F, respectively) identified using the HDX-MS epitope mapping analysis. The epitopes shown in FIG. 28A for the 4A8 antibody include: (i) $^{57}$LVEVKCLNF$^{65}$, (ii) $^{73}$FIETKKFL-LIGKSNIC$^{88}$, (iii) $^{136}$QKKYVKVLMHDVAY$^{149}$, and (iv) $^{181}$YEIKVRSIPDHYFKGF$^{196}$. The epitopes shown in FIG. 28B for the 13A10 antibody include: (i) $^{73}$FIETKKFL-LIGKSNIC$^{88}$, (ii) $^{89}$VKVGEKSLTCKKIDLTT$^{105}$, (iii) $^{136}$QKKYVKVLMHDVAY$^{149}$, and (iv) $^{181}$YEIKVR-SIPDHYFKGF$^{196}$. The epitopes shown in FIG. 28C for PFE A3312F include: (i) $^{24}$SQLEVNGSQHSLTCA$^{38}$, (ii) $^{52}$EICGALVEVKCLNF$^{65}$, (iii) $^{73}$FIETKKFLLIGKSNIC$^{88}$, (iv) $^{89}$VKVGEKSLTCKKIDLTT$^{105}$, (v) $^{104}$TTIVK- PEAPFDLSV$^{117}$, (vi) $^{109}$PEAPFDLSVIYRE$^{121}$, (vii) $^{136}$QKKYVKVLMHDVAY$^{149}$, $^{169}$TLLORKLQPAAM$^{180}$, and (ix) $^{181}$YEIKVRSIPDHYFKGF$^{196}$. The black vertical bars indicate the summed differences in deuteration for each peptide. The lines represent differences in deuteration for each peptide at different time points, i.e., 1 minute ("(2)"), 10 minutes ("(3)"), and 240 minutes ("(1)").

Figure 29C:
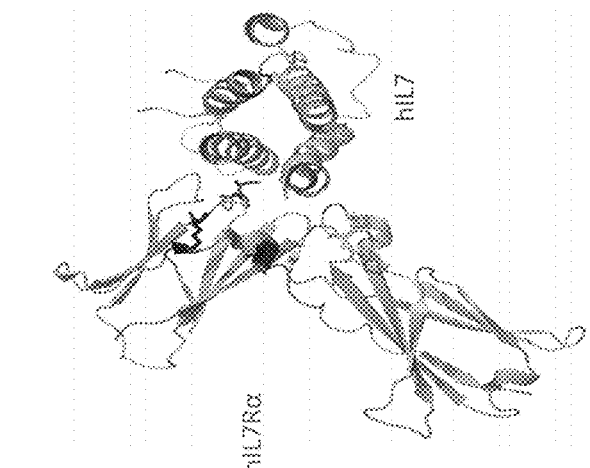
Figure 29B:
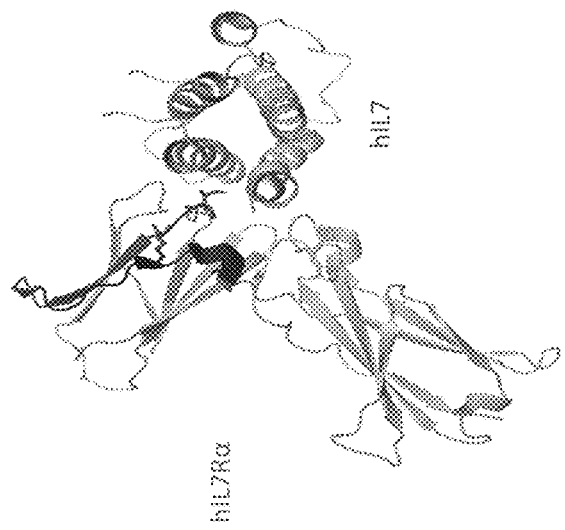
Figure 29A:
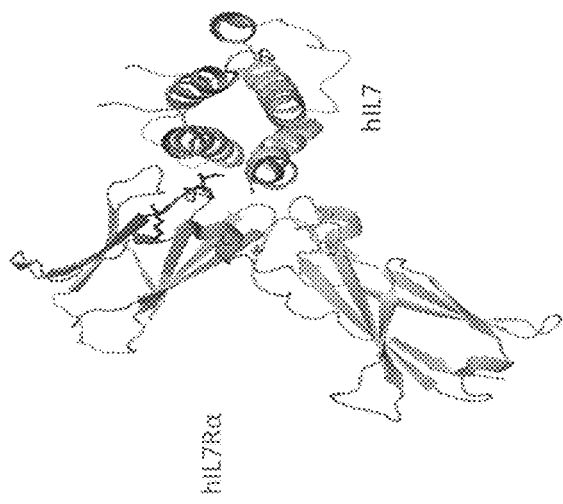

FIGS. 29A, 29B, and 29C show the epitopes of three reference anti-IL-7R antibodies (4A8, 13A10, and PFE A3312F, respectively) mapped onto the crystal structure of the human IL-7Rα protein.

DETAILED DESCRIPTION OF DISCLOSURE

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

As used herein, the terms "IL-7R" and "IL-7 receptor" refer to any form of IL-7R, including variants thereof, that retain at least part of the activity of an IL-7R. The IL-7R is a heterodimer consisting of an α subunit (IL-7Rα or CD127) and the cytokine receptor common γ chain (γc). The IL-7Rα subunit is expressed on various cell types, including naïve and memory T cells and developing B cells. As used herein, in some aspects, the term IL-7R refers to the α subunit and is used interchangeably with IL-7Rα.

Four isoforms of human IL-7Rα have been identified. Isoform 1 (Accession No. NP_002176.2; SEQ ID NO: 1) consists of 459 amino acids and represents the canonical sequence. Isoform 2 (Accession No. P16871-4; SEQ ID NO: 2) consists of 252 amino acids and is soluble. It lacks amino acid residues 253-459, which encode part of the transmembrane domain and the entire cytoplasmic domain. Amino acids 237-252 also differ from the canonical sequence (i.e., Isoform 1). Isoform 3 (Accession No. P16871-2, SEQ ID NO: 3) consists of 298 amino acids and has a truncated cytoplasmic domain. It differs from the canonical sequence at amino acid residues 293-459. Isoform 4 (Accession No. P16871-3; SEQ ID NO: 4) consist of 261 amino acids and is soluble. It differs from the canonical sequence at amino acid residues 237-459.

Below are the amino acid sequences of the four known human IL-7Rα isoforms.

(A) Human IL-7Rα Isoform 1 (Accession No. NP_002176.2; SEQ ID NO: 1, encoded by the nucleotide sequence having Accession No. NM_002185.4; SEQ ID NO: 5):
MTILGTTFGMVFSLLQVVSGESGYAQNGDLEDAELDDYSFSCYSQLEVNG

SQHSLTCAFEDPDVNTTNLEFEICGALVEVKCLNFRKLQEIYFIETKKFL

LIGKSNICVKVGEKSLICKKIDLTTIVKPEAPFDLSVIYREGANDFVVTF

NTSHLQKKYVKVLMHDVAYRQEKDENKWTHVNLSSTKLTLLQRKLQPAAM

YEIKVRSIPDHYFKGFWSEWSPSYYFRIPEINNSSGEMDPILLTISILSF

FSVALLVILACVLWKKRIKPIVWPSLPDHKKTLEHLCKKPRKVSVFGA (B) Human IL-7Ra Isoform 2 (Accession No. P16871-4; SEQ ID NO: 2):
MTILGTTFGMVFSLLQVVSGESGYAQNGDLEDAELDDYSFSCYSQLEVNG

SQHSLTCAFEDPDVNTTNLEFEICGALVEVKCLNFRKLQEIYFIETKKFL

LIGKSNICVKVGEKSLICKKIDLTTIVKPEAPFDLSVIYREGANDFVVTF

NTSHLQKKYVKVLMHDVAYRQEKDENKWTHVNLSSTKLTLLQRKLQPAAM

YEIKVRSIPDHYFKGFWSEWSPSYYFRIPEINNSSGLSLSYGPVSPIIRQ

EL (C) Human IL-7Ra Isoform 3 (Accession No. P16871-2; SEQ ID NO: 3):
MTILGTTFGMVFSLLQVVSGESGYAQNGDLEDAELDDYSFSCYSQLEVNG

SQHSLTCAFEDPDVNTTNLEFEICGALVEVKCLNFRKLQEIYFIETKKFL

LIGKSNICVKVGEKSLICKKIDLTTIVKPEAPFDLSVIYREGANDFVVTF

NTSHLQKKYVKVLMHDVAYRQEKDENKWTHVNLSSTKLTLLQRKLQPAAM

YEIKVRSIPDHYFKGFWSEWSPSYYFRIPEINNSSGEMDPILLTISILSF

FSVALLVILACVLWKKRIKPIVWPSLPDHKKTLEHLCKKPRKVSVFGA (D) Human IL-7Ra Isoform 4 (Accession No. P16871-3; SEQ ID NO: 4):
MTILGTTFGMVFSLLQVVSGESGYAQNGDLEDAELDDYSFSCYSQLEVNG

```
                                                     -continued
SQHSLTCAFEDPDVNTTNLEFEICGALVEVKCLNFRKLQEIYFIETKKFL

LIGKSNICVKVGEKSLICKKIDLTTIVKPEAPFDLSVIYREGANDFVVTF

NTSHLQKKYVKVLMHDVAYRQEKDENKWTHVNLSSTKLTLLQRKLQPAAM

YEIKVRSIPDHYFKGFWSEWSPSYYFRIPEINNSSGLSLSYGPVSPIIRR

LTNNIFVRNQEK.
```

The signal sequence of Isoforms 1-4 corresponds to amino acid residues 1-20 (underlined). Thus, the mature form, e.g., of the canonical sequence (Isoform 1) consists of amino acids 21-459. The extracellular domain of mature human IL-7Rα (e.g., Isoform 1) consists of amino acid residues 21-239 and has the following amino acid sequence:

```
                                               (SEQ ID NO: 6)
ESGYAQNGDLEDAELDDYSFSCYSQLEVNGSQHSLTCAFEDPDVNTTNLE

FEICGALVEVKCLNFRKLQEIYFIETKKFLLIGKSNICVKVGEKSLTCKK

IDLTTIVKPEAPFDLSVIYREGANDFVVTFNTSHLQKKYVKVLMHDVAYR

QEKDENKWTHVNLSSTKLTLLQRKLQPAAMYEIKVRSIPDHYFKGFWSEW

SPSYYFRTPEINNSSGEMD.
```

Cynomolgus IL-7Rα protein consists of the following amino acid sequence (including a signal sequence, which is underlined):

```
                                               (SEQ ID NO: 7)
MTILGTTFGMVFSLLQVVSGESGYAQNGDLEDAELDDYSFSCYSQLEVNG

SQHSLTCAFEDPDVNTTNLEFEICGALVEVKCLSFRKLQEIYFIETKKFL

LIGKSNICVKVGGKSLTCKKIDLTTIVKPEAPFDLSVIYREGANDFVVTF

NTSHLQKKYVKVLMHDVAYRQEKDENKWMHVNLSSTKLTLLQRNLQPEAM

YEIKVRSIPDHYFKGFWSEWSPSYYFRTPEINNSPGEMDPILLTISLLSF

FSVALLVILACVLWKKRIKPIVWPSLPDHKKTLEHLCKKPRKNLNVSFNP

ESFLDCQIHRVDDIQARDEVEGFLQDTFPQQLEESKKQRLGGDVQSPSCP

SEDVVITPESFERDSSLRCLAGNVSACDAPILSSSRSLDCRESGKNGPHV

YQDLLLSLGTTNSTLPPPFSLQSGILTLNPVAQGQPILTSLGSNQEEAYV

TMSSFYQNQ.
```

As used herein, "TSLP" refers to a growth factor that closely resembles IL-7 and plays a role in the maturation and activation of myeloid cells (e.g., monocytes and dendritic cells). TSLP is produced by various cell types, such as fibroblasts, epithelial cells, and stromal cells. Elevated levels of TSLP have been associated with diseases, such as asthma, atopic dermatitis, and inflammatory arthritis, which are also known to be associated with abnormal regulation of IL-7. Nguyen V., et al., *J Immunol Res* 2017: 4807853 (2017).

As used herein, the term "antibody" refers to a protein comprising at least two heavy (H) chains and two light (L) chains inter-connected by disulfide bonds. Each heavy chain is comprised of a heavy chain variable region (abbreviated herein as VH) and a heavy chain constant region (abbreviated herein as CH). In certain antibodies, e.g., naturally occurring IgG antibodies, the heavy chain constant region is comprised of a hinge and three domains, CH1, CH2 and CH3. In certain antibodies, e.g., naturally occurring IgG antibodies, each light chain is comprised of a light chain variable region (abbreviated herein as VL) and a light chain constant region. The light chain constant region is comprised of one domain (abbreviated herein as CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. A heavy chain may have the C-terminal lysine or not. Unless specified otherwise herein, the amino acids in the variable regions are numbered using the Kabat numbering system and those in the constant regions are numbered using the EU system. "Antibody" includes, by way of example, both naturally occurring and non-naturally occurring antibodies; monoclonal and polyclonal antibodies; chimeric and humanized antibodies; human and nonhuman antibodies and wholly synthetic antibodies.

An "IgG antibody", e.g., a human IgG1, IgG2, IgG3 and IgG4 antibody, as used herein, has, in certain embodiments, the structure of a naturally occurring IgG antibody, i.e., it has the same number of heavy and light chains and disulfide bonds as a naturally occurring IgG antibody of the same subclass. For example, an anti-IL-7R IgG1, IgG2, IgG3 or IgG4 antibody consists of two heavy chains (HCs) and two light chains (LCs), wherein the two heavy chains and light chains are linked by the same number and location of disulfide bridges that occur in naturally occurring IgG1, IgG2, IgG3 and IgG4 antibodies, respectively (unless the antibody has been mutated to modify the disulfide bridges).

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, $10^{-8}$ M or less, $5 \times 10^{-9}$ M or less, or between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, at least 95%, at least 97%, or at least 99% sequence identity to the sequence of the given antigen. By way of example, an antibody that binds specifically to human IL-7Rα can, in certain embodiments, also have cross-reactivity with IL-7Rα antigens from certain primate species (e.g., cynomolgus IL-7Rα), but cannot cross-react with IL-7Rα antigens from other species or with an antigen other than IL-7Rα.

As used herein, "isotype" refers to the antibody class (e.g., IgG1, IgG2, IgG3, IgG4, IgM, IgA1, IgA2, IgD, and IgE antibody) that is encoded by the heavy chain constant region genes. The IgG isotype is divided in subclasses in certain species: IgG1, IgG2, IgG3 and IgG4 in humans, and IgG1, IgG2a, IgG2b and IgG3 in mice. In some embodiments, the anti-IL-7R antibodies described herein are of the IgG1 isotype. Immunoglobulins, e.g., IgG1, exist in several allotypes, which differ from each other in at most a few amino acids.

As used herein, the term "allotype" refers to naturally occurring variants within a specific isotype group, wherein the variants differ in a few amino acids (see, e.g., Jefferis et al. (2009) mAbs 1:1). Anti-IL-7R antibodies described herein can be of any allotype. As used herein, antibodies referred to as "IgG1f," "IgG1.1f," or "IgG1.3f" isotype are IgG1, effectorless IgG1.1, and effectorless IgG1.3 antibodies, respectively, of the allotype "f," i.e., having 214R, 356E and 358M according to the EU index as in Kabat, as shown, e.g., in SEQ ID NO: 21.

The term "antigen-binding portion" of an antibody, as used herein, refers to one or more fragments of an antibody that retain the ability to specifically bind to an antigen (e.g., human IL-7Rα). It has been shown that the antigen-binding function of an antibody can be performed by fragments of a full-length antibody. Examples of binding fragments encompassed within the term "antigen-binding portion" of an antibody, e.g., an anti-IL-7R antibody described herein, include (i) a Fab fragment (fragment from papain cleavage) or a similar monovalent fragment consisting of the $V_L$, $V_H$, LC and CH1 domains; (ii) a F(ab')2 fragment (fragment from pepsin cleavage) or a similar bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR) and (vii) a combination of two or more isolated CDRs which can optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

The term "monoclonal antibody," as used herein, refers to an antibody from a population of substantially homogeneous antibodies, i.e., the individual antibodies comprised in the population are substantially similar and bind the same epitope(s) (e.g., the antibodies display a single binding specificity and affinity), except for possible variants that may arise during production of the monoclonal antibody, such variants generally being present in minor amounts. The modifier "monoclonal" indicates the character of the antibody as being obtained from a substantially homogeneous population of antibodies, and is not to be construed as requiring production of the antibody by any particular method. The term "human monoclonal antibody" refers to an antibody from a population of substantially homogeneous antibodies that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The anti-IL-7R antibodies described herein can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other proteins and cellular material.

As used herein, an antibody that "inhibits binding of IL-7 to IL-7Rα" is intended to refer to an antibody that inhibits the binding of IL-7Rα to its ligand, e.g., interleukin-7 (IL-7), e.g., in binding assays using T cells from whole blood that express IL-7Rα, with an $EC_{50}$ of about 1 µg/mL or less, such as about 0.9 µg/mL or less, about 0.85 µg/mL or less, about 0.8 µg/mL or less, about 0.75 µg/mL or less, about 0.7 µg/mL or less, about 0.65 µg/mL or less, about 0.6 µg/mL or less, about 0.55 µg/mL or less, about 0.5 µg/mL or less, about 0.45 µg/mL or less, about 0.4 µg/mL or less, about 0.35 µg/mL or less, about 0.3 µg/mL or less, about 0.25 µg/mL or less, about 0.2 µg/mL or less, about 0.15 µg/mL or less, about 0.1 µg/mL or less, or about 0.05 µg/mL or less, in art-recognized methods, e.g., the FACS-based binding assays described herein.

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Various properties of human FcγRs are known in the art. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans. Human IgG1 binds to most human Fc receptors and is considered equivalent to murine IgG2a with respect to the types of activating Fc receptors that it binds to.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. For IgG, the Fc region comprises immunoglobulin domains CH2 and CH3 and the hinge between CH1 and CH2 domains. Although the definition of the boundaries of the Fc region of an immunoglobulin heavy chain might vary, as defined herein, the human IgG heavy chain Fc region is defined to stretch from an amino acid residue D221 for IgG1, V222 for IgG2, L221 for IgG3 and P224 for IgG4 to the carboxy-terminus of the heavy chain, wherein the numbering is according to the EU index as in Kabat. The CH2 domain of a human IgG Fc region extends from amino acid 237 to amino acid 340, and the CH3 domain is positioned on C-terminal side of a CH2 domain in an Fc region, i.e., it extends from amino acid 341 to amino acid 447 or 446 (if the C-terminal lysine residue is absent) or 445 (if the C-terminal glycine and lysine residues are absent) of an IgG. As used herein, the Fc region can be a native sequence Fc, including any allotypic variant, or a variant Fc (e.g., a non-naturally occurring Fc). Fc can also refer to this region in isolation or in the context of an Fc-comprising protein polypeptide such as a "binding protein comprising an Fc region," also referred to as an "Fc fusion protein" (e.g., an antibody or immunoadhesion).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc include the various allotypes of Fcs (see, e.g., Jefferis et al. (2009) *mAbs* 1:1).

The term "epitope" or "antigenic determinant" refers to a site on an antigen (e.g., IL-7Rα) to which an immunoglobulin or antibody specifically binds, e.g., as defined by the specific method used to identify it. Epitopes can be formed both from contiguous amino acids (usually a linear epitope) or noncontiguous amino acids juxtaposed by tertiary folding of a protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from IL-7Rα) are tested for reactivity with a given antibody (e.g., anti-IL-7R antibody). Methods of determining spatial conformation of epitopes include techniques in the art and those described herein, for example, x-ray crystallography, antigen mutational analysis, 2-dimensional nuclear magnetic resonance and HDX-MS (see, e.g., Epitope Mapping Protocols in Methods in Molecular Biology, Vol. 66, G. E. Morris, Ed. (1996)).

The term "epitope mapping" refers to the process of identification of the molecular determinants for antibody-antigen recognition.

The term "binds to the same epitope" with reference to two or more antibodies means that the antibodies bind to the same segment of amino acid residues, as determined by a given method. Techniques for determining whether antibodies bind to the "same epitope on IL-7Rα" with the antibodies described herein include, for example, epitope mapping methods, such as, x-ray analyses of crystals of antigen: antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments, e.g., BIACORE™ surface plasmon resonance (SPR) analysis. In certain embodiments, an antibody competes with, and inhibits binding of another antibody to a target by at least 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, N.Y., USA 1999. Two antibodies "cross-compete" if antibodies block each other both ways by at least 50%, i.e., regardless of whether one or the other antibody is contacted first with the antigen in the competition experiment.

Competitive binding assays for determining whether two antibodies compete or cross-compete for binding include: competition for binding to T cells expressing IL-7Rα, e.g., by flow cytometry, such as described in the Examples. Other methods include: SPR (e.g., BIACORE™), solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE™ 2000 instrument using the predetermined antigen, e.g., recombinant human IL-7Rα, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human IL-7Rα" refers to an antibody that binds to soluble or cell bound human IL-7Rα with a $K_D$ of $10^{-7}$ M or less, such as approximately less than $10^{-8}$ M, $10^{-9}$ M or $10^{-10}$ M or even lower. An antibody that "cross-reacts with cynomolgus IL-7Rα" refers to an antibody that binds to cynomolgus IL-7Rα with a $K_D$ of $10^{-7}$ M or less, such as approximately less than $10^{-8}$ M, $10^{-9}$ M or $10^{-10}$ M or even lower. In certain embodiments, such antibodies that do not cross-react with IL-7Rα from a non-human species exhibit essentially undetectable binding against these proteins in standard binding assays.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. Available methods for determining the $K_D$ of an antibody include surface plasmon resonance, a biosensor system such as a BIACORE® system or flow cytometry and Scatchard analysis.

As used herein, the term "high affinity" for an IgG antibody refers to an antibody having a $K_D$ of $10^{-8}$ M or less, $10^{-9}$ M or less, or $10^{-10}$ M or less for a target antigen. However, "high affinity" binding can vary for other antibody isotypes. For example, "high affinity" binding for an IgM isotype refers to an antibody having a $K_D$ of $10^{-10}$ M or less, or $10^{-8}$ M or less.

The term "$EC_{50}$" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

"Conservative amino acid substitutions" refer to substitutions of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, a predicted nonessential amino acid residue in an anti-IL-7R antibody is replaced with another amino acid residue from the same side chain family. Methods of identifying nucleotide and amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)).

For nucleic acids, the term "substantial homology" indicates that two nucleic acids, or designated sequences thereof, when optimally aligned and compared, are identical, with appropriate nucleotide insertions or deletions, in at least about 80% of the nucleotides, at least about 90% to 95%, or at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, at least about 90% to 95%, or at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, e.g., as described in the non-limiting examples below.

The percent identity between two nucleotide sequences can be determined using the GAP program in the GCG software package (available at worldwideweb.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS,* 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See worldwideweb.ncbi.nlm.nih.gov.

The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, can be mutated, in accordance with standard techniques to provide gene sequences. For coding sequences, these mutations, can affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

As used herein, the term "immune response" is as understood in the art, and generally refers to a biological response within a vertebrate against foreign agents or abnormal, e.g., cancerous, cells, which response protects the organism against these agents and diseases caused by them. An immune response is mediated by the action of one or more cells of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a $CD4^+$ cell, a $CD8^+$ T cell, or a Treg cell, or activation or inhibition of any other cell of the immune system, e.g., NK cell.

As used herein, the term "aberrant immune response" refers to the failure of a subject's immune system to distinguish self from non-self or the failure to respond to foreign antigens. The term also embraces hyperimmune responses to foreign antigens as in the case of allergic disorders. Thus, the response is present in both autoimmune disorders and allergic disorders. Aberrant immune responses include, but are not limited to, tissue injury and inflammation caused by the production of antibodies to an organism's own tissue, impaired production of cytokines and tissue damage caused by cytotoxic or non-cytotoxic mechanisms of action. In some embodiments, aberrant immune responses are inappropriately regulated immune responses that lead to patient symptoms. Typically, autoimmune responses occur when the immune system of a subject recognizes self-antigens as foreign, leading to the production of self-reactive effector immune cells. Self-reactive effector immune cells include cells from a variety of lineages, including, but not limited to, cytotoxic T cells, helper T cells, and B cells. While the precise mechanisms differ, the presence of autoreactive effector immune cells in a patient suffering from an autoimmune disorder may lead to the destruction of tissues and cells of the patient, resulting in pathologic symptoms. Similarly, the presence of cells that undergo a hypersensitive reaction to foreign antigens to which normal individuals respond in a more restrain manner is indicative of hypersensitivity (allergy). Examples include, but are not limited to, food allergies, hay fever, and allergic asthma. Numerous assays for determining the presence of such cells in a patient, and therefore the presence of an autoimmune disorder, such as an antigen-specific autoimmune disorder in a patient, or an allergic disorder, are known to those of skill in the art and can be readily employed in the subject methods.

As used herein, the term "autoimmune disease" refers to a disease or disorder in which the immune system produces an immune response (e.g., a B cell or a T cell response) against an antigen that is part of the normal host (i.e., an autoantigen), with consequent injury to tissues. An autoantigen may be derived from a host cell, or may be derived from a commensal organism such as the micro-organisms (known as commensal organisms) that normally colonize mucosal surfaces.

Exemplary autoimmune diseases affecting mammals include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (e.g., Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture syndrome, Addison's disease, systemic sclerosis, polymyositis, dermatomyositis, autoimmune hemolytic anemia, pernicious anemia, and the like.

As used herein, the term "inflammatory bowel disease" (IBD) refers to a heterogeneous group of chronic inflammatory disorders of the gastrointestinal tract. In some embodiments, the IBD includes Crohn's disease (CD) and ulcerative colitis (UC).

As used herein, the term "immunosuppressive agent" refers to a molecule, such as a chemical compound, small molecule, steroid, nucleic acid molecule, or other biological agent, that can decrease an immune response such as an inflammatory reaction. Immunosuppressive agents include, but are not limited to an agent of use in treating arthritis (anti-arthritis agent). Specific, non-limiting examples of immunosuppressive agents are non-steroidal anti-inflammatory agents, cyclosporine A, FK506, and anti-CD4. In additional examples, the agent is a biological response modifier, such as KINERET® (anakinra), ENBREL® (etanercept), or REMICADE® (infliximab), a disease-modifying antirheumatic drug (DMARD), such as ARAVA® (leflunomide), a nonsteroidal anti-inflammatory drug (NSAIDs), specifically a Cyclo-Oxygenase-2 (COX-2) inhibitor, such as CELEBREX® (celecoxib) and VIOXX® (rofecoxib), or another product, such as HYALGAN® (hyaluronan) and SYNVISC® (hylan G-F20). Rapamycin is an additional example of an immunosuppressive agent.

The term "inflammation" or an "inflammatory process," as used herein, refers to a complex series of events, including dilatation of arterioles, capillaries and venules, with increased permeability and blood flow, exudation of fluids, including plasma proteins and leukocyte migration into the inflammatory focus. Inflammation may be measured by many methods well known in the art, such as the number of leukocytes, the number of polymorphonuclear neutrophils (PMN), a measure of the degree of PMN activation, such as luminal enhanced-chemiluminescence, or a measure of the amount of proinflammatory cytokines (e.g., IL-6 or TNF-α) present.

An "immunomodulator" or "immunoregulator" refers to an agent, e.g., an agent targeting a component of a signaling pathway that can be involved in modulating, regulating, or modifying an immune response. "Modulating," "regulating," or "modifying" an immune response refers to any alteration in a cell of the immune system or in the activity of such cell (e.g., an effector T cell, such as a Th1 cell). Such modulation includes stimulation or suppression of the immune system which can be manifested by an increase or decrease in the number of various cell types, an increase or decrease in the activity of these cells, or any other changes which can occur within the immune system. Both inhibitory and stimulatory immunomodulators have been identified, some of which can have enhanced function in a tumor microenvironment. In some embodiments, the immunomodulator targets a molecule on the surface of a T cell. An "immunomodulatory target" or "immunoregulatory target"

is a molecule, e.g., a cell surface molecule, that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject afflicted with, or at risk of contracting or suffering a recurrence of, a disease by a method comprising inducing, enhancing, suppressing or otherwise modifying the immune system or an immune response.

As used herein, the term "pathogenic T cells" refer to T cells (e.g., CD4$^+$ or CD8$^+$ T cells) that cause the underlying symptoms and/or damage associated with a disease or disorder, e.g., an inflammatory disease, e.g., an inflammatory bowel disease. In some embodiments, the term is interchangeable with "effector T cells" ($T_{eff}$), which refers to T cells (e.g., CD4$^+$ and CD8$^+$ T cells) with cytolytic activities as well as T helper (Th) cells, e.g., Th1 cells, which can secrete inflammatory cytokines (e.g., TNF-α, IFN-γ, or IL-17) and also activate and direct other immune cells (e.g., monocytes) to produce proinflammatory mediators, and thereby, cause the underlying symptoms and/or damage associated with the disease or disorder. In some embodiments, the effector T cells are Th17 cells, which refer to CD4$^+$ T cells that produce the proinflammatory cytokine IL-17. In some embodiments, the effector T cells are cytotoxic T lymphocytes (CTLs), which refer to CD8$^+$ T cells that have the ability to kill other cells (e.g., through the release of perforin or granzyme B).

As used herein, the term "regulatory T cells" (Tregs) refer to a population of T cells with the ability to reduce or suppress the induction and proliferation of effector T cells, and thereby, modulate an immune response. In some embodiments, Tregs can suppress an immune response by secreting anti-inflammatory cytokines, such as IL-10, TGF-β, and IL-35, which can interfere with the activation and differentiation of naïve T cells into effector T cells. In some embodiments, Tregs can also produce cytolytic molecules, such as Granzyme B, which can induce the apoptosis of effector T cells. In some embodiments, the regulatory T cells are natural regulatory T cells (nTregs) (i.e., developed within the thymus). In some embodiments, the regulatory T cells are induced regulatory T cells (iTregs) (i.e., naïve T cells that differentiate into Tregs in the peripheral tissue upon exposure to certain stimuli). Methods for identifying Tregs are known in the art. For example, Tregs express certain phenotypic markers (e.g., CD25, Foxp3, or CD39) that can be measured using flow cytometry. See, e.g., International Publication No. WO 2017/062035 A1; Gu J., et al., *Cell Mol Immunol* 14(6): 521-528 (2017). In some embodiments, the Tregs are CD45RA$^-$CD39$^+$ T cells.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent to a subject, using any of the various methods and delivery systems known to those skilled in the art. Different routes of administration for the anti-IL-7R antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the terms "inhibits" or "blocks" (e.g., referring to inhibition/blocking of binding of IL-7 to IL-7Rα on cells) are used interchangeably and encompass both partial and complete inhibition/blocking. In some embodiments, the anti-IL-7R antibody inhibits binding of IL-7 to IL-7Rα by at least about 50%, for example, about 60%, 70%, 80%, 90%, 95%, 99%, or 100%, determined, e.g., as further described herein. In some embodiments, the anti-IL-7R antibody inhibits binding of IL-7 to IL-7Rα by no more than 50%, for example, by about 40%, 30%, 20%, 10%, 5% or 1%, determined, e.g., as further described herein.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease or enhancing overall survival. Treatment can be of a subject having a disease or a subject who does not have a disease (e.g., for prophylaxis).

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

The term "weight based" dose or dosing as referred to herein means that a dose that is administered to a patient is calculated based on the weight of the patient. For example, when a patient with 60 kg body weight requires 3 mg/kg of an anti-IL-7R antibody, one can calculate and use the appropriate amount of the anti-IL-7R antibody (i.e., 180 mg) for administration.

The use of the term "fixed dose" with regard to a method of the disclosure means that two or more different antibodies in a single composition (e.g., anti-IL-7R antibody and a second antibody, e.g., an anti-TNFR antibody) are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio of the two antibodies (e.g., anti-IL-7R and anti-TNFR) is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody (e.g., anti-IL-7R antibody) to mg second antibody. For example, a 2:1 ratio of an anti-IL-7R antibody and an anti-TNF receptor antibody, such as atrosab, can mean that a vial or an injection can contain about 480 mg of the anti-IL-7R antibody and 240 mg of the anti-TNFR antibody, or about 2 mg/ml of the anti-IL-7R antibody and 1 mg/ml of the anti-TNFR antibody.

The use of the term "flat dose" with regard to the methods and dosages described herein means a dose that is administered to a patient without regard for the weight or body surface area (BSA) of the patient. The flat dose is therefore not provided as a mg/kg dose, but rather as an absolute amount of the agent (e.g., the anti-IL-7R antibody). For example, a 60 kg person and a 100 kg person would receive the same dose of an antibody (e.g., 480 mg of an anti-IL-7R antibody).

As used herein, the terms "ug" and "uM" are used interchangeably with "µg" and "µM," respectively.

Various aspects described herein are described in further detail in the following subsections.

I. Anti-Human IL-7R Antibodies

Described herein are antibodies, e.g., fully human antibodies, which are characterized by particular functional features or properties. For example, the antibodies specifically bind human IL-7Rα, and more specifically, a particular domain (e.g., a functional domain) within the extracellular domain of human IL-7Rα. In some embodiments, the antibodies specifically bind to the site on IL-7Rα to which IL-7 binds. In certain embodiments, the antibodies are antagonist antibodies, i.e., they inhibit or suppress IL-7-mediated expansion and/or survival of pathogenic T cells (e.g., effector CD8+ T cells). In certain embodiments, anti-IL-7R antibodies disclosed herein cross-react with IL-7Rα from one or more non-human primates, such as cynomolgus IL-7Rα. In some embodiments, the antibodies specifically bind to the extracellular region of human IL-7Rα and the extracellular region of cynomolgus IL-7Rα. In certain embodiments, the antibodies bind to human IL-7Rα with high affinity.

Anti-IL-7R antibodies described herein exhibit one or more of the following functional properties:

(a) capable of binding to soluble and/or membrane bound human IL-7Rα;
(b) capable of binding to soluble and/or membrane bound cyno IL-7Rα;
(c) capable of binding to IL-7Rα expressed on T cells (CD4⁻CD45RA⁺, CD4⁺CD45RA⁻, CD8⁺CD45RA⁻, and/or CD8⁺CD45RA⁻) in whole blood, e.g., human whole blood;
(d) not capable of binding to IL-7Rα expressed on non-T cells (e.g., monocytes) in whole blood, e.g., human whole blood;
(e) not capable of effectively blocking thymic stromal lymphopoietin (TSLP)-mediated activation of monocytes;
(f) not capable of agonizing IL-7 receptor signaling upon binding to IL-7Rα, e.g., minimal pSTAT5 activation;
(g) capable of restoring a T regulatory cells (Treg) function and/or promoting a Treg survival;
(h) capable of blocking an expansion of IL-17 and/or IFN-gamma producing cells;
(i) capable of maintaining a drug free remission longer than that by, e.g., CTLA4-Ig (ORENCIA®);
(j) capable of blocking inflammation and mucosal damage (e.g., induced by pathogenic T cells), in an intestinal tissue;
(k) capable of decreasing a frequency of T effector cells, e.g., in the mesenteric lymph nodes (MLN) and/or lamina propria (LP);
(l) capable of treating a subject with an inflammatory disease, e.g., inflammatory bowel disease;
(m) capable of binding to human IL-7Rα at an epitope selected from the group consisting of: $^{24}$SQLEVNGSQHSLTCAF$^{39}$ (SEQ ID NO: 8), $^{73}$FIETKKFLLIGKSNIC$^{88}$ (SEQ ID NO: 9), $^{89}$VKVGEKSLTCKKIDLTT$^{105}$ (SEQ ID NO: 10), $^{136}$QKKYVKVLMHDVAY$^{149}$ (SEQ ID NO: 11), $^{181}$YEIKVRSIPDHYFKGF$^{196}$ (SEQ ID NO: 12), and combinations thereof, e.g., as determined by hydrogen/deuterium exchange mass spectrometry (HDX-MS); and/or
(n) capable of binding to human IL-7Rα at one or more amino acid residues selected from the group consisting of H33, E75, F79, I82, K84, M144, R186, H191, Y192, and combinations thereof, e.g., as determined by mass spectrometry-based protein footprinting approaches, such as photochemical oxidation of protein (FPOP) and glycine ethyl ester (GEE) labeling.

In some embodiments, anti-IL-7R antibodies described herein bind to human IL-7Rα with high affinity, for example, with a $K_D$ of $10^{-7}$ M or less, $10^{-8}$ M or less, $10^{-9}$ M or less, $10^{-10}$ M or less, $10^{-11}$ M or less, $10^{-12}$ M or less, $10^{-12}$ M to $10^{-7}$ M, $10^{-11}$ M to $10^{-7}$ M, $10^{-10}$ M to $10^{-7}$ M, or $10^{-9}$ M to $10^{-7}$ M. In certain embodiments, an anti-IL-7R antibody binds to soluble human IL-7Rα, e.g., as determined by BIACORE™, with a $K_D$ of $10^{-7}$ M or less, $10^{-8}$ M or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. In certain embodiments, an anti-IL-7R antibody binds to bound (e.g., cell membrane bound) human IL-7Rα, such as on human T cells but not on human non-T cells, e.g., as determined by flow cytometry and Scatchard plot, with a $K_D$ of $10^{-7}$ M or less, $10^{-8}$ M or less, $10^{-9}$ M (1 nM) or less, $5 \times 10^{-10}$ M or less, $10^{-10}$ M or less, $10^{-12}$ M to $10^{-7}$ M, $10^{-11}$ M to $10^{-8}$ M, $10^{-10}$ M to $10^{-8}$ M, $10^{-9}$ M to $10^{-8}$ M, $10^{-11}$ M to $10^{-9}$ M, or $10^{-10}$ M to $10^{-9}$ M. In some embodiments, an anti-IL-7R antibody disclosed herein binds to bound (e.g., cell membrane bound) human IL-7Rα, such as on human T cells but not on human non-T cells, e.g., as determined by flow cytometry, with an $EC_{50}$ of 10 ug/mL or less, 5 ug/mL or less, 1 ug/mL or less, 0.9 ug/mL or less, 0.8 ug/mL or less, 0.7 ug/mL or less, 0.6 ug/mL or less, 0.5 ug/mL or less, 0.4 ug/mL or less, 0.3 ug/mL or less, 0.2 ug/mL or less, 0.1 ug/mL or less, 0.05 ug/mL or less, or 0.01 ug/mL or less. In some embodiments, anti-IL-7R antibodies described herein bind to cyno IL-7Rα, for example, with a $K_D$ of $10^{-7}$ M or less, $10^{-8}$ M or less, $10^{-9}$ M or less, $10^{-10}$ M or less, $10^{-11}$ M or less, $10^{-12}$ M or less, $10^{-12}$ M to $10^{-7}$ M, $10^{-11}$ M to $10^{-7}$ M, $10^{-10}$ M to $10^{-7}$ M, or $10^{-9}$ M to $10^{-7}$ M. In certain embodiments, an anti-IL-7R antibody binds to soluble cyno IL-7Rα, e.g., as determined by BIACORE™, with a $K_D$ of $10^{-7}$ M or less, $10^{-8}$ M or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. Anti-IL-7R antibodies of the present disclosure can bind to bound (e.g., membrane bound) cynomolgus IL-7Rα, such as on cyno T cells but not on cyno non-T cells, e.g., with an $EC_{50}$ of 100 nM or less, 10 nM or less, 100 nM to 0.01 nM, 100 nM to 0.1 nM, 100 nM to 1 nM, or 10 nM to 1 nM, e.g., as measured by flow cytometry. In certain embodiments, an anti-IL-7R antibody binds to bound (e.g., cell membrane bound) cyno IL-7Rα, such as on cyno T cells but not on cyno non-T cells, e.g., as determined by flow cytometry and Scatchard plot, with a $K_D$ of $10^{-7}$ M or less, $10^{-8}$ M or less, $10^{-9}$ M (1 nM) or less, $5 \times 10^{-10}$ M or less, $10^{-10}$ M or less, $10^{-12}$ M to $10^{-7}$ M, $10^{-11}$ M to $10^{-8}$ M, $10^{-10}$ M to $10^{-8}$ M, $10^{-9}$ M to $10^{-8}$ M, $10^{-11}$ M to $10^{-9}$ M, or $10^{-10}$ M to $10^{-9}$ M.

Standard assays to evaluate the binding ability of the antibodies toward IL-7Rα of various species are known in the art, including for example, ELISAs, Western blots, and RIAs. Suitable assays are also described in the Examples. The binding kinetics (e.g., binding affinity) of the antibodies can also be assessed by standard assays known in the art, such as by Biacore analysis. Assays to evaluate the effects of the antibodies on functional properties of immune cells (e.g., ligand binding, STAT5 phosphorylation/activation, cytokine production) are described in further detail infra and in the Examples.

In some embodiments, the anti-IL-7R antibodies disclosed herein are selective for IL-7Rα expressed on T cells (e.g., CD4+CD45RA+, CD4+CD45RA−, CD8−CD45RA+, CD8+CD45RA−) but not on non-T cells (e.g., monocytes). Accordingly, in some embodiments, the anti-IL-7R antibodies can effectively block the binding of IL-7 to IL-7Rα on T cells but cannot block the binding of TSLP to IL-7Rα expressed on non-T cells (e.g., monocytes). In some embodiments, the anti-IL-7R antibodies can inhibit or reduce IL-7-mediated phosphorylation of STAT5 ("pSTAT5 activation") in T cells. In some embodiments, pSTAT5 activation is inhibited or reduced by at least 5%, 10%, 20%, 30%, 40%, 50%, 60%, 70%, 80%, 90%, or 100% compared to a reference (e.g., corresponding T cells that are not treated with the anti-IL-7R antibodies disclosed herein). In some embodiments, the anti-IL-7R antibodies disclosed herein do not reduce or prevent TSLP-mediated activation of monocytes.

In some embodiments, anti-IL-7R antibodies described herein are capable of modulating (e.g., increasing) the ratio of regulatory T cells to effector T cells in a subject in need thereof. In some embodiments, the anti-IL-7R antibodies modulate the ratio by restoring a function and/or promoting the survival of Tregs (e.g., CD45RA−CD39+ T cells) in the subject. In certain embodiments, the anti-IL-7R antibodies of the present disclosure increases a Treg function (e.g., ability to suppress T cell proliferation and/or IL-10 production) by at least 5%, at least 10%, at least 20%, at least 30%, at least 40%, at least 50%, at least 60%, at least 70%, at least 80%, at least 90%, or at least 100%, compared to a reference (e.g., a corresponding Treg in a subject who did not receive the anti-IL-7R antibody). In some embodiments, the frequency of Tregs in the subject is increased by at least 5%, at least 10%, at least 20%, at least 30%, at least 40%, at least 50%, at least 60%, at least 70%, at least 80%, at least 90%, or at least 100%, compared to a reference (e.g., a corresponding Treg in a subject who did not receive the anti-IL-7R antibody).

In some embodiments, the anti-IL-7R antibodies disclosed herein modulate the ratio of regulatory T cells to effector T cells by blocking an expansion of effector T cells (e.g., IL-17 and/or IFN-γ producing T cells) in the subject. In certain embodiments, the frequency of effector T cells in the subject is decreased by at least 5%, at least 10%, at least 20%, at least 30%, at least 40%, at least 50%, at least 60%, at least 70%, at least 80%, at least 90%, or at least 100%, compared to a reference (e.g., a corresponding Treg in a subject who did not receive the anti-IL-7R antibody). In certain embodiments, the anti-IL-7R antibodies of the present disclosure modulate the ratio by both restoring a function and/or promoting the survival of Tregs and blocking the expansion of effector T cells in the subject.

In some embodiments, the ratio of regulatory T cells to effector T cells is increased by at least 5%, at least 10%, at least 20%, at least 30%, at least 40%, at least 50%, at least 60%, at least 70%, at least 80%, at least 90%, or at least 100% compared to a reference (e.g., corresponding ratio in a subject who did not receive the anti-IL-7R antibody).

In some embodiments, anti-IL-7R antibodies described herein bind to an epitope, e.g., a conformational epitope, in the extracellular portion of human IL-7Rα, e.g., in the Ig like domain of the extracellular region, i.e., amino acids 21 to 239 of SEQ ID NO: 1. In certain embodiments, an anti-IL-7R antibody binds to, or to an epitope within, a region consisting of amino acid residues 44 to 59 of SEQ ID NO: 1 (i.e., residues 24 to 39 of SEQ ID NO: 6) (SQLEVNG-SQHSLTCAF, "Epitope 1"; SEQ ID NO: 8). In some embodiments, an anti-IL-7R antibody binds to, or to an epitope within, a region consisting of amino acid residues 93 to 108 of SEQ ID NO: 1 (i.e., residues 73 to 88 of SEQ ID NO: 6) (FIETKKFLLIGKSNIC, "Epitope 2"; SEQ ID NO: 9). In other embodiments, an anti-IL-7R antibody binds to, or to an epitope within, a region consisting of amino acid residues 109 to 125 of SEQ ID NO: 1 (i.e., residues 89 to 105 of SEQ ID NO: 6) (VKVGEKSLTCKKIDLTT, "Epitope 3"; SEQ ID NO: 10). In some embodiments, an anti-IL-7R antibody binds to, or to an epitope within, a region consisting of amino acid residues 156 to 169 of SEQ ID NO: 1 (i.e., residues 136 to 149 of SEQ ID NO: 6) (QKKYVKVLMHDVAY, "Epitope 4"; SEQ ID NO: 11). In other embodiments, an anti-IL-7R antibody binds to, or to an epitope within, a region consisting of amino acid residues 201 to 216 of SEQ ID NO: 1 (i.e., residues 181 to 196 of SEQ ID NO: 6) (YEIKVRSIPDHYFKGF, "Epitope 5"; SEQ ID NO: 12).

In some embodiments, an anti-IL-7R antibody of the present disclosure binds to an epitope (or region of human IL-7Rα) comprising one or more of amino acid residues H53, E95, F99, I102, K104, M164, R206, H211, and Y212 of SEQ ID NO: 1 (i.e., H33, E75, F79, I82, K84, M144, R186, H191, and Y192 of SEQ ID NO: 6). In some embodiments, an anti-IL-7R antibody disclosed herein does not bind significantly, or only with significantly reduced binding affinity, to a human IL-7Rα in which one or more of amino acid residues H53, E95, F99, I102, K104, M164, R206, H211, and Y212 of SEQ ID NO: 1 is changed to another amino acid, e.g., in a non-conservative amino acid substitution.

In some embodiments, anti-IL-7R antibodies disclosed herein are not native antibodies or are not naturally-occurring antibodies. For example, in certain embodiments, the anti-IL-7R antibodies have post-translational modifications that are different from those of antibodies that are naturally occurring, such as by having more, less or a different type of post-translational modification.

In some embodiments, the anti-IL-7R antibodies do not have agonist activity, as determined, e.g., by measuring pSTAT activation after culturing T cells with the anti-IL-7R antibody, in which such antibodies do not enhance activity beyond anti-IL-7R antibody alone. In certain embodiments, anti-IL-7R antibodies block the interaction of IL-7Rα with IL-7 without promoting agonist activity.

In some embodiments, the anti-IL-7R antibodies of the present disclosure are not capable of blocking thymic stromal lymphopoietin (TSLP)-mediated activation of monocytes.

In some embodiments, the anti-IL-7R antibodies are capable of maintaining a drug free remission longer than that by, e.g., CTLA4-Ig (ORENCIA®).

In some embodiments, the anti-IL-7R antibodies are capable of blocking inflammation and mucosal damage (e.g., induced by pathogenic T cells), in an intestinal tissue. In some embodiments, the anti-IL-7R antibodies are capable of decreasing a frequency of T effector cells, e.g., in the mesenteric lymph nodes (MLN) and/or lamina propria (LP). In some embodiments, the anti-IL-7R antibodies are capable of treating a subject with an inflammatory disease, e.g., inflammatory bowel disease.

In some embodiments, an anti-IL-7R antibody of the present disclosure comprises a heavy chain CDR1, CDR2, and CDR3 and a light chain CDR1, CDR2, and CDR3, wherein the heavy chain CDR3 comprises the amino acid sequence set forth in SEQ ID NO: 15. In some embodiments, the heavy chain CDR1 comprises the amino acid sequence set forth in SEQ ID NO: 13. In some embodiments, the heavy chain CDR2 comprises the amino acid sequence set forth in SEQ ID NO: 14. In certain embodiments, the light chain CDR1 comprises the amino acid sequence set forth in SEQ ID NO: 16. In other embodiments, the light chain CDR2 comprises the amino acid sequence set forth in SEQ ID NO: 17. In some embodiments, the light chain CDR3 comprises the amino acid sequence set forth in SEQ ID NO: 18.

In some embodiments, an anti-IL-7R antibody comprises a heavy chain CDR1, CDR2, and CDR3 and a light chain CDR1, CDR2, and CDR3, wherein the heavy chain CDR1, CDR2, and CDR3 comprises the CDR1, CDR2, and CDR3 sequences set forth as SEQ ID NOs: 13, 14, and 15, respectively, wherein the light chain CDR1, CDR2, and CDR3 comprises the CDR1, CDR2, and CDR3 sequences set forth as SEQ ID NOs: 16, 17, and 18, respectively, and wherein the anti-IL-7R antibody has one or more of the properties disclosed herein.

Figure 18A:
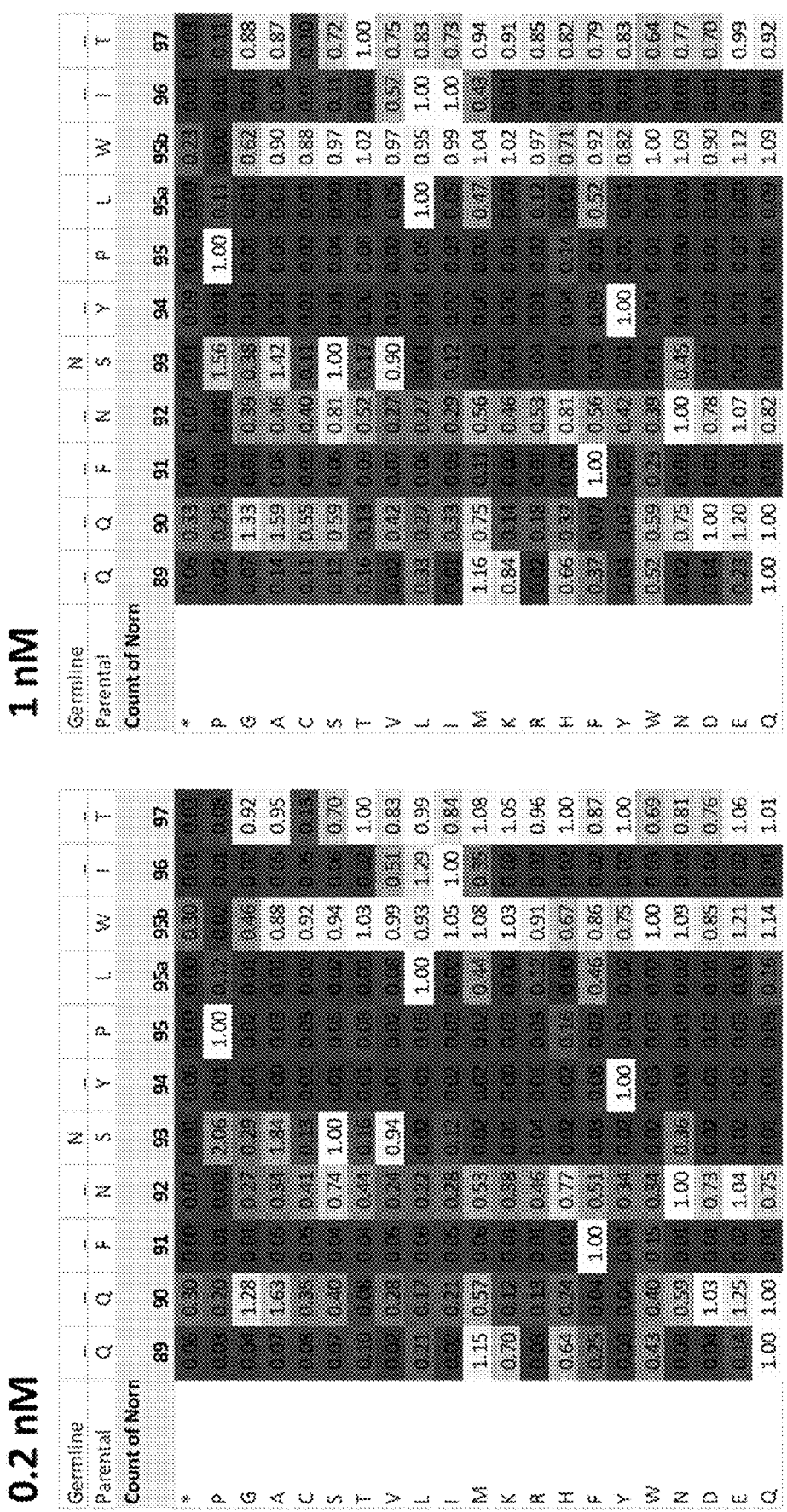
Figure 18B:
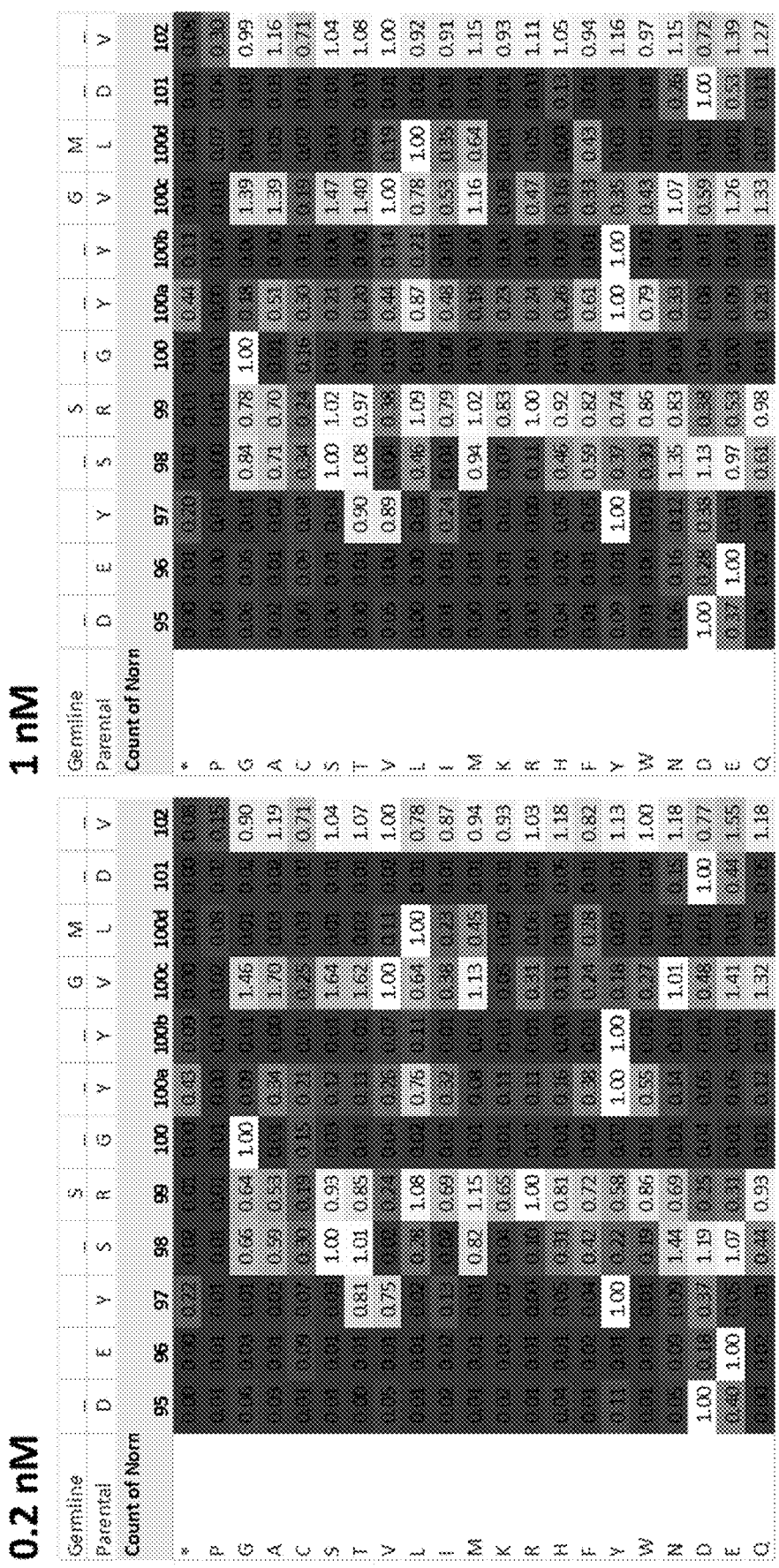
Figure 18C:
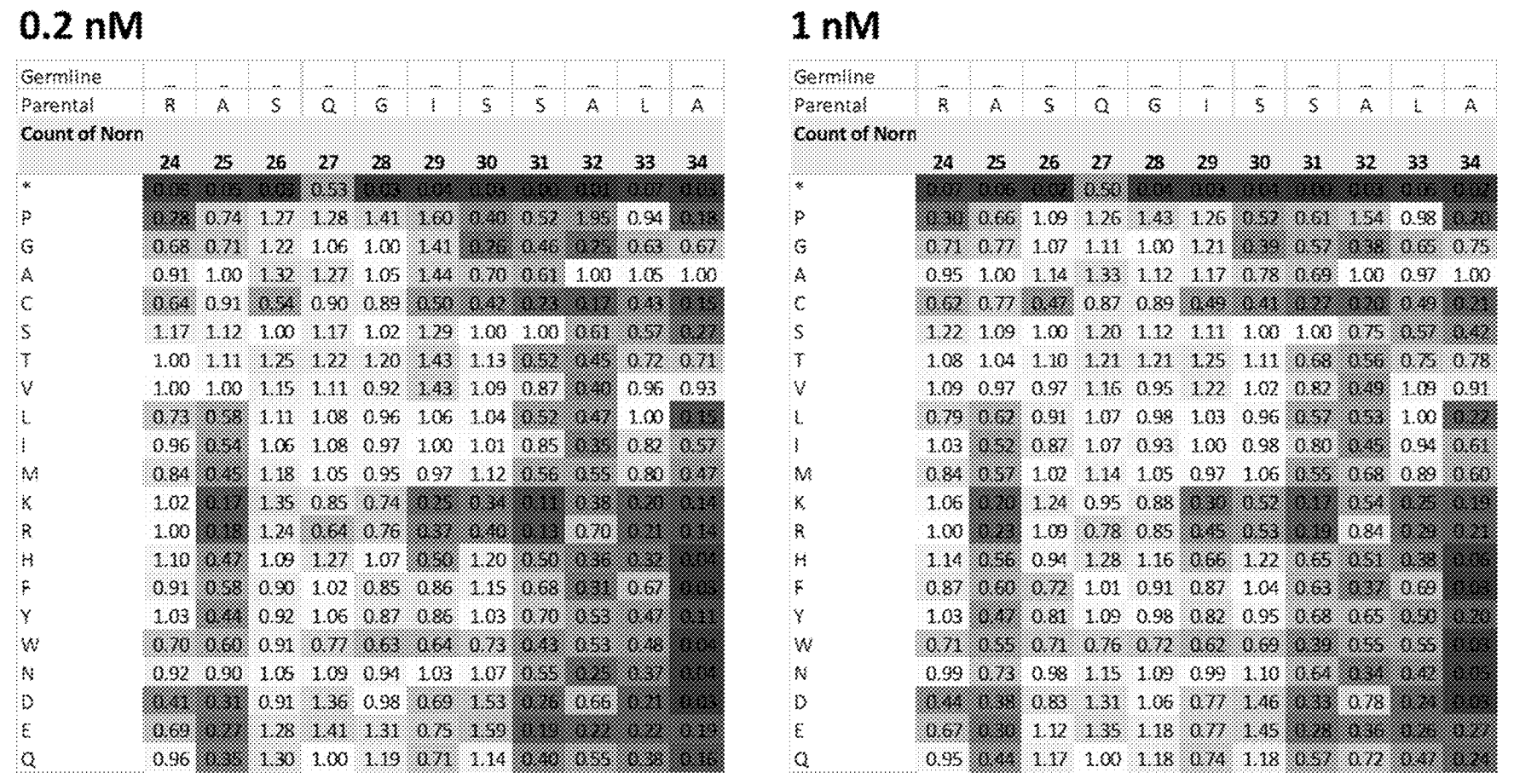
Figure 18D:
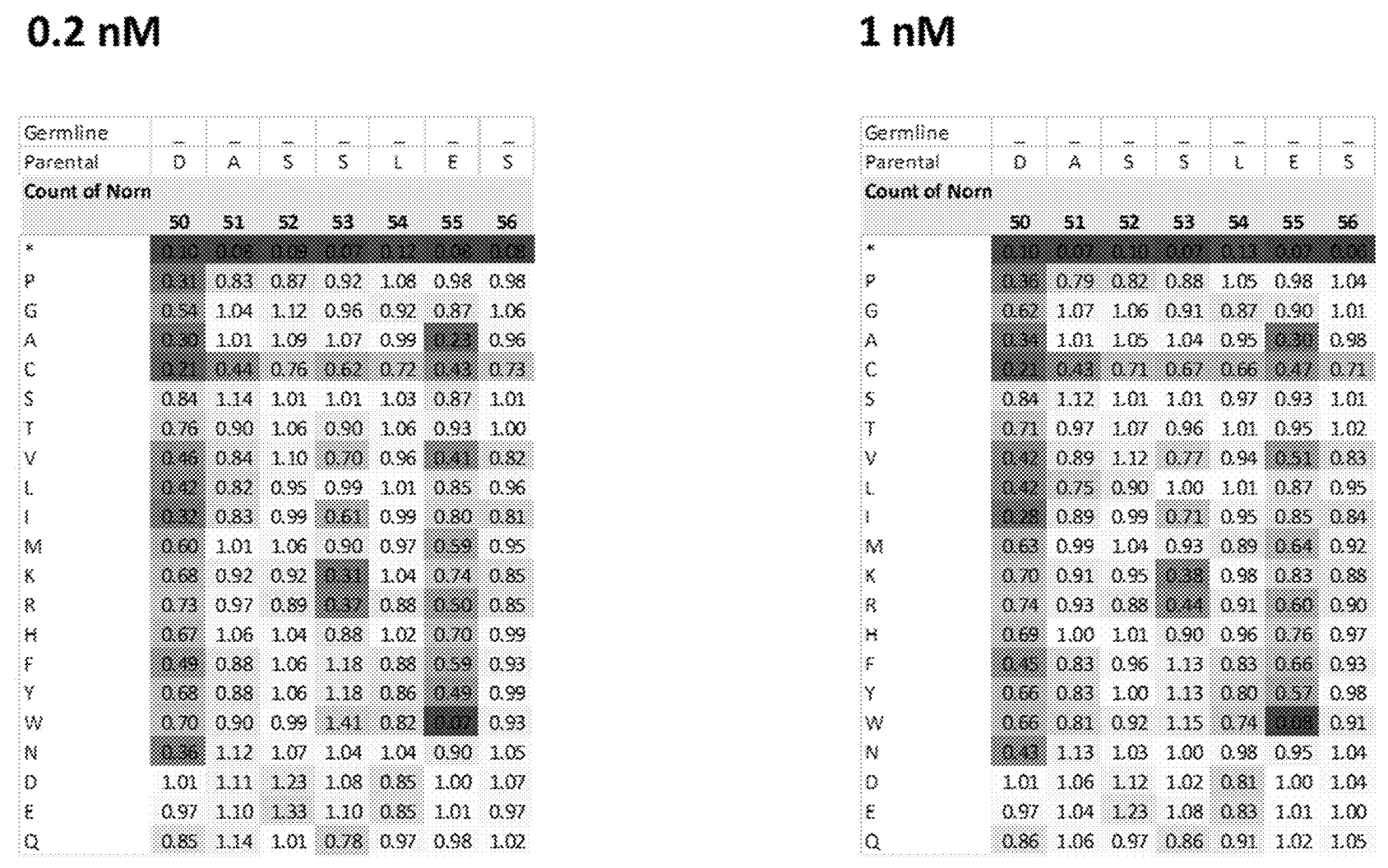
Figure 18E:
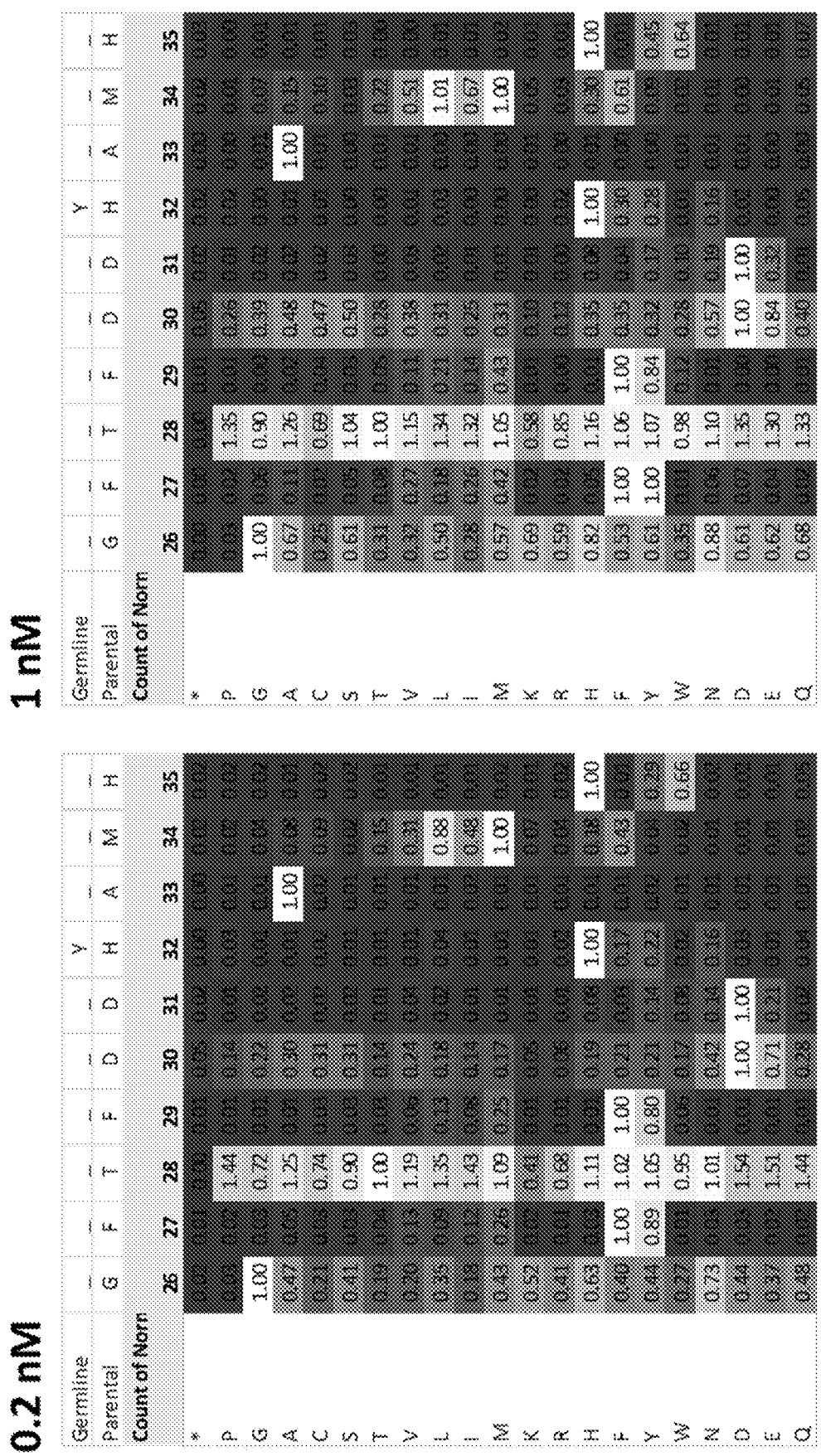
Figure 18F:
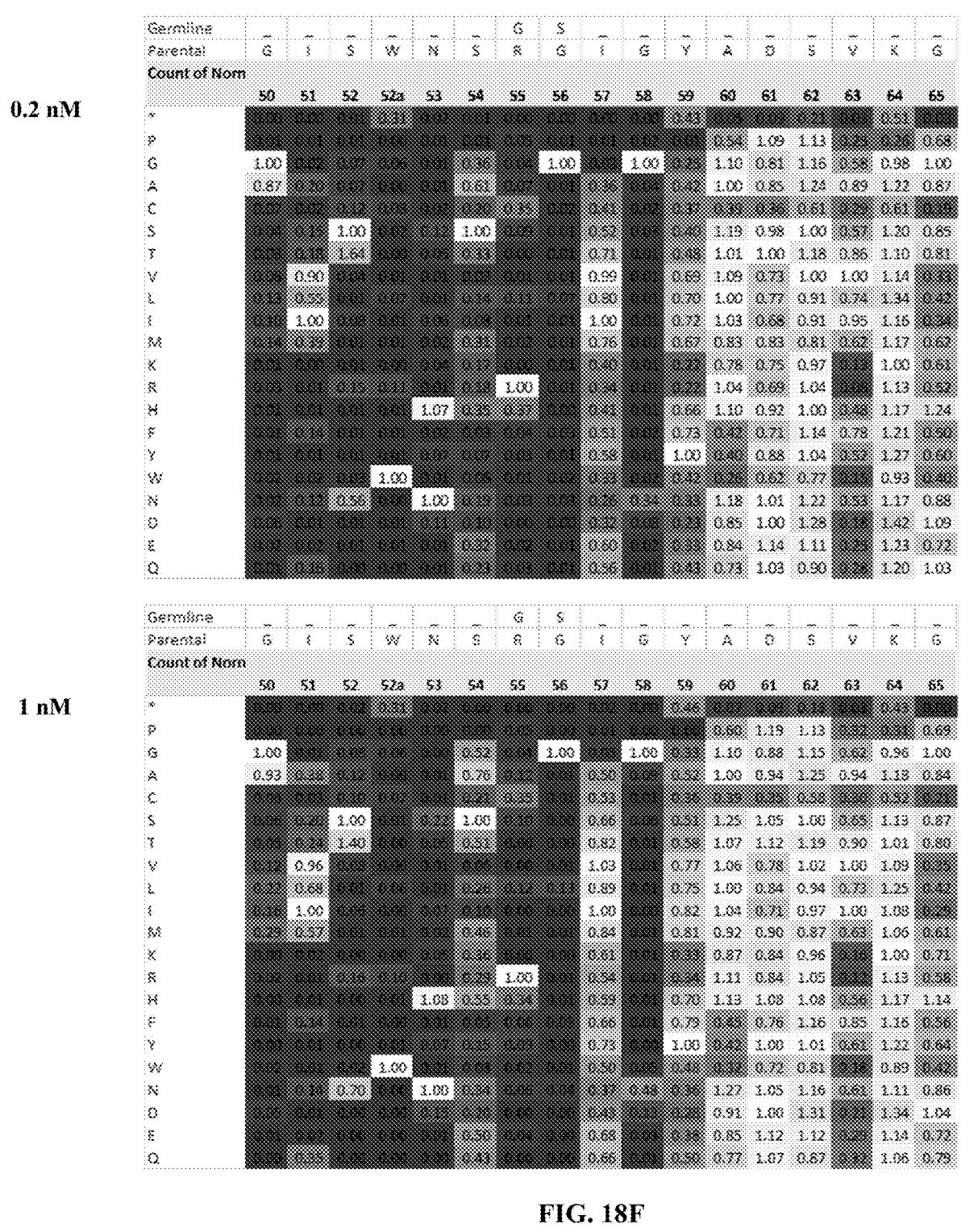

In some aspects, an anti-IL-7R antibody of the present disclosure comprises a heavy chain CDR1, CDR2, and CDR3, and a light chain CDR1, CDR2, and CDR3, wherein the heavy chain CDR3 comprises one or more amino acid modifications (e.g., one, two, three, or four substitutions, e.g., such as those shown in FIG. 18B as having an enrichment ratio of ≥1.00) relative to SEQ ID NO: 15. In some aspects, the heavy chain CDR1 comprises one or more amino acid modifications (e.g., one, two, or three substitutions, e.g., such as those shown in FIG. 18E as having an enrichment ratio of ≥1.00) relative to SEQ ID NO: 13. In certain aspects, the heavy chain CDR2 comprises one or more amino acid modifications (e.g. one, two, three, four, five, six, seven, eight, or nine substitutions, e.g., such as those shown in FIG. 18F as having an enrichment ratio of ≥1.00) relative to SEQ ID NO: 14. In further aspects, the light chain CDR1 comprises one or more amino acid modifications (e.g., one, two, three, four, five, six, seven, eight, or nine substitutions, e.g., such as those shown in FIG. 18C as having an enrichment ratio of ≥1.00) relative to SEQ ID NO: 16. In some aspects, the light chain CDR2 comprises one or more amino acid modifications (e.g., one, two, three, four, five, or six substitutions, e.g., such as those shown in FIG. 18D as having an enrichment ratio of ≥1.00) relative to SEQ ID NO: 17. In certain aspects, the light chain CDR3 comprises one or more amino acid modifications (e.g., one, two, three, four, five, six, or seven substitutions, e.g., such as those shown in FIG. 18A as having an enrichment ratio of ≥1.00) relative to SEQ ID NO: 18.

In some aspects, the heavy chain CDR1 of an anti-IL-7R antibody disclosed herein comprises the amino acid sequence $GX_1X_2FDDHAX_3H$ (SEQ ID NO: 260), wherein $X_1$ is F or Y; $X_2$ is T, P, A, S, V, L, I, M, H, F, Y, N, D, E, or Q; and $X_3$ is L or M. In certain aspects, $X_2$ is D or E. In further aspects, $X_2$ is D. In other aspects, $X_2$ is E. Non-limiting examples of heavy chain CDR1 sequences of an IL-7R antibody disclosed herein are provided in Table 13.

In some aspects, the heavy chain CDR2 of an anti-IL-7R antibody disclosed herein comprises the amino acid sequence $GIX_1WX_2SRGX_3GYX_4X_5X_6X_7X_8X_9$ (SEQ ID NO: 261), wherein $X_1$ is S or T; $X_2$ is H or N; $X_3$ is I or V; $X_4$ is G, A, S, T, V, L, I, R, H, or N; $X_5$ is P, T, N, D, E, Q, S, H, or Y; $X_6$ is P, G, A, S, T, V, R, H, F. Y, N, D, or E; $X_7$ is V or I; $X_8$ is A, S, T, V, L, I, M, K, R, H, F, Y, N, D, E, or Q; and $X_9$ is G, H, D, or Q. In certain aspects, $X_1$ is T. Non-limiting examples of heavy chain CDR2 sequences of an IL-7R antibody disclosed herein are provided in Table 14.

In some aspects, the heavy chain CDR3 of an anti-IL-7R antibody disclosed herein comprises the amino acid sequence $DEYX_1X_2GYYX_3LDX_4$ (SEQ ID NO: 262), wherein $X_1$ is S, T, N, D, or E; $X_2$ is L, M, R, or S; $X_3$ is G, A, S, T, V, M, N, E, or Q; and $X_4$ is A, S, T, V, R, H, Y, W, N, E, Q, or M. In certain aspects, $X_3$ is A, S, or T. In some aspects, $X_3$ is A. In other aspects, $X_3$ is S. In further aspects, $X_3$ is T. In some aspects, $X_4$ is E. Non-limiting examples of heavy chain CDR3 sequences of an IL-7R antibody disclosed herein are provided in Table 15.

In some aspects, the light chain CDR1 of an anti-IL-7R antibody of the present disclosure comprises the amino acid sequence $X_1X_2X_3X_4X_5X_6X_7SX_8X_9A$ (SEQ ID NO: 263), wherein $X_1$ is S, T, V, K, R, H, Y, or I; $X_2$ is A, S, T, or V; $X_3$ is P, G, A, S, T, V, L, I, M, K, R, H, N, E, or Q; $X_4$ is P, G, A, S, T, V, L, I, M, H, F, Y, N, D, E, or Q; $X_5$ is P, G, A, S, T, H, E, Q, M, N, or D; $X_6$ is P, G, A, S, T, V, L, I, or N; $X_7$ 1S S, T, V, L, I, M, H, F, Y, N, D, E, or Q; $X_8$ is P or A; and $X_9$ is A, L, or V. In certain aspects, $X_6$ is P. In some aspects, $X_8$ is P. In further aspects, $X_7$ is D or E. In certain aspects, $X_7$ is D. In some aspects, $X_7$ is E. Non-limiting examples of light chain CDR1 sequences of an IL-7R antibody disclosed herein are provided in Table 16.

In some aspects, the light chain CDR2 of an anti-IL-7R antibody disclosed herein comprises the amino acid sequence $DX_1X_2X_3X_4X_5X_6$ (SEQ ID NO: 264), wherein $X_1$ is G, A, S, M, H, N, D, E, or Q; $X_2$ is G, A, S, T, V, M, H, F, Y, N, D, E, or Q; $X_3$ is A, S, F, Y, W, N, D, E, or L; $X_4$ is P, S, T, L, K, H, or N; $X_5$ is D, E, or Q; and $X_6$ is G, S, T, N, D, Q, P, or E. Non-limiting examples of light chain CDR2 sequences of an IL-7R antibody disclosed herein are provided in Table 17.

In some aspects, the light chain CDR3 of an anti-IL-7R antibody disclosed herein comprises the amino acid sequence $X_1X_2FX_3X_4YPLX_5X_6X_7$ (SEQ ID NO: 265), wherein $X_1$ is M or Q; $X_2$ is G, A, D, E, or Q; $X_3$ is N or E; $X_4$ is P, A, or S; $X_5$ is T, I, M, K, W, N, E, or Q; $X_6$ is L or I; and $X_7$ is T, M, K, H, Y, E, or Q. In certain aspects, $X_2$ is A. In some aspects, $X_4$ is P or A. In certain aspects, $X_4$ is P. In other aspects, $X_4$ is A. Non-limiting examples of light chain CDR3 sequences of an IL-7R antibody disclosed herein are provided in Table 18.

In some aspects, an anti-IL-7R antibody disclosed herein comprises a heavy chain CDR1, CDR2, and CDR3, and a light chain CDR1, CDR2, and CDR3, wherein:
  (i) the heavy chain CDR1 comprises an amino acid sequence set forth in SEQ ID NOs: 31 to 46;
  (ii) the heavy chain CDR2 comprises an amino acid sequence set forth in SEQ ID NO: 14;
  (iii) the heavy chain CDR3 comprises an amino acid sequence set forth in SEQ ID NO: 15;
  (iv) the light chain CDR1 comprises an amino acid sequence set forth in SEQ ID NO: 16;
  (v) the light chain CDR2 comprises an amino acid sequence set forth in SEQ ID NO: 17; and
  (vi) the light chain CDR3 comprises an amino acid sequence set forth in SEQ ID NO: 18.

In some aspects, an anti-IL-7R antibody disclosed herein comprises a heavy chain CDR1, CDR2, and CDR3, and a light chain CDR1, CDR2, and CDR3, wherein:
  (i) the heavy chain CDR1 comprises an amino acid sequence set forth in SEQ ID NO: 13;
  (ii) the heavy chain CDR2 comprises an amino acid sequence set forth in SEQ ID NOs: 47 to 96
  (iii) the heavy chain CDR3 comprises an amino acid sequence set forth in SEQ ID NO: 15;
  (iv) the light chain CDR1 comprises an amino acid sequence set forth in SEQ ID NO: 16;
  (v) the light chain CDR2 comprises an amino acid sequence set forth in SEQ ID NO: 17; and
  (vi) the light chain CDR3 comprises an amino acid sequence set forth in SEQ ID NO: 18.

In some aspects, an anti-IL-7R antibody disclosed herein comprises a heavy chain CDR1, CDR2, and CDR3, and a light chain CDR1, CDR2, and CDR3, wherein:
  (i) the heavy chain CDR1 comprises an amino acid sequence set forth in SEQ ID NO: 13;
  (ii) the heavy chain CDR2 comprises an amino acid sequence set forth in SEQ ID NO: 14;
  (iii) the heavy chain CDR3 comprises an amino acid sequence set forth in SEQ ID NOs: 97 to 122;
  (iv) the light chain CDR1 comprises an amino acid sequence set forth in SEQ ID NO: 16;
  (v) the light chain CDR2 comprises an amino acid sequence set forth in SEQ ID NO: 17; and
  (vi) the light chain CDR3 comprises an amino acid sequence set forth in SEQ ID NO: 18.

In some aspects, an anti-IL-7R antibody disclosed herein comprises a heavy chain CDR1, CDR2, and CDR3, and a light chain CDR1, CDR2, and CDR3, wherein:
  (i) the heavy chain CDR1 comprises an amino acid sequence set forth in SEQ ID NO: 13;
  (ii) the heavy chain CDR2 comprises an amino acid sequence set forth in SEQ ID NO: 14;
  (iii) the heavy chain CDR3 comprises an amino acid sequence set forth in SEQ ID NO: 15;
  (iv) the light chain CDR1 comprises an amino acid sequence set forth in SEQ ID NOs: 123 to 194;
  (v) the light chain CDR2 comprises an amino acid sequence set forth in SEQ ID NO: 17; and
  (vi) the light chain CDR3 comprises an amino acid sequence set forth in SEQ ID NO: 18.

In some aspects, an anti-IL-7R antibody disclosed herein comprises a heavy chain CDR1, CDR2, and CDR3, and a light chain CDR1, CDR2, and CDR3, wherein:
  (i) the heavy chain CDR1 comprises an amino acid sequence set forth in SEQ ID NO: 13;
  (ii) the heavy chain CDR2 comprises an amino acid sequence set forth in SEQ ID NO: 14;
  (iii) the heavy chain CDR3 comprises an amino acid sequence set forth in SEQ ID NO: 15;
  (iv) the light chain CDR1 comprises an amino acid sequence set forth in SEQ ID NO: 16;
  (v) the light chain CDR2 comprises an amino acid sequence set forth in SEQ ID NOs: 195 to 237; and
  (vi) the light chain CDR3 comprises an amino acid sequence set forth in SEQ ID NO: 18.

In some aspects, an anti-IL-7R antibody disclosed herein comprises a heavy chain CDR1, CDR2, and CDR3, and a light chain CDR1, CDR2, and CDR3, wherein:
  (i) the heavy chain CDR1 comprises an amino acid sequence set forth in SEQ ID NO: 13;
  (ii) the heavy chain CDR2 comprises an amino acid sequence set forth in SEQ ID NO: 14;
  (iii) the heavy chain CDR3 comprises an amino acid sequence set forth in SEQ ID NO: 15;
  (iv) the light chain CDR1 comprises an amino acid sequence set forth in SEQ ID NO: 16;
  (v) the light chain CDR2 comprises an amino acid sequence set forth in SEQ ID NO: 17; and
  (vi) the light chain CDR3 comprises an amino acid sequence set forth in SEQ ID NOs: 238 to 259.

In some aspects, an anti-IL-7R antibody disclosed herein comprises a heavy chain CDR1, CDR2, and CDR3, and a light chain CDR1, CDR2, and CDR3, wherein:
  (i) the heavy chain CDR1 comprises any one of an amino acid sequence set forth in SEQ ID NOs: 13 and 31 to 46;
  (ii) the heavy chain CDR2 comprises any one of an amino acid sequence set forth in SEQ ID NOs: 14 and 47 to 96;
  (iii) the heavy chain CDR3 comprises any one of an amino acid sequence set forth in SEQ ID NOs: 15 and 97 to 122;
  (iv) the light chain CDR1 comprises any one of an amino acid sequence set forth in SEQ ID NOs: 16 and 123 to 194;
  (v) the light chain CDR2 comprises any one of an amino acid sequence set forth in SEQ ID NOs: 17 and 195 to 237; and/or
  (vi) the light chain CDR3 comprises any one of an amino acid sequence set forth in SEQ ID NOs: 18 and 238 to 259.

In some aspects, the heavy chain CDR1 comprises an amino acid sequence set forth in SEQ ID NO: 43 or SEQ ID NO: 44. In some aspects, the heavy chain CDR2 comprises an amino acid sequence set forth in SEQ ID NO: 47. In some aspects, the heavy chain CDR3 comprises an amino acid sequence set forth in SEQ ID NO: 105, SEQ ID NO: 106, SEQ ID NO: 107, or SEQ ID NO: 120. In some aspects, the light chain CDR1 comprises an amino acid sequence set forth in SEQ ID NO: 172, SEQ ID NO: 189, SEQ ID NO: 190, or SEQ ID NO: 192. In some aspects, the light chain CDR3 comprises an amino acid sequence set forth in SEQ ID NO: 240, SEQ ID NO: 244, or SEQ ID NO: 245.

In some aspects, an IL-7R antibody disclosed herein comprises a heavy chain CDR1, CDR2, and CDR3, and a light chain CDR1, CDR2, and CDR3, wherein:
(i) the heavy chain CDR1 comprises an amino acid sequence set forth in SEQ ID NO: 43 or SEQ ID NO: 44;
(ii) the heavy chain CDR2 comprises an amino acid sequence set forth in SEQ ID NO: 14;
(iii) the heavy chain CDR3 comprises an amino acid sequence set forth in SEQ ID NO: 15;
(iv) the light chain CDR1 comprises an amino acid sequence set forth in SEQ ID NO: 16;
(v) the light chain CDR2 comprises an amino acid sequence set forth in SEQ ID NO: 17; and
(vi) the light chain CDR3 comprises an amino acid sequence set forth in SEQ ID NO: 18.

In some aspects, an IL-7R antibody disclosed herein comprises a heavy chain CDR1, CDR2, and CDR3, and a light chain CDR1, CDR2, and CDR3, wherein:
(i) the heavy chain CDR1 comprises an amino acid sequence set forth in SEQ ID NO: 13;
(ii) the heavy chain CDR2 comprises an amino acid sequence set forth in SEQ ID NO: 47;
(iii) the heavy chain CDR3 comprises an amino acid sequence set forth in SEQ ID NO: 15;
(iv) the light chain CDR1 comprises an amino acid sequence set forth in SEQ ID NO: 16;
(v) the light chain CDR2 comprises an amino acid sequence set forth in SEQ ID NO: 17; and
(vi) the light chain CDR3 comprises an amino acid sequence set forth in SEQ ID NO: 18.

In some aspects, an IL-7R antibody disclosed herein comprises a heavy chain CDR1, CDR2, and CDR3, and a light chain CDR1, CDR2, and CDR3, wherein:
(i) the heavy chain CDR1 comprises an amino acid sequence set forth in SEQ ID NO: 13;
(ii) the heavy chain CDR2 comprises an amino acid sequence set forth in SEQ ID NO: 14;
(iii) heavy chain CDR3 comprises an amino acid sequence set forth in SEQ ID NO: 105, SEQ ID NO: 106, SEQ ID NO: 107, or SEQ ID NO: 120;
(iv) the light chain CDR1 comprises an amino acid sequence set forth in SEQ ID NO: 16;
(v) the light chain CDR2 comprises an amino acid sequence set forth in SEQ ID NO: 17; and
(vi) the light chain CDR3 comprises an amino acid sequence set forth in SEQ ID NO: 18.

In some aspects, an IL-7R antibody disclosed herein comprises a heavy chain CDR1, CDR2, and CDR3, and a light chain CDR1, CDR2, and CDR3, wherein:
(i) the heavy chain CDR1 comprises an amino acid sequence set forth in SEQ ID NO: 13;
(ii) the heavy chain CDR2 comprises an amino acid sequence set forth in SEQ ID NO: 14;
(iii) the heavy chain CDR3 comprises an amino acid sequence set forth in SEQ ID NO: 15;
(iv) the light chain CDR1 comprises an amino acid sequence set forth in SEQ ID NO: 172, SEQ ID NO: 189, SEQ ID NO: 190, or SEQ ID NO: 192;
(v) the light chain CDR2 comprises an amino acid sequence set forth in SEQ ID NO: 17; and
(vi) the light chain CDR3 comprises an amino acid sequence set forth in SEQ ID NO: 18.

In some aspects, an IL-7R antibody disclosed herein comprises a heavy chain CDR1, CDR2, and CDR3, and a light chain CDR1, CDR2, and CDR3, wherein:
(i) the heavy chain CDR1 comprises an amino acid sequence set forth in SEQ ID NO: 13;
(ii) the heavy chain CDR2 comprises an amino acid sequence set forth in SEQ ID NO: 14;
(iii) the heavy chain CDR3 comprises an amino acid sequence set forth in SEQ ID NO: 15;
(iv) the light chain CDR1 comprises an amino acid sequence set forth in SEQ ID NO: 16;
(v) the light chain CDR2 comprises an amino acid sequence set forth in SEQ ID NO: 17; and
(vi) the light chain CDR3 comprises an amino acid sequence set forth in SEQ ID NO: 240, SEQ ID NO: 244, or SEQ ID NO: 245.

In some aspects, an IL-7R antibody disclosed herein comprises a heavy chain CDR1, CDR2, and CDR3, and a light chain CDR1, CDR2, and CDR3, wherein one of the heavy chain or light chain CDRs comprise an amino acid modification disclosed herein and the other heavy chain or light chain CDRs are not modified relative to the corresponding CDRs of the 18B1 antibody (also referred to herein as "Antibody A") disclosed herein. In some aspects, two of the heavy chain or light chain CDRs comprise an amino acid modification disclosed herein and the other heavy chain or light chain CDRs are not modified relative to the corresponding CDRs of the 18B1 antibody. In further aspects, three of the heavy chain or light chain CDRs comprise an amino acid modification disclosed herein and the other heavy chain or light chain CDRs are not modified relative to the corresponding CDRs of the 18B1 antibody. In certain aspects, four of the heavy chain or light chain CDRs comprise an amino acid modification disclosed herein and the other heavy chain or light chain CDRs are not modified relative to the corresponding CDRs of the 18B1 antibody. In further aspects, five of the heavy chain or light chain CDRs comprise an amino acid modification disclosed herein and the other heavy chain or light chain CDRs are not modified relative to the corresponding CDRs of the 18B1 antibody. In some aspects, all six of the heavy chain and light chain CDRs comprise an amino acid modification disclosed herein relative to the corresponding CDRs of the 18B1 antibody. As described herein, the 18B1 antibody comprises heavy chain CDR1 set forth in SEQ ID NO: 13, heavy chain CDR2 set forth in SEQ ID NO: 14, heavy chain CDR3 set forth in SEQ ID NO: 15, light chain CDR1 set forth in SEQ ID NO: 16, light chain CDR2 set forth in SEQ ID NO: 17, and light chain CDR3 set forth in SEQ ID NO: 18.

In some embodiments, an anti-IL-7R antibody disclosed herein comprise a heavy chain variable region (VH) and a light chain variable region (VL), wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 19, wherein the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth in SEQ ID NO: 20, and wherein the anti-IL-7R antibody has one or more of the properties disclosed herein.

In some embodiments, the anti-IL-7R antibody comprises a VH and a VL, wherein the VH comprises the heavy chain CDR1, CDR2, and CDR3 of SEQ ID NO: 19, wherein the VL comprises the light chain CDR1, CDR2, and CDR3 of SEQ ID NO: 20, and wherein the anti-IL-7R antibody has one or more of the properties disclosed herein.

In some embodiments, an anti-IL-7R antibody of the present disclosure cross-competes for binding to a human IL-7Rα with a reference anti-IL-7R antibody, which comprises a VH and a VL, wherein the VH comprises the amino acid sequence set forth in SEQ ID NO: 19 and wherein the VL comprises the amino acid sequence set forth in SEQ ID NO: 20. In some embodiments, an anti-IL-7R antibody disclosed herein binds to the same epitope on human IL-7Rα as a reference anti-IL-7R antibody, which comprises a VH and a VL, wherein the VH comprises the amino acid sequence set forth in SEQ ID NO: 19 and wherein the VL comprises the amino acid sequence set forth in SEQ ID NO: 20. In some embodiments, the anti-IL-7R antibody and the reference antibody both bind to an epitope selected from the group consisting of SQLEVNGSQHSLTCAF (SEQ ID NO: 8), FIETKKFLLIGKSNIC (SEQ ID NO: 9), VKVGEKSLTCKKIDLTT (SEQ ID NO: 10), QKKYVKVLMHDVAY (SEQ ID NO: 11), YEIKVRSIPDHYFKGF (SEQ ID NO: 12). In some embodiments, the anti-IL-7R antibody and the reference antibody both bind to an epitope comprising one or more of amino acid residues H53, E95, F99, I102, K104, M164, R206, H211, and Y212 of SEQ ID NO: 1 (i.e., H33, E75, F79, I82, K84, M144, R186, H191, and Y192 of SEQ ID NO: 6).

In some embodiments, an anti-IL-7R antibody disclosed herein inhibits the binding of a reference anti-IL-7R antibody to human IL-7Rα by at least 10%, 20%, 30%, 40%, 50%, 60%, 70%, 80%, 90% or by 100%. Competing antibodies bind to the same epitope, an overlapping epitope, or to adjacent epitopes (e.g., as evidenced by steric hindrance). Whether two antibodies compete with each other for binding to a target can be determined using competition experiments known in the art, such as RIA and EIA.

A VH domain, or one or more CDRs thereof, described herein can be linked to a constant domain for forming a heavy chain, e.g., a full length heavy chain. Similarly, a VL domain, or one or more CDRs thereof, described herein can be linked to a constant domain for forming a light chain, e.g., a full length light chain. A full length heavy chain (with the exception of the C-terminal lysine (K) or with the exception of the C-terminal glycine and lysine (GK), which can be absent) and full length light chain combine to form a full length antibody.

In some embodiments, a VH domain described herein can be fused to the constant domain of a human IgG, e.g., IgG1, IgG2, IgG3 or IgG4, which are either naturally-occurring or modified, e.g., as further described herein. For example, a VH domain can comprise the amino acid sequence of any VH domain described herein fused to a human IgG, e.g., an IgG1, constant region, such as the following wild-type human IgG1 constant domain amino acid sequence:
ASTKGPSVFPLAPSSKSTSGGTAALGCLVKDYF-
PEPVTVSWNSGALTSGVHTFPAVLQSSGLYSLS-
SVVTVPSSSLGTQTYICNVNHKPSNTKVDKKVE-
PKSCDKTHTCPPCPAPELLGGPSVFLFPPKPKDT-
LMISRIPEVICVVVDVSHEDPEVKFNWYVDGVE-
VHNAKTKPREEQYNSTYRVVSVLTVLHQDWLN-
GKEYKCKVSNKALPAPIEKTISKAKGQPREPQV-
YTLPPSRDELTKNQVSLICLVKGFYPSDIAVEWE-
SNGQPENNYKTIPPVLDSDGSFFLYSKLTVDKSR-
WQQGNVFSCSVMHEALHNHYTQKSLSLSPGK
(SEQ ID NO: 23)
or that of an allotypic variant of SEQ ID NO: 23 and have the following amino acid sequences:
ASTKGPSVFPLAPSSKSTSGGTAALGCLVKDYF-
PEPVTVSWNSGALTSGVHTFPAVLQSSGLYSLS-
SVVTVPSSSLGTQTYICNVNHKPSNTKVDK<u>R</u>VE-
PKSCDKTHTCPPCPAPELLGGPSVFLFPPKPKDT-
LMISRIPEVICVVVDVSHEDPEVKFNWYVDGVE-
VHNAKTKPREEQYNSTYRVVSVLTVLHQDWLN-
GKEYKCKVSNKALPAPIEKTISKAKGQPREPQVY-
TLPPSR<u>EEM</u>TKNQVSLICLVKGFYPSDIAVEWES-
NGQPENNYKTIPPVLDSDGSFFLYSKLTVDKSRW-
QQGNVFSCSVMHEALHNHYTQKSLSLSPGK (SEQ ID NO: 24; allotype specific amino acid residues are in bold and underlined).

In some embodiments, a VH domain of an anti-IL-7R antibody can comprise the amino acid sequence of any VH domain described herein fused to an effectorless constant region, e.g., the following effectorless human IgG1 constant domain amino acid sequences:
ASTKGPSVFPLAPSSKSTSGGTAALGCLVKDYF-
PEPVTVSWNSGALTSGVHTFPAVLQSSGLYSLS-
SVVTVPSSSLGTQTYICNVNHKPSNTKVDK<u>R</u>VE-
PKSCDKTHTCPPCPAPEAEGAPSVFLFPPKPKDT-
LMISRIPEVICVVVDVSHEDPEVKFNWYVDGVE-
VHNAKTKPREEQYNSTYRVVSVLTVLHQDWLN-
GKEYKCKVSNKALP<u>SS</u>IEKTISKAKGQPREPQVY-
TLPPSR<u>EEM</u>TKNQVSLICLVKGFYPSDIAVEWES-
NGQPENNYKTIPPVLDSDGSFFLYSKLTVDKSR-
WQQGNVFSCSVMHEALHNHYTQKSLSLSPGK
(SEQ ID NO: 25; "IgG1.1f," comprising substitutions L234A, L235E, G237A, A330S and P331S, which are underlined).
or
ASTKGPSVFPLAPSSKSTSGGTAALGCLVKDYF-
PEPVTVSWNSGALTSGVHTFPAVLQSSGLYSLS-
SVVTVPSSSLGTQTYICNVNHKPSNTKVDK<u>R</u>VE-
PKSCDKTHTCPPCPAPEAEGAPSVFLFPPKPKDT-
LMISRIPEVICVVVDVSHEDPEVKFNWYVDGVE-
VHNAKTKPREEQYNSTYRVVSVLTVLHQDWLN-
GKEYKCKVSNKALP<u>A</u>PIEKTISKAKGQPREPQV-
YTLPPSR<u>EEM</u>TKNQVSLICLVKGFYPSDIAVEWE-
SNGQPENNYKTIPPVLDSDGSFFLYSKLTVDKSR-
WQQGNVFSCSVMHEALHNHYTQKSLSLSPGK
(SEQ ID NO: 26; "IgG1.3f", comprising substitutions L234A, L235E and G237A, which are underlined).

For example, an allotypic variant of IgG1 comprises an K97R, D239E, and/or L241M (underlined and bolded above) and numbering according to that in SEQ ID NOs: 24-26. Within the full length heavy region and according to EU numbering, these amino acid substitutions are numbered K214R, D356E, and L358M. In some embodiments, the constant region of an anti-IL-7R antibody can further comprises one or more mutations or substitutions at amino acids L117, A118, G120, A213, and P214 (underlined above) as numbered in SEQ ID NOs: 24-26, or L234, A235, G237, A330 and P331, per EU numbering. In further embodiments, the constant region of an anti-IL-7R antibody comprises one or more mutations or substitutions at amino acids L117A, A118E, G120A, A213S, and P214S of SEQ ID NO: 23, or L234A, L235E, G237A, A330S and P331S, per EU numbering. The constant region of an anti-IL-7R antibody may also comprise one or more mutations or substitutions L117A, A118E and G120A of SEQ ID NO: 23, or L234A, L235E and G237A, per EU numbering A VL domain described herein can be fused to the constant domain of a human Kappa or Lambda light chain. For example, a VL domain of an anti-IL-7R antibody can comprise the amino acid sequence of any VL domain described herein fused to the following human IgG1 kappa light chain amino acid sequence:

```
                                          (SEQ ID NO: 20)
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC
```

In certain embodiments, the heavy chain constant region comprises a lysine or another amino acid at the C-terminus, e.g., it comprises the following last amino acids: LSPGK (SEQ ID NO: 28) in the heavy chain. In certain embodiments, the heavy chain constant region is lacking one or more amino acids at the C-terminus, and has, e.g., the C-terminal sequence LSPG (SEQ ID NO: 29) or LSP.

In some embodiments, an anti-IL-7R antibody of the present disclosure comprises a heavy chain (HC) and a light chain (LC), wherein the HC comprises the amino acid sequence set forth in SEQ ID NO: 21 and wherein the LC comprises the amino acid sequence set forth in SEQ ID NO: 22.

II. Engineered and Modified Antibodies

Also provided are engineered and modified antibodies that can be prepared using an antibody having one or more of the VH and/or VL sequences disclosed herein as starting material to engineer a modified antibody, which modified antibody can have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. Sci. U.S.A.* 86: 10029-10033; U.S. Pat. No. 5,225,539 to Winter, and U.S. Pat. Nos. 5,530,101; 5,585,089; 5,693,762 and 6,180,370 to Queen et al.).

Accordingly, an embodiment described herein pertains to an isolated monoclonal antibody comprising a heavy chain variable region (VH) and a light chain variable region (VL), wherein the VH comprises CDR1, CDR2, and CDR3 sequences set forth as SEQ ID NOs: 13, 14, and 15, respectively, wherein the VL comprises CDR1, CDR2, and CDR3 sequences set forth as SEQ ID NOs: 16, 17, and 18, respectively, and wherein the antibody has one or more properties disclosed herein. Thus, the anti-IL-7R antibodies disclosed herein can contain the VH and VL CDR sequences recited above and yet can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline V$_H$ Sequences Reveals about Fifty Groups of V$_H$ Segments with Different Hypervariable Loops" *J. Mol. Biol.* 227:776-798; and Cox, J. P. L. et al. (1994) "A Directory of Human Germ-line V$_H$ Segments Reveals a Strong Bias in their Usage" *Eur. J. Immunol.* 24:827-836; the contents of each of which are expressly incorporated herein by reference.

In some embodiments, the framework sequences for use in the anti-IL-7R antibodies described herein are those that are structurally similar to the framework sequences used by the anti-IL-7R antibodies described herein. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see, e.g., U.S. Pat. Nos. 5,530,101; 5,585,089; 5,693,762 and 6,180,370 to Queen et al.).

Engineered anti-IL-7R antibodies described herein include those in which modifications have been made to framework residues within VH and/or VL, e.g., to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Another type of variable region modification is to mutate amino acid residues within the VH and/or VL CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. In some embodiments, conservative modifications (as discussed above) are introduced. The mutations can be amino acid substitutions, additions or deletions. Moreover, typically no more than one, two, three, four or five residues within a CDR region are altered.

Accordingly, also provided herein are isolated anti-IL-7R antibodies comprising a VH and a VL, wherein the VH comprises (i) a CDR1 region comprising an amino acid sequence set forth in SEQ ID NO: 13 (DHAMH), or an amino acid sequence having one, two, three, four or five amino acid substitutions, deletions or additions as compared to SEQ ID NO: 13; (ii) a CDR2 region comprising an amino acid sequence set forth in SEQ ID NO: 14 (GISWNSRGI-GYADSVKG), or an amino acid sequence having one, two, three, four or five amino acid substitutions, deletions or additions as compared to SEQ ID NO: 14; and (iii) a CDR3 region comprising an amino acid sequence set forth in SEQ ID NO: 15 (DEYSRGYYVLDV), or an amino acid sequence having one, two, three, four or five amino acid substitutions, deletions or additions as compared to SEQ ID NO: 15; wherein the VL comprises (iv) a CDR1 region comprising an amino acid sequence set forth in SEQ ID NO: 16 (RASQGISSALA), or an amino acid sequence having one, two, three, four or five amino acid substitutions, deletions or additions as compared to SEQ ID NO: 16; (v) a CDR2 region comprising an amino acid sequence set forth in SEQ ID NO: 17 (DASSLES), or an amino acid sequence having one, two, three, four or five amino acid substitutions, deletions or additions as compared to SEQ ID NO: 17; and (vi) a CDR3 region comprising an amino acid sequence set forth in SEQ ID NO: 18 (QQFNSYPLWIT), or an amino acid sequence having one, two, three, four or five amino acid substitutions, deletions or additions as compared to SEQ ID NO: 18; and wherein the antibodies have one or more properties disclosed herein. Non-limiting examples of such VH and VL CDR sequences are provided in Table 13 (VH CDR1), Table 14 (VH CDR2), Table 15 (VH CDR3), Table 16 (VL CDR1), Table 17 (VL CDR2), and Table 18 (VL CDR3).

Methionine residues in CDRs of antibodies can be oxidized, resulting in potential chemical degradation and consequent reduction in potency of the antibody. Accordingly, also provided are anti-IL-7R antibodies which have one or more methionine residues in the heavy and/or light chain CDRs replaced with amino acid residues which do not undergo oxidative degradation.

Similarly, deamidation sites can be removed from anti-IL-7R antibodies disclosed herein, particularly in the CDRs.

Anti-IL-7R variable regions described herein can be linked (e.g., covalently linked or fused) to an Fc, e.g., an IgG1, IgG2, IgG3 or IgG4 Fc, which can be of any allotype or isoallotype, e.g., for IgG1: G1m, G1m1(a), G1m2(x), G1m3(f), G1m17(z); for IgG2: G2m, G2m23(n); for IgG3: G3m, G3m21(g1), G3m28(g5), G3m11(b0), G3m5(b1), G3m13(b3), G3m14(b4), G3m10(b5), G3m15(s), G3m16 (t), G3m6(c3), G3m24(c5), G3m26(u), G3m27(v); and for K: Km, Km1, Km2, Km3 (see, e.g., Jefferies et al. (2009) mAbs 1:1).

In certain embodiments, anti-IL-7R variable regions described herein are linked to an effectorless or mostly effectorless Fc, e.g., IgG1.1f or IgG1.3f.

Generally, variable regions described herein can be linked to an Fc comprising one or more modification, typically to alter one or more functional properties of the antibody, such as serum half-life, complement fixation, Fc receptor binding, and/or antigen-dependent cellular cytotoxicity. Furthermore, an antibody described herein can be chemically modified (e.g., one or more chemical moieties can be attached to the antibody) or be modified to alter its glycosylation, to alter one or more functional properties of the antibody. Each of these embodiments is described in further detail below. The numbering of residues in the Fc region is that of the EU index of Kabat.

The Fc region encompasses domains derived from the constant region of an immunoglobulin, including a fragment, analog, variant, mutant or derivative of the constant region. Suitable immunoglobulins include IgG1, IgG2, IgG3, IgG4, and other classes such as IgA, IgD, IgE and IgM. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination.

Ig molecules interact with multiple classes of cellular receptors. For example IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to an Fc receptor (FcR).

In certain embodiments, the Fc region is a variant Fc region, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity.

Generally, variants of the constant region or portions thereof, e.g., CH1, CL, hinge, CH2 or CH3 domains can comprise 1, 2, 3, 4, 5, 6, 7, 8, 9, 10 or more mutations, and/or at most 10, 9, 8, 7, 6, 5, 4, 3, 2 or 1 mutation, or 1-10 or 1-5 mutations, or comprise an amino acid sequence that is at least about 75%, 80%, 85%, 90%, 95%, 96%, 97%, 98%, or 99% identical to that of the corresponding wild-type region or domain (CH1, CL, hinge, CH2, or CH3 domain, respectively), provided that the heavy chain constant region comprising the specific variant retains the necessary biological activity.

For example, one can make modifications in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for C1q and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region can include two, three, four, five, etc. substitutions therein, e.g., of the specific Fc region positions identified herein.

A variant Fc region can also comprise a sequence alteration wherein amino acids involved in disulfide bond formation are removed or replaced with other amino acids. Such removal can avoid reaction with other cysteine-containing proteins present in the host cell used to produce the anti-IL-7R antibodies described herein. Even when cysteine residues are removed, single chain Fc domains can still form a dimeric Fc domain that is held together non-covalently. In other embodiments, the Fc region can be modified to make it more compatible with a selected host cell. For example, one can remove the PA sequence near the N-terminus of a typical native Fc region, which can be recognized by a digestive enzyme in *E. coli* such as proline iminopeptidase. In other embodiments, one or more glycosylation sites within the Fc domain can be removed. Residues that are typically glycosylated (e.g., asparagine) can confer cytolytic response. Such residues can be deleted or substituted with unglycosylated residues (e.g., alanine). In other embodiments, sites involved in interaction with complement, such as the C1q binding site, can be removed from the Fc region. For example, one can delete or substitute the EKK sequence of human IgG1. In certain embodiments, sites that affect binding to Fc receptors can be removed, preferably sites other than salvage receptor binding sites. In other embodiments, an Fc region can be modified to remove an ADCC site. ADCC sites are known in the art; see, for example, Molec. Immunol. 29 (5): 633-9 (1992) with regard to ADCC sites in IgG1. Specific examples of variant Fc domains are disclosed for example, in WO 97/34631 and WO 96/32478.

In one embodiment, the hinge region of Fc is modified such that the number of cysteine residues in the hinge region is altered, e.g., increased or decreased. This approach is described further in U.S. Pat. No. 5,677,425 by Bodmer et al. The number of cysteine residues in the hinge region of Fc is altered to, for example, facilitate assembly of the light and heavy chains or to increase or decrease the stability of the antibody. In one embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320, 322, 330, and/or 331 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region can be modified to decrease antibody dependent cellular cytotoxicity (ADCC) and/or to decrease the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F7324T. Other modifications for enhancing FcγR and complement interactions include but are not limited to substitutions 298 A, 333A, 334A, 326A, 247I, 339D, 339Q, 280H, 290S, 298D, 298V, 243L, 292P, 300L, 396L, 305I, and 396L. These and other modifications are reviewed in Strohl, 2009, *Current Opinion in Biotechnology* 20:685-691.

Fc modifications that increase binding to an Fcγ receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 338, 340, 360, 373, 376, 379, 382, 388, 389, 398, 414, 416, 419, 430, 434, 435, 437, 438 or 439 of the Fc region, wherein the numbering of the residues in the Fc region is that of the EU index as in Kabat (WO00/42072).

Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, 328, 330, and/or 331 (e.g., 330 and 331), wherein numbering is according to the EU index. Exemplary substitutions include but are not limited to 234A, 235E, 236R, 237A, 267R, 269R, 325L, 328R, 330S, and 331S (e.g., 330S, and 331S), wherein numbering is according to the EU index. An Fc variant can comprise 236R/328R. Other modifications for reducing FcγR and complement interactions include substitutions 297A, 234A, 235A, 237A, 318A, 228P, 236E, 268Q, 309L, 330S, 331 S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, *Current Opinion in Biotechnology* 20:685-691.

Optionally, the Fc region can comprise a non-naturally occurring amino acid residue at additional and/or alternative positions known to one skilled in the art (see, e.g., U.S. Pat. Nos. 5,624,821; 6,277,375; 6,737,056; 6,194,551; 7,317, 091; 8,101,720; PCX Patent Publications WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/0201 14).

Fc variants that enhance affinity for an inhibitory receptor FcγRIIb can also be used. Such variants can provide an Fc fusion protein with immunomodulatory activities related to FcγRIIb cells, including for example B cells and monocytes. In one embodiment, the Fc variants provide selectively enhanced affinity to FcγRIIb relative to one or more activating receptors. Modifications for altering binding to FcγRIIb include one or more modifications at a position selected from the group consisting of 234, 235, 236, 237, 239, 266, 267, 268, 325, 326, 327, 328, 330, 331, and 332, according to the EU index. Exemplary substitutions for enhancing FcγRIIb affinity include but are not limited to 234A, 234D, 234E, 234F, 234W, 235D, 235E, 235F, 235R, 235Y, 236D, 236N, 237A, 237D, 237N, 239D, 239E, 266M, 267D, 267E, 268D, 268E, 327D, 327E, 328F, 328W, 328Y, 330S, 331S, and 332E. Exemplary substitutions include 235Y, 236D, 239D, 266M, 267E, 268D, 268E, 328F, 328W, and 328Y. Other Fc variants for enhancing binding to FcγRIIb include 235Y/267E, 236D/267E, 239D/268D, 239D/267E, 267E/268D, 267E/268E, and 267E/328F.

The affinities and binding properties of an Fc region for its ligand can be determined by a variety of in vitro assay methods (biochemical or immunological based assays) known in the art including but not limited to, equilibrium methods (e.g., enzyme-linked immunoabsorbent assay (ELISA), or radioimmunoassay (RIA)), or kinetics (e.g., BIACORE™ analysis), and other methods such as indirect binding assays, competitive inhibition assays, fluorescence resonance energy transfer (FRET), gel electrophoresis and chromatography (e.g., gel filtration). These and other methods can utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental immunology, 4th Ed., Lippincott-Raven, Philadelphia (1999), which focuses on antibody-immunogen interactions.

In certain embodiments, the antibody is modified to increase its biological half-life. Various approaches are possible. For example, this can be done by increasing the binding affinity of the Fc region for FcRn, for example, one or more of more of following residues can be mutated: 252, 254, 256, 433, 435, 436, as described in U.S. Pat. No. 6,277,375. Specific exemplary substitutions include one or more of the following: T252L, T254S, and/or T256F. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 259I, 308F, 428L, 428M, 434S, 434I 1. 434F, 434Y, and 434X1. Other variants that increase Fc binding to FcRn include: 250E, 250Q, 428 L, 428F, 250Q/428L (Hinton et al. 2004, *J. Biol. Chem.* 279(8): 6213-6216, Hinton et al. 2006 *Journal of Immunology* 176:346-356), 256A, 272A, 286A, 305A, 307A, 307Q, 31 1A, 312A, 376A, 378Q, 380A, 382A, 434A (Shields et al., *Journal of Biological Chemistry,* 2001, 276(9):6591-6604), 252F, 252T, 252Y, 252W, 254T, 256S, 256R, 256Q, 256E, 256D, 256T, 309P, 31 1 S, 433R, 433S, 4331, 433P, 433Q, 434H, 434F, 434Y, 252Y/254T/256E, 433K/434F/436H, 308T/309P/311S (Dall'Acqua et al. *Journal of Immunology,* 2002, 169:5171-5180, Dall'Acqua et al., 2006, *Journal of Biological Chemistry* 281:23514-23524). Other modifications for modulating FcRn binding are described in Yeung et al., 2010, *J Immunol,* 182:7663-7671.

In certain embodiments, hybrid IgG isotypes with particular biological characteristics can be used. For example, an IgG1/IgG3 hybrid variant can be constructed by substituting IgG1 positions in the CH2 and/or CH3 region with the amino acids from IgG3 at positions where the two isotypes differ. Thus a hybrid variant IgG antibody can be constructed that comprises one or more substitutions, e.g., 274Q, 276K, 300F, 339T, 356E, 358M, 384S, 392N, 397M, 422I, 435R, and 436F. In other embodiments described herein, an IgG1/IgG2 hybrid variant can be constructed by substituting IgG2 positions in the CH2 and/or CH3 region with amino acids from IgG1 at positions where the two isotypes differ. Thus a hybrid variant IgG antibody can be constructed that comprises one or more substitutions, e.g., one or more of the following amino acid substitutions: 233E, 234L, 235L, –236G (referring to an insertion of a glycine at position 236), and 327A.

Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A, which has been shown to exhibit enhanced FcγRIIIa binding and ADCC activity (Shields et al., 2001). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006). In addition, IgG1 mutants containing L235V, F243L, R292P, Y300L and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al., 2007; Nordstrom et al., 2011). Other Fc mutants that can be used include: S298A/E333A/L334A, S239D/I332E, S239D/I332E/A330L, L235V/F243L/R292P/Y300L/P396L, and M428L/N434S.

In certain embodiments, an Fc is chosen that has reduced binding to FcγRs. An exemplary Fc, e.g., IgG1 Fc, with reduced FcγR binding comprises the following three amino acid substitutions: L234A, L235E and G237A.

In certain embodiments, an Fc is chosen that has reduced complement fixation. An exemplary Fc, e.g., IgG1 Fc, with reduced complement fixation has the following two amino acid substitutions: A330S and P331S.

In certain embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S.

When using an IgG4 constant domain, it can include the substitution S228P, which mimics the hinge sequence in IgG1 and thereby stabilizes IgG4 molecules.

In still other embodiments, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation can increase the affinity of the antibody for antigen. Such an approach is described in further detail in U.S. Pat. Nos. 5,714,350 and 6,350,861 by Co et al.

Glycosylation of the constant region on N297 can be prevented by mutating the N297 residue to another residue, e.g., N297A, and/or by mutating an adjacent amino acid, e.g., 298 to thereby reduce glycosylation on N297.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant anti-IL-7R antibodies described herein to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Led 3 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17: 176-180).

Another modification of the anti-IL-7R antibodies described herein is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. In some embodiments, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the anti-IL-7R antibodies described herein. See for example, EP 0 154 316 by Nishimura et al. and EP 0 401 384 by Ishikawa et al.

III. Antibody Physical Properties

Anti-IL-7R antibodies, e.g., those described herein, have some or all of the physical characteristics described herein, such as the characteristics described in the Examples.

Anti-IL-7R antibodies described herein can contain one or more glycosylation sites in either the light or heavy chain variable region. Such glycosylation sites can result in increased immunogenicity of the antibody or an alteration of the pK of the antibody due to altered antigen binding (Marshall et al., (1972) *Annu Rev Biochem* 41:673-702; Gala and Morrison (2004) *J. Immunol* 172:5489-94; Wallick et al., (1988) *J Exp Med* 168: 1099-109; Spiro (2002) Glycobiology 12:43R-56R; Parekh et al., (1985) *Nature* 316:452-7; Mimura et al., (2000) *Mol Immunol* 37:697-706). Glycosylation has been known to occur at motifs containing an N-X-S/T sequence. In some embodiments, an anti-IL-7R antibody does not contain variable region glycosylation. This can be achieved either by selecting antibodies that do not contain the glycosylation motif in the variable region or by mutating residues within the glycosylation region.

In some embodiments, the anti-IL-7R antibodies described herein do not contain asparagine isomerism sites. The deamidation of asparagine can occur on N-G or D-G sequences and result in the creation of an isoaspartic acid residue that introduces a kink into the polypeptide chain and decreases its stability (isoaspartic acid effect).

Each antibody will have a unique isoelectric point (pi), which generally falls in the pH range between 6 and 9.5. The pi for an IgG1 antibody typically falls within the pH range of 7-9.5 and the pi for an IgG4 antibody typically falls within the pH range of 6-8. There is speculation that antibodies with a pi outside the normal range can have some unfolding and instability under in vivo conditions. Thus, an anti-IL-7R antibody can contain a pi value that falls in the normal range. This can be achieved either by selecting antibodies with a pi in the normal range or by mutating charged surface residues.

Each antibody will have a characteristic melting temperature, with a higher melting temperature indicating greater overall stability in vivo (Krishnamurthy R and Manning M C (2002) *Curr Pharm Biotechnol* 3:361-71). Generally, the $T_M i$ (the temperature of initial unfolding) can be greater than 60° C., greater than 65° C., or greater than 70° C. The melting point of an antibody can be measured using differential scanning calorimetry (Chen et al., (2003) *Pharm Res* 20: 1952-60; Ghirlando et al., (1999) *Immunol Lett* 68:47-52) or circular dichroism (Murray et al., (2002) *J. Chromatogr Sci* 40:343-9).

In one embodiment, antibodies are selected that do not degrade rapidly. Degradation of an antibody can be measured using capillary electrophoresis (CE) and MALDI-MS (Alexander A J and Hughes D E (1995) *Anal Chem* 67:3626-32).

In some embodiments, antibodies are selected that have minimal aggregation effects, which can lead to the triggering of an unwanted immune response and/or altered or unfavorable pharmacokinetic properties. Generally, antibodies are acceptable with aggregation of 25% or less, 20% or less, 15% or less, 10% or less, or 5% or less. Aggregation can be measured by several techniques, including size-exclusion column (SEC), high performance liquid chromatography (HPLC), and light scattering.

IV. Methods of Engineering Antibodies

As discussed above, the anti-IL-7R antibodies having VH and VL sequences disclosed herein can be used to create new anti-IL-7R antibodies by modifying the VH and/or VL sequences, or the constant region(s) attached thereto. Thus, in another aspect described herein, the structural features of an anti-IL-7R antibody described herein are used to create structurally related anti-IL-7R antibodies that retain at least one functional property of the anti-IL-7R antibodies described herein, such as binding to human IL-7Rα and cynomolgus IL-7Ra. For example, one or more CDR regions of an anti-IL-7R antibody disclosed herein can be combined recombinantly with known framework regions and/or other CDRs to create additional, recombinantly-engineered, anti-IL-7R antibodies, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, provided herein are methods for preparing an anti-IL-7R antibody comprising:
(a) providing: (i) a heavy chain variable region antibody sequence comprising a CDR1 sequence set forth as SEQ ID NO: 13 or any one of the sequences provided in Table 13, a CDR2 sequence set forth as SEQ ID NO: 14 or any one of the sequences provided in Table 14, and/or a CDR3 sequence set forth as SEQ ID NO: 15 or any one of the sequences provided in Table 15; and (ii) a light chain variable region antibody sequence comprising a CDR1 sequence set forth as SEQ ID NO: 16 or any one of the sequences provided in Table 16, a CDR2 sequence set forth as SEQ ID NO: 17 or any one of the sequences provided in Table 17, and/or a CDR3 sequence set forth as SEQ ID NO: 18 or any one of the sequences provided in Table 18;
(b) altering at least one amino acid residue within the heavy chain variable region antibody sequence and/or the light chain variable region antibody sequence to create at least one altered antibody sequence; and
(c) expressing the altered antibody sequence as a protein.

Standard molecular biology techniques can be used to prepare and express the altered antibody sequence. In some embodiments, the antibody encoded by the altered antibody sequence(s) is one that retains one, some or all of the functional properties of the anti-IL-7R antibodies described herein. The functional properties of the altered antibodies can be assessed using standard assays available in the art and/or described herein, such as those set forth in the Examples (e.g., ELISAs, FACS).

In some embodiments, mutations can be introduced randomly or selectively along all or part of an anti-IL-7R antibody coding sequence and the resulting modified anti-IL-7R antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

V. Nucleic Acids, Vectors, and Cells

Also described herein are nucleic acid molecules that encode the anti-IL-7R antibodies described herein. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and can or cannot contain intronic sequences. In certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

In some embodiments, the nucleic acids described herein are those encoding the VH and VL sequences of the anti-IL-7R antibodies of the present disclosure. In some embodiments, the nucleic acids described herein encode VH and VL sequences that are homologous to the anti-IL-7R antibodies disclosed herein. In some embodiments, the nucleic acids encode VH and VL sequences that are at least 70% identical, for example, at least 75%, at least 80%, at least 85%, at least 90%, at least 95%, or at least 99% identical, to nucleic acid molecules encoding the VH and VL sequences of the anti-IL-7R antibodies disclosed herein.

In some embodiments, the nucleic acid molecules described herein can be modified to delete specific sequences, e.g., restriction enzyme recognition sequences. In some embodiments, the nucleic acid molecules comprise conservative substitutions (i.e., substitutions that do not alter the resulting amino acid sequence upon translation of nucleic acid molecule), e.g., for codon optimization.

A method for making an anti-IL-7R antibody as disclosed herein can comprise expressing the heavy chain and the light chains in a cell line comprising the nucleotide sequences encoding the heavy and light chains with a signal peptide, e.g., SEQ ID NOs: 21 and 22, respectively. Host cells comprising these nucleotide sequences are encompassed herein. In some embodiments, the host cells are derived from a CHOZN cell line.

Once DNA fragments encoding VH and VL segments are obtained, these DNA fragments can be further manipulated by standard recombinant DNA techniques, for example, to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2, and/or CH3). The sequences of human heavy chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG1 region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

Present disclosure further provides cells (e.g., host cells) expressing (e.g., recombinantly) anti-IL-7R antibodies described herein and related polynucleotides and expression vectors. Provided herein are also vectors comprising polynucleotides comprising nucleotide sequences encoding anti-IL-7R antibodies or a fragment thereof. In some embodiments, the vectors can be used for recombinantly expressing anti-IL-7R antibodies described herein in host cells, e.g., in mammalian cells, e.g., CHOZN cells. In some embodiments, the vectors can be used for gene therapy. Suitable vectors for the disclosure include expression vectors, viral vectors, and plasmid vectors.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the disclosure can include polynucleotides encoding the antibody or antigen binding porting thereof described herein. In some embodiments, the coding sequences for the antibody or antigen binding porting thereof is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired antibody or antigen binding porting thereof.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; lentivirus; adenovirus; adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

VI. Antibody Production

Anti-IL-7R antibodies described herein can be produced using a variety of known techniques, such as the standard somatic cell hybridization technique described by Kohler and Milstein, *Nature* 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized anti-IL-7R antibodies described herein can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693, 762 and 6,180,370 to Queen et al).

In one embodiment, the anti-IL-7R antibodies described herein are human monoclonal antibodies. Such human monoclonal antibodies directed against IL-7Rα can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HUMAB-MOUSE® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see, e.g., Lonberg, et al., (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGK monoclonal (Lonberg, N. et al. (1994), supra; reviewed in Lonberg, N. (1994) Handbook of Experimental Pharmacology 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al., (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *Immunol.* 152:2912-2920; Taylor, L. et al. (1994) *International Immunology* 6: 579-591; and Fishwild, D. et al. (1996) *Nature Biotechnology* 14: 845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In certain embodiments, the anti-IL-7R antibodies described herein are raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-IL-7R antibodies described herein. For example, an alternative transgenic system referred to as the XENOMOUSE® (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-IL-7R antibodies described herein. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-IL-7R antibodies described herein.

Additional mouse systems described in the art for raising human antibodies, e.g., human anti-IL-7R antibodies, include (i) the VelocImmune® mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MeMo® mouse (Merus Biopharmaceuticals, Inc.), in which the mouse contains unrearranged human heavy chain variable regions but a single rearranged human common light chain variable region. Such mice, and use thereof to raise antibodies, are described in, for example, WO 2009/157771, US 2010/0069614, WO 2011/072204, WO 2011/097603, WO 2011/163311, WO 2011/163314, WO 2012/148873, US 2012/0070861 and US 2012/0073004.

Human monoclonal anti-IL-7R antibodies described herein can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal anti-IL-7R antibodies described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

VI.A. Immunizations

To generate fully human antibodies to IL-7Rα, transgenic or transchromosomal mice containing human immunoglobulin genes (e.g., HCol2, HCo7 or KM mice) can be immunized with a purified or enriched preparation of the IL-7Rα antigen and/or cells expressing IL-7Rα or fragment thereof, as described for other antigens, for example, by Lonberg et al., (1994) *Nature* 368(6474): 856-859; Fishwild et al., (1996) *Nature Biotechnology* 14: 845-851 and WO 98/24884. Alternatively, mice can be immunized with DNA encoding human IL-7Rα or fragment thereof. In some embodiments, the mice can be 6-16 weeks of age upon the first infusion. For example, a purified or enriched preparation (5-50 μg) of the recombinant IL-7Rα antigen can be used to immunize the HuMAb mice intraperitoneally. In the event that immunizations using a purified or enriched preparation of the IL-7Rα antigen do not result in antibodies, mice can also be immunized with cells expressing IL-7Rα, e.g., a cell line, to promote immune responses. Exemplary cell lines include IL-7Rα-overexpressing stable CHO cell line (CHOZN).

Cumulative experience with various antigens has shown that the HuMAb transgenic mice respond best when initially immunized intraperitoneally (IP) or subcutaneously (SC) with antigen in Ribi's adjuvant, followed by every other week IP/SC immunizations (up to a total of 10) with antigen in Ribi's adjuvant. The immune response can be monitored over the course of the immunization protocol with plasma samples being obtained by retroorbital bleeds. The plasma can be screened by ELISA and FACS (as described below), and mice with sufficient titers of anti-IL-7R human immunoglobulin can be used for fusions. Mice can be boosted intravenously with antigen 3 days before sacrifice and removal of the spleen and lymph nodes. It is expected that 2-3 fusions for each immunization can need to be performed. Between 6 and 24 mice are typically immunized for each antigen. Usually, HCo7, HCol2, and KM strains are used. In addition, both HCo7 and HCo12 transgene can be bred together into a single mouse having two different human heavy chain transgenes (HCo7/HCo12).

VI.B. Generation of Hybridomas Producing Monoclonal Antibodies to IL-7Rα

To generate hybridomas producing human monoclonal anti-IL-7R antibodies described herein, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to Sp2/0 nonsecreting mouse myeloma cells (ATCC, CRL 1581) with PEG. Cells can be plated in flat bottom microtiter plate, followed by incubation in selective medium. After several weeks, cells can be cultured in medium. Individual wells can then be screened by ELISA for human monoclonal IgM and IgG antibodies. Once extensive hybridoma growth occurs, medium can be observed usually after 10-14 days. The antibody secreting hybridomas can be replaced, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored.

VI.C. Generation of Transfectomas Producing Monoclonal Antibodies to IL-7Rα

Antibodies can be produced in a host cell transfectoma using, for example, a combination of recombinant DNA techniques and gene transfection methods as is well known in the art (Morrison, S. (1985) *Science* 229: 1202).

For example, to express antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the anti-IL-7R antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector.

Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein). Exemplary signal peptide sequences that can be used are known in the art. See, e.g., International Publication No. WO 2018/013818 A2.

In addition to the antibody chain genes, recombinant expression vectors can carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, can depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, recombinant expression vectors can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr– host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like.

Although it is theoretically possible to express the anti-IL-7R antibodies described herein in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6: 12-13).

Certain mammalian host cells for expressing the recombinant anti-IL-7R antibodies described herein include Chinese Hamster Ovary (CHO cells) (including dhfr– CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) Mol. Biol. 759:601-621), NS0 myeloma cells, COS cells and SP2 cells. In particular, for use with NS0 myeloma cells, another expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

VII. Immunoconjugates, Antibody Derivatives and Diagnostics

Anti-IL-7R antibodies described herein can be used for diagnostic purposes, including sample testing and in vivo imaging, and for this purpose the antibody (or binding fragment thereof) can be conjugated to an appropriate detectable agent, to form an immunoconjugate. For diagnostic purposes, appropriate agents are detectable labels that include radioisotopes, for whole body imaging, and radioisotopes, enzymes, fluorescent labels and other suitable antibody tags for sample testing.

The detectable labels that can be linked to any IL-7R antibody described herein can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-STAR® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

In some embodiments, conjugation methods result in linkages which are substantially (or nearly) non-immunogenic, e.g., peptide- (i.e., amide-), sulfide-, (sterically hindered), disulfide-, hydrazone-, and ether linkages. These linkages are nearly non-immunogenic and show reasonable stability within serum (see e.g., Senter, P. D., *Curr. Opin. Chem. Biol.* 13 (2009) 235-244; WO 2009/059278; WO 95/17886).

Depending on the biochemical nature of the moiety and the antibody, different conjugation strategies can be employed. In case the moiety is naturally occurring or recombinant of between 50 to 500 amino acids, there are standard procedures in text books describing the chemistry for synthesis of protein conjugates, which can be easily followed by the skilled artisan (see e.g., Hackenberger, C. P. R., and Schwarzer, D., Angew. *Chem. Int. Ed. Engl.* 47 (2008) 10030-10074). In one embodiment the reaction of a maleinimido moiety with a cysteine residue within the antibody or the moiety is used. This is an especially suited coupling chemistry in case e.g., a Fab or Fab'-fragment of an antibody is used. Alternatively, in one embodiment coupling to the C-terminal end of the antibody or moiety is performed. C-terminal modification of a protein, e.g., of a Fab-fragment, can be performed as described (Sunbul, M. and Yin, J., *Org. Biomol. Chem.* 7 (2009) 3361-3371).

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., *ChemBioChem.* 10 (2009) 425-427). It is also possible to obtain a desired amino acid modification by utilizing the specific enzymatic reactivity of certain enzymes with a natural amino acid in a given sequence context (see, e.g., Taki, M. et al., *Prot. Eng. Des. Sel.* 17 (2004) 119-126; Gautier, A. et al. *Chem. Biol.* 15 (2008) 128-136; and Protease-catalyzed formation of C—N bonds is used by Bordusa, F., Highlights in Bioorganic Chemistry (2004) 389-403). Site specific reaction and covalent coupling can also be achieved by the selective reaction of terminal amino acids with appropriate modifying reagents.

The reactivity of an N-terminal cysteine with benzonitrils (see Ren, H. et al., *Angew. Chem. Int. Ed. Engl.* 48 (2009) 9658-9662) can be used to achieve a site-specific covalent coupling.

Native chemical ligation can also rely on C-terminal cysteine residues (Taylor, E. Vogel; Imperiali, B, *Nucleic Acids and Molecular Biology* (2009), 22 (Protein Engineering), 65-96).

U.S. Pat. No. 6,437,095 B1 describes a conjugation method which is based on the faster reaction of a cysteine within a stretch of negatively charged amino acids with a cysteine located in a stretch of positively charged amino acids.

The moiety can also be a synthetic peptide or peptide mimic. In case a polypeptide is chemically synthesized, amino acids with orthogonal chemical reactivity can be incorporated during such synthesis (see e.g., de Graaf, A. J. et al., *Bioconjug. Chem.* 20 (2009) 1281-1295). Since a great variety of orthogonal functional groups is at stake and can be introduced into a synthetic peptide, conjugation of such peptide to a linker is standard chemistry.

In order to obtain a mono-labeled polypeptide, the conjugate with 1:1 stoichiometry can be separated by chromatography from other conjugation side-products. This procedure can be facilitated by using a dye labeled binding pair member and a charged linker. By using this kind of labeled and highly negatively charged binding pair member, mono conjugated polypeptides are easily separated from non-labeled polypeptides and polypeptides which carry more than one linker, since the difference in charge and molecular weight can be used for separation. The fluorescent dye can be useful for purifying the complex from un-bound components, like a labeled monovalent binder.

In one embodiment the moiety attached to an anti-IL-7R antibody is selected from the group consisting of a binding moiety, a labeling moiety, and a biologically active moiety.

Anti-IL-7R antibodies described herein can also be conjugated to a therapeutic agent to form an immunoconjugate such as an antibody-drug conjugate (ADC). Suitable therapeutic agents include antimetabolites, alkylating agents, DNA minor groove binders, DNA intercalators, DNA cross-linkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. In other embodiments, the linker is a peptidyl linker such as Val-Cit, Ala-Val, Val-Ala-Val, Lys-Lys, Pro-Val-Gly-Val-Val (SEQ ID NO: 30), Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295.

Anti-IL-7R antibodies, e.g., those described herein, can also be used for detecting IL-7Rα, such as human IL-7Rα, e.g., human IL-7Rα in tissues or tissue samples. The antibodies can be used, e.g., in an ELISA assay or in flow cytometry. In certain embodiments, an anti-IL-7R antibody is contacted with cells, e.g., cells in a tissue, for a time appropriate for specific binding to occur, and then a reagent, e.g., an antibody that detects the anti-IL-7R antibody, is added. Exemplary assays are provided in the Examples. The anti-IL-7R antibody can be a fully human antibody, or it can be a chimeric antibody, such as an antibody having human variable regions and murine constant regions or a portion thereof. Wash steps can be included after the incubation with the antibody and/or detection reagent. Anti-IL-7R antibodies for use in these methods do not have to be linked to a label or detection agents, as a separate detection agent can be used.

Other uses for anti-IL-7R antibodies, e.g., as monotherapy or combination therapy, are provided elsewhere herein, e.g., in the section pertaining to therapeutic uses.

VIII. Bispecific Molecules

Antibodies described herein can be used for forming bispecific molecules. An anti-IL-7R antibody disclosed herein can be derivatized or linked to another functional molecule, e.g., another peptide or protein (e.g., another antibody or ligand for a receptor) to generate a bispecific molecule that binds to at least two different binding sites or target molecules. Various cytokines have been described as playing an important role in the onset of many inflammatory diseases, such as in inflammatory bowel disease. Non-limiting examples of such cytokines include TNF-α, TL1α, IL-1β, IL-6, IL-18, IL-12, IL-23, IL-17, and IL-27. Sanchez-Munoz F., et al., World J Gastroenterol 14(27): 4280-4288 (2008). As described supra, regulatory T cells are also thought to be important in treating inflammatory diseases. Some of the cytokines that are known to be important in the induction of regulatory T cells include TGF-β, IL-10, and IL-2. Hoeppli R. E., et al., Front Immunol 6:61 (2015). Accordingly, the anti-IL-7R antibodies disclosed herein can be linked to an antibody that binds specifically to any of the above cytokines and thereby, regulate the onset of inflammatory diseases and/or the induction of regulatory T cells. In some embodiments, the anti-IL-7R antibodies can be linked to an antibody that treats a disease or disorder, e.g., an inflammatory disease. Non-limiting examples such antibodies include Natalizumab (TYSABRI®), Infliximab, Adalimumab, Ustekinumab, Golimumab, Tocilizumab, Vedolizumab, Secokinumab.

The antibody described herein can in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody binding portion thereof, peptide or binding mimetic, such that a bispecific molecule results.

Accordingly, provided herein are bispecific molecules comprising at least one first binding specificity for IL-7Rα and a second binding specificity for a second target epitope. In some embodiments, the bispecific molecules can further include a third binding specificity.

In some embodiments, the bispecific molecules described herein comprise as a binding specificity at least one antibody including, e.g., an Fab, Fab', F(ab')$_2$, Fv, or a single chain Fv (scFv). The antibody can also be a light chain or heavy chain dimer, or any minimal fragment thereof such as a Fv or a single chain construct as described in Ladner et al., U.S. Pat. No. 4,946,778, the contents of which is expressly incorporated by reference.

While human monoclonal antibodies are preferred, other antibodies which can be employed in the bispecific molecules described herein are murine, chimeric and humanized monoclonal antibodies.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) J. Exp. Med. 160: 1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Some conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particular embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, mAb×(scFv)$_2$, Fab×F(ab')$_2$ or ligand×Fab fusion protein. A bispecific antibody can comprise an antibody comprising an scFv at the C-terminus of each heavy chain. A bispecific molecule described herein can be a single chain molecule comprising one single chain antibody and a binding determinant, or a single chain bispecific molecule comprising two binding determinants. Bispecific molecules can comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

IX. Kits

Provided herein are kits comprising one or more anti-IL-7R antibodies described herein, or antigen-binding portions thereof, bispecific molecules, or immunoconjugates thereof. In some embodiments, provided herein is a pharmaceutical pack or kit comprising one or more containers filled with one or more of the ingredients of the pharmaceutical compositions described herein, such as one or more antibodies provided herein or an antigen-binding portion thereof, optional an instructing for use. In some embodiments, the kits contain a pharmaceutical composition described herein and any prophylactic or therapeutic agent, such as those described herein.

X. Pharmaceutical Compositions

Provided herein are compositions comprising an antibody or antigen-binding portion thereof described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

In a specific embodiment, pharmaceutical compositions comprise an antibody or antigen-binding portion thereof, a bispecific molecule, or a immunoconjugate described herein, and optionally one or more additional prophylactic or therapeutic agents, in a pharmaceutically acceptable carrier. In a specific embodiment, pharmaceutical compositions comprise an effective amount of an antibody or antigen-binding portion thereof described herein, and optionally one or more additional prophylactic of therapeutic agents, in a pharmaceutically acceptable carrier. In some embodiments, the antibody is the only active ingredient included in the pharmaceutical composition. Pharmaceutical compositions described herein can be useful in modulating (e.g., reducing or inhibiting) IL-7 activity in a T cell (e.g., pathogenic T cell) and treating a disease or disorder, such as an inflammatory disease, e.g., inflammatory bowel disease.

As used herein, "pharmaceutically acceptable carrier" includes any and all solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, can be coated in a material to protect the compound from the action of acids and other natural conditions that can inactivate the compound.

Accordingly, one object of the present disclosure is to provide a pharmaceutical formulation, which improves the stability of the anti-IL-7R antibodies and thus, allows for their long-term storage. In some embodiments, the pharmaceutical formulation disclosed herein comprises: (a) an anti-IL-7R antibody; (b) a buffering agent; (c) a stabilizing agent; (d) a salt; (e) a bulking agent; and/or (f) a surfactant. In some embodiments, the pharmaceutical formulation is stable for at least 1 month, at least 2 months, at least 3 months, at least 6 months, at least 1 year, at least 2 years, at least 3 years, at least 5 years or more. In some embodiments, the formulation is stable when stored at 4° C., 25° C., or 40° C.

Buffering Agent

Buffering agents useful for the present invention can be a weak acid or base used to maintain the acidity (pH) of a solution near a chosen value after the addition of another acid or base. Suitable buffering agents can maximize the stability of the pharmaceutical formulations by maintaining pH control of the formulation. Suitable buffering agents can also ensure physiological compatibility or optimize solubility. Rheology, viscosity and other properties can also dependent on the pH of the formulation. Common buffering agents include, but are not limited to, histidine, citrate, succinate, acetate and phosphate. In some embodiments, a buffering agent comprises histidine (e.g., L-histidine) with isotonicity agents and potentially pH adjustment with an acid or a base known in the art. In certain embodiments, the buffering agent is L-histidine. In certain embodiments, the pH of the formulation is maintained between about 2 and about 10, or between about 4 and about 8.

Stabilizing Agent

Stabilizing agents are added to a pharmaceutical product in order to stabilize that product. Such agents can stabilize proteins in a number of different ways. Common stabilizing agents include, but are not limited to, amino acids such as glycine, alanine, lysine, arginine, or threonine, carbohydrates such as glucose, sucrose, trehalose, raffinose, or maltose, polyols such as glycerol, mannitol, sorbitol, cyclodextrins or dextrans of any kind and molecular weight, or PEG. In one aspect of the invention, the stabilizing agent is chosen in order to maximize the stability of FIX polypeptide in lyophilized preparations. In certain embodiments, the stabilizing agent is sucrose and/or arginine.

Bulking Agent

Bulking agents can be added to a pharmaceutical product in order to add volume and mass to the product, thereby facilitating precise metering and handling thereof. Common bulking agents include, but are not limited to, lactose, sucrose, glucose, mannitol, sorbitol, calcium carbonate, or magnesium stearate.

Surfactant

Surfactants are amphipathic substances with lyophilic and lyophobic groups. A surfactant can be anionic, cationic, zwitterionic, or nonionic. Examples of nonionic surfactants include, but are not limited to, alkyl ethoxylate, nonylphenol ethoxylate, amine ethoxylate, polyethylene oxide, polypropylene oxide, fatty alcohols such as cetyl alcohol or oleyl alcohol, cocamide MEA, cocamide DEA, polysorbates, or dodecyl dimethylamine oxide. In some embodiments, the surfactant is polysorbate 20 or polysorbate 80.

In some embodiments, the pharmaceutical formulation of the present disclosure comprises:
(a) about 0.25 mg/mL to 250 mg/mL (e.g., 10 to 200 mg/mL) of an anti-IL-7R antibody;
(b) about 20 mM histidine;
(c) about 260 mM sucrose;
(d) about 0.5 mM DTPA; and
(e) about 0.05% Tween-80.

The formulation can further comprise one or more of a buffer system, a preservative, a tonicity agent, a chelating agent, a stabilizer and/or a surfactant, as well as various combinations thereof. The use of preservatives, isotonic agents, chelating agents, stabilizers and surfactants in pharmaceutical compositions is well-known to the skilled person. Reference may be made to Remington: The Science and Practice of Pharmacy, 19$^{th}$ edition, 1995.

In some embodiments, the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In some embodiments, the pharmaceutical formulation is a freeze-dried formulation, to which the physician or the patient adds solvents and/or diluents prior to use.

Pharmaceutical compositions described herein also can be administered in combination therapy, i.e., combined with other agents. For example, the combination therapy can include an IL-7R antibody described herein combined with at least one other therapeutic agent. Examples of therapeutic agents that can be used in combination therapy can include other compounds, drugs, and/or agents used for the treatment of a disease or disorder (e.g., an inflammatory disorder). Such compounds, drugs, and/or agents can include, for example, anti-inflammatory drugs or antibodies that block or reduce the production of inflammatory cytokines. In some embodiments, therapeutic agents can include an anti-IP-10 antibody, an anti-TNF-α antibody (e.g., adalimumab (HUMIRA®), golimumab (SIMPONI®), infliximab (REMICADE®), certolizumab pegol (CIMZIA®)), interferon beta-1a (e.g., AVONEX®, REBIF®), interferon beta-1b (e.g., BETASERON®, EXTAVIA®), glatiramer acetate (e.g., COPAXONE®, GLATOPA®), mitoxantrone (e.g., NOVANTRONE®), non-steroidal anti-inflammatory drugs (NSAIDs), analgesics, corticosteroids, and combinations thereof. In some embodiments, therapeutic agents can include compounds, drugs, and/or agents that can induce the generation of regulatory T cells (e.g., induced regulatory T cells). Non-limiting examples of such therapeutic agents include TGF-β, IL-10, IL-2, and combinations thereof.

The pharmaceutical compounds described herein can include one or more pharmaceutically acceptable salts. A "pharmaceutically acceptable salt" refers to a salt that retains the desired biological activity of the parent compound and does not impart any undesired toxicological effects (see, e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein can also include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that can be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of presence of microorganisms can be ensured both by sterilization procedures, supra, and by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition can comprise a preservative or can be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, the compositions can include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of an anti-IL-7R antibody, e.g., described herein, the dosage ranges from about 0.0001 to 100 mg/kg, and more usually 0.01 to 5 or 10 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months.

In some embodiments, the anti-IL-7R antibody is administered at a flat dose (flat dose regimen). In other embodiments, the anti-IL-7R antibody is administered at a fixed dose with another antibody. In certain embodiments, the anti-IL-7R antibody is administered at a dose based on body weight.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and until the patient shows partial or complete amelioration of symptoms of disease. Thereafter, the patient can be administered a prophylactic regime.

Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A composition described herein can be administered via one or more routes of administration using one or more of a variety of methods known in the art. As will be appreciated by the skilled artisan, the route and/or mode of administration will vary depending upon the desired results. Routes of administration for the anti-IL-7R antibodies described herein can include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein could potentially be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a particular embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use with anti-IL-7R antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

XI. Uses and Methods

The anti-IL-7R antibodies of the present disclosure and the compositions comprising such antibodies (e.g., pharmaceutical composition, formulations, polynucleotides, vectors, and cells) can be used for the treatment of an inflammatory disease (e.g., by modulating the ratio of regulatory T cells to effector T cells in a subject).

Accordingly, in one aspect, the present disclosure provides methods for treating an inflammatory disease in a subject in need thereof, comprising administering a therapeutically effective dose of an anti-IL-7R antibody to the subject. Examples of inflammatory diseases that can be treated with the present anti-IL-7R antibodies include, but not limited to, inflammatory bowel disease (IBD), Crohn's disease (CD), ulcerative colitis (UC), irritable bowel syndrome, rheumatoid arthritis (RA), psoriasis, psoriatic arthritis, systemic lupus erythematosus (SLE), lupus nephritis, type I diabetes, Grave's disease, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogren's syndrome, autoimmune nephritis, Goodpasture syndrome, chronic inflammatory demyelinating polyneuropathy, allergy, asthma and other autoimmune diseases that are a result of either acute or chronic inflammation.

In some embodiments, the anti-IL-7R antibodies are suitable for use in the treatment of individuals with inflammatory bowel disease. Inflammatory Bowel Disease (IBD) is a disease that may affect any part of the gastrointestinal tract from mouth to anus, causing a wide variety of symptoms. IBD primarily causes abdominal pain, diarrhea (which may be bloody), vomiting or weight loss, but may also cause complications outside of the gastrointestinal tract such as skin rashes, arthritis, inflammation of the eye, fatigue and lack of concentration. Patients with IBD can be divided into two major classes, those with ulcerative colitis (UC) and those with Crohn's disease (CD). CD generally involves the ileum and colon, but it can affect any region of the intestine and is often discontinuous (focused areas of disease spread throughout the intestine). UC always involves the rectum (colonic) and is more continuous. In CD, the inflammation is transmural, resulting in abscesses, fistulas and strictures, whereas in UC, the inflammation is typically confined to the mucosa. There is no known pharmaceutical or surgical cure for Crohn's disease, whereas some patients with UC can be cured by surgical removal of the colon. Treatment options are restricted to controlling symptoms, maintaining remission and preventing relapse. Efficacy in inflammatory bowel disease in the clinic may be measured as a reduction in the Crohn's Disease Activity Index (CDAI) score for CD which is scoring scale based on laboratory tests and a quality of life questionnaire. In animal models, efficacy is mostly measured by increase in weight and also a disease activity index (DAI), which is a combination of stool consistency, weight and blood in stool.

In some embodiments, the anti-IL-7R antibodies of the present disclosure are suitable for use in the treatment of individuals with rheumatoid arthritis. Rheumatoid arthritis (RA) is a systemic disease that affects nearly if not all of the body and is one of the most common forms of arthritis. It is characterized by inflammation of the joint, which causes pain, stiffness, warmth, redness and swelling. This inflammation is a consequence of inflammatory cells invading the joints, and these inflammatory cells release enzymes that may digest bone and cartilage. As a result, this inflammation can lead to severe bone and cartilage damage and to joint deterioration and severe pain, among other physiologic effects. The involved joint can lose its shape and alignment, resulting in pain and loss of movement. There are several animal models for rheumatoid arthritis known in the art. For example, in the collagen-induced arthritis (CIA) model, mice develop an inflammatory arthritis that resembles human rheumatoid arthritis. Since CIA shares similar immunological and pathological features with RA, this makes it a suitable model for screening potential human anti-inflammatory compounds. Efficacy in this model is measured by decrease in joint swelling. Efficacy in RA in the clinic is measured by the ability to reduce symptoms in patients which is measured as a combination of joint swelling, erythrocyte sedimentation rate, C-reactive protein levels and levels of serum factors, such as anti-citrullinated protein antibodies.

In some embodiments, the anti-IL-7R antibodies as disclosed herein are suitable for use in the treatment of individuals with psoriasis. Psoriasis is a T-cell mediated inflammatory disorder of the skin that can cause considerable discomfort. It is a disease for which there is currently no cure and it affects people of all ages. Although individuals with mild psoriasis can often control their disease with topical agents, more than one million patients worldwide require ultraviolet light treatments or systemic immunosuppressive therapy. Unfortunately, the inconvenience and risks of ultraviolet radiation and the toxicities of many therapies limit their long-term use. Moreover, patients usually have recurrence of psoriasis, and in some cases rebound shortly after stopping immunosuppressive therapy. A recently developed model of psoriasis based on the transfer of CD4+ T cells mimics many aspects of human psoriasis and therefore can be used to identify compounds suitable for use in treatment of psoriasis (Davenport et al., *Internat. Immunopharmacol* 2: 653-672, 2002). Efficacy in this model is measured by reduction in skin pathology using a scoring system. Similarly, efficacy in patients is measured by a decrease in skin pathology.

In some embodiments, the anti-IL-7R antibodies are suitable for use in the treatment of individuals with psoriatic arthritis. Psoriatic arthritis (PA) is a type of inflammatory arthritis that occurs in a subset of patients with psoriasis. In these patients, the skin pathology/symptoms are accompanied by a joint swelling similar to that seen in rheumatoid arthritis. It features patchy, raised, red areas of skin inflammation with scaling. Psoriasis often affects the tips of the elbows and knees, the scalp, the navel and around the genital areas or anus. Approximately 10% of patients who have psoriasis also develop an associated inflammation of their joints.

In terms of the present disclosure, prophylactic, palliative, symptomatic and/or curative treatments may represent separate aspects of the disclosure. An antibody of the invention can be administered parenterally, such as intravenously, such as intramuscularly, such as subcutaneously. Alternatively, an antibody of the invention can be administered via a non-parenteral route, such as orally or topically. An antibody of the invention can be administered prophylactically. An antibody of the invention can be administered therapeutically (on demand).

All of the references cited above, as well as all references cited herein, are incorporated herein by reference in their entireties.

The following examples are offered by way of illustration and not by way of limitation.

EXAMPLES

Example 1: Characterization of the Human Anti-IL-7R Antibody

An anti-IL-7R antibody disclosed herein (comprising VH as set forth in SEQ ID NO: 19 and VL as set forth in SEQ ID NO: 20, see Table 12) ("Antibody A") was assayed for binding to IL-7Rα-expressing cells. IL-7Rα is expressed primarily on human T cells and to a lesser extent on monocytes.

As shown in Table 1 (below), Antibody A was able to bind IL-7Rα expressed on various subsets of T cells (CD4+CD45RA+, CD4+CD45RA−, CD8−CD45RA+, and CD8+CD45RA−) from whole blood ($EC_{50}$ value ranging from about 1.4 to 3.3 nM). Moreover, Antibody A did not agonize IL-7Rα signaling (see Table 2) and was able to efficiently block IL-7 from binding to the IL-7Rα expressed on CD4−CD45RA+ T cells (as measured by pSTAT5 activation). Compared to a reference anti-IL-7R antibody ("PFE A3312F"), Antibody A was much more potent in blocking the IL-7 binding to IL-7Rα. When CD4+CD45RA+ T cells from whole blood were stimulated with IL-7 (e.g., 2.0 ng/mL) in the presence of Antibody A, there was minimal pSTAT5 activation (IC50=2.1±1.4 nM). In contrast, with PFE A3312F, pSTAT5 activation was significantly higher (IC50=15.8±4.0).

TABLE 1

In vitro properties of Antibody A compared to a reference anti-IL-7R monoclonal antibody (PFE A3312F)

| Cell Type | Subsets | Assay | Stimuli | Anti-IL-7R Antibody | PFE A3312F |
|---|---|---|---|---|---|
| T cells (Whole Blood) | CD4+CD45RA+ | Binding EC50 nM | — | 1.4 ± 0.7 | 1.5 ± 0.5 |
|  | CD4+CD45RA− |  |  | 3.3 ± 1.6 | 3.1 ± 0.9 |
|  | CD8+CD45RA+ |  |  | 2.0 ± 0.9 | 1.7 ± 0.4 |
|  | CD8+CD45RA− |  |  | 1.9 ± 1.4 | 2.7 ± 0.8 |
| T cells (Whole Blood) | CD4+CD45RA+ | pSTAT5 IC50 (nM) | IL-7 (0.25 ng/mL) | 0.6 ± 0.7 | 1.0 ± 0.9 |
|  | CD4+CD45RA+ |  | IL-7 (2.0 ng/mL) | 2.1 ± 1.4 | 15.8 ± 4.0 |
| Monocytes | Purified | MCP1 Production IC50 (nM) | TSLP | 24 ± 4.5 | 0.08 ± 0.3 |

Antibody A also differed from the reference antibody in its ability to block TSLP-mediated activation of monocytes. As shown in Table 1 (last row), monocytes that were stimulated with TSLP in the presence of PFE A3312F failed to produce monocyte chemoattractant protein-1 (MCP-1) (IC50=0.08±0.3 nM), suggesting that PFE A3312F was able to bind to IL-7Rα expressed on the monocytes and effectively block the binding of TSLP to IL-7Rα. In contrast, with Antibody A, the TSLP-stimulated monocytes produced significantly higher amounts of MCP1 (IC50=24±4.5).

Next, to assess whether the inability to block TSLP-stimulated activation of monocyte was due to binding issues, whole blood from human donors were incubated with varying concentrations of Antibody A. Then, the mean fluorescence intensity (MFI) of the binding of Antibody A to IL-7Rα expressed on non-T cells (CD3) was measured using flow cytometry. As shown in FIG. 1, even at concentrations as high as 70 nM, there was minimal binding of Antibody A to the non-T cells.

Collectively, the above data indicate that, compare to other known antibodies (PFE A3312F), the anti-IL-7R antibody disclosed herein (Antibody A) is more potent at blocking IL-7 binding and is selective for IL-7Rα expressed on T cells but not on non-T cells (e.g., monocytes and other CD3⁻ cells in whole blood).

Example 2: Analysis of the Agonistic Activity of the Anti-IL-7R Antibody

Next, to assess whether the binding of the anti-IL-7R antibody can induce IL-7Rα signaling, peripheral blood mononuclear cells (PBMCs) and whole blood were incubated with different concentrations of Antibody A (100, 50, 25, 13, 6, 3, 2, 1, and 0 nM). An isotype control antibody and IL-7 (2 nM) were used as negative and positive controls, respectively.

As shown in Table 2, at all concentrations tested, Antibody A did not induce pSTAT5 activation, as compared to the negative control. This result demonstrates that Antibody A does not agonize signaling upon binding to IL-7Rα.

TABLE 2

In vitro agonistic activity on human PBMCs and human whole blood as assessed using pSTAT5 activation

| | PBMCs | | | | | |
|---|---|---|---|---|---|---|
| | d355 + BMS DR alone | | d173 + BMS DR alone | | d341 + BMS DR alone | |
| Anti-IL-7R antibody (Antibody A) (nM) | Anti-IL-7R antibody alone (pSTAT5 activation) | % of control | Anti-IL-7R antibody alone (pSTAT5 activation) | % of control | Anti-IL-7R antibody alone (pSTAT5 activation) | % of control |
| 100 | 786 | 2 | 1836 | 6 | 1083 | 2 |
| 50 | 868 | 2 | 915 | 0 | 1386 | 3 |
| 25 | 894 | 3 | 1072 | 1 | 1333 | 3 |
| 13 | 1038 | 4 | 1060 | 1 | 1373 | 3 |
| 6 | 941 | 3 | 1031 | 1 | 1476 | 4 |
| 3 | 938 | 3 | 1467 | 4 | 1711 | 5 |
| 2 | 896 | 3 | 1075 | 1 | 1582 | 4 |
| 1 | 1174 | 5 | 1467 | 4 | 1787 | 5 |
| 0 | 597 | 0 | 841 | 0 | 797 | 0 |
| Isotype ctrl | 934 | 3 | 1174 | 2 | 1325 | 3 |
| 2 nM IL-7 stim | 11520 | 100 | 16575 | 100 | 19406 | 100 |

| | Whole Blood | | | | | |
|---|---|---|---|---|---|---|
| | d232 + BMS DR alone | | d331 + BMS DR alone | | d344 + BMS DR alone | |
| Anti-IL-7R antibody (Antibody A) (nM) | Anti-IL-7R antibody alone (pSTAT5 activation) | % of control | Anti-IL-7R antibody alone (pSTAT5 activation) | % of control | Anti-IL-7R antibody alone (pSTAT5 activation) | % of control |
| 100 | 14704 | −4 | 1055 | −10 | 8328 | −20 |
| 50 | 17982 | 0 | 1001 | −15 | 9524 | −9 |
| 25 | 16463 | −2 | 1140 | −3 | 11526 | 10 |
| 13 | 15041 | −4 | 1031 | −12 | 11212 | 7 |
| 6 | 19004 | 1 | 976 | −17 | 10891 | 4 |
| 3 | 15281 | −4 | 958 | −19 | 9132 | −13 |
| 2 | 21046 | 3 | 1016 | −14 | 14779 | 41 |
| 1 | 17489 | −1 | 1045 | −11 | 10224 | −2 |
| 0 | 18350 | 0 | 1178 | 0 | 10459 | 0 |
| Isotype ctrl | 18648 | 0 | 952 | −19 | 14024 | 34 |
| 2 nM IL-7 stim | 85984 | 100 | 7371 | 526 | 33102 | 216 |

Example 3: Cross-Reactivity of the Anti-IL-7R Antibody in Cynomolgus Monkey

To assess the cross-reactivity of Antibody A, the binding affinity to human and cyno IL-7Rα was assessed using Surface Plasmon Resonance (SPR). Briefly, experiments were performed on a BIACORE™ T200 instrument (GE Healthcare, Chicago, Ill., USA) in a running buffer consisting of 10 mM NaPO4, 130 mM NaCl, 0.05% p20 (PBS-T) at either pH 7.4 or pH 6.0. The chip surface was prepared by immobilizing protein A on flow cell 1, 2, 3, and 4 of a CM5 sensor chip using ethyl(dimethylaminopropyl) carbodiimide/NHS to a density of 4000 RU. Antibody A was captured using a contact time of 30 seconds at 10 µl/min. Purified extracellular domain constructs (generated in house) of his-tagged human-IL7R or cynomolgus-IL7R were tested for binding using a 2 fold serial dilution from 500 nM to 7.8 nM, with 180 s association time and 360 s dissociation time at 30 µl/min. Regeneration between cycles was accomplished using 2×30 second injections of 10 mM glycine-HCL pH 1.5. The data were analyzed using the Biacore T200 Evaluation software (GE Healthcare), and fit to a 1:1 Langmuir model.

As shown in Table 3, Antibody A was able to bind to both human and cyno IL-7Rα with similar affinity. For instance, at pH 7.4, Antibody A bound to human and cyno IL-7Rα with KD values of 1.3 nM and 1.7 nM, respectively. At pH 6.0, binding was approximately 4-fold weaker, suggesting that the binding of anti-IL-7R to both human and cyno IL-7Rα is pH dependent. In contrast, PFE A3312F did not demonstrate pH-dependent binding, with KD values of 4.4 nM at pH 7.4 and 3.9 nM at pH 6.0. SPR analysis also demonstrated very weak binding to all human and cyno FcγRs at neural pH, and stronger binding at pH 6.0, as expected for hIgG1.3f isotype.

TABLE 3

Binding affinity of anti-IL-7R antibody (Antibody A) to human and cyno IL-7Rα

| Target | Temperature | pH | ka (1/Ms) | kd (1/s) | KD (nM) |
|---|---|---|---|---|---|
| human IL-7Rα | 37° C. | 7.4 | 3.1E+05 | 4.0E−04 | 1.3 |
|  |  | 6.0 | 2.4E+05 | 1.3E−03 | 5.3 |
| cyno IL-7Rα | 37° C. | 7.4 | 2.9E+05 | 5.0E−04 | 1.7 |
|  |  | 6.0 | 2.3E+05 | 1.6E−03 | 7.0 |

To confirm the above cross-reactivity data, cellular binding and functional blockade were also assessed. Briefly, a single dose (0.1, 0.5, or 3.0 mg/kg) of Antibody A was administered to cynomolgus monkeys. Then, at day 8 post-administration, PBMCs were isolated from the animals. To measure the ability to block IL-7 binding to cyno IL-7Rα, the PBMCs were stimulated with recombinant cyno IL-7 (5 pM) for 15 minutes and pSTAT5 activity and receptor occupancy on CD4$^+$ T cells were assessed using flow cytometry.

As shown in FIG. 2A, at a serum anti-IL-7R antibody concentration of about 310-350 ng/mL (~2.1-2.3 nM), greater than 95% of the IL-7Rα expressed on the cyno CD4$^+$ T cells were occupied. Similarly, as shown in FIG. 2B, there was a direct inverse correlation between serum anti-IL-7R antibody concentration and pSTAT5 activity. At serum concentration of between 670-2200 ng/mL (4.5-15 nM), there was greater than 90% STAT5 inhibition. Based on these results, trough concentrations of approximately 2-15 nM would be required to fully block the IL-7Rα in vivo.

The above data, collectively, demonstrate that the anti-IL-7R antibody disclosed herein (Antibody A) is fully cross-reactive in cynomolgus monkeys and can effectively bind to and block IL-7-induced signaling of cyno IL-7Rα.

Example 4: Additional Characteristics of the Anti-IL-7R Antibody

Analytical and biophysical characteristics of Antibody A are provided in Table 4.

The analytical and biophysical properties of Antibody A were favorable for continued development. The identity of the antibody was confirmed by mass spectrometry analysis (Intact Mass Analysis & Peptide Mapping). The antibody was >99% monomeric as tested by analytical size exclusion chromatography. A single N glycosylation site was confirmed at N297 on the heavy chain with a glycan profile matching the glycan profile of CHO-expressed monoclonal antibodies (G0F, G1F & G2F). Charge variant profile as determined by imaged capillary isoelectric focusing showed a pI for the main peak at 8.5 (60%) with 34% acidic and 6% basic variants. Thermal stability (Tm1=70.0° C., Tm2=75.4° C., Tm3=84.2° C.) was within the range for a typical human IgG1.3f monoclonal antibody.

TABLE 4

Analytical and biophysical characteristics of the anti-IL-7R antibody

| Property | Method | Results |
|---|---|---|
| Identity | LC-MS | Intact Mass confirmed |
|  | LC-MS/MS peptide map | Sequence confirmed by tryptic peptide map with 100% coverage of heavy chain and light chain. Glycosylation occupancy of 99.8%) |
| Purity/Homogeneity | SEC | 99.6% monomer, 0.4% HMW |
|  | SEC-MALS | Expected monomer mass |
|  | LC-MS | 56% G0F, 40% G1F, and 4% G2F observed on heavy chain. |
|  | cIEF | Main Peak pI = 8.53 (59.8%); Acidic variants = 34.4%; Basic variants = 5.8% |
|  | SDS-PAGE | Reduced: 2 predominant bands of ~50 kDa & ~25 kDa Non-Reduced: Predominant band of ~150 kDa with minor fragments of ~100 kDa, ~25 kDa (artifacts of SDS-running conditions) |
| Thermal Stability | DSC | Tm1 = 70.0° C., Tm2 = 75.4° C., Tm3 = 84.2° C. |

Stability characteristics of Antibody A are provided in Table 5.

TABLE 5

Stability of the anti-IL-7R antibody (Antibody A)

| Property | Method(s) | Results |
| --- | --- | --- |
| Freeze/Thaw (2 h @ −80° C., 4 h @ RT × 3) | UV, SEC, DLS, iCIEF | No freeze/thaw stability risk revealed |
| Solubility/Concentration Profile | UV, SEC | At least 150 mg/mL in platform formulation buffer (20 mM histidine, 260 mM sucrose, 0.05 mM DTPA, 0.05% Tween-80, pH 6.0) |
| pH Screen for Conformational and Colloidal Stability | Optim2 (Tm and Tagg onset) | Optimal conformational stability = pH 6-8 Optimal colloidal stability = pH 5-6 |
| Buffer and Excipient Screening | Optim2 (Tm and Tagg onset) | Stabilizers: sucrose, sorbitol, glycerol |
| Accelerated Stability 150 mg/mL 12 w @ 4° C., 25° C., and 40° C. in truncated platform formulation (20 mM histidine, 260 mM sucrose, 0.05 mM DTPA, 0.05% Tween-80, pH 6.0) | SEC, cIEF, HIC, LC-MS/MS (peptide mapping and intact mass), Biacore, bioassay, UV-Vis, DLS | 12 w @ 40° C. = no changes in HMW or LMW observed 12 w @ 25° C. = <0.1%/month increase in HMW 0.3%/month increase in LMW 12 w @ 40° C. = ~1%/month increase in HMW ~1.3%/month increase in LMW No increase in Rh, or Pd noted 12 w @ 40° C. = 5.5%/month N54 deamidation in HC CDR2, 3.4%/month D30/31 deamidation in HC CDR1, 10%/month VSNK deamidation |
| Agitation Stability Study (Conducted at 150 mg/mL) | 350 rpm @ RT in formulation buffer ± 0.05% PS80 for 7 days | No agitation-induced HMW formation observed |
| Viscosity Assessment | Determine concentration-viscosity profile | Solution reached 8 cP at 100 mg/mL, and 18.8 cP at 140 mg/mL. Viscosity was predicted to limit syringeable formulation concentration to ~125 mg/mL |

A preliminary formulation evaluation, including search for optimal pH, buffer composition, and excipients, and an accelerated stability study was performed for the anti-IL-7R antibody disclosed herein using HEK derived material. No physical stability issues were observed during freeze thaw stress (5 cycles) in a truncated platform formulation (20 mM histidine, 260 mM sucrose, 0.05 mM DTPA, pH 6.0), or due to agitation stresses, with or without surfactant, at 150 mg/mL. Addition of a surfactant was not assessed during these investigations. Forced degradation studies at 150 mg/mL were set up at 4, 25 and 40° C. Chemical modifications in the CDR region were observed under the highest stress condition (3 months at 40° C.), which correlated with changes in both KD and Rmax in an SPR activity assay. Minor chemical changes were observed at the same CDR sites under storage at 25° C. storage. No changed were observed in the activity of samples stored at 4 or 25° C. Expected VSNK deamidation changes were also observed.

The feasibility evaluations performed using HEK-derived material also demonstrated time and temperature dependent changes in both HMW and LMW variants (increases of ~1%/month and ~1.3%/month, respectively at 40° C.). HMW remained unchanged under storage at 4° C., while increasing 0.3%/month at 25° C. The LMW formation observed under storage at 40° C. was characterized by accurate mass as the cumulative species of 1 Fab loss, as well as the Fab arm, putatively the result of chemical clipping at a conserved sequence in the upper hinge region. Changes in HMW and LMW from these HEK-derived studies are within expectations for an IgG1.3 mAb and support molecule progression.

The viscosity limitation for Antibody A was noted as a liability in early lead optimization. The viscosity-concentration profile measured during the course of the formulation assessments demonstrated 8 cP viscosity at 100 mg/mL, and ~19 cP at 140 mg/mL. Based on the viscosity profile of Antibody A, it was estimated that ~125 mg/mL concentration would be the upper limit of what would be syringeable using a conventional device.

Example 5: Pharmacokinetics (PK) of the Anti-IL-7R Antibody in NOD Scid Gamma (NSG)-Human PBMC Transfer Mice As Antibody A does not cross-react with the mouse IL-7Rα the NSG-human PBMC transfer mice enabled the evaluation of the influence of target mediated clearance on PK. Additionally, Antibody A was shown to exhibit differential pH-dependent binding affinity to IL-7Rα, e.g., relative to PFE A3312F (see Example 3). For mAbs exhibiting short half-life due to target mediated clearance, pH-dependent antigen binding was demonstrated to result in an improved PK profile. See Igawa T., et al., Nat Biotechnol 28(11): 1203-7 (2010). Therefore, this model was also used to evaluate if pH-dependent target binding would translate to improved pharmacokinetics.

Briefly, the NSG-human PBMC transfer mice received a single administration of Antibody A or the reference PFE A3312F antibody. The mice received one of two doses intravenously: 0.5 mg/kg or 5 mg/kg. Then, the mice were bled at various time points post-administration, and the serum antibody concentration was determined. As shown in FIG. 3, the PK of PFE A3312F was nonlinear, as the blood clearance (CL) decreased by 5.7-fold between 0.5 and 5 mg/kg doses (see Table 6), presumably due to target mediated drug disposition (TMDD). While the PK of Antibody A at 5 mg/kg was similar to PFE A3312F, a significant improvement in exposure was observed at the lower dose (0.5 mg/kg). Not to be bound by any one theory, as target mediated drug clearance is generally more apparent at a lower dose range, the improved PK observed at the lower dose was postulated to be due to differential pH-dependent binding affinity of the anti-IL-7R antibody to IL-7Rα.

TABLE 6

Pharmacokinetic parameters following a single IV dose in NSG-human PBMC transfer mice

|  | Anti-IL-7R Antibody (Antibody A) | | PFE A3312F | |
| --- | --- | --- | --- | --- |
| IV Dose (mg/kg) | 0.5 | 5.0 | 0.5 | 5.0 |
| N (number of mice) | 6 | 6 | 5 | 5 |
| AUClast (μM*h) | 4.1 | 51.2 | 0.7 | 49.6 |
| $T_{1/2}$ (h) | 38 | 54 | 56 | 39 |
| CL (mL/h/kg) | 0.8 | 0.6 | 4.0 | 0.7 |

Example 6: Pharmacokinetics (PK) of the Anti-IL-7R Antibody in Cynomolgus Monkeys To further assess the PK of Antibody A, cynomolgus monkeys received a single dose of Antibody A or the reference PFE A3312F antibody at one of the following doses: 0.1 mg/kg, 0.5 mg/kg, or 3 mg/kg intravenously. Then, the animals were bled at various time points post-administration, and the in vivo potency (PK, RO, and ex vivo pSTAT5 activation) of the antibodies were compared.

As shown in FIG. 4, in animals that received ≥0.5 mg/kg of either of the antibodies, anti-drug antibodies (ADA) (dotted line) were detected on and after day 10, resulting in lower antibody serum concentrations (solid line) in the animals. As shown in FIG. 5, the pharmacokinetics of Antibody A and PFE A3312F were non-linear at the tested doses, suggesting TMDD. However, as shown in Table 7, the mean exposures (AUCs) of Antibody A were higher (1.6 to 2.1-fold) relative to PFE A3312F. Similarly, the clearance values of Antibody A were also higher: at doses of 0.1, 0.5 and 3 mg/kg, the values were 1.15±0.20, 0.64±0.10 and 0.44±0.02 mL/h/kg, respectively, while those of A3312F were 1.76±0.22, 1.16±0.39 and 0.94±0.12 mL/h/kg, respectively (Table 7).

During the 3-week evaluation period, there were no anti-IL-7R antibody-related clinical observations or adverse effects on body weight, hematology (with WBC differential), serum clinical chemistry or T/B/NK cell phenotyping ($CD4^+$ and $CD8^+$ shown in FIGS. 7A-7C).

The above results suggest that compared to the reference antibody, the anti-IL-7R antibody disclosed herein (Antibody A) has similar in vivo potency but exhibits improved pharmacokinetics in cynomolgus monkeys with minimal toxicity issues.

Example 7: Analysis of the Immunogenicity of the Anti-IL-7R Antibody

The potential immunogenicity risk of Antibody A was evaluated by in silico methods as well as by in vitro DC:T cell proliferation assays. The in silico iDAB analysis showed some binding potential for the VL CDR3 and a framework mutation at position 71 of the VH from a serine to a phenylalanine (F71S). The in vitro DC:T cell proliferation assay, which consisted of 40 PBMC donors incubated with dendritic cells pulsed with Antibody A, showed significant immunogenic responses (~30-50% of the donors) for the non-RACIR batches of Antibody A (see P1-066930-3 and P1-066930-9 in FIG. 8). Interestingly, these results correlated with the observed severity of ADA in the earlier described monkey studies (see, e.g., Example 6). The RACIR batch of Antibody A had minimal immunogenicity in the donors (~12.5%), comparable to the control protein (Avastin). Given the low response for the RACIR material in the assay, it was predicted that Antibody A would be safe to use in clinic, e.g., to treat an inflammatory disease disclosed herein.

Example 8: Analysis of the Ability of the Anti-IL-7R Antibody to Block IL-7 Signaling in Human T Cells To further assess the ability of Antibody A to inhibit the binding of IL-7 to IL-7Rα, peripheral blood from healthy volunteers (NHV), ulcerative colitis (UC) patients, and Crohn's disease (CD) patients were acquired. Then, the PBCMs were incubated ex vivo and stimulated with IL-7 in

TABLE 7

Pharmacokinetic parameters following a single IV dose in NSG-human PBMC transfer mice

|  | Anti-IL-7R Antibody (Antibody A) | | | PFE A3312F | | |
| --- | --- | --- | --- | --- | --- | --- |
| IV Dose (mg/kg) | 0.1 | 0.5 | 3 | 0.1 | 0.5 | 3 |
| N (number of mice) | 3 | 3 | 3 | 3 | 3 | 3 |
| AUClast (μM * h) | 0.6 ± 1 | 5.3 ± 0.8 | 46.4 ± 2.4 | 0.4 ± 0.1 | 3.1 ± 1.1 | 21.8 ± 2.7 |
| CL (mL/h/kg) | 1.15 ± 0.20 | 0.64 ± 0.10 | 0.44 ± 0.02 | 1.76 ± 0.22 | 1.16 ± 0.39 | 0.94 ± 0.12 |
| Vss (mL/kg) | 39 ± 1 | 42 ± 0 | 41 ± 1 | 41 ± 0 | 48 ± 1 | 49 ± 1 |

There was a good correlation between pSTAT5 inhibition and serum concentration of Antibody A in the cynomolgus monkeys. See FIG. 6. With increased exposure to Antibody A (as evidenced by increase in serum antibody concentration), there was a corresponding decrease in IL-7 mediated pSTAT5 activation. This was true in both monkeys that received the present anti-IL-7R antibody or PFE A3312 (IC50=~2 nm).

the presence of Antibody A for approximately 15 minutes. Afterwards, pSTAT5 activity in the T cells was analyzed using flow cytometry.

As shown in Table 8, there was minimal pSTAT5 activity in the T cells from all individuals tested, suggesting that Antibody A can effectively block the binding of IL-7 to human IL-7Rα from both healthy and disease patients. No statistical differences were observed between the NHV and UC or CD donor responses. This result shows that the anti-IL-7R antibody disclosed herein (Antibody A) could be efficacious in treating inflammatory diseases in vivo by effectively blocking IL-7 signaling in pathogenic T cells.

TABLE 8

Pharmacokinetic parameters following a single IV dose in NSG-human PBMC transfer mice

| $IC_{50}$ (nM) | CD4+CD45RA+ | CD4+CD45RA− | CD8+CD45RA+[a] | CD8+CD45RA−[b] |
|---|---|---|---|---|
| NHV (n = 19) | 0.60 ± 0.3 | 0.52 ± 0.3 | 0.43 ± 0.29 | 0.38 ± 0.30 |
| UC (n = 21) | 0.34 ± 0.2 | 0.28 ± 0.2 | 0.29 ± 0.40 | 0.22 ± 0.18 |
| CD (n = 10) | 0.36 ± 0.3 | 0.36 ± 0.4 | 0.29 ± 0.22 | 0.23 ± 0.30 |

[a], [b]IC50 were calculated only when CD8 T cells responded to IL-7

Example 9: Epitope Mapping Analysis

Hydrogen/deuterium exchange mass spectrometry (HDX-MS), in combination with orthogonal covalent labeling footprinting techniques, such as fast photochemical oxidation of proteins (FPOP) and glycine ethyl ester labeling (GEE) were utilized to probe binding epitopes of hIL7Rα upon interaction with Antibody A.

HDX-MX

Prior to epitope mapping experiments, non-deuterated experiments were carried out to generate a list of common peptides for recombinant human hIL7Rα (10 μM), generated in house, and protein complexes of hIL7Rα with Fab of Antibody A (1:1 molar ratio). The samples were injected into Waters Enzymate BEH pepsin enzyme column (2.1×30 mm), and digested for 3 min at 15° C. The cooling chamber of the UPLC system, which housed all the chromatographic elements, was held at 0.0±0.1° C. for the entire time of the measurements. The injected peptides were trapped and desalted for 3 min at 40 μL/min and then separated in 6 min by a 5-40% acetonitrile-water gradient at 65 μL/min. The separation column was a 1.0 mm×100.0 mm ACQUITY UPLC BEH C18 column (Waters) containing 1.7-μm particles and the back pressure averaged 8500 psi at 0.1° C. Xevo G2 mass spectrometer was used for data acquisition. The instrument configuration was as follows: capillary voltage 3.2 kV, trap collision energy 6 V, sampling cone voltage 35 V, source temperature 80° C. and desolvation temperature 175° C. Mass spectra were acquired over an m/z range of 100 to 1900. Mass accuracy was ensured by calibration with 500 nM [Glu1]-fibrinopeptide B, and was less than 10 ppm throughout all experiments. Identification of the peptic peptides was accomplished through a combination of exact mass analysis and MSE using ProteinLynx Global SERVER 2.5 (Waters).

In the HDX-MS experiments, 5 μL of each sample (hIL7Rα or hIL7Rα with Fab of Antibody A, respectively) was diluted into 55 μL of $D_2O$ buffer (10 mM phosphate buffer, $D_2O$, pH 7.0) to start the labeling reactions. The reactions were carried out for different periods of time: 1 min, 10 min and 240 min. By the end of each labeling reaction period, the reaction was quenched by adding quenching buffer (100 mM phosphate buffer with 4M GdnCl and 0.4M TCEP, pH 2.5, 1:1, v/v). 50 μL of quenched sample was digested online using exact same conditions as in non-deuterated experiments. All comparison experiments were performed under identical experimental conditions such that deuterium levels were not corrected for back exchange and are therefore reported as relative. All experiments were performed in duplicate. The error of measuring the mass of each peptide was ±0.20 Da in this experimental setup, consistent with previously obtained values. Deuterium uptake was calculated by subtraction of the centroid of the isotopic distribution for peptide ions from undeuterated protein from the centroid of the isotopic distribution for peptide ions from the deuterium-labeled sample. The resulting relative deuterium levels were plotted versus the exchange time with use of the software program DYNAMX 3.0™ (Waters).

FFOP

FPOP experiments were performed on hIL7Rα and hIL7Rα/Fab (Antibody A)complex (1:1 molar ratio, 10 μM final concentration). A KrF excimer laser was used to generate hydroxyl radicals by the photolysis of $H_2O_2$, and the excitation wavelength was set to be 248 nm. Immediate before labeling, 5 μL of histidine and $H_2O_2$ each was added to a protein aliquot. The final volume of protein solution was 50 μL, and the final concentrations of histidine, and $H_2O_2$ were 500 μM and 15 mM, respectively. The laser energy was adjusted to 28 mJ/pulse (7.4 Hz). Both FPOP and no laser control experiments were performed in triplicates. Each replicate was collected in a micro-centrifuge tube containing 11 μL of quenching solution (800 nM of catalase tetramer and 200 mM of methionine). The samples were denatured, reduced, alkylated and digested with chymotrypsin. Data acquisition was performed on Thermo Q Exactive Plus mass spectrometer with Waters Acquity UPLC system. Byonic search engine was used to provide sequencing coverage and identify oxidation sites. Relative oxidation levels for tryptic peptides were calculated using Byologic software (Protein Metrics, San Carlos, Calif.). Only peptides with statistically significant difference in relative oxidation between free and bound state (based on student T-test p value<0.01) were considered for further analysis. Residue level analysis was done with Byologic software and manually verified for each replicate. Only residues with statistically significant difference in oxidation between hIL7Rα free and hIL7Rα/Fab-Antibody A (based on student T-test p value<0.01) were considered protected residues.

GEE Labeling

GEE labeling was initiated by mixing 10 μL of each sample (hPAI1 or hPAI1 with mAb at 1 mg/mL) with 1 μL of 2 M GEE and 1 μL of 50 mM 1-ethyl-3-(3-dimethylaminopropyl) carbodiimide (EDC) at room temperature for 1 min. The reaction was quenched by adding 10 μL of 1 M ammonium acetate to sample. 17.5 μL of each GEE labeled sample was subjected to enzymatic digestion. The sample was denatured in the presence of 0.5% Rapigest surfactant, reduced by DTT at 56° C. for 30 min, alkylated by IAM at room temp for 30 min in dark, and digested by chymotrypsin at 37° C. for overnight in Tris pH 7.4 followed by acidic quench. The digested samples were analyzed on Thermo Q Exactive Plus mass spectrometry and the GEE modification levels were monitored on hIL7Rα in the absence/presence of Antibody A.

Results

As shown in FIG. 9, sequence coverage of 97.3% of hIL7R was obtained using HDX-MS analysis. The analysis revealed the following discontinuous epitopes, which cover four distinct regions within the hIL7R: (i) Region 1: $^{24}$SQLEVNGSQHSLTCAF$^{39}$; (ii) Region 2: $^{73}$FIETKKFLLIGKSNIC$^{88}$, $^{89}$VKVGEKSLTCKKIDLTT$^{105}$; (iii) Region 3: $^{136}$QKKYVKVLMHDVAY$^{149}$; and (iv) Region 4: $^{181}$YEIKVRSIPDHYFKGF$^{196}$. Based on the relative deuterium uptake differences, the peptide regions can be ranked as region 1>2, 3, 4, with region 1 having the most significant change in deuterium uptake (FIG. 10).

With the FPOP analysis, the following five epitopes of the hIL7R were identified: (i) Region 1: $^{24}$SQLEVNGSQHS$^{35}$; (ii) Region 2: $^{73}$FIETKKF$^{79}$ and $^{80}$LLIGKSNICVKVGEKSL$^{95}$; (iii) Region 3: $^{144}$MHDVAY$^{149}$; and (iv) Region 4: $^{182}$EIKVRSIPDHYFKGF$^{193}$. These epitopes overlapped with the discontinuous regions identified above using the HDX-MS analysis. Also, as shown in Table 9, the identified epitopes also exhibited decrease in oxidation levels in comparison with the controls. The most protected residues were identified as follows: (i) Region 1: H33; (ii) Region 2: F79, I82, and K84; (iii) Region 3: M144; and (iv) Region 4: R186, H191, and Y192.

TABLE 9

Residue level extend of oxidation after FPOP for chymotryptic peptides of hIL7Rα

| Peptide | 24SQLEVDGSQHSL35 | 73FIETKKF79 | | 80LLIGKSNICVKVGEKSL96 | | 144MHDVAY149 | | | 182EIKVRSIPDHYF193 | |
|---|---|---|---|---|---|---|---|---|---|---|
| AA Residue No | H33 | F73 | F79 | I82 | K84 | M144 | H145 | Y149 | R186 | H191 | Y192 |
| % Oxidation IL7R | 0.13 | 1.40 | 0.83 | 3.35 | 1.25 | 29.22 | 0.05 | 0.36 | 1.15 | 0.09 | 2.61 |
| % Oxidation IL7R-Antibody A | 0.07 | 1.35 | 0.38 | 1.18 | 0.37 | 16.42 | 0.05 | 0.33 | 0.19 | 0.03 | 0.28 |
| p value | 0.001 | 0.287 | 0.0003 | 0.00001 | 0.0001 | 0.0001 | 0.107 | 0.296 | 0.0001 | 0.000002 | 0.000001 |
| STDEV (IL7R) | 0.01 | 0.09 | 0.07 | 0.09 | 0.12 | 0.93 | 0.00 | 0.04 | 0.12 | 0.00 | 0.09 |
| STDEV (IL7R-Antibody A) | 0.01 | 0.09 | 0.05 | 0.13 | 0.02 | 1.64 | 0.00 | 0.07 | 0.02 | 0.00 | 0.04 |

Residues which show a significant difference in the level of oxidation (p value <0.01) upon binding with Antibody A in comparison with hIL7Rα control are considered most protected residues. Calculations represents n = 3 replicates per condition.

Lastly, GEE-labeling (which was used to provide complementary data on residues with limited oxidation propensity, which may be silent to FPOP, in particular aspartic acid and glutamic acid) identified E75 as the most protected residue on hIL7Rα upon interaction with Antibody A (Table 10).

The human efficacious dose was projected by targeting 95% RO at trough following once-every two weeks dosing. The monkey PK/PD study demonstrated that more than 95% RO resulted in 90% inhibition of pSTAT5. See Example 3. Therefore, RO rather than pSTAT5 coverage was used for

TABLE 10

Extend of GEE labeling for chymotryptic peptides of hIL7Rα

| Peptide | $^{24}$SQLEVDGSQHSL$^{35}$ | $^{73}$FIETKKF$^{79}$ | $^{80}$LLIGKSNICVKVGEKSL$^{96}$ | $^{144}$MHDVAY$^{149}$ | $^{182}$EIKVRSIPDHYF$^{193}$ |
|---|---|---|---|---|---|
| Residue No | E27 | E75 | E93 | D146 | E182/D190 |
| % GEE Labeling IL7R | 0.16 | 4.07 | 0.76 | ND | 1.75 |
| % GEE labeling IL7R-Antibody A | 0.16 | 2.65 | 0.65 | ND | 1.43 |
| p value | 0.460 | 0.004 | 0.020 | NA | 0.017 |
| STDEV (IL7R) | 0.01 | 0.27 | 0.06 | NA | 0.13 |
| STDEV (IL7R_mAb) | 0.02 | 0.42 | 0.02 | NA | 0.12 |

Residues which show a significant difference in the level of GEE labeling (p value <0.01) upon binding with Antibody A in comparison with hIL7Rα control are considered most protected residues. Calculations represent n = 2 replicates per condition.

Based on the above analysis, epitopes of hIL7Rα upon interaction with Antibody A were mapped to linear sequence of hIL7Rα. (FIG. 11A), and further mapped to crystal structure (FIG. 11B).

In summary, hydrogen/deuterium exchange mass spectrometry (HDX-MS) experiments indicated that Antibody A binding sites on human IL7Rα are mapped to the residues in the following peptide sequences: $^{24}$SQLEVNGSQHSLT-CAF$^{39}$, $^{73}$FIETKKFLLIGKSNIC$^{88}$, 89VKVGEKSLTCK-KIDLTT$^{105}$, $^{136}$QKKYVKVLMHDVAY$^{149}$, and $^{181}$YEI-KVRSIPDHYFKGF$^{196}$. Additional mass spectrometry-based protein footprinting approaches including FPOP, and GEE labeling provided amino-acid resolution of Antibody A binding sites on human IL7Rα in the following amino acids: H33, E75, F79, I82, K84, M144, R186, H191 and Y192.

Example 10: Projected Human Dose

Human PK/RO/PD for the anti-IL-7R antibody disclosed herein were projected using a mechanistic target mediated drug disposition model that was recently reported for PFE A3312F (nbc.aapsmeeting.org/event/member/373852) (FIGS. 12A and 12B). This mechanistic model was able to capture the time course of PK/RO/PD following administration of PFE A3312F mAb in human clinical study.

To enable simulation of human PK and PD of the anti-IL-7R antibody, while most of the model parameters were similar to the reported model, clearance was assumed to be 2-fold lower in human (relative to PFE A3312F). This was supported by the 2-fold lower CL relative to A3312F observed in monkeys at a pharmacologically relevant dose (3 mg/kg; FIG. 4). Additionally, the binding affinity of the anti-IL-7R antibody was similar between monkeys and humans, particularly at pH 7.4 (see Example 3). Therefore, PK projections assumed that this difference in CL would translate to humans. Given the similar in-vivo potency of the present anti-IL-7R antibody and A3312F in monkeys (FIG. 5), the binding kinetics of these two antibodies were assumed to be similar in humans dose projections because pSTAT5 inhibition was more variable in monkeys and humans.

Integrating the above information, it was estimated that a maintenance SC dose of 110 mg for a 70-kg adult every other week (Q2W) would achieve 95% IL-7R RO during treatment with the present anti-IL-7R antibody. The SC loading dose to enable achievement of this RO after the first dose was calculated to be 140 mg (FIG. 13).

Predicted human steady-state exposure and PK parameters at this dose are listed in Table 11. As expected, due to nonlinear pharmacokinetics, the projected half-life of the anti-IL-7R antibody in humans was protected to increase with increasing dose. The projected half-life was 53 hours at the efficacious dose of 110 mg but it was estimated to be longer at higher doses (e.g., 85 hours at 125 mg).

TABLE 11

Pharmacokinetic parameters following a single IV dose in NSG-human PBMC transfer mice

| PK Parameter | Projected Human Dose and PK Parameter Estimates of Anti-IL-7R Antibody 110 mg SC every 2 weeks |
|---|---|
| $Cmax_{ss}$ (nM) | 40.6 |
| $AUC(tau)_{ss}$ (nM*h) | 7893 |
| CL (mL/h/kg) | 0.56 |
| $Ctrough_{ss}$ (nM) | 6.0 |
| Terminal $T_{1/2}$ (h) | 53 |

Example 11: Mutational Scan Analysis of Antibody 18B1

In order to carry out the mutational scan, the antibody 18B1 (Antibody A, Table 12) was first reformatted as scFv and confirmed binding for against full length hIL-7R binding via mRNA display (Xu L et al. (2002) Chemistry & Biology 9: 933; Roberts R W and J W Szostak (1997) Proc. Natl. Acad. Sci. USA 94:12297; Kurz et al. (2000) Nucleic Acids Res. 28(18):E83). The binding data of the reformatted antibody is provided in FIGS. 14A and 14B.

Once binding was confirmed, we next constructed a mutational scan library in which each library variant contained only a single mutation within the CDR. All six CDRs of the antibody were mutated, with each position in the CDR mutated to all possible amino acids at that position. The specific positions that were mutated are shown in FIG. 15. This library of 18B1 scFv variants was taken through a single round of selection against hIL-7R using mRNA display. Results from the single round of selection is provided in FIG. 16. Selection output was analyzed via next generation sequencing (NGS), and heat maps were generated to visualize NGS data and to readily identify 1) CDR positions critical for binding, 2) CDR positions where mutations are tolerated, and 3) mutations that can improve binding of the antibody to hIL-7R. FIGS. 17A and 17B provide a schematic of the overall process. Heat map results are provided in FIGS. 18A-18F.

Alanine substitution variants of 18B1 antibody were made to confirm above NGS data. Briefly, a series of single mutation variants were designed where a single alanine mutation was introduced to a position in the CDR. This was done for all positions of the six CDRs, except for CDR positions that already encodes an alanine. These alanine substitution variants were gene synthesized, transiently expressed in Expi293 as IgG1.3, and purified using protein A resin.

18B1 and alanine substitution variants were tested for their binding to hIL-7R via biacore. Briefly, CM5 chip (with Fc on the chip surface) was used to capture 12.5 nM of the antibody, hIL-7R was introduced as ligand at 30, 10, and 3.3 nM in HBS-P, pH 7.4, 37 C. See FIGS. 20A and 20B. Affinity ($K_D$) of each variant binding to hIL-7R was obtained using this approach, and compared against the enrichment ratio (ER) obtained through NGS heat map analysis for the same variant. FIG. 19 provides the values for each of the antibody variants.

As shown in FIG. 21, several of the 18B1 variants were able to bind to hIL-7R with similar affinity as the 18B1 antibody (i.e., Antibody A). And, as shown in FIGS. 22 and 23, alanine mutations with the heavy chain CDR3 and the light chain CDR3 appeared to have the greatest impact on binding. Lastly, as shown in FIG. 24, results shown in the heat maps correlated well to measured $K_D$ values for the alanine variants. FIG. 25 provides a crystal structure of the Fab fragment of the 18B1 antibody in which the residues that are critical for binding (red) and residues that could improve binding (blue) are shown.

Example 12: Internalization Analysis of 18B1 Antibody Upon Binding to IL-7 Receptor α-Chain (IL-7Rα)

To further characterize the anti-IL-7R antibodies disclosed herein, the 18B1 antibody (i.e., Antibody A) was tested for its internalization upon binding to to IL-7Rα expressed on monkey leukocytes. Briefly, cynomolgus monkeys received a subcutaneous administration of the 18B1 antibody at one of the following doses: (i) 2 mg/kg, (ii) 10 mg/kg, and (iii) 50 mg/kg. Animals that did not receive the 18B1 antibody were used as controls. Then, at various time points post-administration, peripheral blood was collected from the animals, and the mean fluorescence intensity (MFI) of IL-7Rα expression on CD3+ leukocytes was assessed using flow cytometry.

As shown in FIG. 26, the IL-7Rα expression on the CD3+ leukocytes remained largely consistent throughout the duration of the experiment in all the animals treated with the 18B1 antibody. Compared to the control animals, administration of the 18B1 antibody did not result in decreased expression of IL-7Rα on the CD3+ leukocytes.

This result demonstrates that the 18B1 antibody disclosed herein does not induce the internalization of the IL-7Rα upon binding, which confirms that the antibody does not have any agonistic effect.

Example 13: Analysis of the Potency of the 18B1 Antibody

The assess the potency of the anti-IL-7R antibodies disclosed herein, the ability of the 18B1 antibody to inhibit keyhole limpet hemocyanin (KLH)-induced antibody response was measured. Briefly, cynomolgus monkeys (both male and female) received a subcutaneous administration of the 18B1 antibody at one of the following doses: (i) 2 mg/kg, (ii) 10 mg/kg, and (iii) 50 mg/kg. Animals that did not receive the 18B1 antibody were used as controls. Then, at day 15 post antibody administration, all the animals were immunized with KLH (10 mg; intramuscularly in the posterior quadriceps). Then, at various time points, peripheral blood was collected from the animals (from the femoral, cephalic, or saphenous vein) and the endpoint titers (EPT) of KLH-specific IgM and IgG antibodies in the sera were measured using ELISA.

As shown in FIGS. 27A and 27B, upon immunization with KLH, an increase in KLH-specific IgM and IgG antibodies were observed in all the treatment groups. For KLH-specific IgM response, there were no significant differences among the treatment groups (see FIG. 27A). However, in animals treated with the 18B1 antibody, there was a statistically significant decrease (up to 80% suppression) in KLH-specific IgG responses at 2 ("day 29"), 3 ("day 36"), and 4 ("day 43") weeks post KLH immunization compared to the control animals (i.e., animals that were immunized with KLH but did not receive the 18B1 antibody) (see FIG. 27B). The observed inhibition of KLH-specific IgG response was dose-independent, as the response appeared to be comparable in all the animals treated with the 18B1 antibody, regardless of the dosage.

The above data demonstrates the potency of the disclosed anti-IL-7R antibodies, and that even at a dose as low as 2 mg/kg, the 18B1 antibody can effectively inhibit KLH-specific IgG response. Not to be bound by any one theory, the suppression of KLH-specific IgG but not IgM response suggests that the 18B1 antibody can inhibit antibody class switching recombination in B cells that undergoing isotype switching.

Example 14: Additional Epitope Mapping Analysis

To further characterize the anti-IL-7R antibodies of the present disclosure, the binding epitopes of three reference antibodies (i.e., 4A8, 13A10, and PFE A3312F) were determined and compared to the binding epitopes of the antibody 18B1 (Antibody A, Table 12). The binding epitopes were determined as described earlier in Example 9.

As shown in FIGS. 28A-28C, based on HDX-MS experiments, the binding sites for the 4A8 antibody were mapped to the residues in the following peptide sequences: (i) $^{57}$LVEVKCLNF$^{65}$, (ii) $^{73}$FIETKKFLLIGKSNIC$^{88}$, (iii) $^{136}$QKKYVKVLMHDVAY$^{149}$, and (iv) $^{181}$YEIKVR-SIPDHYFKGF$^{196}$. The binding sites for the 13A10 antibody were mapped to the following peptide sequences: (i) $^{73}$FIETKKFLLIGKSNIC$^{88}$, (ii) $^{89}$VKVGEKSLTCK-KIDLTT$^{105}$, (iii) $^{136}$QKKYVKVLMHDVAY$^{149}$, and (iv)

$^{181}$YEIKVRSIPDHYFKGF$^{196}$. And, the binding sites for PFE A3312F were mapped to the following peptide sequences: (i) $^{24}$SQLEVNGSQHSLTCA$^{38}$, (ii) $^{52}$EICGALVEVKCLNF$^{65}$, (iii) $^{73}$FIETKKFLLIGKSNIC$^{88}$, (iv) $^{89}$VKVGEKSLTCKKIDLTT$^{105}$, (v) $^{104}$TTIVKPEAPFDLSV$^{117}$, (vi) $^{109}$PEAPFDLSVIYRE$^{121}$, (vii) $^{136}$QKKYVKVLMHDVAY$^{149}$, (viii) $^{169}$TLLQRKLQPAAM$^{180}$, and (ix) $^{181}$YEIKVRSIPDHYFKGF$^{196}$. FIGS. 29A-29C show the binding sites for the 4A8, 13A10, and PFE A3312F mapped onto a crystal structure of the human IL-7Rα protein.

Compared to the data provided in Example 9 (see also FIGS. 10 and 11B), the above results demonstrate that the antibody 18B1 disclosed in the present application bind to different regions on the human IL-7Rα protein compared to the reference antibodies described in this Example.

TABLE 12

| SEQ ID | Description | Sequences |
|---|---|---|
| 19 | Anti-IL-7R Antibody (Antibody A) Heavy Chain Variable Region (VH) | EVQLVESGGGLVQPGRSLRLSCAASGFTFDDHAMHWVRQAPGKGLEWVSGISWNSRGIGYADSVK GRFTIFRDNAKNSLYLQMNSLRAEDTALYYCAKDEYSRGYYVLDVWGQGTTVTVSS |
| 20 | Anti-IL-7R Antibody (Antibody A) Light Chain Variable Region (VL) | AIQLTQSPSSLSASVGDRVTITCRASQGISSALAWYQQKPGKAPKLLIYDASSLESGVPSRFSGS GSGTDFTLTISSLQPEDFATYYCQQFNSYPLWITFGQGTRLEIK |
| 21 | Anti-IL-7R Antibody (Antibody A) Heavy Chain | EVQLVESGGGLVQPGRSLRLSCAASGFTFDDHAMHWVRQAPGKGLEWVSGISWNSRGIGYADSVK GRFTIFRDNAKNSLYLQMNSLRAEDTALYYCAKDEYSRGYYVLDVWGQGTTVTVSSASTKGPSVF PLAPSSKSTSGGTAALGCLVKDYFPEPVTVSWNSGALTSGVHTFPAVLQSSGLYSLSSVVTVPSS SLGTQTYICNVNHKPSNTKVDKRVEPKSCDKTHTCPPCPAPEAEGAPSVFLFPPKPKDTLMISRT PEVTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSLSLSPG |
| 22 | Anti-IL-7R Antibody (Antibody A) Light Chain | AIQLTQSPSSLSASVGDRVTITCRASQGISSALAWYQQKPGKAPKLLIYDASSLESGVPSRFSGS GSGTDFTLTISSLQPEDFATYYCQQFNSYPLWITFGQGTRLEIKRTVAAPSVFIFPPSDEQLKSG TASVVCLLNNFYPREAKVQWKVDNALQSGNSQESVTEQDSKDSTYSLSSTLTLSKADYEKHKVYA CEVTHQGLSSPVTKSFNRGEC |

TABLE 13

Exemplary Heavy Chain CDR1 Sequences

| | 26 | 27 | 28 | 29 | 30 | 31 | 32 | 33 | 34 | 35 |
|---|---|---|---|---|---|---|---|---|---|---|
| "18B1" (SEQ ID NO: 31) | G | F | T | F | D | D | H | A | M | H |
| F27Y (SEQ ID NO: 32) | G | Y | T | F | D | D | H | A | M | H |
| T28P (SEQ ID NO: 33) | G | F | P | F | D | D | H | A | M | H |
| T28A (SEQ ID NO: 34) | G | F | A | F | D | D | H | A | M | H |
| T28V (SEQ ID NO: 35) | G | F | V | F | D | D | H | A | M | H |
| T28L (SEQ ID NO: 36) | G | F | L | F | D | D | H | A | M | H |

TABLE 13-continued

Exemplary Heavy Chain CDR1 Sequences

| | 26 | 27 | 28 | 29 | 30 | 31 | 32 | 33 | 34 | 35 |
|---|---|---|---|---|---|---|---|---|---|---|
| T28I (SEQ ID NO: 37) | G | F | I | F | D | D | H | A | M | H |
| T28M (SEQ ID NO: 38) | G | F | M | F | D | D | H | A | M | H |
| T28H (SEQ ID NO: 39) | G | F | H | F | D | D | H | A | M | H |
| T28F (SEQ ID NO: 40) | G | F | F | F | D | D | H | A | M | H |
| T28Y (SEQ ID NO: 41) | G | F | Y | F | D | D | H | A | M | H |
| T28N (SEQ ID NO: 42) | G | F | N | F | D | D | H | A | M | H |
| T28D (SEQ ID NO: 43) | G | F | D | F | D | D | H | A | M | H |
| T28E (SEQ ID NO: 44) | G | F | E | F | D | D | H | A | M | H |
| T28Q (SEQ ID NO: 45) | G | F | Q | F | D | D | H | A | M | H |
| M34L (SEQ ID NO: 46) | G | F | T | F | D | D | H | A | L | H |

TABLE 14

Exemplary Heavy Chain CDR2 Sequences

| | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|
| "18B1" (SEQ ID NO: 14) | G | I | S | W | N | S | R | G | I | G | Y | A | D | S | V | K | G |
| S52T (SEQ ID NO: 47) | G | I | T | W | N | S | R | G | I | G | Y | A | D | S | V | K | G |
| N53H (SEQ ID NO: 48) | G | I | S | W | H | S | R | G | I | G | Y | A | D | S | V | K | G |

TABLE 14-continued

Exemplary Heavy Chain CDR2 Sequences

| | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|
| I57V (SEQ ID NO: 49) | G | I | S | W | N | S | R | G | V | G | Y | A | D | S | V | K | G |
| A60G (SEQ ID NO: 50) | G | I | S | W | N | S | R | G | I | G | Y | G | D | S | V | K | G |
| A60S (SEQ ID NO: 51) | G | I | S | W | N | S | R | G | I | G | Y | S | D | S | V | K | G |
| A60T (SEQ ID NO: 52) | G | I | S | W | N | S | R | G | I | G | Y | T | D | S | V | K | G |
| A60V (SEQ ID NO: 53) | G | I | S | W | N | S | R | G | I | G | Y | V | D | S | V | K | G |
| A60L (SEQ ID NO: 54) | G | I | S | W | N | S | R | G | I | G | Y | L | D | S | V | K | G |
| A60I (SEQ ID NO: 55) | G | I | S | W | N | S | R | G | I | G | Y | I | D | S | V | K | G |
| A60R (SEQ ID NO: 56) | G | I | S | W | N | S | R | G | I | G | Y | R | D | S | V | K | G |
| A60H (SEQ ID NO: 57) | G | I | S | W | N | S | R | G | I | G | Y | H | D | S | V | K | G |
| A60N (SEQ ID NO: 58) | G | I | S | W | N | S | R | G | I | G | Y | N | D | S | V | K | G |
| D61P (SEQ ID NO: 59) | G | I | S | W | N | S | R | G | I | G | Y | A | P | S | V | K | G |
| D61T (SEQ ID NO: 60) | G | I | S | W | N | S | R | G | I | G | Y | A | T | S | V | K | G |
| D61N (SEQ ID NO: 61) | G | I | S | W | N | S | R | G | I | G | Y | A | N | S | V | K | G |
| D61E (SEQ ID NO: 62) | G | I | S | W | N | S | R | G | I | G | Y | A | E | S | V | K | G |
| D61Q (SEQ ID NO: 63) | G | I | S | W | N | S | R | G | I | G | Y | A | Q | S | V | K | G |

TABLE 14-continued

Exemplary Heavy Chain CDR2 Sequences

| | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|
| D61S (SEQ ID NO: 64) | G | I | S | W | N | S | R | G | I | G | Y | A | S | S | V | K | G |
| D61H (SEQ ID NO: 65) | G | I | S | W | N | S | R | G | I | G | Y | A | H | S | V | K | G |
| S62P (SEQ ID NO: 66) | G | I | S | W | N | S | R | G | I | G | Y | A | D | P | V | K | G |
| S62G (SEQ ID NO: 67) | G | I | S | W | N | S | R | G | I | G | Y | A | D | G | V | K | G |
| S62A (SEQ ID NO: 68) | G | I | S | W | N | S | R | G | I | G | Y | A | D | A | V | K | G |
| S62T (SEQ ID NO: 69) | G | I | S | W | N | S | R | G | I | G | Y | A | D | T | V | K | G |
| S62V (SEQ ID NO: 70) | G | I | S | W | N | S | R | G | I | G | Y | A | D | V | V | K | G |
| S62R (SEQ ID NO: 71) | G | I | S | W | N | S | R | G | I | G | Y | A | D | R | V | K | G |
| S62H (SEQ ID NO: 72) | G | I | S | W | N | S | R | G | I | G | Y | A | D | H | V | K | G |
| S62F (SEQ ID NO: 73) | G | I | S | W | N | S | R | G | I | G | Y | A | D | F | V | K | G |
| S62Y (SEQ ID NO: 74) | G | I | S | W | N | S | R | G | I | G | Y | A | D | Y | V | K | G |
| S62N (SEQ ID NO: 75) | G | I | S | W | N | S | R | G | I | G | Y | A | D | N | V | K | G |
| S62D (SEQ ID NO: 76) | G | I | S | W | N | S | R | G | I | G | Y | A | D | D | V | K | G |
| S62E (SEQ ID NO: 77) | G | I | S | W | N | S | R | G | I | G | Y | A | D | E | V | K | G |
| V63I (SEQ ID NO: 78) | G | I | S | W | N | S | R | G | I | G | Y | A | D | S | I | K | G |

TABLE 14-continued

Exemplary Heavy Chain CDR2 Sequences

| | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|
| K64A (SEQ ID NO: 79) | G | I | S | W | N | S | R | G | I | G | Y | A | D | S | V | A | G |
| K64S (SEQ ID NO: 80) | G | I | S | W | N | S | R | G | I | G | Y | A | D | S | V | S | G |
| K64T (SEQ ID NO: 81) | G | I | S | W | N | S | R | G | I | G | Y | A | D | S | V | T | G |
| K64V (SEQ ID NO: 82) | G | I | S | W | N | S | R | G | I | G | Y | A | D | S | V | V | G |
| K64L (SEQ ID NO: 83) | G | I | S | W | N | S | R | G | I | G | Y | A | D | S | V | L | G |
| K64I (SEQ ID NO: 84) | G | I | S | W | N | S | R | G | I | G | Y | A | D | S | V | I | G |
| K64M (SEQ ID NO: 85) | G | I | S | W | N | S | R | G | I | G | Y | A | D | S | V | M | G |
| K64R (SEQ ID NO: 86) | G | I | S | W | N | S | R | G | I | G | Y | A | D | S | V | R | G |
| K64H (SEQ ID NO: 87) | G | I | S | W | N | S | R | G | I | G | Y | A | D | S | V | H | G |
| K64F (SEQ ID NO: 88) | G | I | S | W | N | S | R | G | I | G | Y | A | D | S | V | F | G |
| K64Y (SEQ ID NO: 89) | G | I | S | W | N | S | R | G | I | G | Y | A | D | S | V | Y | G |
| K64N (SEQ ID NO: 90) | G | I | S | W | N | S | R | G | I | G | Y | A | D | S | V | N | G |
| K64D (SEQ ID NO: 91) | G | I | S | W | N | S | R | G | I | G | Y | A | D | S | V | D | G |
| K64E (SEQ ID NO: 92) | G | I | S | W | N | S | R | G | I | G | Y | A | D | S | V | E | G |
| K64Q (SEQ ID NO: 93) | G | I | S | W | N | S | R | G | I | G | Y | A | D | S | V | Q | G |

TABLE 14-continued

Exemplary Heavy Chain CDR2 Sequences

| | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|
| G65H (SEQ ID NO: 94) | G | I | S | W | N | S | R | G | I | G | Y | A | D | S | V | K | H |
| G65D (SEQ ID NO: 95) | G | I | S | W | N | S | R | G | I | G | Y | A | D | S | V | K | D |
| G6SQ (SEQ ID NO: 96) | G | I | S | W | N | S | R | G | I | G | Y | A | D | S | V | K | Q |

TABLE 15

Exemplary Heavy Chain CDR3 Sequences

| | 95 | 96 | 97 | 98 | 99 | 100 | 100a | 100b | 100c | 100d | 101 | 102 |
|---|---|---|---|---|---|---|---|---|---|---|---|---|
| "18B1" (SEQ ID NO: 15) | D | E | Y | S | R | G | Y | Y | V | L | D | V |
| S98T (SEQ ID NO: 97) | D | E | Y | T | R | G | Y | Y | V | L | D | V |
| S98N (SEQ ID NO: 98) | D | E | Y | N | R | G | Y | Y | V | L | D | V |
| S98D (SEQ ID NO: 99) | D | E | Y | D | R | G | Y | Y | V | L | D | V |
| S98E (SEQ ID NO: 100) | D | E | Y | E | R | G | Y | Y | V | L | D | V |
| R99L (SEQ ID NO: 101) | D | E | Y | S | L | G | Y | Y | V | L | D | V |
| R99M (SEQ ID NO: 102) | D | E | Y | S | M | G | Y | Y | V | L | D | V |
| R99S (SEQ ID NO: 103) | D | E | Y | S | S | G | Y | Y | V | L | D | V |
| V100cG (SEQ ID NO: 104) | D | E | Y | S | R | G | Y | Y | G | L | D | V |
| V100cA (SEQ ID NO: 105) | D | E | Y | S | R | G | Y | Y | A | L | D | V |

TABLE 15-continued

Exemplary Heavy Chain CDR3 Sequences

| | 95 | 96 | 97 | 98 | 99 | 100 | 100a | 100b | 100c | 100d | 101 | 102 |
|---|---|---|---|---|---|---|---|---|---|---|---|---|
| V100cS (SEQ ID NO: 106) | D | E | Y | S | R | G | Y | Y | S | L | D | V |
| V100cT (SEQ ID NO: 107) | D | E | Y | S | R | G | Y | Y | T | L | D | V |
| V100cM (SEQ ID NO: 108) | D | E | Y | S | R | G | Y | Y | M | L | D | V |
| V100cN (SEQ ID NO: 109) | D | E | Y | S | R | G | Y | Y | N | L | D | V |
| V100cE (SEQ ID NO: 110) | D | E | Y | S | R | G | Y | Y | E | L | D | V |
| V100cQ (SEQ ID NO: 111) | D | E | Y | S | R | G | Y | Y | 12 | L | D | V |
| V102A (SEQ ID NO: 112) | D | E | Y | S | R | G | Y | Y | V | L | D | A |
| V102S (SEQ ID NO: 113) | D | E | Y | S | R | G | Y | Y | V | L | D | S |
| V102T (SEQ ID NO: 114) | D | E | Y | S | R | G | Y | Y | V | L | D | T |
| V102R (SEQ ID NO: 115) | D | E | Y | S | R | G | Y | Y | V | L | D | R |
| V102H (SEQ ID NO: 116) | D | E | Y | S | R | G | Y | Y | V | L | D | H |
| V102Y (SEQ ID NO: 117) | D | E | Y | S | R | G | Y | Y | V | L | D | Y |
| V102W (SEQ ID NO: 118) | D | E | Y | S | R | G | Y | Y | V | L | D | W |
| V102N (SEQ ID NO: 119) | D | E | Y | S | R | G | Y | Y | V | L | D | N |
| V102E (SEQ ID NO: 120) | D | E | Y | S | R | G | Y | Y | V | L | D | E |

TABLE 15-continued

Exemplary Heavy Chain CDR3 Sequences

| | 95 | 96 | 97 | 98 | 99 | 100 | 100a | 100b | 100c | 100d | 101 | 102 |
|---|---|---|---|---|---|---|---|---|---|---|---|---|
| V102Q (SEQ ID NO: 121) | D | E | Y | S | R | G | Y | Y | V | L | D | Q |
| V102M (SEQ ID NO: 122) | D | E | Y | S | R | G | Y | Y | V | L | D | M |

TABLE 16

Exemplary Light Chain CDR1 Sequences

| | 24 | 25 | 26 | 27 | 28 | 29 | 30 | 31 | 32 | 33 | 34 |
|---|---|---|---|---|---|---|---|---|---|---|---|
| "18B1" (SEQ ID NO: 16) | R | A | S | Q | G | I | S | S | A | L | A |
| R24S (SEQ ID NO: 123) | S | A | S | Q | G | I | S | S | A | L | A |
| R24T (SEQ ID NO: 124) | T | A | S | Q | G | I | S | S | A | L | A |
| R24V (SEQ ID NO: 125) | V | A | S | Q | G | I | S | S | A | L | A |
| R24K (SEQ ID NO: 126) | K | A | S | Q | G | I | S | S | A | L | A |
| R24H (SEQ ID NO: 127) | H | A | S | Q | G | I | S | S | A | L | A |
| R24Y (SEQ ID NO: 128) | Y | A | S | Q | G | I | S | S | A | L | A |
| R24I (SEQ ID NO: 129) | I | A | S | Q | G | I | S | S | A | L | A |
| A25S (SEQ ID NO: 130) | R | S | S | Q | G | I | S | S | A | L | A |
| A25T (SEQ ID NO: 131) | R | T | S | Q | G | I | S | S | A | L | A |
| A25V (SEQ ID NO: 132) | R | V | S | Q | G | I | S | S | A | L | A |

TABLE 16-continued

Exemplary Light Chain CDR1 Sequences

| | 24 | 25 | 26 | 27 | 28 | 29 | 30 | 31 | 32 | 33 | 34 |
|---|---|---|---|---|---|---|---|---|---|---|---|
| S26P (SEQ ID NO: 133) | R | A | P | Q | G | I | S | S | A | L | A |
| S26G (SEQ ID NO: 134) | R | A | G | Q | G | I | S | S | A | L | A |
| S26A (SEQ ID NO: 135) | R | A | A | Q | G | I | S | S | A | L | A |
| S26T (SEQ ID NO: 136) | R | A | T | Q | G | I | S | S | A | L | A |
| S26V (SEQ ID NO: 137) | R | A | V | Q | G | I | S | S | A | L | A |
| S26L (SEQ ID NO: 138) | R | A | L | Q | G | I | S | S | A | L | A |
| S26I (SEQ ID NO: 139) | R | A | I | Q | G | I | S | S | A | L | A |
| S26M (SEQ ID NO: 140) | R | A | M | Q | G | I | S | S | A | L | A |
| S26K (SEQ ID NO: 141) | R | A | K | Q | G | I | S | S | A | L | A |
| S26R (SEQ ID NO: 142) | R | A | R | Q | G | I | S | S | A | L | A |
| S26H (SEQ ID NO: 143) | R | A | H | Q | G | I | S | S | A | L | A |
| S26N (SEQ ID NO: 144) | R | A | N | Q | G | I | S | S | A | L | A |
| S26E (SEQ ID NO: 145) | R | A | E | Q | G | I | S | S | A | L | A |
| S26Q (SEQ ID NO: 146) | R | A | Q | Q | G | I | S | S | A | L | A |
| Q27P (SEQ ID NO: 147) | R | A | S | P | G | I | S | S | A | L | A |

TABLE 16-continued

Exemplary Light Chain CDR1 Sequences

| | 24 | 25 | 26 | 27 | 28 | 29 | 30 | 31 | 32 | 33 | 34 |
|---|---|---|---|---|---|---|---|---|---|---|---|
| Q27G (SEQ ID NO: 148) | R | A | S | G | G | I | S | S | A | L | A |
| Q27A (SEQ ID NO: 149) | R | A | S | A | G | I | S | S | A | L | A |
| Q27S (SEQ ID NO: 150) | R | A | S | S | G | I | S | S | A | L | A |
| Q27T (SEQ ID NO: 151) | R | A | S | T | G | I | S | S | A | L | A |
| Q27V (SEQ ID NO: 152) | R | A | S | V | G | I | S | S | A | L | A |
| Q27L (SEQ ID NO: 153) | R | A | S | L | G | I | S | S | A | L | A |
| Q27I (SEQ ID NO: 154) | R | A | S | I | G | I | S | S | A | L | A |
| Q27M (SEQ ID NO: 155) | R | A | S | M | G | I | S | S | A | L | A |
| Q27H (SEQ ID NO: 156) | R | A | S | H | G | I | S | S | A | L | A |
| Q27F (SEQ ID NO: 157) | R | A | S | F | G | I | S | S | A | L | A |
| Q27Y (SEQ ID NO: 158) | R | A | S | Y | G | I | S | S | A | L | A |
| Q27N (SEQ ID NO: 159) | R | A | S | N | G | I | S | S | A | L | A |
| Q27D (SEQ ID NO: 160) | R | A | S | D | G | I | S | S | A | L | A |
| Q27E (SEQ ID NO: 161) | R | A | S | E | G | I | S | S | A | L | A |
| G28P (SEQ ID NO: 162) | R | A | S | Q | P | I | S | S | A | L | A |

TABLE 16-continued

Exemplary Light Chain CDR1 Sequences

| | 24 | 25 | 26 | 27 | 28 | 29 | 30 | 31 | 32 | 33 | 34 |
|---|---|---|---|---|---|---|---|---|---|---|---|
| G28A (SEQ ID NO: 163) | R | A | S | Q | A | I | S | S | A | L | A |
| G28S (SEQ ID NO: 164) | R | A | S | Q | S | I | S | S | A | L | A |
| G28T (SEQ ID NO: 165) | R | A | S | Q | T | I | S | S | A | L | A |
| G28H (SEQ ID NO: 166) | R | A | S | Q | H | I | S | S | A | L | A |
| G28E (SEQ ID NO: 167) | R | A | S | Q | E | I | S | S | A | L | A |
| G28Q (SEQ ID NO: 168) | R | A | S | Q | Q | I | S | S | A | L | A |
| G28M (SEQ ID NO: 169) | R | A | S | Q | M | I | S | S | A | L | A |
| G28N (SEQ ID NO: 170) | R | A | S | Q | N | I | S | S | A | L | A |
| G28D (SEQ ID NO: 171) | R | A | S | Q | D | I | S | S | A | L | A |
| I29P (SEQ ID NO: 172) | R | A | S | Q | G | P | S | S | A | L | A |
| I29G (SEQ ID NO: 173) | R | A | S | Q | G | G | S | S | A | L | A |
| I29A (SEQ ID NO: 174) | R | A | S | Q | G | A | S | S | A | L | A |
| I29S (SEQ ID NO: 175) | R | A | S | Q | G | S | S | S | A | L | A |
| I29T (SEQ ID NO: 176) | R | A | S | Q | G | T | S | S | A | L | A |
| I29V (SEQ ID NO: 177) | R | A | S | Q | G | V | S | S | A | L | A |

TABLE 16-continued

Exemplary Light Chain CDR1 Sequences

| | 24 | 25 | 26 | 27 | 28 | 29 | 30 | 31 | 32 | 33 | 34 |
|---|---|---|---|---|---|---|---|---|---|---|---|
| I29L (SEQ ID NO: 178) | R | A | S | Q | G | L | S | S | A | L | A |
| I29N (SEQ ID NO: 179) | R | A | S | Q | G | N | S | S | A | L | A |
| S30T (SEQ ID NO: 180) | R | A | S | Q | G | I | T | S | A | L | A |
| S30V (SEQ ID NO: 181) | R | A | S | Q | G | I | V | S | A | L | A |
| S30L (SEQ ID NO: 182) | R | A | S | Q | G | I | L | S | A | L | A |
| S30I (SEQ ID NO: 183) | R | A | S | Q | G | I | I | S | A | L | A |
| S30M (SEQ ID NO: 184) | R | A | S | Q | G | I | M | S | A | L | A |
| S30H (SEQ ID NO: 185) | R | A | S | Q | G | I | H | S | A | L | A |
| S30F (SEQ ID NO: 186) | R | A | S | Q | G | I | F | S | A | L | A |
| S30Y (SEQ ID NO: 187) | R | A | S | Q | G | I | Y | S | A | L | A |
| S30N (SEQ ID NO: 188) | R | A | S | Q | G | I | N | S | A | L | A |
| S30D (SEQ ID NO: 189) | R | A | S | Q | G | I | D | S | A | L | A |
| S30E (SEQ ID NO: 190) | R | A | S | Q | G | I | E | S | A | L | A |
| S30Q (SEQ ID NO: 191) | R | A | S | Q | G | I | Q | S | A | L | A |
| A32P (SEQ ID NO: 192) | R | A | S | Q | G | I | S | S | P | L | A |

TABLE 16-continued

Exemplary Light Chain CDR1 Sequences

| | 24 | 25 | 26 | 27 | 28 | 29 | 30 | 31 | 32 | 33 | 34 |
|---|---|---|---|---|---|---|---|---|---|---|---|
| L33A (SEQ ID NO: 193) | R | A | S | Q | G | I | S | S | A | A | A |
| L33V (SEQ ID NO: 194) | R | A | S | Q | G | I | S | S | A | V | A |

TABLE 17

Exemplary Light Chain CDR2 Sequences

| | 50 | 51 | 52 | 53 | 54 | 55 | 56 |
|---|---|---|---|---|---|---|---|
| "18B1" (SEQ ID NO: 17) | D | A | S | S | L | E | S |
| A51G (SEQ ID NO: 195) | D | G | S | S | L | E | S |
| A51S (SEQ ID NO: 196) | D | S | S | S | L | E | S |
| A51M (SEQ ID NO: 197) | D | M | S | S | L | E | S |
| A51H (SEQ ID NO: 198) | D | H | S | S | L | E | S |
| A51N (SEQ ID NO: 199) | D | N | S | S | L | E | S |
| A51D (SEQ ID NO: 200) | D | D | S | S | L | E | S |
| A51E (SEQ ID NO: 201) | D | E | S | S | L | E | S |
| A51Q (SEQ ID NO: 202) | D | Q | S | S | L | E | S |
| S52G (SEQ ID NO: 203) | D | A | G | S | L | E | S |
| S52A (SEQ ID NO: 204) | D | A | A | S | L | E | S |
| S52T (SEQ ID NO: 205) | D | A | T | S | L | E | S |
| S52V (SEQ ID NO: 206) | D | A | V | S | L | E | S |
| S52M (SEQ ID NO: 207) | D | A | M | S | L | E | S |
| S52H (SEQ ID NO: 208) | D | A | H | S | L | E | S |
| S52F (SEQ ID NO: 209) | D | A | F | S | L | E | S |
| S52Y (SEQ ID NO: 210) | D | A | Y | S | L | E | S |
| S52N (SEQ ID NO: 211) | D | A | N | S | L | E | S |
| S52D (SEQ ID NO: 212) | D | A | D | S | L | E | S |
| S52E (SEQ ID NO: 213) | D | A | E | S | L | E | S |
| S52Q (SEQ ID NO: 214) | D | A | Q | S | L | E | S |
| S53A (SEQ ID NO: 215) | D | A | S | A | L | E | S |

TABLE 17-continued

Exemplary Light Chain CDR2 Sequences

| | 50 | 51 | 52 | 53 | 54 | 55 | 56 |
|---|---|---|---|---|---|---|---|
| S53F (SEQ ID NO: 216) | D | A | S | F | L | E | S |
| S53Y (SEQ ID NO: 217) | D | A | S | Y | L | E | S |
| S53W (SEQ ID NO: 218) | D | A | S | W | L | E | S |
| S53N (SEQ ID NO: 219) | D | A | S | N | L | E | S |
| S53D (SEQ ID NO: 220) | D | A | S | D | L | E | S |
| S53E (SEQ ID NO: 221) | D | A | S | E | L | E | S |
| S53L (SEQ ID NO: 222) | D | A | S | L | L | E | S |
| L54P (SEQ ID NO: 223) | D | A | S | S | P | E | S |
| L54S (SEQ ID NO: 224) | D | A | S | S | S | E | S |
| L54T (SEQ ID NO: 225) | D | A | S | S | T | E | S |
| L54K (SEQ ID NO: 226) | D | A | S | S | K | E | S |
| L54H (SEQ ID NO: 227) | D | A | S | S | H | E | S |
| L54N (SEQ ID NO: 228) | D | A | S | S | N | E | S |
| E55D (SEQ ID NO: 229) | D | A | S | S | L | D | S |
| E55Q (SEQ ID NO: 230) | D | A | S | S | L | Q | S |
| S56G (SEQ ID NO: 231) | D | A | S | S | L | E | G |
| S56T (SEQ ID NO: 232) | D | A | S | S | L | E | T |
| S56N (SEQ ID NO: 233) | D | A | S | S | L | E | N |
| S56D (SEQ ID NO: 234) | D | A | S | S | L | E | D |
| S56Q (SEQ ID NO: 235) | D | A | S | S | L | E | Q |
| S56P (SEQ ID NO: 236) | D | A | S | S | L | E | P |
| S56E (SEQ ID NO: 237) | D | A | S | S | L | E | E |

TABLE 18

Exemplary Light Chain CDR3 Sequences

| | 89 | 90 | 91 | 92 | 93 | 94 | 95 | 95a | 95b | 96 | 97 |
|---|---|---|---|---|---|---|---|---|---|---|---|
| "18E1" (SEQ ID NO: 18) | Q | Q | F | N | S | Y | P | L | W | I | T |
| Q89M (SEQ ID NO: 238) | M | Q | F | N | S | Y | P | L | W | I | T |

TABLE 18-continued

Exemplary Light Chain CDR3 Sequences

| | 89 | 90 | 91 | 92 | 93 | 94 | 95 | 95a | 95b | 96 | 97 |
|---|---|---|---|---|---|---|---|---|---|---|---|
| Q90G (SEQ ID NO: 239) | Q | G | F | N | S | Y | P | L | W | I | T |
| Q90A (SEQ ID NO: 240) | Q | A | F | N | S | Y | P | L | W | I | T |
| Q90D (SEQ ID NO: 241) | Q | D | F | N | S | Y | P | L | W | I | T |
| Q90E (SEQ ID NO: 242) | Q | E | F | N | S | Y | P | L | W | I | T |
| N92E (SEQ ID NO: 243) | Q | Q | F | E | S | Y | P | L | W | I | T |
| S93P (SEQ ID NO: 244) | Q | Q | F | N | P | Y | P | L | W | I | T |
| S93A (SEQ ID NO: 245) | Q | Q | F | N | A | Y | P | L | W | I | T |
| W95bT (SEQ ID NO: 246) | Q | Q | F | N | S | Y | P | L | T | I | T |
| W95bI (SEQ ID NO: 247) | Q | Q | F | N | S | Y | P | L | I | I | T |
| W95bM (SEQ ID NO: 248) | Q | Q | F | N | S | Y | P | L | M | I | T |
| W95bK (SEQ ID NO: 249) | Q | Q | F | N | S | Y | P | L | K | I | T |
| W95bN (SEQ ID NO: 250) | Q | Q | F | N | S | Y | P | L | N | I | T |
| W95bE (SEQ ID NO: 251) | Q | Q | F | N | S | Y | P | L | E | I | T |
| W95bQ (SEQ ID NO: 252) | Q | Q | F | N | S | Y | P | L | Q | I | T |
| I96L (SEQ ID NO: 253) | Q | Q | F | N | S | Y | P | L | W | L | T |

TABLE 18-continued

Exemplary Light Chain CDR3 Sequences

| | 89 | 90 | 91 | 92 | 93 | 94 | 95 | 95a | 95b | 96 | 97 |
|---|---|---|---|---|---|---|---|---|---|---|---|
| T97M (SEQ ID NO: 254) | Q | Q | F | N | S | Y | P | L | W | I | M |
| T97K (SEQ ID NO: 255) | Q | Q | F | N | S | Y | P | L | W | I | K |
| T97H (SEQ ID NO: 256) | Q | Q | F | N | S | Y | P | L | W | I | H |
| T97Y (SEQ ID NO: 257) | Q | Q | F | N | S | Y | P | L | W | I | Y |
| T97E (SEQ ID NO: 258) | Q | Q | F | N | S | Y | P | L | W | I | E |
| T97Q (SEQ ID NO: 259) | Q | Q | F | N | S | Y | P | L | W | I | Q |

What is claimed:

1. An isolated antibody or antigen-binding portion thereof, which specifically binds to an alpha-chain of a human IL-7 receptor (IL-7R), said anti-IL-7R antibody and antigen-binding portion thereof comprising a heavy chain (HC) CDR1, CDR2, and CDR3, and a light chain (LC) CDR1, CDR2, and CDR3, wherein:
   (i) the heavy chain CDR1 comprises the amino acid sequence set forth in SEQ ID NO: 13;
   (ii) the heavy chain CDR2 comprises the amino acid sequence set forth in SEQ ID NO: 14;
   (iii) the heavy chain CDR3 comprises the amino acid sequence set forth in SEQ ID NO: 15;
   (iv) the light chain CDR1 comprises the amino acid sequence set forth in SEQ ID NO: 16;
   (v) the light chain CDR2 comprises the amino acid sequence set forth in SEQ ID NO: 17; and
   (vi) the light chain CDR3 comprises the amino acid sequence set forth in SEQ ID NO: 18.

2. An immunoconjugate comprising the anti-IL-7R antibody or antigen-binding portion thereof of claim 1, linked to an immunotherapeutic agent.

3. A kit comprising the anti-IL-7R antibody or antigen-binding portion thereof of claim 1, and an instruction for use.

4. The anti-IL-7R antibody or antigen-binding portion thereof of claim 1, which comprises a heavy chain variable region (VH) and a light chain variable region (VL), wherein the VH comprises the amino acid sequence set forth in SEQ ID NO: 19 and the VL comprises the amino acid sequence set forth in SEQ ID NO: 20.

5. The anti-IL-7R antibody or antigen-binding portion thereof of claim 4, wherein the anti-IL-7R antibody comprises a heavy chain and a light chain, wherein the heavy chain comprises the amino acid sequence set forth in SEQ ID NO: 21 and the light chain comprises the amino acid sequence set forth in SEQ ID NO: 22.

6. The anti-IL-7R antibody or antigen-binding portion thereof of claim 1, wherein the antibody is selected from the group consisting of: an IgG1, IgG2, IgG3, and IgG4.

7. The anti-IL-7R antibody or antigen-binding portion thereof of claim 6, wherein the antibody is an IgG1 antibody.

8. The anti-IL-7R antibody or antigen-binding portion thereof of claim 7, comprising an effectorless IgG1 Fc.

9. The anti-IL-7R antibody or antigen-binding portion thereof of claim 4, wherein the antibody is selected from the group consisting of: an IgG1, IgG2, IgG3, and IgG4.

10. The anti-IL-7R antibody or antigen-binding portion thereof of claim 9, wherein the antibody is an IgG1 antibody.

11. The anti-IL-7R antibody or antigen-binding portion thereof of claim 10, comprising an effectorless IgG1 Fc.

12. The anti-IL-7R antibody or antigen-binding portion thereof of claim 1, wherein the antigen-binding portion thereof is Fab, F(ab')2, Fv, or scFv.

13. The anti-IL-7R antibody or antigen-binding portion thereof of claim 4, wherein the antigen-binding portion thereof is Fab, F(ab')2, Fv, or scFv.

14. A composition comprising the anti-IL7R antibody or antigen-binding portion thereof of claim 1, and a pharmaceutically acceptable carrier.

15. A composition comprising the anti-IL7R antibody or antigen-binding portion thereof of claim 4, and a pharmaceutically acceptable carrier.

16. A composition comprising the anti-IL7R antibody or antigen-binding portion thereof of claim 5, and a pharmaceutically acceptable carrier.

17. A composition comprising the anti-IL7R antibody or antigen-binding portion thereof of claim 6, and a pharmaceutically acceptable carrier.

18. A composition comprising the anti-IL7R antibody or antigen-binding portion thereof of claim 7, and a pharmaceutically acceptable carrier.

19. A composition comprising the anti-IL7R antibody or antigen-binding portion thereof of claim 8, and a pharmaceutically acceptable carrier.

20. A composition comprising the anti-IL7R antibody or antigen-binding portion thereof of claim 9, and a pharmaceutically acceptable carrier.

21. A composition comprising the anti-IL7R antibody or antigen-binding portion thereof of claim 10, and a pharmaceutically acceptable carrier.

22. A composition comprising the anti-IL7R antibody or antigen-binding portion thereof of claim 11, and a pharmaceutically acceptable carrier.

23. A composition comprising the anti-IL7R antibody or antigen-binding portion thereof of claim 12, and a pharmaceutically acceptable carrier.

24. A composition comprising the anti-IL7R antibody or antigen-binding portion thereof of claim 13, and a pharmaceutically acceptable carrier.

25. The immunoconjugate of claim 2, wherein the immunotherapeutic agent is an antimetabolite, an alkylating agent, a DNA minor groove binder, a DNA intercalator, a DNA crosslinker, a histone deacetylase inhibitor, a nuclear export inhibitor, a proteasome inhibitor, a topoisomerase I or II inhibitor, a heat shock protein inhibitor, a tyrosine kinase inhibitor, an antibiotic, or an anti-mitotic agent.

* * * * *

SEQUENCE LISTING

<160> NUMBER OF SEQ ID NOS: 265

<210> SEQ ID NO 1
<211> LENGTH: 298
<212> TYPE: PRT
<213> ORGANISM: Homo sapiens

<400> SEQUENCE: 1

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Ile Tyr Arg Glu Gly Ala Asn
    130                 135                 140

Asp Phe Val Val Thr Phe Asn Thr Ser His Leu Gln Lys Lys Tyr Val
145                 150                 155                 160

```
Lys Val Leu Met His Asp Val Ala Tyr Arg Gln Glu Lys Asp Glu Asn
            165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
            195                 200                 205

Pro Asp His Tyr Phe Lys Gly Phe Trp Ser Glu Trp Ser Pro Ser Tyr
            210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
            245                 250                 255

Val Ile Leu Ala Cys Val Leu Trp Lys Lys Arg Ile Lys Pro Ile Val
            260                 265                 270

Trp Pro Ser Leu Pro Asp His Lys Lys Thr Leu Glu His Leu Cys Lys
            275                 280                 285

Lys Pro Arg Lys Val Ser Val Phe Gly Ala
            290                 295

<210> SEQ ID NO 2
<211> LENGTH: 252
<212> TYPE: PRT
<213> ORGANISM: Homo sapiens

<400> SEQUENCE: 2

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
            35                  40                  45

Asn Gly Ser Gln His Ser Leu Thr Cys Ala Phe Glu Asp Pro Asp Val
        50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
            85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
            115                 120                 125

Pro Glu Ala Pro Phe Asp Leu Ser Val Ile Tyr Arg Glu Gly Ala Asn
            130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
            165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
            195                 200                 205

Pro Asp His Tyr Phe Lys Gly Phe Trp Ser Glu Trp Ser Pro Ser Tyr
            210                 215                 220
```

```
Tyr Phe Arg Thr Pro Glu Ile Asn Asn Ser Ser Gly Leu Ser Leu Ser
225                 230                 235                 240

Tyr Gly Pro Val Ser Pro Ile Ile Arg Gln Glu Leu
            245                 250

<210> SEQ ID NO 3
<211> LENGTH: 298
<212> TYPE: PRT
<213> ORGANISM: Homo sapiens

<400> SEQUENCE: 3

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Ile Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
            260                 265                 270

Trp Pro Ser Leu Pro Asp His Lys Lys Thr Leu Glu His Leu Cys Lys
        275                 280                 285

Lys Pro Arg Lys Val Ser Val Phe Gly Ala
    290                 295

<210> SEQ ID NO 4
<211> LENGTH: 261
<212> TYPE: PRT
<213> ORGANISM: Homo sapiens
```

<400> SEQUENCE: 4

```
Met Thr Ile Leu Gly Thr Thr Phe Gly Met Val Phe Ser Leu Leu Gln
  1               5                  10                  15
Val Val Ser Gly Glu Ser Gly Tyr Ala Gln Asn Gly Asp Leu Glu Asp
             20                  25                  30
Ala Glu Leu Asp Asp Tyr Ser Phe Ser Cys Tyr Ser Gln Leu Glu Val
         35                  40                  45
Asn Gly Ser Gln His Ser Leu Thr Cys Ala Phe Glu Asp Pro Asp Val
 50                  55                  60
Asn Thr Thr Asn Leu Glu Phe Glu Ile Cys Gly Ala Leu Val Glu Val
 65                  70                  75                  80
Lys Cys Leu Asn Phe Arg Lys Leu Gln Glu Ile Tyr Phe Ile Glu Thr
                 85                  90                  95
Lys Lys Phe Leu Leu Ile Gly Lys Ser Asn Ile Cys Val Lys Val Gly
             100                 105                 110
Glu Lys Ser Leu Thr Cys Lys Lys Ile Asp Leu Thr Thr Ile Val Lys
         115                 120                 125
Pro Glu Ala Pro Phe Asp Leu Ser Val Ile Tyr Arg Glu Gly Ala Asn
130                 135                 140
Asp Phe Val Val Thr Phe Asn Thr Ser His Leu Gln Lys Lys Tyr Val
145                 150                 155                 160
Lys Val Leu Met His Asp Val Ala Tyr Arg Gln Glu Lys Asp Glu Asn
                 165                 170                 175
Lys Trp Thr His Val Asn Leu Ser Ser Thr Lys Leu Thr Leu Leu Gln
             180                 185                 190
Arg Lys Leu Gln Pro Ala Ala Met Tyr Glu Ile Lys Val Arg Ser Ile
         195                 200                 205
Pro Asp His Tyr Phe Lys Gly Phe Trp Ser Glu Trp Ser Pro Ser Tyr
210                 215                 220
Tyr Phe Arg Thr Pro Glu Ile Asn Asn Ser Ser Gly Leu Ser Leu Ser
225                 230                 235                 240
Tyr Gly Pro Val Ser Pro Ile Ile Arg Arg Leu Trp Asn Ile Phe Val
                 245                 250                 255
Arg Asn Gln Glu Lys
             260
```

<210> SEQ ID NO 5
<211> LENGTH: 4643
<212> TYPE: DNA
<213> ORGANISM: Homo sapiens

<400> SEQUENCE: 5

```
gtggttagat aagtataaag ccctagatct aagcttctct gtcttcctcc ctccctccct    60
tcctcttact ctcattcatt tcatacacac tggctcacac atctactctc tctctctatc   120
tctctcagaa tgacaattct aggtacaact tttggcatgg ttttttcttt acttcaagtc   180
gtttctggag aaagtggcta tgctcaaaat ggagacttgg aagatgcaga actggatgac   240
tactcattct catgctatag ccagttggaa gtgaatggat cgcagcactc actgacctgt   300
gcttttgagg acccagatgt caacatcacc aatctggaat ttgaaatatg tggggccctc   360
gtggaggtaa agtgcctgaa tttcaggaaa ctacaagaga tatatttcat cgagacaaag   420
aaattcttac tgattggaaa gagcaatata tgtgtgaagg ttggagaaaa gagtctaacc   480
tgcaaaaaaa tagacctaac cactatagtt aaacctgagg ctccttttga cctgagtgtc   540
```

```
gtctatcggg aaggagccaa tgactttgtg gtgacattta atacatcaca cttgcaaaag    600
aagtatgtaa aagttttaat gcacgatgta gcttaccgcc aggaaaagga tgaaaacaaa    660
tggacgcatg tgaatttatc cagcacaaag ctgacactcc tgcagagaaa gctccaaccg    720
gcagcaatgt atgagattaa agttcgatcc atccctgatc actattttaa aggcttctgg    780
agtgaatgga gtccaagtta ttacttcaga actccagaga tcaataatag ctcaggggag    840
atggatccta tcttactaac catcagcatt ttgagttttt tctctgtcgc tctgttggtc    900
atcttggcct gtgtgttatg gaaaaaaagg attaagccta tcgtatggcc cagtctcccc    960
gatcataaga agactctgga acatctttgt aagaaaccaa gaaaaatttt aaatgtgagt   1020
ttcaatcctg aaagtttcct ggactgccag attcataggg tggatgacat tcaagctaga   1080
gatgaagtgg aagttttct gcaagatacg tttcctcagc aactagaaga atctgagaag   1140
cagaggcttg gaggggatgt gcagagcccc aactgcccat ctgaggatgt agtcatcact   1200
ccagaaagct ttggaagaga ttcatccctc acatgcctgg ctgggaatgt cagtgcatgt   1260
gacgccccta ttctctcctc ttccaggtcc ctagactgca gggagagtgg caagaatggg   1320
cctcatgtgt accaggacct cctgcttagc cttgggacta caaacagcac gctgcccct   1380 ccattttctc tccaatctgg aatcctgaca ttgaacccag ttgctcaggg tcagcccatt   1440
cttacttccc tgggatcaaa tcaagaagaa gcatatgtca ccatgtccag cttctaccaa   1500
aaccagtgaa gtgtaagaaa cccagactga acttaccgtg agcgacaaag atgatttaaa   1560
agggaagtct agagttccta gtctccctca cagcacagag aagacaaaat tagcaaaacc   1620
ccactacaca gtctgcaaga ttctgaaaca ttgctttgac cactcttcct gagttcagtg   1680
gcactcaaca tgagtcaaga gcatcctgct tctaccatgt ggatttggtc acaaggttta   1740
aggtgaccca atgattcagc tatttaaaaa aaaagagga aagaatgaaa gagtaaagga   1800
aatgattgag gagtgaggaa ggcaggaaga gagcatgaga ggaaagaaag aaaggaaaat   1860
aaaaaatgat agttgccatt attaggattt aatatatatc cagtgctttg caagtgctct   1920
gcgcaccttg tctcactcca tcctgacaat aatcctggga ggtgtgtgca attactacga   1980
ctactctctt ttttatagat cattaaattc agaactaagg agttaagtaa cttgtccaag   2040
ttgttcacac agtgaaggga ggggccaaga tatgatggct gggagtctaa ttgcagttcc   2100
ctgagccatg tgcctttctc ttcactgagg actgccccat tcttgagtgc aaacgtcac   2160 tagtaacagg gtgtgcctag ataatttatg atccaaactg agtcagtttg gaaagtgaaa   2220
gggaaactta catataatcc ctccgggaca atgagcaaaa actaggactg tccccagaca   2280
aatgtgaaca tacatatcat cacttaaatt aaaatggcta tgagaaagaa agaggggag   2340 aaacagtctt gcgggtgtga agtcccatga ccagccatgt caaaagaagg taaagaagtc   2400
aagaaaaagc catgaagccc atttggtttc attttctga aaataggctc aagagggaat   2460
aaattagaaa ctcacaattt ctcttgtttg ttaccaagac agtgattctc ttgctgctac   2520
cacccaactg catccgtcca tgatctcaga ggaaactgtc gctgaccctg acatgggta   2580 cgtttgacga gtgagaggag gcatgacccc tccatgtgt atagacacta ccccaaccta   2640
aattcatccc taaattgtcc caagttctcc agcaatagag gctgccacaa acttcaggga   2700
gaaagagtta caagtacatg caatgagtga actgactgtg gctacaatct tgaagatata   2760
cggaagagac gtattattaa tgcttgacat atatcatctt gcctttcttg gtctagactg   2820
acttctaatg actaactcaa agtcaaggca actgagtaat gtcagctcag caaagtgcag   2880
caaacccatc tcccacaggc ctccaaaccc tggctgttca cagaaccaca aagggcagat   2940
```

```
gctgcacaga aaactagaga aggggtcata ggttcatggt tttgtttgag atttgttgct   3000 actgttttc  tgttttgaat tttcttcttt gttctgtttt tactttattt aggggactaa   3060 ggtgttctg  atattttagt tttcttgttt gttttgtttt gtgttgtctg tgaatggggt   3120
tttaactgtg gatgaatgga ccttatctgt tggcttaaag gactggtaag atcagaccat   3180
cttattcttc aggtgaatgt tttactttcc aaagtgctct cctctgcacc agcagtaata   3240
aatacaatgc cataatccct taggtttgcc tagtgctttt gcaattttca aagcacttcc   3300
ataagcattc cttccacctc cttgataggc atttatggaa agcctgctac atgtcaatca   3360
tactgttagg cacaggggac ctaaagacac ataaaaggat ggcattctgc ctcataaatt   3420 gcaaaccta  atgaaagtga ctgcttggta acaaattat  tattatatta taaaatgcta   3480
taaaagagcc atattgaaag tgccctgttg gagacagggc aaatgccaca aaaatgatgt   3540
aaatttacat ggaggaaaag tagaatctgc ctggtttgta ggcagcagaa gacattttc    3600 atcagtgggc aggtgttctt tacctttgt  agaaatggga gtcaagtctc aaataggagg   3660
ctccacaaaa tctcatgcca ggtctctgat accttattca cagaagttct ttgaagtatt   3720
tattgttatt ttctttgact tatgggaaaa ctgggacaca ggaagacagg taaattaccc   3780
aacctcacac gttaagtcag aactgggagc cataattttg tatccctggt ataaatagac   3840
aatctcttga agaaatgaag agatgaccat agaaaaacat cgagatatct ccagctctaa   3900
aatcctttgt ttcaatgttg tttggcatat gttatctttg gaatttagtg tctgagcctc   3960
tgtctgttac tgtagtattt aaaatgcatg tattataatc atataatcat aactgctgtt   4020
aattcttgat tatataccta gggacaatgt gtaatgtaag attactaatt ggttctgccc   4080
aatctccttt cagattttat taggaaaaaa aaataaacct cctgatcgga gacaatgtat   4140
taatcagaag tgtaaactgc cagttctata tagcatgaaa tgaaaagaca gctaatttgg   4200
tccaacaaac atgactgggt ctagggcacc caggctgatt cagctgattt cctaccagcc   4260
tttgcctctt ccttcaatgt ggtttccatg ggaatttgct tcagaaaagc caagtatggg   4320
ctgttcagag gtgcacacct gcattttctt agctcttcta gagggctaa  gagacttggt   4380 acgggccagg aagaatatgt ggcagagctc ctggaaatga tgcagattag gtggcatttt   4440
tgtcagctct gtggtttatt gttgggacta ttctttaaaa tatccattgt tcactacagt   4500
gaagatctct gatttaaccg tgtactatcc acatgcatta caaacatttc gcagagctgc   4560
ttagtatata agcgtacaat gtatgtaata accatctcat atttaattaa atggtataga   4620
agaacaaaaa aaaaaaaaaa aaa                                           4643
```

<210> SEQ ID NO 6
<211> LENGTH: 219
<212> TYPE: PRT
<213> ORGANISM: Homo sapiens

<400> SEQUENCE: 6

```
Glu Ser Gly Tyr Ala Gln Asn Gly Asp Leu Glu Asp Ala Glu Leu Asp
1               5                   10                  15

Asp Tyr Ser Phe Ser Cys Tyr Ser Gln Leu Glu Val Asn Gly Ser Gln
            20                  25                  30

His Ser Leu Thr Cys Ala Phe Glu Asp Pro Asp Val Asn Thr Thr Asn
        35                  40                  45

Leu Glu Phe Glu Ile Cys Gly Ala Leu Val Glu Val Lys Cys Leu Asn
    50                  55                  60
```

```
Phe Arg Lys Leu Gln Glu Ile Tyr Phe Ile Glu Thr Lys Lys Phe Leu
 65                  70                  75                  80

Leu Ile Gly Lys Ser Asn Ile Cys Val Lys Val Gly Glu Lys Ser Leu
                 85                  90                  95

Thr Cys Lys Lys Ile Asp Leu Thr Thr Ile Val Lys Pro Glu Ala Pro
            100                 105                 110

Phe Asp Leu Ser Val Ile Tyr Arg Glu Gly Ala Asn Asp Phe Val Val
        115                 120                 125

Thr Phe Asn Thr Ser His Leu Gln Lys Lys Tyr Val Lys Val Leu Met
    130                 135                 140

His Asp Val Ala Tyr Arg Gln Glu Lys Asp Glu Asn Lys Trp Thr His
145                 150                 155                 160

Val Asn Leu Ser Ser Thr Lys Leu Thr Leu Leu Gln Arg Lys Leu Gln
                165                 170                 175

Pro Ala Ala Met Tyr Glu Ile Lys Val Arg Ser Ile Pro Asp His Tyr
            180                 185                 190

Phe Lys Gly Phe Trp Ser Glu Trp Ser Pro Ser Tyr Tyr Phe Arg Thr
        195                 200                 205

Pro Glu Ile Asn Asn Ser Ser Gly Glu Met Asp
    210                 215

<210> SEQ ID NO 7
<211> LENGTH: 459
<212> TYPE: PRT
<213> ORGANISM: Macaca fascicularis

<400> SEQUENCE: 7

Met Thr Ile Leu Gly Thr Thr Phe Gly Met Val Phe Ser Leu Leu Gln
  1               5                  10                  15

Val Val Ser Gly Glu Ser Gly Tyr Ala Gln Asn Gly Asp Leu Glu Asp
                 20                  25                  30

Ala Glu Leu Asp Asp Tyr Ser Phe Ser Cys Tyr Ser Gln Leu Glu Val
             35                  40                  45

Asn Gly Ser Gln His Ser Leu Thr Cys Ala Phe Glu Asp Pro Asp Val
 50                  55                  60

Asn Thr Thr Asn Leu Glu Phe Glu Ile Cys Gly Ala Leu Val Glu Val
 65                  70                  75                  80

Lys Cys Leu Ser Phe Arg Lys Leu Gln Glu Ile Tyr Phe Ile Glu Thr
                 85                  90                  95

Lys Lys Phe Leu Leu Ile Gly Lys Ser Asn Ile Cys Val Lys Val Gly
            100                 105                 110

Gly Lys Ser Leu Thr Cys Lys Lys Ile Asp Leu Thr Thr Ile Val Lys
        115                 120                 125

Pro Glu Ala Pro Phe Asp Leu Ser Val Ile Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Met His Val Asn Leu Ser Ser Thr Lys Leu Thr Leu Leu Gln
            180                 185                 190

Arg Asn Leu Gln Pro Glu Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220
```

```
Tyr Phe Arg Thr Pro Glu Ile Asn Asn Ser Pro Gly Glu Met Asp Pro
225                 230                 235                 240

Ile Leu Leu Thr Ile Ser Leu Leu Ser Phe Phe Ser Val Ala Leu Leu
                245                 250                 255

Val Ile Leu Ala Cys Val Leu Trp Lys Lys Arg Ile Lys Pro Ile Val
            260                 265                 270

Trp Pro Ser Leu Pro Asp His Lys Lys Thr Leu Glu His Leu Cys Lys
        275                 280                 285

Lys Pro Arg Lys Asn Leu Asn Val Ser Phe Asn Pro Glu Ser Phe Leu
    290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Lys
                325                 330                 335

Lys Gln Arg Leu Gly Gly Asp Val Gln Ser Pro Ser Cys Pro Ser Glu
            340                 345                 350

Asp Val Val Ile Thr Pro Glu Ser Phe Glu Arg Asp Ser Ser Leu Arg
        355                 360                 365

Cys Leu Ala Gly Asn Val Ser Ala Cys Asp Ala Pro Ile Leu Ser Ser
370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
                405                 410                 415

Pro Pro Phe Ser Leu Gln Ser Gly Ile Leu Thr Leu Asn Pro Val Ala
            420                 425                 430

Gln Gly Gln Pro Ile Leu Thr Ser Leu Gly Ser Asn Gln Glu Glu Ala
        435                 440                 445

Tyr Val Thr Met Ser Ser Phe Tyr Gln Asn Gln
    450                 455

<210> SEQ ID NO 8
<211> LENGTH: 16
<212> TYPE: PRT
<213> ORGANISM: Artificial Sequence
<220> FEATURE:
<223> OTHER INFORMATION: Epitope 1

<400> SEQUENCE: 8

Ser Gln Leu Glu Val Asn Gly Ser Gln His Ser Leu Thr Cys Ala Phe
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Epitope 2

<400> SEQUENCE: 9

Phe Ile Glu Thr Lys Lys Phe Leu Leu Ile Gly Lys Ser Asn Ile Cys
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: Epitope 3
```

```
<400> SEQUENCE: 10

Val Lys Val Gly Glu Lys Ser Leu Thr Cys Lys Lys Ile Asp Leu Thr
1               5                   10                  15

Thr

<210> SEQ ID NO 11
<211> LENGTH: 14
<212> TYPE: PRT
<213> ORGANISM: Artificial Sequence
<220> FEATURE:
<223> OTHER INFORMATION: Epitope 4

<400> SEQUENCE: 11

Gln Lys Lys Tyr Val Lys Val Leu Met His Asp Val Ala Tyr
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Epitope 5

<400> SEQUENCE: 12

Tyr Glu Ile Lys Val Arg Ser Ile Pro Asp His Tyr Phe Lys Gly Phe
1               5                   10                  15

<210> SEQ ID NO 13
<211> LENGTH: 5
<212> TYPE: PRT
<213> ORGANISM: Artificial Sequence
<220> FEATURE:
<223> OTHER INFORMATION: Heavy Chain CDR1

<400> SEQUENCE: 13

Asp His Ala Met His
1               5

<210> SEQ ID NO 14
<211> LENGTH: 17
<212> TYPE: PRT
<213> ORGANISM: Artificial Sequence
<220> FEATURE:
<223> OTHER INFORMATION: Heavy Chain CDR2

<400> SEQUENCE: 14

Gly Ile Ser Trp Asn Ser Arg Gly Ile Gly Tyr Ala Asp Ser Val Lys
1               5                   10                  15

Gly

<210> SEQ ID NO 15
<211> LENGTH: 12
<212> TYPE: PRT
<213> ORGANISM: Artificial Sequence
<220> FEATURE:
<223> OTHER INFORMATION: Heavy Chain CDR3

<400> SEQUENCE: 15

Asp Glu Tyr Ser Arg Gly Tyr Tyr Val Leu Asp Val
1               5                   10

<210> SEQ ID NO 16
<211> LENGTH: 11
<212> TYPE: PRT
<213> ORGANISM: Artificial Sequence
```

<220> FEATURE:
<223> OTHER INFORMATION: Light Chain CDR1

<400> SEQUENCE: 16

Arg Ala Ser Gln Gly Ile Ser Ser Ala Leu Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Light Chain CDR2

<400> SEQUENCE: 17

Asp Ala Ser Ser Leu Glu Ser
1               5

<210> SEQ ID NO 18
<211> LENGTH: 11
<212> TYPE: PRT
<213> ORGANISM: Artificial Sequence
<220> FEATURE:
<223> OTHER INFORMATION: Light Chain CDR3

<400> SEQUENCE: 18

Gln Gln Phe Asn Ser Tyr Pro Leu Trp Ile Thr
1               5                   10

<210> SEQ ID NO 19
<211> LENGTH: 121
<212> TYPE: PRT
<213> ORGANISM: Artificial Sequence
<220> FEATURE:
<223> OTHER INFORMATION: Heavy Chain Variable Region (VH)

<400> SEQUENCE: 19

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp His
            20                  25                  30

Ala Met His Trp Val Arg Gln Ala Pro Gly Lys Gly Leu Glu Trp Val
        35                  40                  45

Ser Gly Ile Ser Trp Asn Ser Arg Gly Ile Gly Tyr Ala Asp Ser Val
    50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Glu Tyr Ser Arg Gly Tyr Tyr Val Leu Asp Val Trp Gly
            100                 105                 110

Gln Gly Thr Thr Val Thr Val Ser Ser
        115                 120

<210> SEQ ID NO 20
<211> LENGTH: 109
<212> TYPE: PRT
<213> ORGANISM: Artificial Sequence
<220> FEATURE:
<223> OTHER INFORMATION: Light Chain Variable region (VL)

<400> SEQUENCE: 20

Ala Ile Gln Leu Thr Gln Ser Pro Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Trp Ile Thr Phe Gly Gln Gly Thr Arg Leu Glu Ile Lys
            100                 105

<210> SEQ ID NO 21
<211> LENGTH: 450
<212> TYPE: PRT
<213> ORGANISM: Artificial Sequence
<220> FEATURE:
<223> OTHER INFORMATION: Heavy Chain

<400> SEQUENCE: 21

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp His
            20                  25                  30

Ala Met His Trp Val Arg Gln Ala Pro Gly Lys Gly Leu Glu Trp Val
            35                  40                  45

Ser Gly Ile Ser Trp Asn Ser Arg Gly Ile Gly Tyr Ala Asp Ser Val
    50                  55                  60

Lys Gly Arg Phe Thr Ile Phe Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Glu Tyr Ser Arg Gly Tyr Tyr Val Leu Asp Val Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Glu Gly
225                 230                 235                 240

```
Ala Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 22
<211> LENGTH: 216
<212> TYPE: PRT
<213> ORGANISM: Artificial Sequence
<220> FEATURE:
<223> OTHER INFORMATION: Light Chain

<400> SEQUENCE: 22

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
            85                  90                  95

Trp Ile Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
            130                 135                 140
```

```
Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
            165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
        210                 215

<210> SEQ ID NO 23
<211> LENGTH: 330
<212> TYPE: PRT
<213> ORGANISM: Homo sapiens

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 24
<211> LENGTH: 330
<212> TYPE: PRT
<213> ORGANISM: Homo sapiens

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 25
<211> LENGTH: 330
<212> TYPE: PRT
<213> ORGANISM: Artificial Sequence
<220> FEATURE:
<223> OTHER INFORMATION: IgG1.1f Constant Region

<400> SEQUENCE: 25

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 26
<211> LENGTH: 330
<212> TYPE: PRT
<213> ORGANISM: Artificial Sequence
<220> FEATURE:
<223> OTHER INFORMATION: IgG1.3f Constant Region

<400> SEQUENCE: 26

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 107
<212> TYPE: PRT
<213> ORGANISM: Homo sapiens

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
            35                  40                  45
Ser Gly Asn Ser Gln Glu Ser Val Thr Glu Gln Asp Ser Lys Asp Ser
 50                  55                  60
Thr Tyr Ser Leu Ser Ser Thr Leu Thr Leu Ser Lys Ala Asp Tyr Glu
 65                  70                  75                  80
Lys His Lys Val Tyr Ala Cys Glu Val Thr His Gln Gly Leu Ser Ser
                 85                  90                  95
Pro Val Thr Lys Ser Phe Asn Arg Gly Glu Cys
            100                 105
```

```
<210> SEQ ID NO 28
<211> LENGTH: 5
<212> TYPE: PRT
<213> ORGANISM: Artificial Sequence
<220> FEATURE:
<223> OTHER INFORMATION: LSPGK (C-terminal end of heavy chain)

<400> SEQUENCE: 28

Leu Ser Pro Gly Lys
1               5
```

```
<210> SEQ ID NO 29
<211> LENGTH: 4
<212> TYPE: PRT
<213> ORGANISM: Artificial Sequence
<220> FEATURE:
<223> OTHER INFORMATION: LSPG (C-terminal end of heavy chain)

<400> SEQUENCE: 29

Leu Ser Pro Gly
1
```

```
<210> SEQ ID NO 30
<211> LENGTH: 5
<212> TYPE: PRT
<213> ORGANISM: Artificial Sequence
<220> FEATURE:
<223> OTHER INFORMATION: Linker

<400> SEQUENCE: 30

Pro Val Gly Val Val
1               5
```

```
<210> SEQ ID NO 31
<211> LENGTH: 10
<212> TYPE: PRT
<213> ORGANISM: Artificial Sequence
<220> FEATURE:
<223> OTHER INFORMATION: HC CDR1 (18B1)

<400> SEQUENCE: 31

Gly Phe Thr Phe Asp Asp His Ala Met His
1               5                   10
```

```
<210> SEQ ID NO 32
<211> LENGTH: 10
<212> TYPE: PRT
<213> ORGANISM: Artificial Sequence
<220> FEATURE:
<223> OTHER INFORMATION: HC CDR1 (F27Y)

<400> SEQUENCE: 32

Gly Tyr Thr Phe Asp Asp His Ala Met His
1               5                   10
```

```
<210> SEQ ID NO 33
<211> LENGTH: 10
<212> TYPE: PRT
<213> ORGANISM: Artificial Sequence
<220> FEATURE:
<223> OTHER INFORMATION: HC CDR1 (T28P)

<400> SEQUENCE: 33

Gly Phe Pro Phe Asp Asp His Ala Met His
1               5                   10

<210> SEQ ID NO 34
<211> LENGTH: 10
<212> TYPE: PRT
<213> ORGANISM: Artificial Sequence
<220> FEATURE:
<223> OTHER INFORMATION: HC CDR1 (T28A)

<400> SEQUENCE: 34

Gly Phe Ala Phe Asp Asp His Ala Met His
1               5                   10

<210> SEQ ID NO 35
<211> LENGTH: 10
<212> TYPE: PRT
<213> ORGANISM: Artificial Sequence
<220> FEATURE:
<223> OTHER INFORMATION: HC CDR1 (T28V)

<400> SEQUENCE: 35

Gly Phe Val Phe Asp Asp His Ala Met His
1               5                   10

<210> SEQ ID NO 36
<211> LENGTH: 10
<212> TYPE: PRT
<213> ORGANISM: Artificial Sequence
<220> FEATURE:
<223> OTHER INFORMATION: HC CDR1 (T28L)

<400> SEQUENCE: 36

Gly Phe Leu Phe Asp Asp His Ala Met His
1               5                   10

<210> SEQ ID NO 37
<211> LENGTH: 10
<212> TYPE: PRT
<213> ORGANISM: Artificial Sequence
<220> FEATURE:
<223> OTHER INFORMATION: HC CDR1 (T28I)

<400> SEQUENCE: 37

Gly Phe Ile Phe Asp Asp His Ala Met His
1               5                   10

<210> SEQ ID NO 38
<211> LENGTH: 10
<212> TYPE: PRT
<213> ORGANISM: Artificial Sequence
<220> FEATURE:
<223> OTHER INFORMATION: HC CDR1 (T28M)

<400> SEQUENCE: 38

Gly Phe Met Phe Asp Asp His Ala Met His
1               5                   10
```

```
<210> SEQ ID NO 39
<211> LENGTH: 10
<212> TYPE: PRT
<213> ORGANISM: Artificial Sequence
<220> FEATURE:
<223> OTHER INFORMATION: HC CDR1 (T28H)

<400> SEQUENCE: 39

Gly Phe His Phe Asp Asp His Ala Met His
1               5                   10

<210> SEQ ID NO 40
<211> LENGTH: 10
<212> TYPE: PRT
<213> ORGANISM: Artificial Sequence
<220> FEATURE:
<223> OTHER INFORMATION: HC CDR1 (T28F)

<400> SEQUENCE: 40

Gly Phe Phe Phe Asp Asp His Ala Met His
1               5                   10

<210> SEQ ID NO 41
<211> LENGTH: 10
<212> TYPE: PRT
<213> ORGANISM: Artificial Sequence
<220> FEATURE:
<223> OTHER INFORMATION: HC CDR1 (T28Y)

<400> SEQUENCE: 41

Gly Phe Tyr Phe Asp Asp His Ala Met His
1               5                   10

<210> SEQ ID NO 42
<211> LENGTH: 10
<212> TYPE: PRT
<213> ORGANISM: Artificial Sequence
<220> FEATURE:
<223> OTHER INFORMATION: HC CDR1 (T28N)

<400> SEQUENCE: 42

Gly Phe Asn Phe Asp Asp His Ala Met His
1               5                   10

<210> SEQ ID NO 43
<211> LENGTH: 10
<212> TYPE: PRT
<213> ORGANISM: Artificial Sequence
<220> FEATURE:
<223> OTHER INFORMATION: HC CDR1 (T28D)

<400> SEQUENCE: 43

Gly Phe Asp Phe Asp Asp His Ala Met His
1               5                   10

<210> SEQ ID NO 44
<211> LENGTH: 10
<212> TYPE: PRT
<213> ORGANISM: Artificial Sequence
<220> FEATURE:
<223> OTHER INFORMATION: HC CDR1 (T28E)

<400> SEQUENCE: 44

Gly Phe Glu Phe Asp Asp His Ala Met His
1               5                   10
```

```
<210> SEQ ID NO 45
<211> LENGTH: 10
<212> TYPE: PRT
<213> ORGANISM: Artificial Sequence
<220> FEATURE:
<223> OTHER INFORMATION: HC CDR1 (T28Q)

<400> SEQUENCE: 45

Gly Phe Gln Phe Asp Asp His Ala Met His
1               5                   10

<210> SEQ ID NO 46
<211> LENGTH: 10
<212> TYPE: PRT
<213> ORGANISM: Artificial Sequence
<220> FEATURE:
<223> OTHER INFORMATION: HC CDR1 (M34L)

<400> SEQUENCE: 46

Gly Phe Thr Phe Asp Asp His Ala Leu His
1               5                   10

<210> SEQ ID NO 47
<211> LENGTH: 17
<212> TYPE: PRT
<213> ORGANISM: Artificial Sequence
<220> FEATURE:
<223> OTHER INFORMATION: HC CDR2 (S52T)

<400> SEQUENCE: 47

Gly Ile Thr Trp Asn Ser Arg Gly Ile Gly Tyr Ala Asp Ser Val Lys
1               5                   10                  15

Gly

<210> SEQ ID NO 48
<211> LENGTH: 17
<212> TYPE: PRT
<213> ORGANISM: Artificial Sequence
<220> FEATURE:
<223> OTHER INFORMATION: HC CDR2 (N53H)

<400> SEQUENCE: 48

Gly Ile Ser Trp His Ser Arg Gly Ile Gly Tyr Ala Asp Ser Val Lys
1               5                   10                  15

Gly

<210> SEQ ID NO 49
<211> LENGTH: 17
<212> TYPE: PRT
<213> ORGANISM: Artificial Sequence
<220> FEATURE:
<223> OTHER INFORMATION: HC CDR2 (I57V)

<400> SEQUENCE: 49

Gly Ile Ser Trp Asn Ser Arg Gly Val Gly Tyr Ala Asp Ser Val Lys
1               5                   10                  15

Gly

<210> SEQ ID NO 50
<211> LENGTH: 17
<212> TYPE: PRT
<213> ORGANISM: Artificial Sequence
<220> FEATURE:
<223> OTHER INFORMATION: HC CDR2 (A60G)
```

```
<400> SEQUENCE: 50

Gly Ile Ser Trp Asn Ser Arg Gly Ile Gly Tyr Gly Asp Ser Val Lys
1               5                   10                  15

Gly

<210> SEQ ID NO 51
<211> LENGTH: 17
<212> TYPE: PRT
<213> ORGANISM: Artificial Sequence
<220> FEATURE:
<223> OTHER INFORMATION: HC CDR2 (A60S)

<400> SEQUENCE: 51

Gly Ile Ser Trp Asn Ser Arg Gly Ile Gly Tyr Ser Asp Ser Val Lys
1               5                   10                  15

Gly

<210> SEQ ID NO 52
<211> LENGTH: 17
<212> TYPE: PRT
<213> ORGANISM: Artificial Sequence
<220> FEATURE:
<223> OTHER INFORMATION: HC CDR2 (A60T)

<400> SEQUENCE: 52

Gly Ile Ser Trp Asn Ser Arg Gly Ile Gly Tyr Thr Asp Ser Val Lys
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: HC CDR2 (A60V)

<400> SEQUENCE: 53

Gly Ile Ser Trp Asn Ser Arg Gly Ile Gly Tyr Val Asp Ser Val Lys
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: HC CDR2 (A60L)

<400> SEQUENCE: 54

Gly Ile Ser Trp Asn Ser Arg Gly Ile Gly Tyr Leu Asp Ser Val Lys
1               5                   10                  15

Gly

<210> SEQ ID NO 55
<211> LENGTH: 17
<212> TYPE: PRT
<213> ORGANISM: Artificial Sequence
<220> FEATURE:
<223> OTHER INFORMATION: HC CDR2 (A60I)
```

```
<400> SEQUENCE: 55

Gly Ile Ser Trp Asn Ser Arg Gly Ile Gly Tyr Ile Asp Ser Val Lys
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: HC CDR2 (A60R)

<400> SEQUENCE: 56

Gly Ile Ser Trp Asn Ser Arg Gly Ile Gly Tyr Arg Asp Ser Val Lys
1               5                   10                  15

Gly

<210> SEQ ID NO 57
<211> LENGTH: 17
<212> TYPE: PRT
<213> ORGANISM: Artificial Sequence
<220> FEATURE:
<223> OTHER INFORMATION: HC CDR2 (A60H)

<400> SEQUENCE: 57

Gly Ile Ser Trp Asn Ser Arg Gly Ile Gly Tyr His Asp Ser Val Lys
1               5                   10                  15

Gly

<210> SEQ ID NO 58
<211> LENGTH: 17
<212> TYPE: PRT
<213> ORGANISM: Artificial Sequence
<220> FEATURE:
<223> OTHER INFORMATION: HC CDR2 (A60N)

<400> SEQUENCE: 58

Gly Ile Ser Trp Asn Ser Arg Gly Ile Gly Tyr Asn Asp Ser Val Lys
1               5                   10                  15

Gly

<210> SEQ ID NO 59
<211> LENGTH: 17
<212> TYPE: PRT
<213> ORGANISM: Artificial Sequence
<220> FEATURE:
<223> OTHER INFORMATION: HC CDR2 (D61P)

<400> SEQUENCE: 59

Gly Ile Ser Trp Asn Ser Arg Gly Ile Gly Tyr Ala Pro Ser Val Lys
1               5                   10                  15

Gly

<210> SEQ ID NO 60
<211> LENGTH: 17
<212> TYPE: PRT
<213> ORGANISM: Artificial Sequence
<220> FEATURE:
<223> OTHER INFORMATION: HC CDR2 (D61T)
```

```
<400> SEQUENCE: 60

Gly Ile Ser Trp Asn Ser Arg Gly Ile Gly Tyr Ala Thr Ser Val Lys
1               5                   10                  15
Gly

<210> SEQ ID NO 61
<211> LENGTH: 17
<212> TYPE: PRT
<213> ORGANISM: Artificial Sequence
<220> FEATURE:
<223> OTHER INFORMATION: HC CDR2 (D61N)

<400> SEQUENCE: 61

Gly Ile Ser Trp Asn Ser Arg Gly Ile Gly Tyr Ala Asn Ser Val Lys
1               5                   10                  15
Gly

<210> SEQ ID NO 62
<211> LENGTH: 17
<212> TYPE: PRT
<213> ORGANISM: Artificial Sequence
<220> FEATURE:
<223> OTHER INFORMATION: HC CDR2 (D61E)

<400> SEQUENCE: 62

Gly Ile Ser Trp Asn Ser Arg Gly Ile Gly Tyr Ala Glu Ser Val Lys
1               5                   10                  15
Gly

<210> SEQ ID NO 63
<211> LENGTH: 17
<212> TYPE: PRT
<213> ORGANISM: Artificial Sequence
<220> FEATURE:
<223> OTHER INFORMATION: HC CDR2 (D61Q)

<400> SEQUENCE: 63

Gly Ile Ser Trp Asn Ser Arg Gly Ile Gly Tyr Ala Gln Ser Val Lys
1               5                   10                  15
Gly

<210> SEQ ID NO 64
<211> LENGTH: 17
<212> TYPE: PRT
<213> ORGANISM: Artificial Sequence
<220> FEATURE:
<223> OTHER INFORMATION: HC CDR2 (D61S)

<400> SEQUENCE: 64

Gly Ile Ser Trp Asn Ser Arg Gly Ile Gly Tyr Ala Ser Ser Val Lys
1               5                   10                  15
Gly

<210> SEQ ID NO 65
<211> LENGTH: 17
<212> TYPE: PRT
<213> ORGANISM: Artificial Sequence
<220> FEATURE:
<223> OTHER INFORMATION: HC CDR2 (D61H)
```

-continued

```
<400> SEQUENCE: 65

Gly Ile Ser Trp Asn Ser Arg Gly Ile Gly Tyr Ala His Ser Val Lys
1               5                   10                  15
Gly

<210> SEQ ID NO 66
<211> LENGTH: 17
<212> TYPE: PRT
<213> ORGANISM: Artificial Sequence
<220> FEATURE:
<223> OTHER INFORMATION: HC CDR2 (S62P)

<400> SEQUENCE: 66

Gly Ile Ser Trp Asn Ser Arg Gly Ile Gly Tyr Ala Asp Pro Val Lys
1               5                   10                  15
Gly

<210> SEQ ID NO 67
<211> LENGTH: 17
<212> TYPE: PRT
<213> ORGANISM: Artificial Sequence
<220> FEATURE:
<223> OTHER INFORMATION: HC CDR2 (S62G)

<400> SEQUENCE: 67

Gly Ile Ser Trp Asn Ser Arg Gly Ile Gly Tyr Ala Asp Gly Val Lys
1               5                   10                  15
Gly

<210> SEQ ID NO 68
<211> LENGTH: 17
<212> TYPE: PRT
<213> ORGANISM: Artificial Sequence
<220> FEATURE:
<223> OTHER INFORMATION: HC CDR2 (S62A)

<400> SEQUENCE: 68

Gly Ile Ser Trp Asn Ser Arg Gly Ile Gly Tyr Ala Asp Ala Val Lys
1               5                   10                  15
Gly

<210> SEQ ID NO 69
<211> LENGTH: 17
<212> TYPE: PRT
<213> ORGANISM: Artificial Sequence
<220> FEATURE:
<223> OTHER INFORMATION: HC CDR2 (S62T)

<400> SEQUENCE: 69

Gly Ile Ser Trp Asn Ser Arg Gly Ile Gly Tyr Ala Asp Thr Val Lys
1               5                   10                  15
Gly

<210> SEQ ID NO 70
<211> LENGTH: 17
<212> TYPE: PRT
<213> ORGANISM: Artificial Sequence
<220> FEATURE:
<223> OTHER INFORMATION: HC CDR2 (S62V)
```

```
<400> SEQUENCE: 70

Gly Ile Ser Trp Asn Ser Arg Gly Ile Gly Tyr Ala Asp Val Val Lys
1               5                   10                  15

Gly

<210> SEQ ID NO 71
<211> LENGTH: 17
<212> TYPE: PRT
<213> ORGANISM: Artificial Sequence
<220> FEATURE:
<223> OTHER INFORMATION: HC CDR2 (S62R)

<400> SEQUENCE: 71

Gly Ile Ser Trp Asn Ser Arg Gly Ile Gly Tyr Ala Asp Arg Val Lys
1               5                   10                  15

Gly

<210> SEQ ID NO 72
<211> LENGTH: 17
<212> TYPE: PRT
<213> ORGANISM: Artificial Sequence
<220> FEATURE:
<223> OTHER INFORMATION: HC CDR2 (S62H)

<400> SEQUENCE: 72

Gly Ile Ser Trp Asn Ser Arg Gly Ile Gly Tyr Ala Asp His Val Lys
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: HC CDR2 (S62F)

<400> SEQUENCE: 73

Gly Ile Ser Trp Asn Ser Arg Gly Ile Gly Tyr Ala Asp Phe Val Lys
1               5                   10                  15

Gly

<210> SEQ ID NO 74
<211> LENGTH: 17
<212> TYPE: PRT
<213> ORGANISM: Artificial Sequence
<220> FEATURE:
<223> OTHER INFORMATION: HC CDR2 (S62Y)

<400> SEQUENCE: 74

Gly Ile Ser Trp Asn Ser Arg Gly Ile Gly Tyr Ala Asp Tyr Val Lys
1               5                   10                  15

Gly

<210> SEQ ID NO 75
<211> LENGTH: 17
<212> TYPE: PRT
<213> ORGANISM: Artificial Sequence
<220> FEATURE:
<223> OTHER INFORMATION: HC CDR2 (S62N)
```

```
<400> SEQUENCE: 75

Gly Ile Ser Trp Asn Ser Arg Gly Ile Gly Tyr Ala Asp Asn Val Lys
1               5                   10                  15
Gly

<210> SEQ ID NO 76
<211> LENGTH: 17
<212> TYPE: PRT
<213> ORGANISM: Artificial Sequence
<220> FEATURE:
<223> OTHER INFORMATION: HC CDR2 (S62D)

<400> SEQUENCE: 76

Gly Ile Ser Trp Asn Ser Arg Gly Ile Gly Tyr Ala Asp Asp Val Lys
1               5                   10                  15
Gly

<210> SEQ ID NO 77
<211> LENGTH: 17
<212> TYPE: PRT
<213> ORGANISM: Artificial Sequence
<220> FEATURE:
<223> OTHER INFORMATION: HC CDR2 (S62E)

<400> SEQUENCE: 77

Gly Ile Ser Trp Asn Ser Arg Gly Ile Gly Tyr Ala Asp Glu Val Lys
1               5                   10                  15
Gly

<210> SEQ ID NO 78
<211> LENGTH: 17
<212> TYPE: PRT
<213> ORGANISM: Artificial Sequence
<220> FEATURE:
<223> OTHER INFORMATION: HC CDR2 (V63I)

<400> SEQUENCE: 78

Gly Ile Ser Trp Asn Ser Arg Gly Ile Gly Tyr Ala Asp Ser Ile Lys
1               5                   10                  15
Gly

<210> SEQ ID NO 79
<211> LENGTH: 17
<212> TYPE: PRT
<213> ORGANISM: Artificial Sequence
<220> FEATURE:
<223> OTHER INFORMATION: HC CDR2 (K64A)

<400> SEQUENCE: 79

Gly Ile Ser Trp Asn Ser Arg Gly Ile Gly Tyr Ala Asp Ser Val Ala
1               5                   10                  15
Gly

<210> SEQ ID NO 80
<211> LENGTH: 17
<212> TYPE: PRT
<213> ORGANISM: Artificial Sequence
<220> FEATURE:
<223> OTHER INFORMATION: HC CDR2 (K64S)
```

-continued

```
<400> SEQUENCE: 80

Gly Ile Ser Trp Asn Ser Arg Gly Ile Gly Tyr Ala Asp Ser Val Ser
1               5                   10                  15

Gly

<210> SEQ ID NO 81
<211> LENGTH: 17
<212> TYPE: PRT
<213> ORGANISM: Artificial Sequence
<220> FEATURE:
<223> OTHER INFORMATION: HC CDR2 (K64T)

<400> SEQUENCE: 81

Gly Ile Ser Trp Asn Ser Arg Gly Ile Gly Tyr Ala Asp Ser Val Thr
1               5                   10                  15

Gly

<210> SEQ ID NO 82
<211> LENGTH: 17
<212> TYPE: PRT
<213> ORGANISM: Artificial Sequence
<220> FEATURE:
<223> OTHER INFORMATION: HC CDR2 (K64V)

<400> SEQUENCE: 82

Gly Ile Ser Trp Asn Ser Arg Gly Ile Gly Tyr Ala Asp Ser Val Val
1               5                   10                  15

Gly

<210> SEQ ID NO 83
<211> LENGTH: 17
<212> TYPE: PRT
<213> ORGANISM: Artificial Sequence
<220> FEATURE:
<223> OTHER INFORMATION: HC CDR2 (K64L)

<400> SEQUENCE: 83

Gly Ile Ser Trp Asn Ser Arg Gly Ile Gly Tyr Ala Asp Ser Val Leu
1               5                   10                  15

Gly

<210> SEQ ID NO 84
<211> LENGTH: 17
<212> TYPE: PRT
<213> ORGANISM: Artificial Sequence
<220> FEATURE:
<223> OTHER INFORMATION: HC CDR2 (K64I)

<400> SEQUENCE: 84

Gly Ile Ser Trp Asn Ser Arg Gly Ile Gly Tyr Ala Asp Ser Val Ile
1               5                   10                  15

Gly

<210> SEQ ID NO 85
<211> LENGTH: 17
<212> TYPE: PRT
<213> ORGANISM: Artificial Sequence
<220> FEATURE:
<223> OTHER INFORMATION: HC CDR2 (K64M)
```

-continued

```
<400> SEQUENCE: 85

Gly Ile Ser Trp Asn Ser Arg Gly Ile Gly Tyr Ala Asp Ser Val Met
1               5                   10                  15

Gly

<210> SEQ ID NO 86
<211> LENGTH: 17
<212> TYPE: PRT
<213> ORGANISM: Artificial Sequence
<220> FEATURE:
<223> OTHER INFORMATION: HC CDR2 (K64R)

<400> SEQUENCE: 86

Gly Ile Ser Trp Asn Ser Arg Gly Ile Gly Tyr Ala Asp Ser Val Arg
1               5                   10                  15

Gly

<210> SEQ ID NO 87
<211> LENGTH: 17
<212> TYPE: PRT
<213> ORGANISM: Artificial Sequence
<220> FEATURE:
<223> OTHER INFORMATION: HC CDR2 (K64H)

<400> SEQUENCE: 87

Gly Ile Ser Trp Asn Ser Arg Gly Ile Gly Tyr Ala Asp Ser Val His
1               5                   10                  15

Gly

<210> SEQ ID NO 88
<211> LENGTH: 17
<212> TYPE: PRT
<213> ORGANISM: Artificial Sequence
<220> FEATURE:
<223> OTHER INFORMATION: HC CDR2 (K64F)

<400> SEQUENCE: 88

Gly Ile Ser Trp Asn Ser Arg Gly Ile Gly Tyr Ala Asp Ser Val Phe
1               5                   10                  15

Gly

<210> SEQ ID NO 89
<211> LENGTH: 17
<212> TYPE: PRT
<213> ORGANISM: Artificial Sequence
<220> FEATURE:
<223> OTHER INFORMATION: HC CDR2 (K64Y)

<400> SEQUENCE: 89

Gly Ile Ser Trp Asn Ser Arg Gly Ile Gly Tyr Ala Asp Ser Val Tyr
1               5                   10                  15

Gly

<210> SEQ ID NO 90
<211> LENGTH: 17
<212> TYPE: PRT
<213> ORGANISM: Artificial Sequence
<220> FEATURE:
<223> OTHER INFORMATION: HC CDR2 (K64N)
```

```
<400> SEQUENCE: 90

Gly Ile Ser Trp Asn Ser Arg Gly Ile Gly Tyr Ala Asp Ser Val Asn
1               5                   10                  15

Gly

<210> SEQ ID NO 91
<211> LENGTH: 17
<212> TYPE: PRT
<213> ORGANISM: Artificial Sequence
<220> FEATURE:
<223> OTHER INFORMATION: HC CDR2 (K64D)

<400> SEQUENCE: 91

Gly Ile Ser Trp Asn Ser Arg Gly Ile Gly Tyr Ala Asp Ser Val Asp
1               5                   10                  15

Gly

<210> SEQ ID NO 92
<211> LENGTH: 17
<212> TYPE: PRT
<213> ORGANISM: Artificial Sequence
<220> FEATURE:
<223> OTHER INFORMATION: HC CDR2 (K64E)

<400> SEQUENCE: 92

Gly Ile Ser Trp Asn Ser Arg Gly Ile Gly Tyr Ala Asp Ser Val Glu
1               5                   10                  15

Gly

<210> SEQ ID NO 93
<211> LENGTH: 17
<212> TYPE: PRT
<213> ORGANISM: Artificial Sequence
<220> FEATURE:
<223> OTHER INFORMATION: HC CDR2 (K64Q)

<400> SEQUENCE: 93

Gly Ile Ser Trp Asn Ser Arg Gly Ile Gly Tyr Ala Asp Ser Val Gln
1               5                   10                  15

Gly

<210> SEQ ID NO 94
<211> LENGTH: 17
<212> TYPE: PRT
<213> ORGANISM: Artificial Sequence
<220> FEATURE:
<223> OTHER INFORMATION: HC CDR2 (G65H)

<400> SEQUENCE: 94

Gly Ile Ser Trp Asn Ser Arg Gly Ile Gly Tyr Ala Asp Ser Val Lys
1               5                   10                  15

His

<210> SEQ ID NO 95
<211> LENGTH: 17
<212> TYPE: PRT
<213> ORGANISM: Artificial Sequence
<220> FEATURE:
<223> OTHER INFORMATION: HC CDR2 (G65D)
```

```
<400> SEQUENCE: 95

Gly Ile Ser Trp Asn Ser Arg Gly Ile Gly Tyr Ala Asp Ser Val Lys
1               5                   10                  15

Asp

<210> SEQ ID NO 96
<211> LENGTH: 17
<212> TYPE: PRT
<213> ORGANISM: Artificial Sequence
<220> FEATURE:
<223> OTHER INFORMATION: HC CDR2 (G65Q)

<400> SEQUENCE: 96

Gly Ile Ser Trp Asn Ser Arg Gly Ile Gly Tyr Ala Asp Ser Val Lys
1               5                   10                  15

Gln

<210> SEQ ID NO 97
<211> LENGTH: 12
<212> TYPE: PRT
<213> ORGANISM: Artificial Sequence
<220> FEATURE:
<223> OTHER INFORMATION: HC CDR3 (S98T)

<400> SEQUENCE: 97

Asp Glu Tyr Thr Arg Gly Tyr Tyr Val Leu Asp Val
1               5                   10

<210> SEQ ID NO 98
<211> LENGTH: 12
<212> TYPE: PRT
<213> ORGANISM: Artificial Sequence
<220> FEATURE:
<223> OTHER INFORMATION: HC CDR3 (S98N)

<400> SEQUENCE: 98

Asp Glu Tyr Asn Arg Gly Tyr Tyr Val Leu Asp Val
1               5                   10

<210> SEQ ID NO 99
<211> LENGTH: 12
<212> TYPE: PRT
<213> ORGANISM: Artificial Sequence
<220> FEATURE:
<223> OTHER INFORMATION: HC CDR3 (S98D)

<400> SEQUENCE: 99

Asp Glu Tyr Asp Arg Gly Tyr Tyr Val Leu Asp Val
1               5                   10

<210> SEQ ID NO 100
<211> LENGTH: 12
<212> TYPE: PRT
<213> ORGANISM: Artificial Sequence
<220> FEATURE:
<223> OTHER INFORMATION: HC CDR3 (S98E)

<400> SEQUENCE: 100

Asp Glu Tyr Glu Arg Gly Tyr Tyr Val Leu Asp Val
1               5                   10

<210> SEQ ID NO 101
<211> LENGTH: 12
<212> TYPE: PRT
<213> ORGANISM: Artificial Sequence
```

```
<220> FEATURE:
<223> OTHER INFORMATION: HC CDR3 (R99L)

<400> SEQUENCE: 101

Asp Glu Tyr Ser Leu Gly Tyr Tyr Val Leu Asp Val
1               5                   10

<210> SEQ ID NO 102
<211> LENGTH: 12
<212> TYPE: PRT
<213> ORGANISM: Artificial Sequence
<220> FEATURE:
<223> OTHER INFORMATION: HC CDR3 (R99M)

<400> SEQUENCE: 102

Asp Glu Tyr Ser Met Gly Tyr Tyr Val Leu Asp Val
1               5                   10

<210> SEQ ID NO 103
<211> LENGTH: 12
<212> TYPE: PRT
<213> ORGANISM: Artificial Sequence
<220> FEATURE:
<223> OTHER INFORMATION: HC CDR3 (R99S)

<400> SEQUENCE: 103

Asp Glu Tyr Ser Ser Gly Tyr Tyr Val Leu Asp Val
1               5                   10

<210> SEQ ID NO 104
<211> LENGTH: 12
<212> TYPE: PRT
<213> ORGANISM: Artificial Sequence
<220> FEATURE:
<223> OTHER INFORMATION: HC CDR3 (V100cG)

<400> SEQUENCE: 104

Asp Glu Tyr Ser Arg Gly Tyr Tyr Gly Leu Asp Val
1               5                   10

<210> SEQ ID NO 105
<211> LENGTH: 12
<212> TYPE: PRT
<213> ORGANISM: Artificial Sequence
<220> FEATURE:
<223> OTHER INFORMATION: HC CDR3 (V100cA)

<400> SEQUENCE: 105

Asp Glu Tyr Ser Arg Gly Tyr Tyr Ala Leu Asp Val
1               5                   10

<210> SEQ ID NO 106
<211> LENGTH: 12
<212> TYPE: PRT
<213> ORGANISM: Artificial Sequence
<220> FEATURE:
<223> OTHER INFORMATION: HC CDR3 (V100cS)

<400> SEQUENCE: 106

Asp Glu Tyr Ser Arg Gly Tyr Tyr Ser Leu Asp Val
1               5                   10

<210> SEQ ID NO 107
<211> LENGTH: 12
<212> TYPE: PRT
<213> ORGANISM: Artificial Sequence
```

```
<220> FEATURE:
<223> OTHER INFORMATION: HC CDR3 (V100cT)

<400> SEQUENCE: 107

Asp Glu Tyr Ser Arg Gly Tyr Tyr Thr Leu Asp Val
1               5                   10

<210> SEQ ID NO 108
<211> LENGTH: 12
<212> TYPE: PRT
<213> ORGANISM: Artificial Sequence
<220> FEATURE:
<223> OTHER INFORMATION: HC CDR3 (V100cM)

<400> SEQUENCE: 108

Asp Glu Tyr Ser Arg Gly Tyr Tyr Met Leu Asp Val
1               5                   10

<210> SEQ ID NO 109
<211> LENGTH: 12
<212> TYPE: PRT
<213> ORGANISM: Artificial Sequence
<220> FEATURE:
<223> OTHER INFORMATION: HC CDR3 (V100cN)

<400> SEQUENCE: 109

Asp Glu Tyr Ser Arg Gly Tyr Tyr Asn Leu Asp Val
1               5                   10

<210> SEQ ID NO 110
<211> LENGTH: 12
<212> TYPE: PRT
<213> ORGANISM: Artificial Sequence
<220> FEATURE:
<223> OTHER INFORMATION: HC CDR3 (V100cE)

<400> SEQUENCE: 110

Asp Glu Tyr Ser Arg Gly Tyr Tyr Glu Leu Asp Val
1               5                   10

<210> SEQ ID NO 111
<211> LENGTH: 12
<212> TYPE: PRT
<213> ORGANISM: Artificial Sequence
<220> FEATURE:
<223> OTHER INFORMATION: HC CDR3 (V100cQ)

<400> SEQUENCE: 111

Asp Glu Tyr Ser Arg Gly Tyr Tyr Gln Leu Asp Val
1               5                   10

<210> SEQ ID NO 112
<211> LENGTH: 12
<212> TYPE: PRT
<213> ORGANISM: Artificial Sequence
<220> FEATURE:
<223> OTHER INFORMATION: HC CDR3 (V102A)

<400> SEQUENCE: 112

Asp Glu Tyr Ser Arg Gly Tyr Tyr Val Leu Asp Ala
1               5                   10

<210> SEQ ID NO 113
<211> LENGTH: 12
<212> TYPE: PRT
<213> ORGANISM: Artificial Sequence
```

```
<220> FEATURE:
<223> OTHER INFORMATION: HC CDR3 (V102S)

<400> SEQUENCE: 113

Asp Glu Tyr Ser Arg Gly Tyr Tyr Val Leu Asp Ser
1               5                   10

<210> SEQ ID NO 114
<211> LENGTH: 12
<212> TYPE: PRT
<213> ORGANISM: Artificial Sequence
<220> FEATURE:
<223> OTHER INFORMATION: HC CDR3 (V102T)

<400> SEQUENCE: 114

Asp Glu Tyr Ser Arg Gly Tyr Tyr Val Leu Asp Thr
1               5                   10

<210> SEQ ID NO 115
<211> LENGTH: 12
<212> TYPE: PRT
<213> ORGANISM: Artificial Sequence
<220> FEATURE:
<223> OTHER INFORMATION: HC CDR3 (V102R)

<400> SEQUENCE: 115

Asp Glu Tyr Ser Arg Gly Tyr Tyr Val Leu Asp Arg
1               5                   10

<210> SEQ ID NO 116
<211> LENGTH: 12
<212> TYPE: PRT
<213> ORGANISM: Artificial Sequence
<220> FEATURE:
<223> OTHER INFORMATION: HC CDR3 (V102H)

<400> SEQUENCE: 116

Asp Glu Tyr Ser Arg Gly Tyr Tyr Val Leu Asp His
1               5                   10

<210> SEQ ID NO 117
<211> LENGTH: 12
<212> TYPE: PRT
<213> ORGANISM: Artificial Sequence
<220> FEATURE:
<223> OTHER INFORMATION: HC CDR3 (V102Y)

<400> SEQUENCE: 117

Asp Glu Tyr Ser Arg Gly Tyr Tyr Val Leu Asp Tyr
1               5                   10

<210> SEQ ID NO 118
<211> LENGTH: 12
<212> TYPE: PRT
<213> ORGANISM: Artificial Sequence
<220> FEATURE:
<223> OTHER INFORMATION: HC CDR3 (V102W)

<400> SEQUENCE: 118

Asp Glu Tyr Ser Arg Gly Tyr Tyr Val Leu Asp Trp
1               5                   10

<210> SEQ ID NO 119
<211> LENGTH: 12
<212> TYPE: PRT
<213> ORGANISM: Artificial Sequence
```

```
<220> FEATURE:
<223> OTHER INFORMATION: HC CDR3 (V102N)

<400> SEQUENCE: 119

Asp Glu Tyr Ser Arg Gly Tyr Tyr Val Leu Asp Asn
1               5                   10

<210> SEQ ID NO 120
<211> LENGTH: 12
<212> TYPE: PRT
<213> ORGANISM: Artificial Sequence
<220> FEATURE:
<223> OTHER INFORMATION: HC CDR3 (V102E)

<400> SEQUENCE: 120

Asp Glu Tyr Ser Arg Gly Tyr Tyr Val Leu Asp Glu
1               5                   10

<210> SEQ ID NO 121
<211> LENGTH: 12
<212> TYPE: PRT
<213> ORGANISM: Artificial Sequence
<220> FEATURE:
<223> OTHER INFORMATION: HC CDR3 (V102Q)

<400> SEQUENCE: 121

Asp Glu Tyr Ser Arg Gly Tyr Tyr Val Leu Asp Gln
1               5                   10

<210> SEQ ID NO 122
<211> LENGTH: 12
<212> TYPE: PRT
<213> ORGANISM: Artificial Sequence
<220> FEATURE:
<223> OTHER INFORMATION: HC CDR3 (V102M)

<400> SEQUENCE: 122

Asp Glu Tyr Ser Arg Gly Tyr Tyr Val Leu Asp Met
1               5                   10

<210> SEQ ID NO 123
<211> LENGTH: 11
<212> TYPE: PRT
<213> ORGANISM: Artificial Sequence
<220> FEATURE:
<223> OTHER INFORMATION: LC CDR1 (R24S)

<400> SEQUENCE: 123

Ser Ala Ser Gln Gly Ile Ser Ser Ala Leu Ala
1               5                   10

<210> SEQ ID NO 124
<211> LENGTH: 11
<212> TYPE: PRT
<213> ORGANISM: Artificial Sequence
<220> FEATURE:
<223> OTHER INFORMATION: LC CDR1 (R24T)

<400> SEQUENCE: 124

Thr Ala Ser Gln Gly Ile Ser Ser Ala Leu Ala
1               5                   10

<210> SEQ ID NO 125
<211> LENGTH: 11
<212> TYPE: PRT
<213> ORGANISM: Artificial Sequence
```

```
<220> FEATURE:
<223> OTHER INFORMATION: LC CDR1 (R24V)

<400> SEQUENCE: 125

Val Ala Ser Gln Gly Ile Ser Ser Ala Leu Ala
1               5                   10

<210> SEQ ID NO 126
<211> LENGTH: 11
<212> TYPE: PRT
<213> ORGANISM: Artificial Sequence
<220> FEATURE:
<223> OTHER INFORMATION: LC CDR1 (R24K)

<400> SEQUENCE: 126

Lys Ala Ser Gln Gly Ile Ser Ser Ala Leu Ala
1               5                   10

<210> SEQ ID NO 127
<211> LENGTH: 11
<212> TYPE: PRT
<213> ORGANISM: Artificial Sequence
<220> FEATURE:
<223> OTHER INFORMATION: LC CDR1 (R24H)

<400> SEQUENCE: 127

His Ala Ser Gln Gly Ile Ser Ser Ala Leu Ala
1               5                   10

<210> SEQ ID NO 128
<211> LENGTH: 11
<212> TYPE: PRT
<213> ORGANISM: Artificial Sequence
<220> FEATURE:
<223> OTHER INFORMATION: LC CDR1 (R24Y)

<400> SEQUENCE: 128

Tyr Ala Ser Gln Gly Ile Ser Ser Ala Leu Ala
1               5                   10

<210> SEQ ID NO 129
<211> LENGTH: 11
<212> TYPE: PRT
<213> ORGANISM: Artificial Sequence
<220> FEATURE:
<223> OTHER INFORMATION: LC CDR1 (R24I)

<400> SEQUENCE: 129

Ile Ala Ser Gln Gly Ile Ser Ser Ala Leu Ala
1               5                   10

<210> SEQ ID NO 130
<211> LENGTH: 11
<212> TYPE: PRT
<213> ORGANISM: Artificial Sequence
<220> FEATURE:
<223> OTHER INFORMATION: LC CDR1 (A25S)

<400> SEQUENCE: 130

Arg Ser Ser Gln Gly Ile Ser Ser Ala Leu Ala
1               5                   10

<210> SEQ ID NO 131
<211> LENGTH: 11
<212> TYPE: PRT
<213> ORGANISM: Artificial Sequence
```

```
<220> FEATURE:
<223> OTHER INFORMATION: LC CDR1 (A25T)

<400> SEQUENCE: 131

Arg Thr Ser Gln Gly Ile Ser Ser Ala Leu Ala
1               5                   10

<210> SEQ ID NO 132
<211> LENGTH: 11
<212> TYPE: PRT
<213> ORGANISM: Artificial Sequence
<220> FEATURE:
<223> OTHER INFORMATION: LC CDR1 (A25V)

<400> SEQUENCE: 132

Arg Val Ser Gln Gly Ile Ser Ser Ala Leu Ala
1               5                   10

<210> SEQ ID NO 133
<211> LENGTH: 11
<212> TYPE: PRT
<213> ORGANISM: Artificial Sequence
<220> FEATURE:
<223> OTHER INFORMATION: LC CDR1 (S26P)

<400> SEQUENCE: 133

Arg Ala Pro Gln Gly Ile Ser Ser Ala Leu Ala
1               5                   10

<210> SEQ ID NO 134
<211> LENGTH: 11
<212> TYPE: PRT
<213> ORGANISM: Artificial Sequence
<220> FEATURE:
<223> OTHER INFORMATION: LC CDR1 (S26G)

<400> SEQUENCE: 134

Arg Ala Gly Gln Gly Ile Ser Ser Ala Leu Ala
1               5                   10

<210> SEQ ID NO 135
<211> LENGTH: 11
<212> TYPE: PRT
<213> ORGANISM: Artificial Sequence
<220> FEATURE:
<223> OTHER INFORMATION: LC CDR1 (S26A)

<400> SEQUENCE: 135

Arg Ala Ala Gln Gly Ile Ser Ser Ala Leu Ala
1               5                   10

<210> SEQ ID NO 136
<211> LENGTH: 11
<212> TYPE: PRT
<213> ORGANISM: Artificial Sequence
<220> FEATURE:
<223> OTHER INFORMATION: LC CDR1 (S26T)

<400> SEQUENCE: 136

Arg Ala Thr Gln Gly Ile Ser Ser Ala Leu Ala
1               5                   10

<210> SEQ ID NO 137
<211> LENGTH: 11
<212> TYPE: PRT
<213> ORGANISM: Artificial Sequence
```

```
<220> FEATURE:
<223> OTHER INFORMATION: LC CDR1 (S26V)

<400> SEQUENCE: 137

Arg Ala Val Gln Gly Ile Ser Ser Ala Leu Ala
1               5                   10

<210> SEQ ID NO 138
<211> LENGTH: 11
<212> TYPE: PRT
<213> ORGANISM: Artificial Sequence
<220> FEATURE:
<223> OTHER INFORMATION: LC CDR1 (S26L)

<400> SEQUENCE: 138

Arg Ala Leu Gln Gly Ile Ser Ser Ala Leu Ala
1               5                   10

<210> SEQ ID NO 139
<211> LENGTH: 11
<212> TYPE: PRT
<213> ORGANISM: Artificial Sequence
<220> FEATURE:
<223> OTHER INFORMATION: LC CDR1 (S26I)

<400> SEQUENCE: 139

Arg Ala Ile Gln Gly Ile Ser Ser Ala Leu Ala
1               5                   10

<210> SEQ ID NO 140
<211> LENGTH: 11
<212> TYPE: PRT
<213> ORGANISM: Artificial Sequence
<220> FEATURE:
<223> OTHER INFORMATION: LC CDR1 (S26M)

<400> SEQUENCE: 140

Arg Ala Met Gln Gly Ile Ser Ser Ala Leu Ala
1               5                   10

<210> SEQ ID NO 141
<211> LENGTH: 11
<212> TYPE: PRT
<213> ORGANISM: Artificial Sequence
<220> FEATURE:
<223> OTHER INFORMATION: LC CDR1 (S26K)

<400> SEQUENCE: 141

Arg Ala Lys Gln Gly Ile Ser Ser Ala Leu Ala
1               5                   10

<210> SEQ ID NO 142
<211> LENGTH: 11
<212> TYPE: PRT
<213> ORGANISM: Artificial Sequence
<220> FEATURE:
<223> OTHER INFORMATION: LC CDR1 (S26R)

<400> SEQUENCE: 142

Arg Ala Arg Gln Gly Ile Ser Ser Ala Leu Ala
1               5                   10

<210> SEQ ID NO 143
<211> LENGTH: 11
<212> TYPE: PRT
<213> ORGANISM: Artificial Sequence
```

```
<220> FEATURE:
<223> OTHER INFORMATION: LC CDR1 (S26H)

<400> SEQUENCE: 143

Arg Ala His Gln Gly Ile Ser Ser Ala Leu Ala
1               5                   10

<210> SEQ ID NO 144
<211> LENGTH: 11
<212> TYPE: PRT
<213> ORGANISM: Artificial Sequence
<220> FEATURE:
<223> OTHER INFORMATION: LC CDR1 (S26N)

<400> SEQUENCE: 144

Arg Ala Asn Gln Gly Ile Ser Ser Ala Leu Ala
1               5                   10

<210> SEQ ID NO 145
<211> LENGTH: 11
<212> TYPE: PRT
<213> ORGANISM: Artificial Sequence
<220> FEATURE:
<223> OTHER INFORMATION: LC CDR1 (S26E)

<400> SEQUENCE: 145

Arg Ala Glu Gln Gly Ile Ser Ser Ala Leu Ala
1               5                   10

<210> SEQ ID NO 146
<211> LENGTH: 11
<212> TYPE: PRT
<213> ORGANISM: Artificial Sequence
<220> FEATURE:
<223> OTHER INFORMATION: LC CDR1 (S26Q)

<400> SEQUENCE: 146

Arg Ala Gln Gln Gly Ile Ser Ser Ala Leu Ala
1               5                   10

<210> SEQ ID NO 147
<211> LENGTH: 11
<212> TYPE: PRT
<213> ORGANISM: Artificial Sequence
<220> FEATURE:
<223> OTHER INFORMATION: LC CDR1 (Q27P)

<400> SEQUENCE: 147

Arg Ala Ser Pro Gly Ile Ser Ser Ala Leu Ala
1               5                   10

<210> SEQ ID NO 148
<211> LENGTH: 11
<212> TYPE: PRT
<213> ORGANISM: Artificial Sequence
<220> FEATURE:
<223> OTHER INFORMATION: LC CDR1 (Q27G)

<400> SEQUENCE: 148

Arg Ala Ser Gly Gly Ile Ser Ser Ala Leu Ala
1               5                   10

<210> SEQ ID NO 149
<211> LENGTH: 11
<212> TYPE: PRT
<213> ORGANISM: Artificial Sequence
```

```
<220> FEATURE:
<223> OTHER INFORMATION: LC CDR1 (Q27A)

<400> SEQUENCE: 149

Arg Ala Ser Ala Gly Ile Ser Ser Ala Leu Ala
1               5                   10

<210> SEQ ID NO 150
<211> LENGTH: 11
<212> TYPE: PRT
<213> ORGANISM: Artificial Sequence
<220> FEATURE:
<223> OTHER INFORMATION: LC CDR1 (Q27S)

<400> SEQUENCE: 150

Arg Ala Ser Ser Gly Ile Ser Ser Ala Leu Ala
1               5                   10

<210> SEQ ID NO 151
<211> LENGTH: 11
<212> TYPE: PRT
<213> ORGANISM: Artificial Sequence
<220> FEATURE:
<223> OTHER INFORMATION: LC CDR1 (Q27T)

<400> SEQUENCE: 151

Arg Ala Ser Thr Gly Ile Ser Ser Ala Leu Ala
1               5                   10

<210> SEQ ID NO 152
<211> LENGTH: 11
<212> TYPE: PRT
<213> ORGANISM: Artificial Sequence
<220> FEATURE:
<223> OTHER INFORMATION: LC CDR1 (Q27V)

<400> SEQUENCE: 152

Arg Ala Ser Val Gly Ile Ser Ser Ala Leu Ala
1               5                   10

<210> SEQ ID NO 153
<211> LENGTH: 11
<212> TYPE: PRT
<213> ORGANISM: Artificial Sequence
<220> FEATURE:
<223> OTHER INFORMATION: LC CDR1 (Q27L)

<400> SEQUENCE: 153

Arg Ala Ser Leu Gly Ile Ser Ser Ala Leu Ala
1               5                   10

<210> SEQ ID NO 154
<211> LENGTH: 11
<212> TYPE: PRT
<213> ORGANISM: Artificial Sequence
<220> FEATURE:
<223> OTHER INFORMATION: LC CDR1 (Q27I)

<400> SEQUENCE: 154

Arg Ala Ser Ile Gly Ile Ser Ser Ala Leu Ala
1               5                   10

<210> SEQ ID NO 155
<211> LENGTH: 11
<212> TYPE: PRT
<213> ORGANISM: Artificial Sequence
```

```
<220> FEATURE:
<223> OTHER INFORMATION: LC CDR1 (Q27M)

<400> SEQUENCE: 155

Arg Ala Ser Met Gly Ile Ser Ser Ala Leu Ala
1               5                   10

<210> SEQ ID NO 156
<211> LENGTH: 11
<212> TYPE: PRT
<213> ORGANISM: Artificial Sequence
<220> FEATURE:
<223> OTHER INFORMATION: LC CDR1 (Q27H)

<400> SEQUENCE: 156

Arg Ala Ser His Gly Ile Ser Ser Ala Leu Ala
1               5                   10

<210> SEQ ID NO 157
<211> LENGTH: 11
<212> TYPE: PRT
<213> ORGANISM: Artificial Sequence
<220> FEATURE:
<223> OTHER INFORMATION: LC CDR1 (Q27F)

<400> SEQUENCE: 157

Arg Ala Ser Phe Gly Ile Ser Ser Ala Leu Ala
1               5                   10

<210> SEQ ID NO 158
<211> LENGTH: 11
<212> TYPE: PRT
<213> ORGANISM: Artificial Sequence
<220> FEATURE:
<223> OTHER INFORMATION: LC CDR1 (Q27Y)

<400> SEQUENCE: 158

Arg Ala Ser Tyr Gly Ile Ser Ser Ala Leu Ala
1               5                   10

<210> SEQ ID NO 159
<211> LENGTH: 11
<212> TYPE: PRT
<213> ORGANISM: Artificial Sequence
<220> FEATURE:
<223> OTHER INFORMATION: LC CDR1 (Q27N)

<400> SEQUENCE: 159

Arg Ala Ser Asn Gly Ile Ser Ser Ala Leu Ala
1               5                   10

<210> SEQ ID NO 160
<211> LENGTH: 11
<212> TYPE: PRT
<213> ORGANISM: Artificial Sequence
<220> FEATURE:
<223> OTHER INFORMATION: LC CDR1 (Q27D)

<400> SEQUENCE: 160

Arg Ala Ser Asp Gly Ile Ser Ser Ala Leu Ala
1               5                   10

<210> SEQ ID NO 161
<211> LENGTH: 11
<212> TYPE: PRT
<213> ORGANISM: Artificial Sequence
```

```
<220> FEATURE:
<223> OTHER INFORMATION: LC CDR1 (Q27E)

<400> SEQUENCE: 161

Arg Ala Ser Glu Gly Ile Ser Ser Ala Leu Ala
1               5                   10

<210> SEQ ID NO 162
<211> LENGTH: 11
<212> TYPE: PRT
<213> ORGANISM: Artificial Sequence
<220> FEATURE:
<223> OTHER INFORMATION: LC CDR1 (G28P)

<400> SEQUENCE: 162

Arg Ala Ser Gln Pro Ile Ser Ser Ala Leu Ala
1               5                   10

<210> SEQ ID NO 163
<211> LENGTH: 11
<212> TYPE: PRT
<213> ORGANISM: Artificial Sequence
<220> FEATURE:
<223> OTHER INFORMATION: LC CDR1 (G28A)

<400> SEQUENCE: 163

Arg Ala Ser Gln Ala Ile Ser Ser Ala Leu Ala
1               5                   10

<210> SEQ ID NO 164
<211> LENGTH: 11
<212> TYPE: PRT
<213> ORGANISM: Artificial Sequence
<220> FEATURE:
<223> OTHER INFORMATION: LC CDR1 (G28S)

<400> SEQUENCE: 164

Arg Ala Ser Gln Ser Ile Ser Ser Ala Leu Ala
1               5                   10

<210> SEQ ID NO 165
<211> LENGTH: 11
<212> TYPE: PRT
<213> ORGANISM: Artificial Sequence
<220> FEATURE:
<223> OTHER INFORMATION: LC CDR1 (G28T)

<400> SEQUENCE: 165

Arg Ala Ser Gln Thr Ile Ser Ser Ala Leu Ala
1               5                   10

<210> SEQ ID NO 166
<211> LENGTH: 11
<212> TYPE: PRT
<213> ORGANISM: Artificial Sequence
<220> FEATURE:
<223> OTHER INFORMATION: LC CDR1 (G28H)

<400> SEQUENCE: 166

Arg Ala Ser Gln His Ile Ser Ser Ala Leu Ala
1               5                   10

<210> SEQ ID NO 167
<211> LENGTH: 11
<212> TYPE: PRT
<213> ORGANISM: Artificial Sequence
```

```
<220> FEATURE:
<223> OTHER INFORMATION: LC CDR1 (G28E)

<400> SEQUENCE: 167

Arg Ala Ser Gln Glu Ile Ser Ser Ala Leu Ala
1               5                   10

<210> SEQ ID NO 168
<211> LENGTH: 11
<212> TYPE: PRT
<213> ORGANISM: Artificial Sequence
<220> FEATURE:
<223> OTHER INFORMATION: LC CDR1 (G28Q)

<400> SEQUENCE: 168

Arg Ala Ser Gln Gln Ile Ser Ser Ala Leu Ala
1               5                   10

<210> SEQ ID NO 169
<211> LENGTH: 11
<212> TYPE: PRT
<213> ORGANISM: Artificial Sequence
<220> FEATURE:
<223> OTHER INFORMATION: LC CDR1 (G28M)

<400> SEQUENCE: 169

Arg Ala Ser Gln Met Ile Ser Ser Ala Leu Ala
1               5                   10

<210> SEQ ID NO 170
<211> LENGTH: 11
<212> TYPE: PRT
<213> ORGANISM: Artificial Sequence
<220> FEATURE:
<223> OTHER INFORMATION: LC CDR1 (G28N)

<400> SEQUENCE: 170

Arg Ala Ser Gln Asn Ile Ser Ser Ala Leu Ala
1               5                   10

<210> SEQ ID NO 171
<211> LENGTH: 11
<212> TYPE: PRT
<213> ORGANISM: Artificial Sequence
<220> FEATURE:
<223> OTHER INFORMATION: LC CDR1 (G28D)

<400> SEQUENCE: 171

Arg Ala Ser Gln Asp Ile Ser Ser Ala Leu Ala
1               5                   10

<210> SEQ ID NO 172
<211> LENGTH: 11
<212> TYPE: PRT
<213> ORGANISM: Artificial Sequence
<220> FEATURE:
<223> OTHER INFORMATION: LC CDR1 (I29P)

<400> SEQUENCE: 172

Arg Ala Ser Gln Gly Pro Ser Ser Ala Leu Ala
1               5                   10

<210> SEQ ID NO 173
<211> LENGTH: 11
<212> TYPE: PRT
<213> ORGANISM: Artificial Sequence
```

```
<220> FEATURE:
<223> OTHER INFORMATION: LC CDR1 (I29G)

<400> SEQUENCE: 173

Arg Ala Ser Gln Gly Gly Ser Ser Ala Leu Ala
1               5                   10

<210> SEQ ID NO 174
<211> LENGTH: 11
<212> TYPE: PRT
<213> ORGANISM: Artificial Sequence
<220> FEATURE:
<223> OTHER INFORMATION: LC CDR1 (I29A)

<400> SEQUENCE: 174

Arg Ala Ser Gln Gly Ala Ser Ser Ala Leu Ala
1               5                   10

<210> SEQ ID NO 175
<211> LENGTH: 11
<212> TYPE: PRT
<213> ORGANISM: Artificial Sequence
<220> FEATURE:
<223> OTHER INFORMATION: LC CDR1 (I29S)

<400> SEQUENCE: 175

Arg Ala Ser Gln Gly Ser Ser Ser Ala Leu Ala
1               5                   10

<210> SEQ ID NO 176
<211> LENGTH: 11
<212> TYPE: PRT
<213> ORGANISM: Artificial Sequence
<220> FEATURE:
<223> OTHER INFORMATION: LC CDR1 (I29T)

<400> SEQUENCE: 176

Arg Ala Ser Gln Gly Thr Ser Ser Ala Leu Ala
1               5                   10

<210> SEQ ID NO 177
<211> LENGTH: 11
<212> TYPE: PRT
<213> ORGANISM: Artificial Sequence
<220> FEATURE:
<223> OTHER INFORMATION: LC CDR1 (I29V)

<400> SEQUENCE: 177

Arg Ala Ser Gln Gly Val Ser Ser Ala Leu Ala
1               5                   10

<210> SEQ ID NO 178
<211> LENGTH: 11
<212> TYPE: PRT
<213> ORGANISM: Artificial Sequence
<220> FEATURE:
<223> OTHER INFORMATION: LC CDR1 (I29L)

<400> SEQUENCE: 178

Arg Ala Ser Gln Gly Leu Ser Ser Ala Leu Ala
1               5                   10

<210> SEQ ID NO 179
<211> LENGTH: 11
<212> TYPE: PRT
<213> ORGANISM: Artificial Sequence
```

<220> FEATURE:
<223> OTHER INFORMATION: LC CDR1 (I29N)

<400> SEQUENCE: 179

Arg Ala Ser Gln Gly Asn Ser Ser Ala Leu Ala
1               5                   10

<210> SEQ ID NO 180
<211> LENGTH: 11
<212> TYPE: PRT
<213> ORGANISM: Artificial Sequence
<220> FEATURE:
<223> OTHER INFORMATION: LC CDR1 (S30T)

<400> SEQUENCE: 180

Arg Ala Ser Gln Gly Ile Thr Ser Ala Leu Ala
1               5                   10

<210> SEQ ID NO 181
<211> LENGTH: 11
<212> TYPE: PRT
<213> ORGANISM: Artificial Sequence
<220> FEATURE:
<223> OTHER INFORMATION: LC CDR1 (S30V)

<400> SEQUENCE: 181

Arg Ala Ser Gln Gly Ile Val Ser Ala Leu Ala
1               5                   10

<210> SEQ ID NO 182
<211> LENGTH: 11
<212> TYPE: PRT
<213> ORGANISM: Artificial Sequence
<220> FEATURE:
<223> OTHER INFORMATION: LC CDR1 (S30L)

<400> SEQUENCE: 182

Arg Ala Ser Gln Gly Ile Leu Ser Ala Leu Ala
1               5                   10

<210> SEQ ID NO 183
<211> LENGTH: 11
<212> TYPE: PRT
<213> ORGANISM: Artificial Sequence
<220> FEATURE:
<223> OTHER INFORMATION: LC CDR1 (S30I)

<400> SEQUENCE: 183

Arg Ala Ser Gln Gly Ile Ile Ser Ala Leu Ala
1               5                   10

<210> SEQ ID NO 184
<211> LENGTH: 11
<212> TYPE: PRT
<213> ORGANISM: Artificial Sequence
<220> FEATURE:
<223> OTHER INFORMATION: LC CDR1 (S30M)

<400> SEQUENCE: 184

Arg Ala Ser Gln Gly Ile Met Ser Ala Leu Ala
1               5                   10

<210> SEQ ID NO 185
<211> LENGTH: 11
<212> TYPE: PRT
<213> ORGANISM: Artificial Sequence

```
<220> FEATURE:
<223> OTHER INFORMATION: LC CDR1 (S30M)

<400> SEQUENCE: 185

Arg Ala Ser Gln Gly Ile His Ser Ala Leu Ala
1               5                   10

<210> SEQ ID NO 186
<211> LENGTH: 11
<212> TYPE: PRT
<213> ORGANISM: Artificial Sequence
<220> FEATURE:
<223> OTHER INFORMATION: LC CDR1 (S30F)

<400> SEQUENCE: 186

Arg Ala Ser Gln Gly Ile Phe Ser Ala Leu Ala
1               5                   10

<210> SEQ ID NO 187
<211> LENGTH: 11
<212> TYPE: PRT
<213> ORGANISM: Artificial Sequence
<220> FEATURE:
<223> OTHER INFORMATION: LC CDR1 (S30Y)

<400> SEQUENCE: 187

Arg Ala Ser Gln Gly Ile Tyr Ser Ala Leu Ala
1               5                   10

<210> SEQ ID NO 188
<211> LENGTH: 11
<212> TYPE: PRT
<213> ORGANISM: Artificial Sequence
<220> FEATURE:
<223> OTHER INFORMATION: LC CDR1 (S30N)

<400> SEQUENCE: 188

Arg Ala Ser Gln Gly Ile Asn Ser Ala Leu Ala
1               5                   10

<210> SEQ ID NO 189
<211> LENGTH: 11
<212> TYPE: PRT
<213> ORGANISM: Artificial Sequence
<220> FEATURE:
<223> OTHER INFORMATION: LC CDR1 (S30D)

<400> SEQUENCE: 189

Arg Ala Ser Gln Gly Ile Asp Ser Ala Leu Ala
1               5                   10

<210> SEQ ID NO 190
<211> LENGTH: 11
<212> TYPE: PRT
<213> ORGANISM: Artificial Sequence
<220> FEATURE:
<223> OTHER INFORMATION: LC CDR1 (S30E)

<400> SEQUENCE: 190

Arg Ala Ser Gln Gly Ile Glu Ser Ala Leu Ala
1               5                   10

<210> SEQ ID NO 191
<211> LENGTH: 11
<212> TYPE: PRT
<213> ORGANISM: Artificial Sequence
```

```
<220> FEATURE:
<223> OTHER INFORMATION: LC CDR1 (S30Q)

<400> SEQUENCE: 191

Arg Ala Ser Gln Gly Ile Gln Ser Ala Leu Ala
1               5                   10

<210> SEQ ID NO 192
<211> LENGTH: 11
<212> TYPE: PRT
<213> ORGANISM: Artificial Sequence
<220> FEATURE:
<223> OTHER INFORMATION: LC CDR1 (A32P)

<400> SEQUENCE: 192

Arg Ala Ser Gln Gly Ile Ser Ser Pro Leu Ala
1               5                   10

<210> SEQ ID NO 193
<211> LENGTH: 11
<212> TYPE: PRT
<213> ORGANISM: Artificial Sequence
<220> FEATURE:
<223> OTHER INFORMATION: LC CDR1 (L33A)

<400> SEQUENCE: 193

Arg Ala Ser Gln Gly Ile Ser Ser Ala Ala Ala
1               5                   10

<210> SEQ ID NO 194
<211> LENGTH: 11
<212> TYPE: PRT
<213> ORGANISM: Artificial Sequence
<220> FEATURE:
<223> OTHER INFORMATION: LC CDR1 (L33V)

<400> SEQUENCE: 194

Arg Ala Ser Gln Gly Ile Ser Ser Ala Val Ala
1               5                   10

<210> SEQ ID NO 195
<211> LENGTH: 7
<212> TYPE: PRT
<213> ORGANISM: Artificial Sequence
<220> FEATURE:
<223> OTHER INFORMATION: LC CDR2 (A51G)

<400> SEQUENCE: 195

Asp Gly Ser Ser Leu Glu Ser
1               5

<210> SEQ ID NO 196
<211> LENGTH: 7
<212> TYPE: PRT
<213> ORGANISM: Artificial Sequence
<220> FEATURE:
<223> OTHER INFORMATION: LC CDR2 (A51S)

<400> SEQUENCE: 196

Asp Ser Ser Ser Leu Glu Ser
1               5

<210> SEQ ID NO 197
<211> LENGTH: 7
<212> TYPE: PRT
<213> ORGANISM: Artificial Sequence
```

```
<220> FEATURE:
<223> OTHER INFORMATION: LC CDR2 (A51M)

<400> SEQUENCE: 197

Asp Met Ser Ser Leu Glu Ser
1               5

<210> SEQ ID NO 198
<211> LENGTH: 7
<212> TYPE: PRT
<213> ORGANISM: Artificial Sequence
<220> FEATURE:
<223> OTHER INFORMATION: LC CDR2 (A51H)

<400> SEQUENCE: 198

Asp His Ser Ser Leu Glu Ser
1               5

<210> SEQ ID NO 199
<211> LENGTH: 7
<212> TYPE: PRT
<213> ORGANISM: Artificial Sequence
<220> FEATURE:
<223> OTHER INFORMATION: LC CDR2 (A51N)

<400> SEQUENCE: 199

Asp Asn Ser Ser Leu Glu Ser
1               5

<210> SEQ ID NO 200
<211> LENGTH: 7
<212> TYPE: PRT
<213> ORGANISM: Artificial Sequence
<220> FEATURE:
<223> OTHER INFORMATION: LC CDR2 (A51D)

<400> SEQUENCE: 200

Asp Asp Ser Ser Leu Glu Ser
1               5

<210> SEQ ID NO 201
<211> LENGTH: 7
<212> TYPE: PRT
<213> ORGANISM: Artificial Sequence
<220> FEATURE:
<223> OTHER INFORMATION: LC CDR2 (A51E)

<400> SEQUENCE: 201

Asp Glu Ser Ser Leu Glu Ser
1               5

<210> SEQ ID NO 202
<211> LENGTH: 7
<212> TYPE: PRT
<213> ORGANISM: Artificial Sequence
<220> FEATURE:
<223> OTHER INFORMATION: LC CDR2 (A51Q)

<400> SEQUENCE: 202

Asp Gln Ser Ser Leu Glu Ser
1               5

<210> SEQ ID NO 203
<211> LENGTH: 7
<212> TYPE: PRT
<213> ORGANISM: Artificial Sequence
```

```
<220> FEATURE:
<223> OTHER INFORMATION: LC CDR2 (S52G)

<400> SEQUENCE: 203

Asp Ala Gly Ser Leu Glu Ser
1               5

<210> SEQ ID NO 204
<211> LENGTH: 7
<212> TYPE: PRT
<213> ORGANISM: Artificial Sequence
<220> FEATURE:
<223> OTHER INFORMATION: LC CDR2 (S52A)

<400> SEQUENCE: 204

Asp Ala Ala Ser Leu Glu Ser
1               5

<210> SEQ ID NO 205
<211> LENGTH: 7
<212> TYPE: PRT
<213> ORGANISM: Artificial Sequence
<220> FEATURE:
<223> OTHER INFORMATION: LC CDR2 (S52T)

<400> SEQUENCE: 205

Asp Ala Thr Ser Leu Glu Ser
1               5

<210> SEQ ID NO 206
<211> LENGTH: 7
<212> TYPE: PRT
<213> ORGANISM: Artificial Sequence
<220> FEATURE:
<223> OTHER INFORMATION: LC CDR2 (S52V)

<400> SEQUENCE: 206

Asp Ala Val Ser Leu Glu Ser
1               5

<210> SEQ ID NO 207
<211> LENGTH: 7
<212> TYPE: PRT
<213> ORGANISM: Artificial Sequence
<220> FEATURE:
<223> OTHER INFORMATION: LC CDR2 (S52M)

<400> SEQUENCE: 207

Asp Ala Met Ser Leu Glu Ser
1               5

<210> SEQ ID NO 208
<211> LENGTH: 7
<212> TYPE: PRT
<213> ORGANISM: Artificial Sequence
<220> FEATURE:
<223> OTHER INFORMATION: LC CDR2 (S52H)

<400> SEQUENCE: 208

Asp Ala His Ser Leu Glu Ser
1               5

<210> SEQ ID NO 209
<211> LENGTH: 7
<212> TYPE: PRT
<213> ORGANISM: Artificial Sequence
```

```
<220> FEATURE:
<223> OTHER INFORMATION: LC CDR2 (S52F)

<400> SEQUENCE: 209

Asp Ala Phe Ser Leu Glu Ser
1               5

<210> SEQ ID NO 210
<211> LENGTH: 7
<212> TYPE: PRT
<213> ORGANISM: Artificial Sequence
<220> FEATURE:
<223> OTHER INFORMATION: LC CDR2 (S52Y)

<400> SEQUENCE: 210

Asp Ala Tyr Ser Leu Glu Ser
1               5

<210> SEQ ID NO 211
<211> LENGTH: 7
<212> TYPE: PRT
<213> ORGANISM: Artificial Sequence
<220> FEATURE:
<223> OTHER INFORMATION: LC CDR2 (S52N)

<400> SEQUENCE: 211

Asp Ala Asn Ser Leu Glu Ser
1               5

<210> SEQ ID NO 212
<211> LENGTH: 7
<212> TYPE: PRT
<213> ORGANISM: Artificial Sequence
<220> FEATURE:
<223> OTHER INFORMATION: LC CDR2 (S52D)

<400> SEQUENCE: 212

Asp Ala Asp Ser Leu Glu Ser
1               5

<210> SEQ ID NO 213
<211> LENGTH: 7
<212> TYPE: PRT
<213> ORGANISM: Artificial Sequence
<220> FEATURE:
<223> OTHER INFORMATION: LC CDR2 (S52E)

<400> SEQUENCE: 213

Asp Ala Glu Ser Leu Glu Ser
1               5

<210> SEQ ID NO 214
<211> LENGTH: 7
<212> TYPE: PRT
<213> ORGANISM: Artificial Sequence
<220> FEATURE:
<223> OTHER INFORMATION: LC CDR2 (S52Q)

<400> SEQUENCE: 214

Asp Ala Gln Ser Leu Glu Ser
1               5

<210> SEQ ID NO 215
<211> LENGTH: 7
<212> TYPE: PRT
<213> ORGANISM: Artificial Sequence
```

```
<220> FEATURE:
<223> OTHER INFORMATION: LC CDR2 (S53A)

<400> SEQUENCE: 215

Asp Ala Ser Ala Leu Glu Ser
1               5

<210> SEQ ID NO 216
<211> LENGTH: 7
<212> TYPE: PRT
<213> ORGANISM: Artificial Sequence
<220> FEATURE:
<223> OTHER INFORMATION: LC CDR2 (S53F)

<400> SEQUENCE: 216

Asp Ala Ser Phe Leu Glu Ser
1               5

<210> SEQ ID NO 217
<211> LENGTH: 7
<212> TYPE: PRT
<213> ORGANISM: Artificial Sequence
<220> FEATURE:
<223> OTHER INFORMATION: LC CDR2 (S53Y)

<400> SEQUENCE: 217

Asp Ala Ser Tyr Leu Glu Ser
1               5

<210> SEQ ID NO 218
<211> LENGTH: 7
<212> TYPE: PRT
<213> ORGANISM: Artificial Sequence
<220> FEATURE:
<223> OTHER INFORMATION: LC CDR2 (S53W)

<400> SEQUENCE: 218

Asp Ala Ser Trp Leu Glu Ser
1               5

<210> SEQ ID NO 219
<211> LENGTH: 7
<212> TYPE: PRT
<213> ORGANISM: Artificial Sequence
<220> FEATURE:
<223> OTHER INFORMATION: LC CDR2 (S53N)

<400> SEQUENCE: 219

Asp Ala Ser Asn Leu Glu Ser
1               5

<210> SEQ ID NO 220
<211> LENGTH: 7
<212> TYPE: PRT
<213> ORGANISM: Artificial Sequence
<220> FEATURE:
<223> OTHER INFORMATION: LC CDR2 (S53D)

<400> SEQUENCE: 220

Asp Ala Ser Asp Leu Glu Ser
1               5

<210> SEQ ID NO 221
<211> LENGTH: 7
<212> TYPE: PRT
<213> ORGANISM: Artificial Sequence
```

```
<220> FEATURE:
<223> OTHER INFORMATION: LC CDR2 (S53E)

<400> SEQUENCE: 221

Asp Ala Ser Glu Leu Glu Ser
1               5

<210> SEQ ID NO 222
<211> LENGTH: 7
<212> TYPE: PRT
<213> ORGANISM: Artificial Sequence
<220> FEATURE:
<223> OTHER INFORMATION: LC CDR2 (S53L)

<400> SEQUENCE: 222

Asp Ala Ser Leu Leu Glu Ser
1               5

<210> SEQ ID NO 223
<211> LENGTH: 7
<212> TYPE: PRT
<213> ORGANISM: Artificial Sequence
<220> FEATURE:
<223> OTHER INFORMATION: LC CDR2 (L54P)

<400> SEQUENCE: 223

Asp Ala Ser Ser Pro Glu Ser
1               5

<210> SEQ ID NO 224
<211> LENGTH: 7
<212> TYPE: PRT
<213> ORGANISM: Artificial Sequence
<220> FEATURE:
<223> OTHER INFORMATION: LC CDR2 (L54S)

<400> SEQUENCE: 224

Asp Ala Ser Ser Ser Glu Ser
1               5

<210> SEQ ID NO 225
<211> LENGTH: 7
<212> TYPE: PRT
<213> ORGANISM: Artificial Sequence
<220> FEATURE:
<223> OTHER INFORMATION: LC CDR2 (L54T)

<400> SEQUENCE: 225

Asp Ala Ser Ser Thr Glu Ser
1               5

<210> SEQ ID NO 226
<211> LENGTH: 7
<212> TYPE: PRT
<213> ORGANISM: Artificial Sequence
<220> FEATURE:
<223> OTHER INFORMATION: LC CDR2 (L54K)

<400> SEQUENCE: 226

Asp Ala Ser Ser Lys Glu Ser
1               5

<210> SEQ ID NO 227
<211> LENGTH: 7
<212> TYPE: PRT
<213> ORGANISM: Artificial Sequence
```

```
<220> FEATURE:
<223> OTHER INFORMATION: LC CDR2 (L54H)

<400> SEQUENCE: 227

Asp Ala Ser Ser His Glu Ser
1               5

<210> SEQ ID NO 228
<211> LENGTH: 7
<212> TYPE: PRT
<213> ORGANISM: Artificial Sequence
<220> FEATURE:
<223> OTHER INFORMATION: LC CDR2 (L54N)

<400> SEQUENCE: 228

Asp Ala Ser Ser Asn Glu Ser
1               5

<210> SEQ ID NO 229
<211> LENGTH: 7
<212> TYPE: PRT
<213> ORGANISM: Artificial Sequence
<220> FEATURE:
<223> OTHER INFORMATION: LC CDR2 (E55D)

<400> SEQUENCE: 229

Asp Ala Ser Ser Leu Asp Ser
1               5

<210> SEQ ID NO 230
<211> LENGTH: 7
<212> TYPE: PRT
<213> ORGANISM: Artificial Sequence
<220> FEATURE:
<223> OTHER INFORMATION: LC CDR2 (E55Q)

<400> SEQUENCE: 230

Asp Ala Ser Ser Leu Gln Ser
1               5

<210> SEQ ID NO 231
<211> LENGTH: 7
<212> TYPE: PRT
<213> ORGANISM: Artificial Sequence
<220> FEATURE:
<223> OTHER INFORMATION: LC CDR2 (S56G)

<400> SEQUENCE: 231

Asp Ala Ser Ser Leu Glu Gly
1               5

<210> SEQ ID NO 232
<211> LENGTH: 7
<212> TYPE: PRT
<213> ORGANISM: Artificial Sequence
<220> FEATURE:
<223> OTHER INFORMATION: LC CDR2 (S56T)

<400> SEQUENCE: 232

Asp Ala Ser Ser Leu Glu Thr
1               5

<210> SEQ ID NO 233
<211> LENGTH: 7
<212> TYPE: PRT
<213> ORGANISM: Artificial Sequence
```

```
<220> FEATURE:
<223> OTHER INFORMATION: LC CDR2 (S56N)

<400> SEQUENCE: 233

Asp Ala Ser Ser Leu Glu Asn
1               5

<210> SEQ ID NO 234
<211> LENGTH: 7
<212> TYPE: PRT
<213> ORGANISM: Artificial Sequence
<220> FEATURE:
<223> OTHER INFORMATION: LC CDR2 (S56D)

<400> SEQUENCE: 234

Asp Ala Ser Ser Leu Glu Asp
1               5

<210> SEQ ID NO 235
<211> LENGTH: 7
<212> TYPE: PRT
<213> ORGANISM: Artificial Sequence
<220> FEATURE:
<223> OTHER INFORMATION: LC CDR2 (S56Q)

<400> SEQUENCE: 235

Asp Ala Ser Ser Leu Glu Gln
1               5

<210> SEQ ID NO 236
<211> LENGTH: 7
<212> TYPE: PRT
<213> ORGANISM: Artificial Sequence
<220> FEATURE:
<223> OTHER INFORMATION: LC CDR2 (S56P)

<400> SEQUENCE: 236

Asp Ala Ser Ser Leu Glu Pro
1               5

<210> SEQ ID NO 237
<211> LENGTH: 7
<212> TYPE: PRT
<213> ORGANISM: Artificial Sequence
<220> FEATURE:
<223> OTHER INFORMATION: LC CDR2 (S56E)

<400> SEQUENCE: 237

Asp Ala Ser Ser Leu Glu Glu
1               5

<210> SEQ ID NO 238
<211> LENGTH: 11
<212> TYPE: PRT
<213> ORGANISM: Artificial Sequence
<220> FEATURE:
<223> OTHER INFORMATION: LC CDR3 (Q89M)

<400> SEQUENCE: 238

Met Gln Phe Asn Ser Tyr Pro Leu Trp Ile Thr
1               5                   10

<210> SEQ ID NO 239
<211> LENGTH: 11
<212> TYPE: PRT
<213> ORGANISM: Artificial Sequence
```

```
<220> FEATURE:
<223> OTHER INFORMATION: LC CDR3 (Q90G)

<400> SEQUENCE: 239

Gln Gly Phe Asn Ser Tyr Pro Leu Trp Ile Thr
1               5                   10

<210> SEQ ID NO 240
<211> LENGTH: 11
<212> TYPE: PRT
<213> ORGANISM: Artificial Sequence
<220> FEATURE:
<223> OTHER INFORMATION: LC CDR3 (Q90A)

<400> SEQUENCE: 240

Gln Ala Phe Asn Ser Tyr Pro Leu Trp Ile Thr
1               5                   10

<210> SEQ ID NO 241
<211> LENGTH: 11
<212> TYPE: PRT
<213> ORGANISM: Artificial Sequence
<220> FEATURE:
<223> OTHER INFORMATION: LC CDR3 (Q90D)

<400> SEQUENCE: 241

Gln Asp Phe Asn Ser Tyr Pro Leu Trp Ile Thr
1               5                   10

<210> SEQ ID NO 242
<211> LENGTH: 11
<212> TYPE: PRT
<213> ORGANISM: Artificial Sequence
<220> FEATURE:
<223> OTHER INFORMATION: LC CDR3 (Q90E)

<400> SEQUENCE: 242

Gln Glu Phe Asn Ser Tyr Pro Leu Trp Ile Thr
1               5                   10

<210> SEQ ID NO 243
<211> LENGTH: 11
<212> TYPE: PRT
<213> ORGANISM: Artificial Sequence
<220> FEATURE:
<223> OTHER INFORMATION: LC CDR3 (N92E)

<400> SEQUENCE: 243

Gln Gln Phe Glu Ser Tyr Pro Leu Trp Ile Thr
1               5                   10

<210> SEQ ID NO 244
<211> LENGTH: 11
<212> TYPE: PRT
<213> ORGANISM: Artificial Sequence
<220> FEATURE:
<223> OTHER INFORMATION: LC CDR3 (S93P)

<400> SEQUENCE: 244

Gln Gln Phe Asn Pro Tyr Pro Leu Trp Ile Thr
1               5                   10

<210> SEQ ID NO 245
<211> LENGTH: 11
<212> TYPE: PRT
<213> ORGANISM: Artificial Sequence
```

<220> FEATURE:
<223> OTHER INFORMATION: LC CDR3 (S93A)

<400> SEQUENCE: 245

Gln Gln Phe Asn Ala Tyr Pro Leu Trp Ile Thr
1               5                   10

<210> SEQ ID NO 246
<211> LENGTH: 11
<212> TYPE: PRT
<213> ORGANISM: Artificial Sequence
<220> FEATURE:
<223> OTHER INFORMATION: LC CDR3 (W95bT)

<400> SEQUENCE: 246

Gln Gln Phe Asn Ser Tyr Pro Leu Thr Ile Thr
1               5                   10

<210> SEQ ID NO 247
<211> LENGTH: 11
<212> TYPE: PRT
<213> ORGANISM: Artificial Sequence
<220> FEATURE:
<223> OTHER INFORMATION: LC CDR3 (W95bI)

<400> SEQUENCE: 247

Gln Gln Phe Asn Ser Tyr Pro Leu Ile Ile Thr
1               5                   10

<210> SEQ ID NO 248
<211> LENGTH: 11
<212> TYPE: PRT
<213> ORGANISM: Artificial Sequence
<220> FEATURE:
<223> OTHER INFORMATION: LC CDR3 (W95bM)

<400> SEQUENCE: 248

Gln Gln Phe Asn Ser Tyr Pro Leu Met Ile Thr
1               5                   10

<210> SEQ ID NO 249
<211> LENGTH: 11
<212> TYPE: PRT
<213> ORGANISM: Artificial Sequence
<220> FEATURE:
<223> OTHER INFORMATION: LC CDR3 (W95bK)

<400> SEQUENCE: 249

Gln Gln Phe Asn Ser Tyr Pro Leu Lys Ile Thr
1               5                   10

<210> SEQ ID NO 250
<211> LENGTH: 11
<212> TYPE: PRT
<213> ORGANISM: Artificial Sequence
<220> FEATURE:
<223> OTHER INFORMATION: LC CDR3 (W95bN)

<400> SEQUENCE: 250

Gln Gln Phe Asn Ser Tyr Pro Leu Asn Ile Thr
1               5                   10

<210> SEQ ID NO 251
<211> LENGTH: 11
<212> TYPE: PRT
<213> ORGANISM: Artificial Sequence

```
<220> FEATURE:
<223> OTHER INFORMATION: LC CDR3 (W95bE)

<400> SEQUENCE: 251

Gln Gln Phe Asn Ser Tyr Pro Leu Glu Ile Thr
1               5                   10

<210> SEQ ID NO 252
<211> LENGTH: 11
<212> TYPE: PRT
<213> ORGANISM: Artificial Sequence
<220> FEATURE:
<223> OTHER INFORMATION: LC CDR3 (W95bQ)

<400> SEQUENCE: 252

Gln Gln Phe Asn Ser Tyr Pro Leu Gln Ile Thr
1               5                   10

<210> SEQ ID NO 253
<211> LENGTH: 11
<212> TYPE: PRT
<213> ORGANISM: Artificial Sequence
<220> FEATURE:
<223> OTHER INFORMATION: LC CDR3 (I96L)

<400> SEQUENCE: 253

Gln Gln Phe Asn Ser Tyr Pro Leu Trp Leu Thr
1               5                   10

<210> SEQ ID NO 254
<211> LENGTH: 11
<212> TYPE: PRT
<213> ORGANISM: Artificial Sequence
<220> FEATURE:
<223> OTHER INFORMATION: LC CDR3 (T97M)

<400> SEQUENCE: 254

Gln Gln Phe Asn Ser Tyr Pro Leu Trp Ile Met
1               5                   10

<210> SEQ ID NO 255
<211> LENGTH: 11
<212> TYPE: PRT
<213> ORGANISM: Artificial Sequence
<220> FEATURE:
<223> OTHER INFORMATION: LC CDR3 (T97K)

<400> SEQUENCE: 255

Gln Gln Phe Asn Ser Tyr Pro Leu Trp Ile Lys
1               5                   10

<210> SEQ ID NO 256
<211> LENGTH: 11
<212> TYPE: PRT
<213> ORGANISM: Artificial Sequence
<220> FEATURE:
<223> OTHER INFORMATION: LC CDR3 (T97H)

<400> SEQUENCE: 256

Gln Gln Phe Asn Ser Tyr Pro Leu Trp Ile His
1               5                   10

<210> SEQ ID NO 257
<211> LENGTH: 11
<212> TYPE: PRT
<213> ORGANISM: Artificial Sequence
```

```
<220> FEATURE:
<223> OTHER INFORMATION: LC CDR3 (T97Y)

<400> SEQUENCE: 257

Gln Gln Phe Asn Ser Tyr Pro Leu Trp Ile Tyr
1               5                   10

<210> SEQ ID NO 258
<211> LENGTH: 11
<212> TYPE: PRT
<213> ORGANISM: Artificial Sequence
<220> FEATURE:
<223> OTHER INFORMATION: LC CDR3 (T97E)

<400> SEQUENCE: 258

Gln Gln Phe Asn Ser Tyr Pro Leu Trp Ile Glu
1               5                   10

<210> SEQ ID NO 259
<211> LENGTH: 11
<212> TYPE: PRT
<213> ORGANISM: Artificial Sequence
<220> FEATURE:
<223> OTHER INFORMATION: LC CDR3 (T97Q)

<400> SEQUENCE: 259

Gln Gln Phe Asn Ser Tyr Pro Leu Trp Ile Gln
1               5                   10

<210> SEQ ID NO 260
<211> LENGTH: 10
<212> TYPE: PRT
<213> ORGANISM: Artificial Sequence
<220> FEATURE:
<223> OTHER INFORMATION: HC CDR1
<220> FEATURE:
<221> NAME/KEY: misc_feature
<222> LOCATION: (1)..(1)
<223> OTHER INFORMATION: Wherein Xaa is Phe or Tyr
<220> FEATURE:
<221> NAME/KEY: misc_feature
<222> LOCATION: (2)..(2)
<223> OTHER INFORMATION: Wherein Xaa is Thr,
      Pro,Ala,Ser,Val,Leu,Ile,Met,His,Phe,Tyr,Asn,Asp,Glu, or Gln
<220> FEATURE:
<221> NAME/KEY: misc_feature
<222> LOCATION: (3)..(3)
<223> OTHER INFORMATION: Wherein Xaa is Leu, or Met
<220> FEATURE:
<221> NAME/KEY: misc_feature
<222> LOCATION: (9)..(9)
<223> OTHER INFORMATION: Xaa can be any naturally occurring amino acid

<400> SEQUENCE: 260

Gly Xaa Xaa Phe Asp Asp His Ala Xaa His
1               5                   10

<210> SEQ ID NO 261
<211> LENGTH: 17
<212> TYPE: PRT
<213> ORGANISM: Artificial Sequence
<220> FEATURE:
<223> OTHER INFORMATION: HC CDR2
<220> FEATURE:
<221> NAME/KEY: misc_feature
<222> LOCATION: (1)..(1)
<223> OTHER INFORMATION: Wherein Xaa is Ser or Thr
<220> FEATURE:
<221> NAME/KEY: misc_feature
<222> LOCATION: (2)..(2)
<223> OTHER INFORMATION: Wherein Xaa is His or Asn
```

```
<220> FEATURE:
<221> NAME/KEY: misc_feature
<222> LOCATION: (3)..(3)
<223> OTHER INFORMATION: Wherein Xaa is Ile or Val
<220> FEATURE:
<221> NAME/KEY: misc_feature
<222> LOCATION: (4)..(4)
<223> OTHER INFORMATION: Wherein Xaa is Gly, Ala, Ser, Thr, Val, Leu,
      Ile, Arg, His, or Asn
<220> FEATURE:
<221> NAME/KEY: misc_feature
<222> LOCATION: (5)..(5)
<223> OTHER INFORMATION: Wherein Xaa is Pro, Thr, Asn, As, Glu, Gln,
      Ser, His, or Tyr
<220> FEATURE:
<221> NAME/KEY: misc_feature
<222> LOCATION: (6)..(6)
<223> OTHER INFORMATION: Wherein  Xaa is
      Pro,Gly,Ala,Ser,Thr,Val,Arg,His,Phe,Tyr,Asn,Asp,Arg, or Glu
<220> FEATURE:
<221> NAME/KEY: misc_feature
<222> LOCATION: (7)..(7)
<223> OTHER INFORMATION: Wherein  Xaa is Val or Ile
<220> FEATURE:
<221> NAME/KEY: misc_feature
<222> LOCATION: (8)..(8)
<223> OTHER INFORMATION: Wherein  Xaa is Ala, Ser, Thr, Val,Leu,
      Ile,Met, Lys, Arg, His, Phe, Tyr, Asn, Asp, Glu, Arg, or Gln
<220> FEATURE:
<221> NAME/KEY: misc_feature
<222> LOCATION: (9)..(9)
<223> OTHER INFORMATION: Wherein  Xaa is Gly, His, Asp, or Gln
<220> FEATURE:
<221> NAME/KEY: misc_feature
<222> LOCATION: (12)..(17)
<223> OTHER INFORMATION: Xaa can be any naturally occurring amino acid

<400> SEQUENCE: 261

Gly Ile Xaa Trp Xaa Ser Arg Gly Xaa Gly Tyr Xaa Xaa Xaa Xaa Xaa
1               5                   10                  15

Xaa

<210> SEQ ID NO 262
<211> LENGTH: 12
<212> TYPE: PRT
<213> ORGANISM: Artificial Sequence
<220> FEATURE:
<223> OTHER INFORMATION: HC CDR3
<220> FEATURE:
<221> NAME/KEY: misc_feature
<222> LOCATION: (1)..(1)
<223> OTHER INFORMATION: Wherein X is Ser,Thr, Asn, Asp, Glu
<220> FEATURE:
<221> NAME/KEY: misc_feature
<222> LOCATION: (2)..(2)
<223> OTHER INFORMATION: Wherein X is Lys, Met, Arg, or Ser
<220> FEATURE:
<221> NAME/KEY: misc_feature
<222> LOCATION: (3)..(3)
<223> OTHER INFORMATION: Wherein Xaa is Gly, Ala, Ser, Thr, Val, Met,
      Asn, Glu, or Gln
<220> FEATURE:
<221> NAME/KEY: misc_feature
<222> LOCATION: (4)..(4)
<223> OTHER INFORMATION: Wherein X is Ala, Ser, Thr, Val, Arg, His, Tyr,
      Trp, Asn, Glu, or Met
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
```

```
<220> FEATURE:
<221> NAME/KEY: misc_feature
<222> LOCATION: (12)..(12)
<223> OTHER INFORMATION: Xaa can be any naturally occurring amino acid

<400> SEQUENCE: 262

Asp Glu Tyr Xaa Xaa Gly Tyr Tyr Xaa Leu Asp Xaa
1               5                   10

<210> SEQ ID NO 263
<211> LENGTH: 11
<212> TYPE: PRT
<213> ORGANISM: Macaca fascicularis
<220> FEATURE:
<221> NAME/KEY: MISC_FEATURE
<222> LOCATION: (1)..(1)
<223> OTHER INFORMATION: Wherein Xaa is Ser, Thr, Val, Lys, Arg, His,
      Tyr or Ile
<220> FEATURE:
<221> NAME/KEY: MISC_FEATURE
<222> LOCATION: (2)..(2)
<223> OTHER INFORMATION: Wherein Xaa is Ala, Ser, Thr, or Val
<220> FEATURE:
<221> NAME/KEY: MISC_FEATURE
<222> LOCATION: (3)..(3)
<223> OTHER INFORMATION: Wherein Xaa is Pro,  Gly, Ala, Ser, Thr, Val,
      Leu, Ile, Met, Lys, Arg, His, Asn, Glu
<220> FEATURE:
<221> NAME/KEY: MISC_FEATURE
<222> LOCATION: (4)..(4)
<223> OTHER INFORMATION: Wherein Xaa is Pro, Gly, Ala, Ser, Thr, Val,
      Leu, Ile, Met, His, Phe, Tyr, Asn, As, Glu
<220> FEATURE:
<221> NAME/KEY: MISC_FEATURE
<222> LOCATION: (5)..(5)
<223> OTHER INFORMATION: Wherein Xaa is Pro, Gly, Aal, Ser, Thr, His,
      Glu, Gln, Met, Asn, or Asp
<220> FEATURE:
<221> NAME/KEY: MISC_FEATURE
<222> LOCATION: (6)..(6)
<223> OTHER INFORMATION: Wherein Xaa is Pro, Gly, Ala, Ser, Thr, Val,
      Leu, Ile, Asn
<220> FEATURE:
<221> NAME/KEY: MISC_FEATURE
<222> LOCATION: (7)..(7)
<223> OTHER INFORMATION: Wherein Xaa is Ser, Thr, Val, Leu, Ile, Met,
      His, Phe, Tyr, Asn, Asp, Glu, or Gln
<220> FEATURE:
<221> NAME/KEY: MISC_FEATURE
<222> LOCATION: (8)..(8)
<223> OTHER INFORMATION: Wherein Xaa is Pro or Ala
<220> FEATURE:
<221> NAME/KEY: MISC_FEATURE
<222> LOCATION: (9)..(9)
<223> OTHER INFORMATION: Wherein Xaa is Ala, Leu, or Val
<220> FEATURE:
<221> NAME/KEY: misc_feature
<222> LOCATION: (10)..(10)
<223> OTHER INFORMATION: Xaa can be any naturally occurring amino acid

<400> SEQUENCE: 263

Xaa Xaa Xaa Xaa Xaa Xaa Xaa Ser Xaa Xaa Ala
1               5                   10

<210> SEQ ID NO 264
<211> LENGTH: 7
<212> TYPE: PRT
<213> ORGANISM: Artificial Sequence
<220> FEATURE:
<223> OTHER INFORMATION: LC CDR2
<220> FEATURE:
<221> NAME/KEY: MISC_FEATURE
<222> LOCATION: (1)..(1)
<223> OTHER INFORMATION: Wherein Xaa is Gly, Ala, Ser, Met, His, Asn,
      Asp, Glu, or Gln
```

```
<220> FEATURE:
<221> NAME/KEY: MISC_FEATURE
<222> LOCATION: (2)..(2)
<223> OTHER INFORMATION: Wherein Xaa is
      Gly,Ala,Ser,Thr,Val,Met,His,Phe,Tyr,Asn,Asp,Glu,Gln
<220> FEATURE:
<221> NAME/KEY: MISC_FEATURE
<222> LOCATION: (3)..(3)
<223> OTHER INFORMATION: Wherein Ala,Ser,Phe,Tyr,Trp,Asn,Asp,Glu,Arg,
      Leu
<220> FEATURE:
<221> NAME/KEY: MISC_FEATURE
<222> LOCATION: (4)..(4)
<223> OTHER INFORMATION: Wherein Xaa is Pro, Ser, Tyr, Leu, Lys, His, or
      Asn
<220> FEATURE:
<221> NAME/KEY: MISC_FEATURE
<222> LOCATION: (5)..(5)
<223> OTHER INFORMATION: Wherein Xaa is Asp, Glu, or Gln
<220> FEATURE:
<221> NAME/KEY: MISC_FEATURE
<222> LOCATION: (6)..(6)
<223> OTHER INFORMATION: Wherein Xaa is Gly, Ser, Thr, Asn, Asp, Gln,
      Pro, Glu
<220> FEATURE:
<221> NAME/KEY: misc_feature
<222> LOCATION: (7)..(7)
<223> OTHER INFORMATION: Xaa can be any naturally occurring amino acid

<400> SEQUENCE: 264

Asp Xaa Xaa Xaa Xaa Xaa Xaa
1               5

<210> SEQ ID NO 265
<211> LENGTH: 11
<212> TYPE: PRT
<213> ORGANISM: Artificial Sequence
<220> FEATURE:
<223> OTHER INFORMATION: LC CDR3
<220> FEATURE:
<221> NAME/KEY: MISC_FEATURE
<222> LOCATION: (1)..(1)
<223> OTHER INFORMATION: wherein Xaa is Met or Gln
<220> FEATURE:
<221> NAME/KEY: MISC_FEATURE
<222> LOCATION: (2)..(2)
<223> OTHER INFORMATION: wherein Xaa is Gly, Ala, Asp, Glu, or Gln
<220> FEATURE:
<221> NAME/KEY: MISC_FEATURE
<222> LOCATION: (3)..(3)
<223> OTHER INFORMATION: wherein Xaa is Asn or Glu
<220> FEATURE:
<221> NAME/KEY: MISC_FEATURE
<222> LOCATION: (4)..(4)
<223> OTHER INFORMATION: wherein Xaa is Pro, Ala, or Ser
<220> FEATURE:
<221> NAME/KEY: MISC_FEATURE
<222> LOCATION: (5)..(5)
<223> OTHER INFORMATION: wherein Xaa is Thr, Ile, Met, Lys, Trp, Asn,
      Glu
<220> FEATURE:
<221> NAME/KEY: MISC_FEATURE
<222> LOCATION: (6)..(6)
<223> OTHER INFORMATION: Wherein Xaa is Leu or Ile
<220> FEATURE:
<221> NAME/KEY: MISC_FEATURE
<222> LOCATION: (7)..(7)
<223> OTHER INFORMATION: Wherein Xaa is Thr, Met, Leu, His, Tyr, Glu or
      Gly
```

```
<220> FEATURE:
<221> NAME/KEY: misc_feature
<222> LOCATION: (9)..(11)
<223> OTHER INFORMATION: Xaa can be any naturally occurring amino acid

<400> SEQUENCE: 265

Xaa Xaa Phe Xaa Xaa Tyr Pro Leu Xaa Xaa Xaa
1               5                   10
```